US011458129B2

(12) United States Patent
Anderson et al.

(10) Patent No.: US 11,458,129 B2
(45) Date of Patent: Oct. 4, 2022

(54) NEUROKININ ANTAGONISTS AND USES THEREOF

(71) Applicant: California Institute of Technology, Pasadena, CA (US)

(72) Inventors: David J. Anderson, Altadena, CA (US); Moriel Zelikowsky, Pasadena, CA (US); Andrea Choe, Los Angeles, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 16/178,460

(22) Filed: Nov. 1, 2018

(65) Prior Publication Data

US 2019/0125738 A1  May 2, 2019

Related U.S. Application Data

(60) Provisional application No. 62/580,834, filed on Nov. 2, 2017.

(51) Int. Cl.
*A61K 31/4545* (2006.01)
*A61P 43/00* (2006.01)
*G01N 33/68* (2006.01)

(52) U.S. Cl.
CPC .......... *A61K 31/4545* (2013.01); *A61P 43/00* (2018.01); *G01N 33/68* (2013.01)

(58) Field of Classification Search
CPC .......................... A61K 31/4545; G01N 33/68
See application file for complete search history.

(56) References Cited

U.S. PATENT DOCUMENTS

| 5,942,523 | A | 8/1999 | Bichon et al. |
| 7,410,970 | B2 | 8/2008 | Janssens et al. |
| 7,435,736 | B2 | 10/2008 | Jenssens et al. |
| 7,544,694 | B2 | 6/2009 | Jenssens et al. |
| 7,560,549 | B2 | 7/2009 | Tomori et al. |
| 8,138,334 | B2 | 3/2012 | Jenssens et al. |
| 9,540,657 | B2 | 1/2017 | Yu et al. |
| 9,585,971 | B2 | 3/2017 | Deverman et al. |
| 2005/0163777 | A1* | 7/2005 | Rosen .................... C07K 16/18 424/145.1 |
| 2005/0256112 | A1* | 11/2005 | Brodney ................. A61P 25/00 514/227.5 |
| 2007/0142431 | A1* | 6/2007 | Chan ...................... A61P 25/24 514/314 |
| 2008/0161393 | A1* | 7/2008 | Barrett ................... A61P 25/06 514/484 |
| 2010/0111359 | A1* | 5/2010 | Bai ........................ A01K 29/005 382/103 |
| 2010/0168215 | A1 | 7/2010 | During et al. |
| 2011/0313372 | A1* | 12/2011 | Eifler ...................... A61K 31/13 604/304 |
| 2013/0123277 | A1* | 5/2013 | Jain ....................... A61P 25/00 514/256 |
| 2014/0125678 | A1* | 5/2014 | Wang ..................... G06F 3/0488 345/473 |
| 2014/0155575 | A1* | 6/2014 | Bai ......................... C07K 7/64 530/321 |
| 2014/0178305 | A1 | 6/2014 | Anderson et al. |
| 2017/0166926 | A1 | 6/2017 | Deverman et al. |
| 2017/0198308 | A1 | 7/2017 | Qi et al. |
| 2017/0296528 | A1 | 10/2017 | Ressler et al. |
| 2018/0221396 | A1* | 8/2018 | Chadeayne ............. A61P 25/24 |
| 2019/0125900 | A1 | 5/2019 | Anderson et al. |

FOREIGN PATENT DOCUMENTS

| WO | WO 1995/32948 | | 7/1995 |
| WO | WO 2004/050626 | * | 6/2004 |
| WO | WO 2005094801 | A1 | 10/2005 |
| WO | WO 2006/050991 | | 5/2006 |
| WO | WO2006/050992 | | 5/2006 |
| WO | WO 2006/130080 | | 12/2006 |
| WO | WO 2007/003965 | * | 1/2007 |
| WO | WO 2008/131779 | | 6/2008 |
| WO | WO 2009/130240 | | 10/2009 |
| WO | WO 2010/083842 | | 11/2010 |
| WO | WO 2017/049252 | A1 | 3/2017 |
| WO | WO 2017/153995 | A1 | 9/2017 |
| WO | WO 2017/165747 | A1 | 9/2017 |

OTHER PUBLICATIONS

Salome et al. (Pharmacology, Biochemistry and Behavior (2006) 533-539). (Year: 2006).*
International Search Report and Written Opinion dated Jan. 29, 2019 in Application No. PCT/US18/58809.
International Search Report and Written Opinion dated Jan. 22, 2019 in Application No. PCT/US2018/058808.
Anthony, Todd et al., "Control of Stress-Induced Persistent Anxiety by an Extra-Amygdala Septohypothalamic Circuit", Cell, Jan. 30, 2014 Elsevier Inc., vol. 156, pp. 522-536.
Beajounan, Jean-Claude et al., "A 25-year adventure in the field of Tachykinins", Peptides 25, 2004 Elsevier Inc., pp. 339-357.
Blanchard, Caroline et al., "Defensive Responses to Predictor Threat in the Rat and Mouse", Current Protocols in Neuroscience, 2005 John Wiley & Sons, Inc., Unit 8.19, Supplement 30, pp. 1-20.
Blanchard, Caroline, "The Mouse Defense Test Battery: pharmacological and behavioral assays for anxiety and panic", European Journal of Pharmacology, 2003 Elvesier, Inc, vol. 463, Issue No. 1-3, pp. 97-116.

(Continued)

*Primary Examiner* — Marcos L Sznaidman

(74) *Attorney, Agent, or Firm* — Knobbe, Martens, Olson & Bear, LLP

(57) ABSTRACT

In some embodiments, methods of inhibiting, ameliorating, reducing the severity of, treating, reducing the likelihood of, or preventing social isolation stress or symptoms thereof in a subject in need thereof are described. In some embodiments, methods of determining a risk of social isolation stress in a subject are described.

23 Claims, 84 Drawing Sheets

Specification includes a Sequence Listing.

(56) References Cited

OTHER PUBLICATIONS

Cai, Haijang et al., "Central amygdala PKC neurons mediate the influence of multiple anorexigenic signals.", Nature Neuroscience, Sep. 2014, vol. 17, No. 9, pp. 1240-1248.

Chou, Kee-Lee et al., "The Association Between Social Isolation and DSM-IV Mood, Anxiety, and Substance Use Disorders: Wave 2 of the National Epidemiologic Survey on Alcohol and Related Conditions", J Clin Psychiatry, Nov. 2011, vol. 72 (11), pp. 1468-1476.

Culman, Juraj et al, "Central tachykinins: mediators of defence reaction and stress reactions." Can. J. Physiol Pharmacol., 1995, vol. 73, pp. 885-891.

Cushman, Jesse, et al., "The Role of the δ Gaba (A) Receptor in Ovarian Cycle-Linked Changes in Hippocampus-Dependent Learning and Memory", Neurochem Research, 2014, vol. 39, pp. 1140-1146.

Deneen, Benjamin, et al., "The Transcription Factor NFIA Controls the Onset of Gliogenesis in the Developing Spinal Cord", Neuron 52, Dec. 21, 2006, vol. 52, pp. 953-968.

Deverman, Benjamin, et al., "Cre-dependent selection yields AAV variants for widespread gene transfer to the adult brain", Nature Biotechnology, Feb. 2016, vol. 34, No. 2, pp. 204-209.

Friedler, Brett, et al. One is the deadliest number: the detrimental effects of social isolation on cerebrovascular diseases and cognition, Acta Neuropathol, 2015, vol. 129, pp. 493-509.

Griebel, Guy et al., "Neuropeptide receptor ligands as drugs for psychiatric diseases: the end of the beginning?", Natures Reviews | Drug Discovery, Jun. 2012, vol. 11, pp. 462-478.

Haubensak, Wulf et al., "Genetic dissection of an amygdala microcircuit that gates conditioned fear", Nature, Nov. 11, 2010, vol. 468, pp. 270-276.

Hong, Weizhe et al., "Antagonistic Control of Social versus Repetitive Self-Grooming Behaviors by Separable Amygdala Neuronal Subsets", Cell 158, Sep. 11, 2014, pp. 1348-1361.

Hong, Weizhe et al., "Automated measurement of mouse social behaviors using depth sensing, video tracking, and machine learning", PNAS, Sep. 9, 2015, pages E5351-E5360.

Hsiao, Elaine et al., "Microbiota Modulate Behavioral and Physiological Abnormalities Associates with Neurodevelopmental Disorders", Cell 155, Dec. 19, 2013, pp. 1451-1463.

Huang, Huang, et al., "Isolation Housing Exacerbates Alzheimer's Disease Like Pathophysiology in Aged APP/PS1 Mice", International Journal of Neuropsychopharmacology, 2015, pp. 1-10.

Kim, Jeansok J., et al., "N-Methyl-D-Aspartate Receptor Antagonist APV Blocks Acquisition but Not Expression of Fear Conditioning", Behavioral Neuroscience, 1991, vol. 105, No. 1, pp. 126-133.

Koch, M, "The Neurobiology of Startle", Progress in Neurobiolgy, 1999, vol. 59, pp. 107-128.

Kunwar, Prabhat, et al., "Ventromedial hypothalamic neurons control a defensive emotion state", eLife Sciences, 2015, vol. 4, No. e06633, pp. 1-30.

Lee, Hyosang et al., "Scalable control of mounting and attack by Esr1+neurons in the ventromedial hypothalmus", Nature, May 29, 2014, vol. 509, pp. 627-632.

Lein, Ed et al., "Genome-wide atlas of gene expression in the adult mouse brain", Nature, Jan. 11, 2007, vol. 445, pp. 168-176.

Lin, John Y., "A user's guide to channelrhodopsin variants: features, limitations and future developments", The Experimental Physiology, The Author Journal compilation, 2010, vol. 96.1, pp. 19-25.

Madisen, Linda et al., "A robust and high-throughput Cre reporting and characterization system for the whole mouse brain", Nature Neuroscrience, Jan. 2010, vol. 13, No. 1, pp. 133-140.

Maggio, J.E, "Tachykinins", Ann. Rev Neurosci, 1988, vol. 11, pp. 13-28.

Mongeau, Raymond et al., "Neural Correlates of Competing Fear Behaviors Evoked by an Innately Aversive Stimulus", The Journal of Neuroscience, May 1, 2003, vol. 29, No. 9, pp. 3855-3868.

Naito, Yuki., et al., "SiDirect 2.0: updated software for designing functional siRNA with reduced seed-dependent off-target effect", BMC Brioinformatics, 2009, vol. 10, No. 392, pp. 1-8.

Shi, Limin, et al., Maternal Influenza Infection Causes Marked Behavioral and Pharmacological Changes in the Offspring, The Journal of Neuroscience, Jan. 1, 2003, vol. 23, No. 1, pp. 297-302.

Sambrook et al. (Molecular Cloning: A Laboratory Manual. Cold Spring Harbor Laboratory Press, N.Y. (1989).

Thompson, Carol L, et al., "Genomic Anatomy of the Hippocampus", Neuron 60, Dec. 26, 2008, pp. 1010-1021.

Williams, J. Bradley, et al., "A Model of Gene-Environment Interaction Reveals Altered Mammary Gland Gene Expression and Increased Tumor Growth Following Social Isolation", Amercian Association Cancer Research Journal, Oct. 2009, vol. 2, No. 10, pp. 850-861.

Yilmaz, Melis, et al., "Rapid Innate Defensive Responses of Mice to Looming Visual Stimuli", Current Biology, Oct. 21, 2013, vol. 23, No. 20, pp. 2011-2015.

Zelikowsky, Moriel, et al., "Neuronal Ensembles in Amygdala, Hippocampus, and Prefrontal Cortex Track Differential Components of Contextual Fear", The Journal of Neuroscience, Jun. 18, 2014, vol. 34, No. 25, pp. 8462-8466.

File History of U.S. Appl. No. 16/178,461.

Andero et al., "A Role for Tac2, NkB, and Nk3 Receptor in Normal and Dysregulated Fear Memory Consolidation", Neuron, vol. 83, pp. 444-454, Jul. 16, 2014.

Dissen et al., "Engineering a Gene Silencing Viral Construct that Targets the Cat Hypothalamus to Induce Permanent Sterility: An Update", Reprod Domest Anim., vol. 52 (Suppl 2), pp. 354-358 (1-9), Apr. 2017.

Foti et al., "Delivering multiple gene products in the brain from a single adeno-associated virus vector", GeneTher., vol. 16, No. 11, pp. 1314-1319 (1-13), Nov. 2009.

Nation et al., "DREADD-induced activation of subfornical organ neurons stimulates thirst and salt appetite", J Neurophysiol., vol. 115, No. 6, pp. 3123-3129 (1-13), Jun. 1, 2016.

Office Action dated Feb. 27, 2020 in U.S. Appl. No. 16/178,461.

Roth, B.L., "DREADDs for Neuroscientists", Neuron, vol. 89, No. 4, pp. 683-694 (1-25), Feb. 17, 2016.

Shen et al., "Triple Transduction with Adeno-Associated Virus Vectors Expressing Tyrosine Hydroxylase, Aromatic-L-Amino-Acid Decarboxylase, and GTP Cyclohydrolase I for Gene Therapy of Parkinson's Disease", Human Gene Therapy, vol. 11, pp. 1509-1519, Jul. 20, 2000.

Wikipedia, Neurokinin B (NKB), pp. 1-6, downloaded on Feb. 15, 2020 from https://en.wikipedia.org/wiki/Neurokinin_B.

Extended European Search Report dated Aug. 5, 2021 in European Application No. 18873410.7 in 9 pages.

Salome et al., Selective Blockade of NK2 or NK2 Receptors Produces Anxiolytic- and Antidepressant-like effects in Gerbils, Pharmacology Biochemistry and Behavior, vol. 83, No. 4, pp. 533-539, 2006.

Office Action dated Jun. 15, 2021 in U.S. Appl. No. 16/178,461 in 22 pages.

Kugler et al., Human Synapsin 1 Gene Promoter Confers Highly Neuron-Specific Long-Term Transgene Expression from an Adenoviral Vector in The Adult Rat Brain Depending On The Transduced Area, Gene Therapy, vol. 10, pp. 337-347, 2003.

U.S. Appl. No. 62/457,123, filed Feb. 9, 2017, Chadeayne.

American Psychiatric Association. (2013). Anxiety disorders. In Diagnostic and statistical manual of mental disorders (5th ed.). https://doi.org/10.1176/appi.books.9780890425596.dsm05.

Notice of Allowance dated Feb. 22, 2022, in U.S. Appl. No. 16/178,461 in 13 pages.

Bailey, N. W., et al., Evolutionary Consequences of Social Isolation, Trends in Ecology & Evolution, vol. 33, Issue 8, pp. 595-607, 2018.

Blanchard, R. J., et al., Aggressive behavior in the rat, Behavioral Biology, vol. 21, Issue 2, pp. 197-224, 1977.

Bourin, M. et al., Animal Models Of Anxiety In Mice, Fundamental & clinical pharmacology. 21. 567-74, 2008.

Cacioppo, J. T., et al., Evolutionary mechanisms for loneliness, Cognition & emotion vol. 28, No. 1, pp. 3-21, 2014.

Cacioppo, J.T., et al., Social isolation. Annals of the New York Academy of Sciences, vol. 1231, pp. 17-22, 2011.

(56) References Cited

OTHER PUBLICATIONS

Extended European Search Report dated Oct. 29, 2021 in EP Application 18873220.0 in 9 pages.
Hawkley, L. C. et al., Loneliness and pathways to disease, Brain, Behavior, and Immunity, vol. 17, Issue1, Supplement, pp. 98-105, 2003.
Mazarati et al., Galanin And Galanin Receptors In Epilepsy, Neuropeptides, No. 38, pp. 331-343, 2004.
Miczek, K. A., et al., Aggressive behavioral phenotypes in mice. Behavioural Brain Research, vol. 125, No. 1-2, pp. 167-181, 2001.
Neumann, I. D., et al., Aggression And Anxiety: Social Context And Neurobiological Links, Behavioral Neuroscience, vol. 4, Article 12, in 16 pages, 2010.
Rinker, J.A., et al., Neuropeptide Y1 receptor signaling in BNST-projecting neurons of the central amygdala modulates binge-like ethanol consumption. Alcoholism: Clin Exptl Res 39: Supp p. 235A, Abstract 898 Jun. 2015.
Roelofs, K., Freeze for action: Neurobiological Mechanisms In Animal And Human Freezing, Philosophical Transactions B., vol. 372, in 10 pages, 2017.
Rorato et al., Activation of TRH Neurons Using DREADDs Stimulates TSH Release and Increases Serum Thyroid Hormone Levels, Exhibit/Poster Hall (BCEC), 2016 in 1 page.
Silva et al., The Neural Circuits Of Innate Fear: Detection, Integration, Action, And Memorization, Learning & Memory, No. 23, pp. 544-555, 2016.
Valzelli, L. The "isolation syndrome" in mice. Psychopharmacologia, vol. 31, pp. 305-320, 1973. (Abstract only).
Wongwitdecha, N., et al., Social isolation increases aggressive behaviour and alters the effects of diazepam in the rat social interaction test, Behavioural Brain Research, vol. 75, Issues 1-2, pp. 27-32, 1996.
Zelikowsky, M. et al., The Neuropeptide Tac2 Controls a Distributed Brain State Induced by Chronic Social Isolation Stress, Cell, vol. 173, No. 5 pp. 1265-1279.e19, 2018.
Cacioppo JT, et al., Loneliness as a specific risk factor for depressive symptoms: cross-sectional and longitudinal analyses. Psychol Aging, vol. 21, No. 1, pp. 140-151, 2006.
Cacioppo, J. et al., Loneliness and Health: Potential Mechanisms, Psychosomatic Medicine, vol. 64, Issue 3, pp. 407-417, 2002.
House JS., et al., Social relationships and health, Science, vol. 29, No. 241(4865), pp. 540-455, 1988.
Valzelli, L. The "isolation syndrome" in mice. Psychopharmacologia, vol. 31, pp. 305-320,1973.

\* cited by examiner

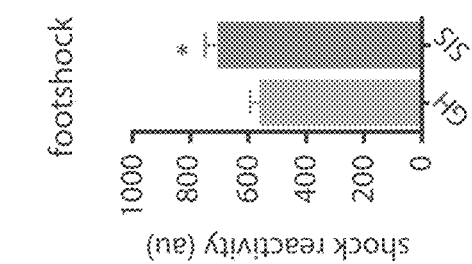
FIG. 1J
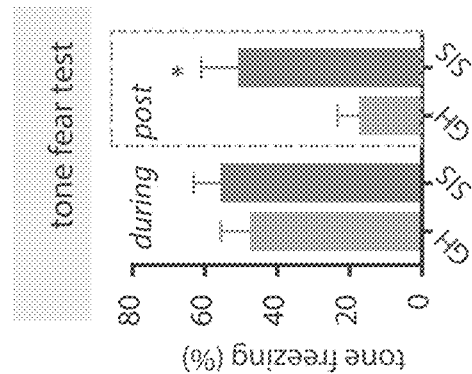
FIG. 1I
FIG. 1H
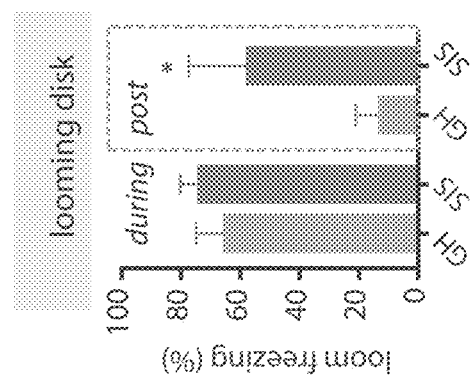
FIG. 1G
FIG. 1F
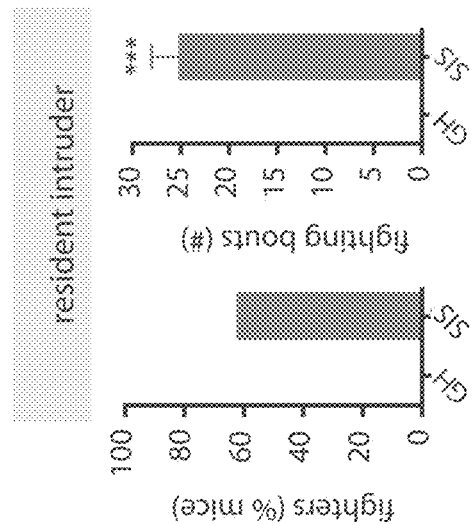

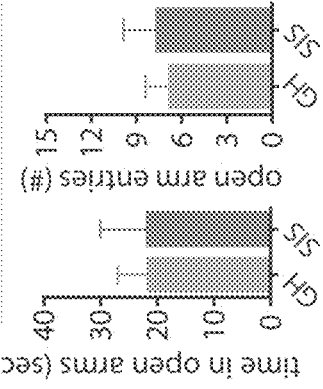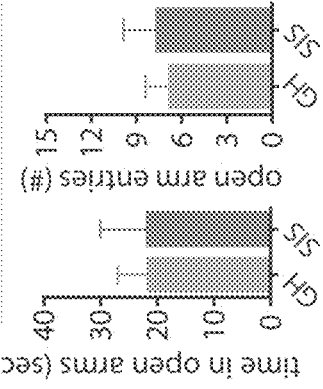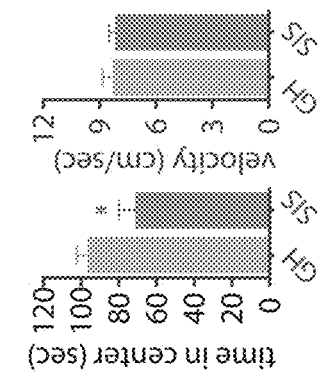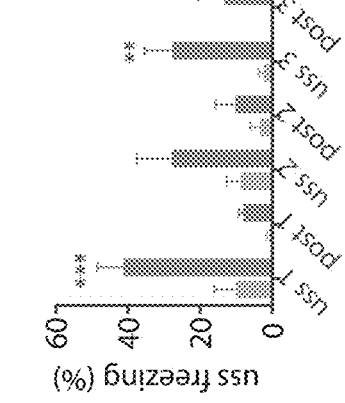

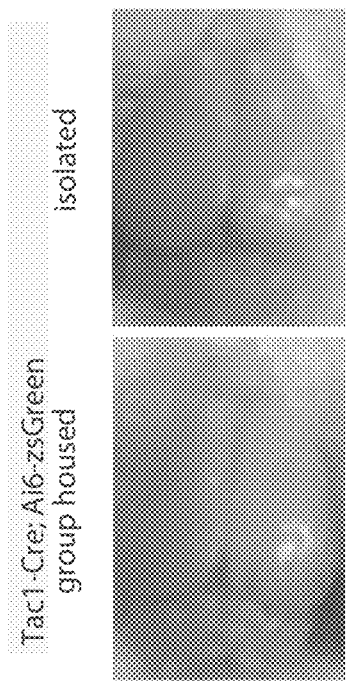
FIG. 2E
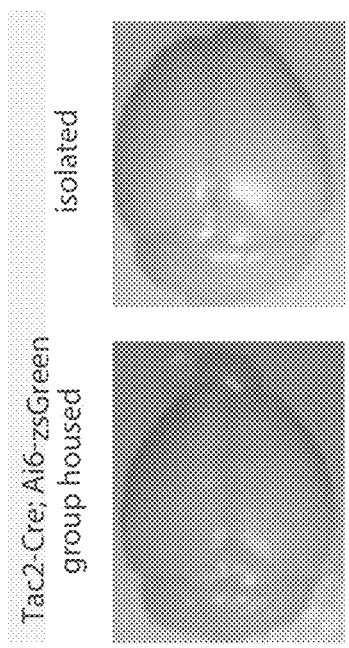
FIG. 2D
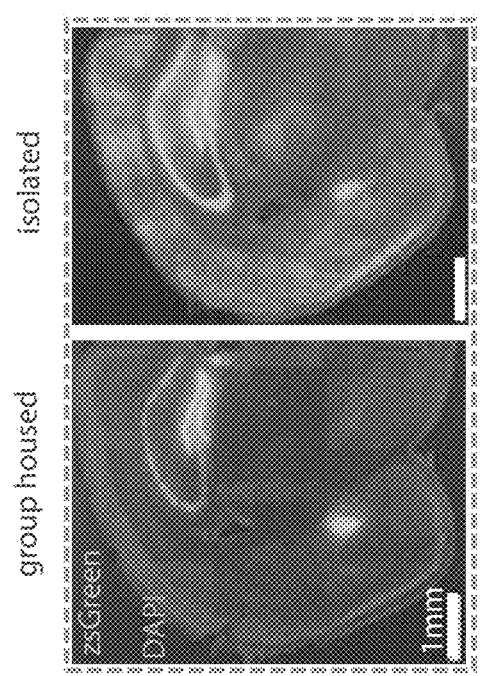
FIG. 2G
FIG. 2F

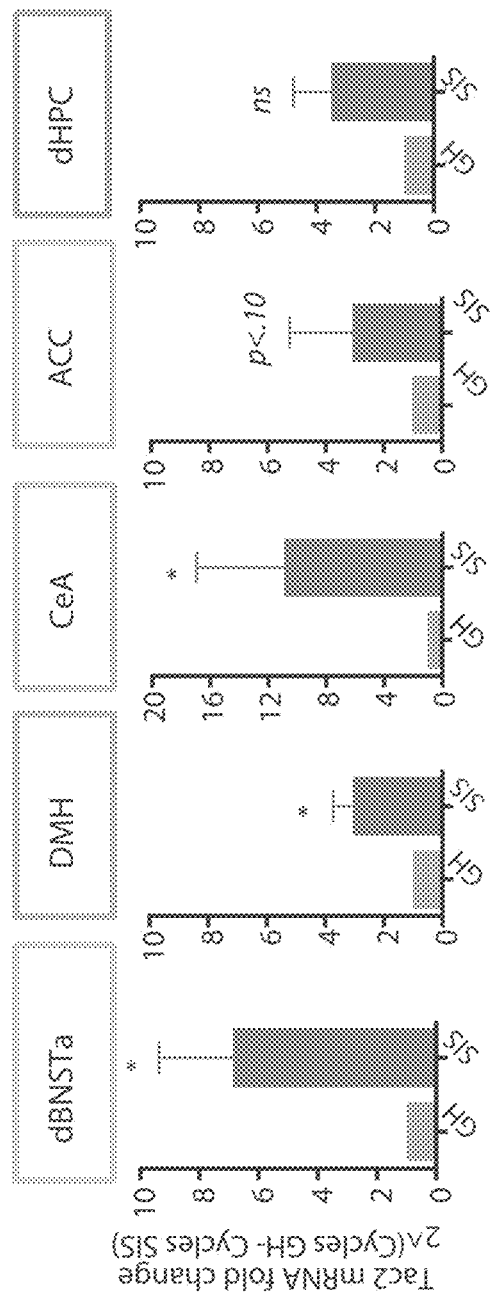
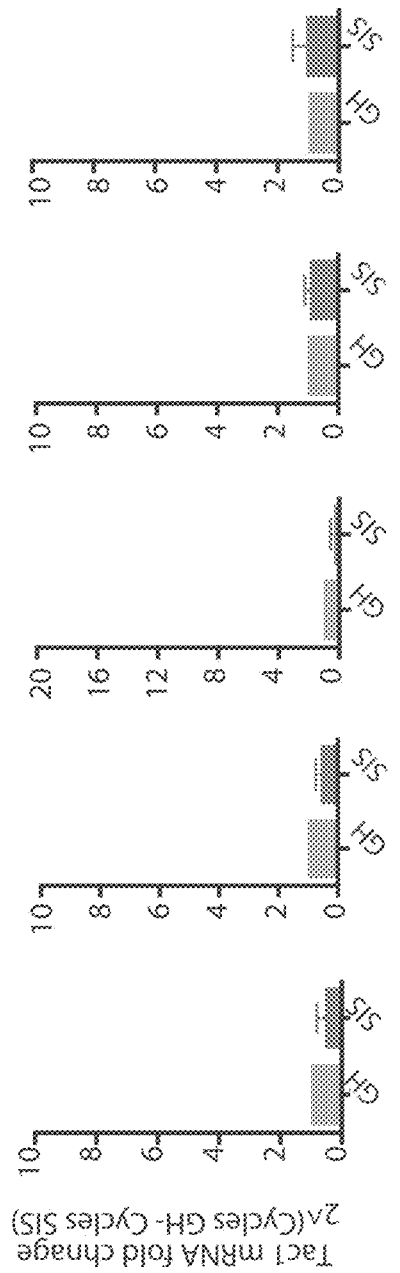

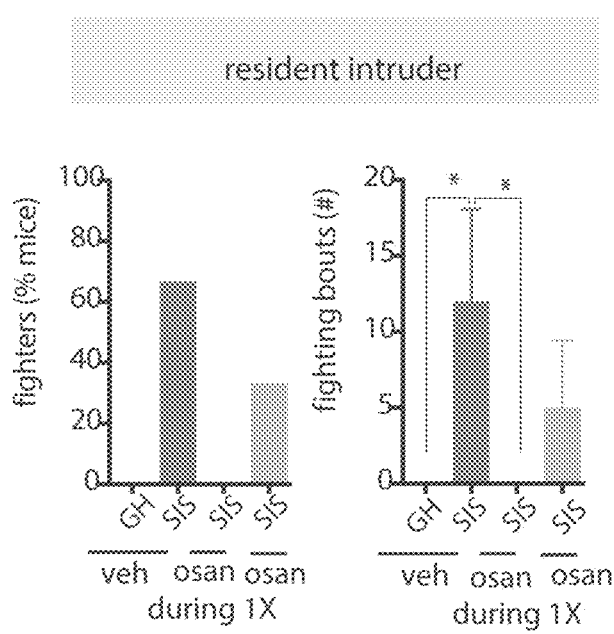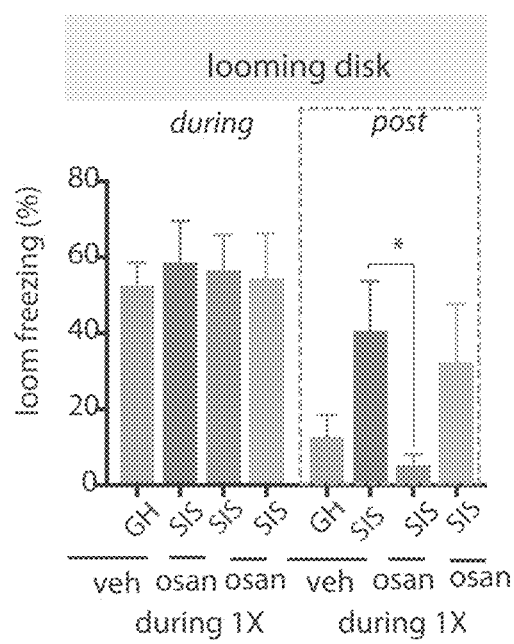
FIG. 3H    FIG. 3I    FIG. 3J

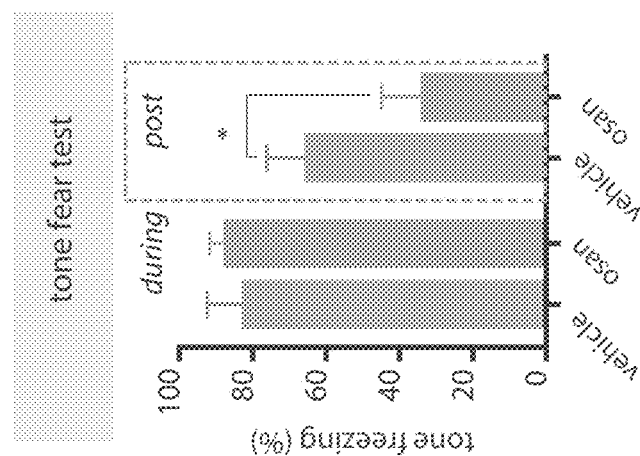
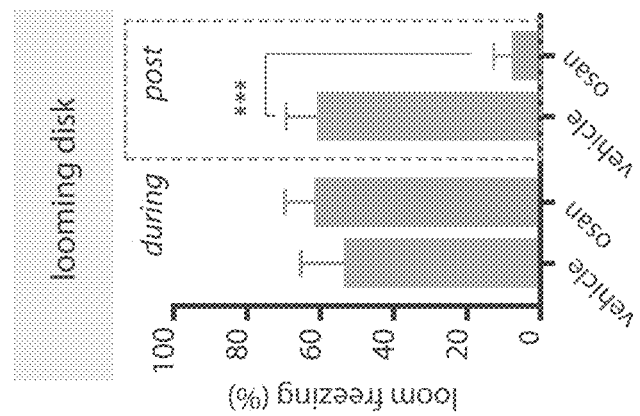
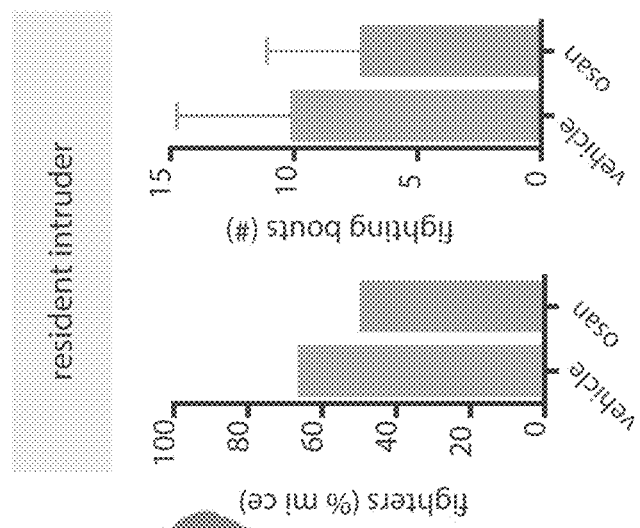
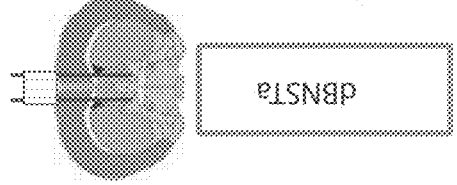
FIG. 4B  FIG. 4C  FIG. 4D  FIG. 4E  FIG. 4F

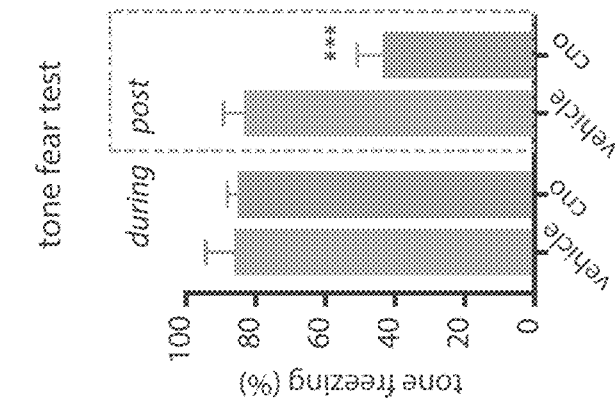
FIG. 5F
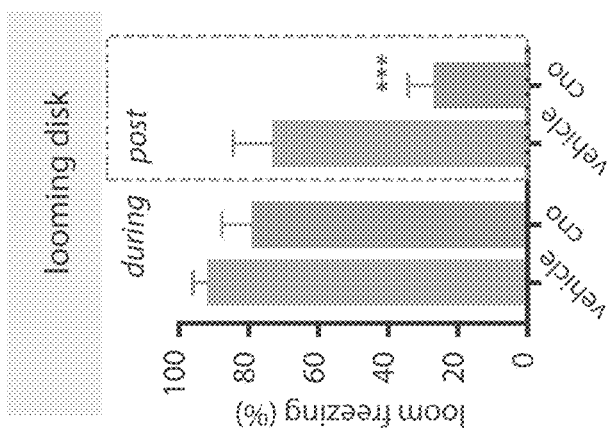
FIG. 5E
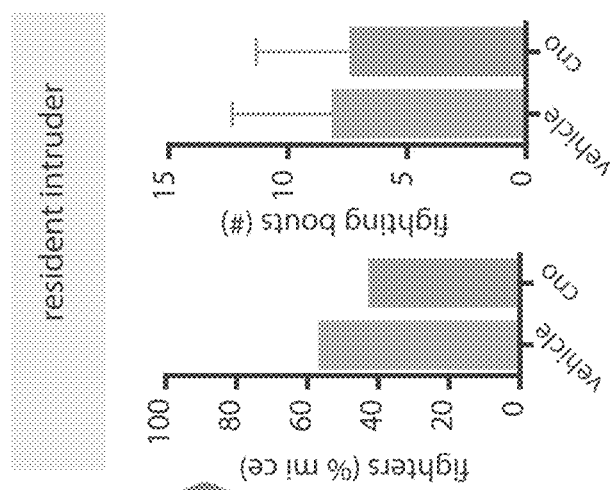
FIG. 5D
FIG. 5C
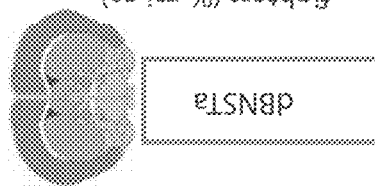
FIG. 5B

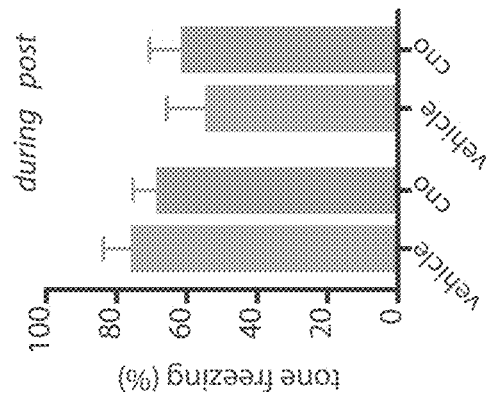
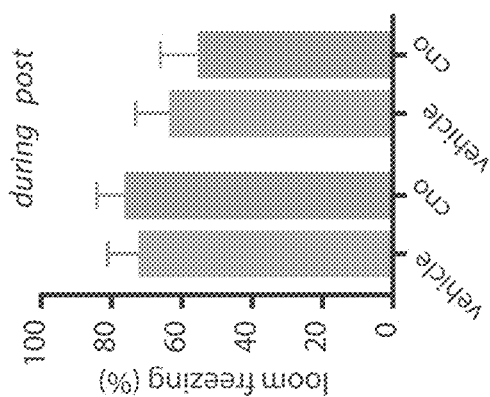
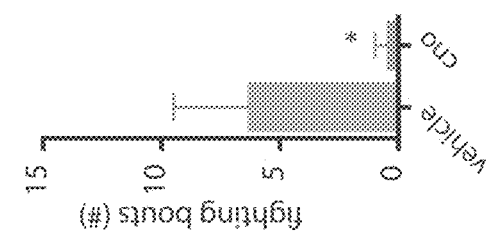
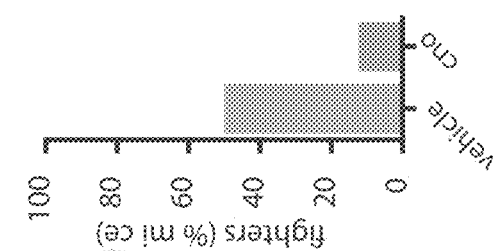
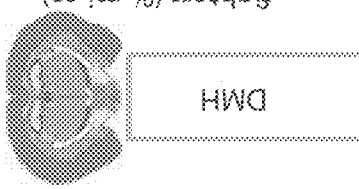

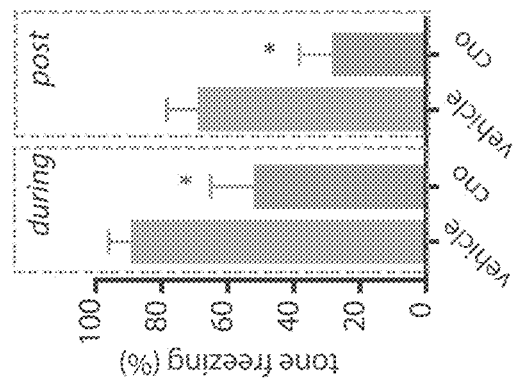
FIG. 5P
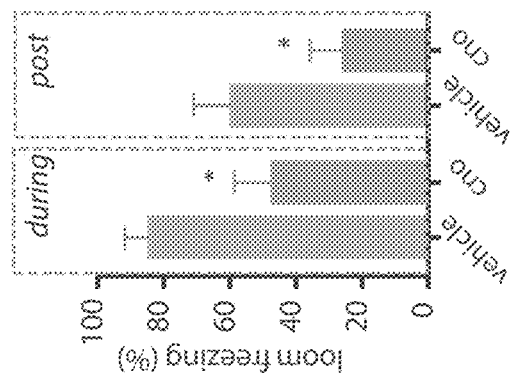
FIG. 5O
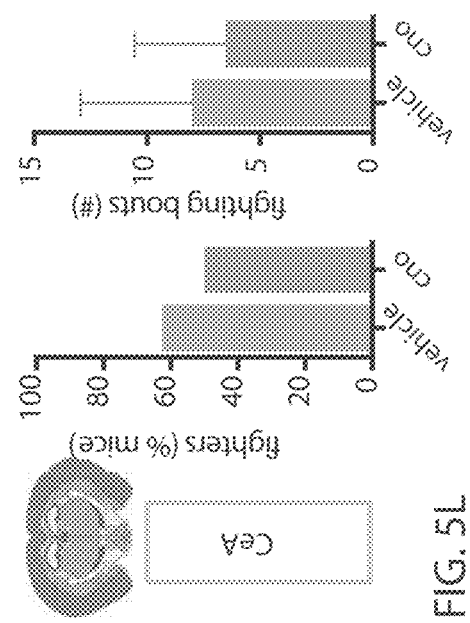
FIG. 5N
FIG. 5M
FIG. 5L

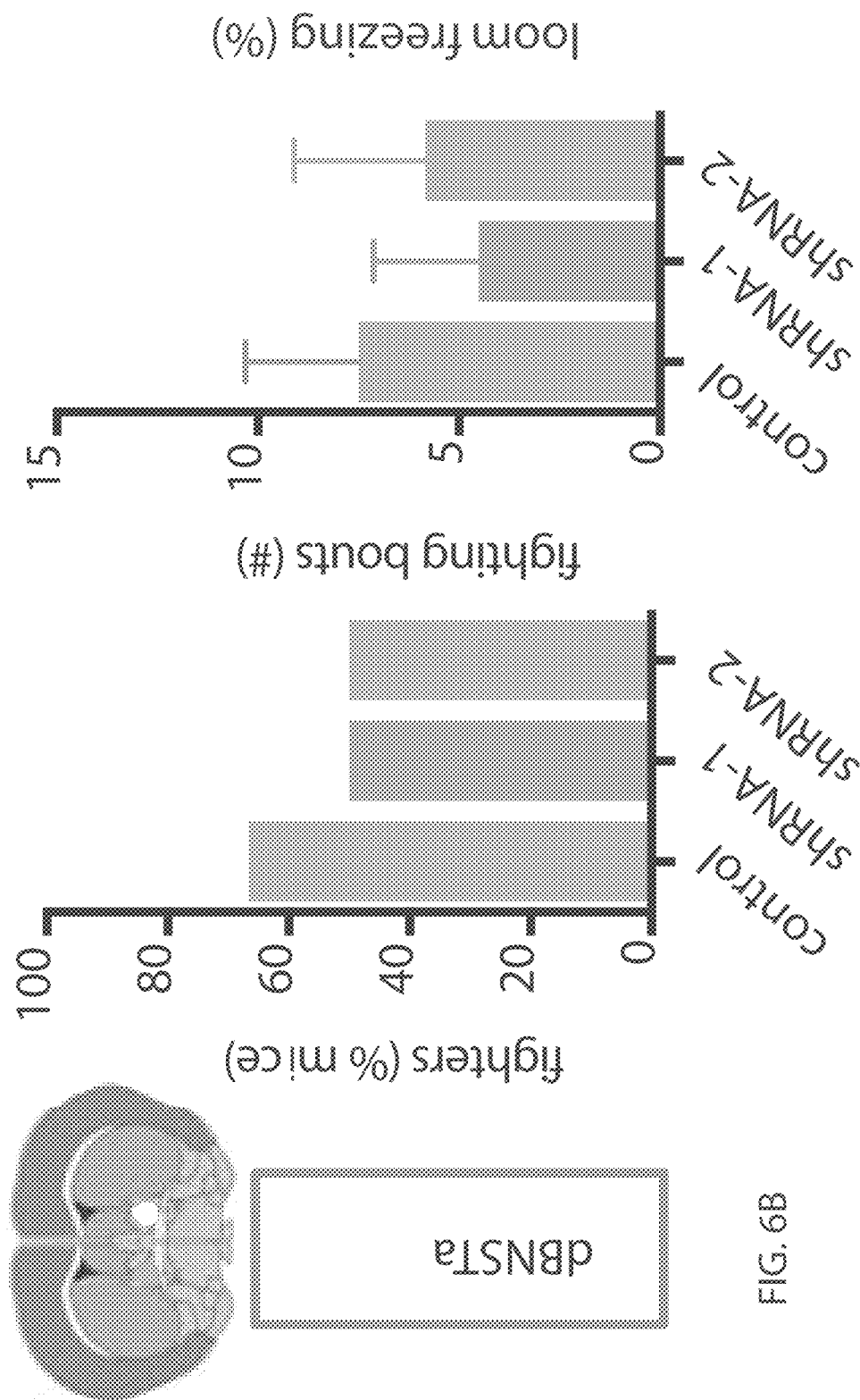

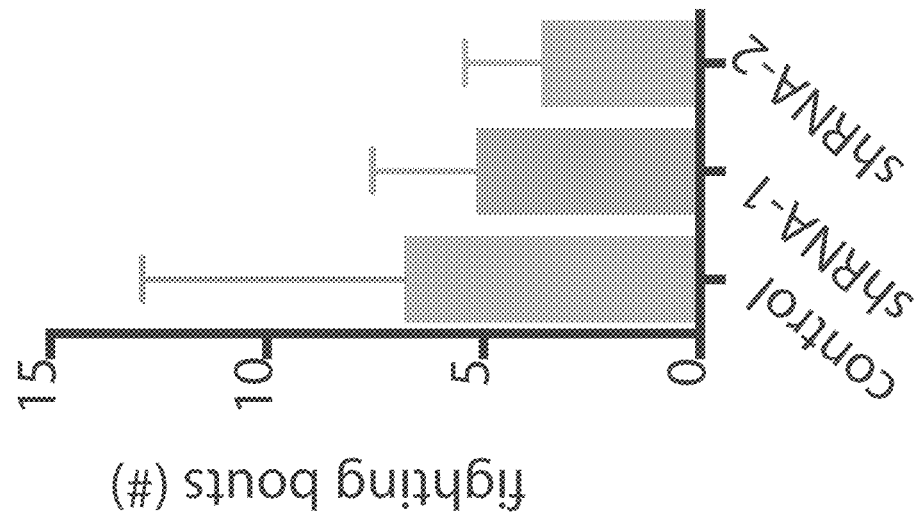
FIG. 6N
FIG. 6M
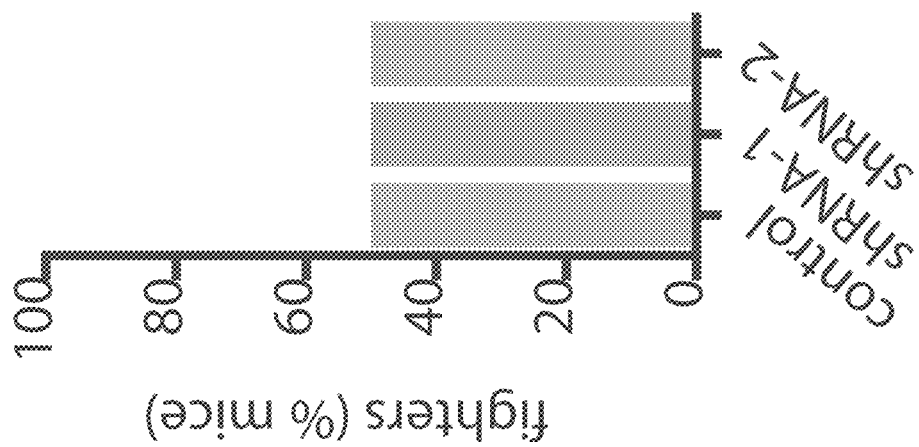
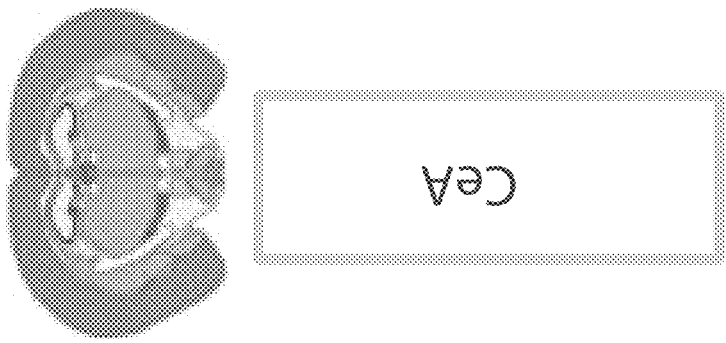
FIG. 6L looming disk baseline fear at test tone fear test

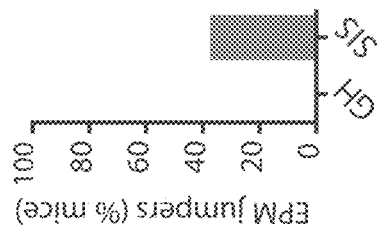
FIG. 8K elevated plus maze
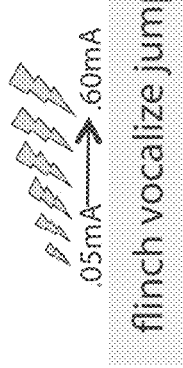
FIG. 8I flinch vocalize jump
FIG. 8G acoustic startle
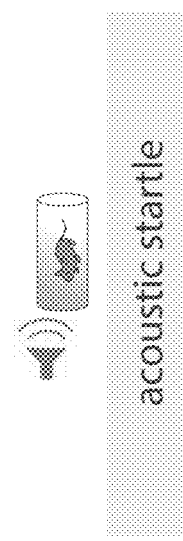
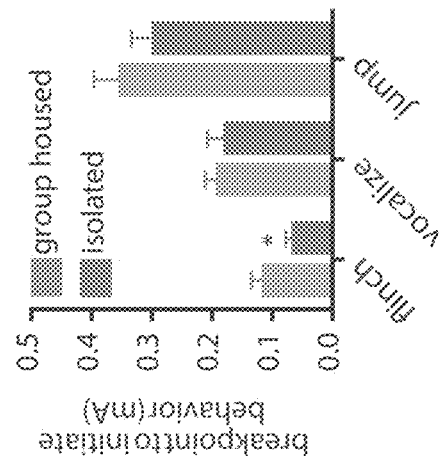
FIG. 8L
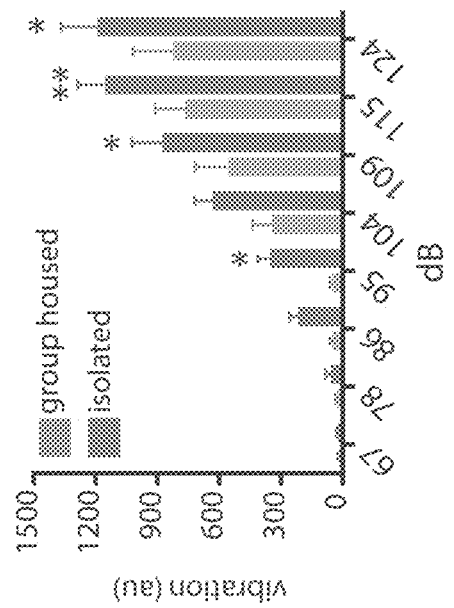
FIG. 8J
FIG. 8H

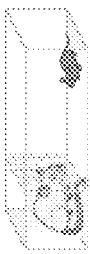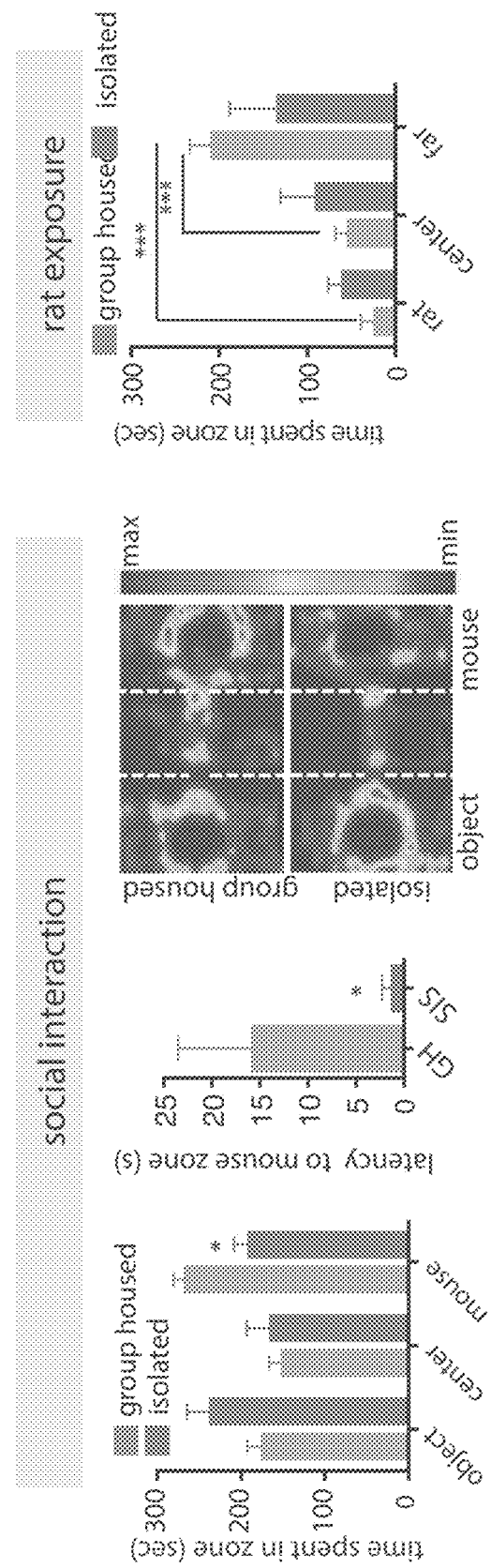

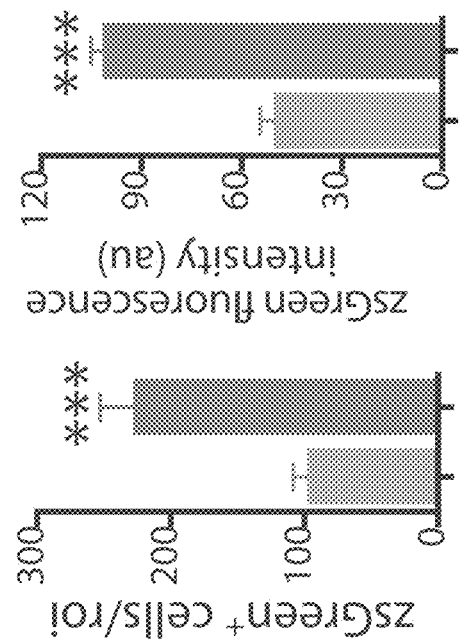
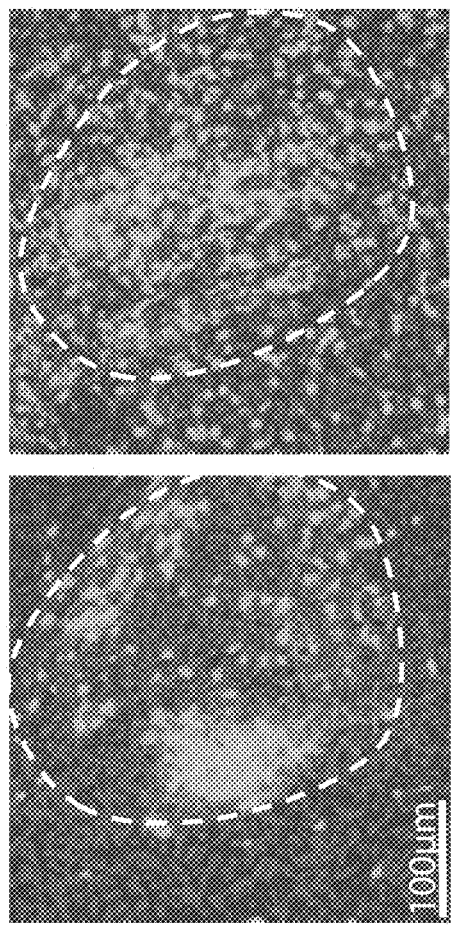
FIG. 9I  FIG. 9J  FIG. 9K  FIG. 9L

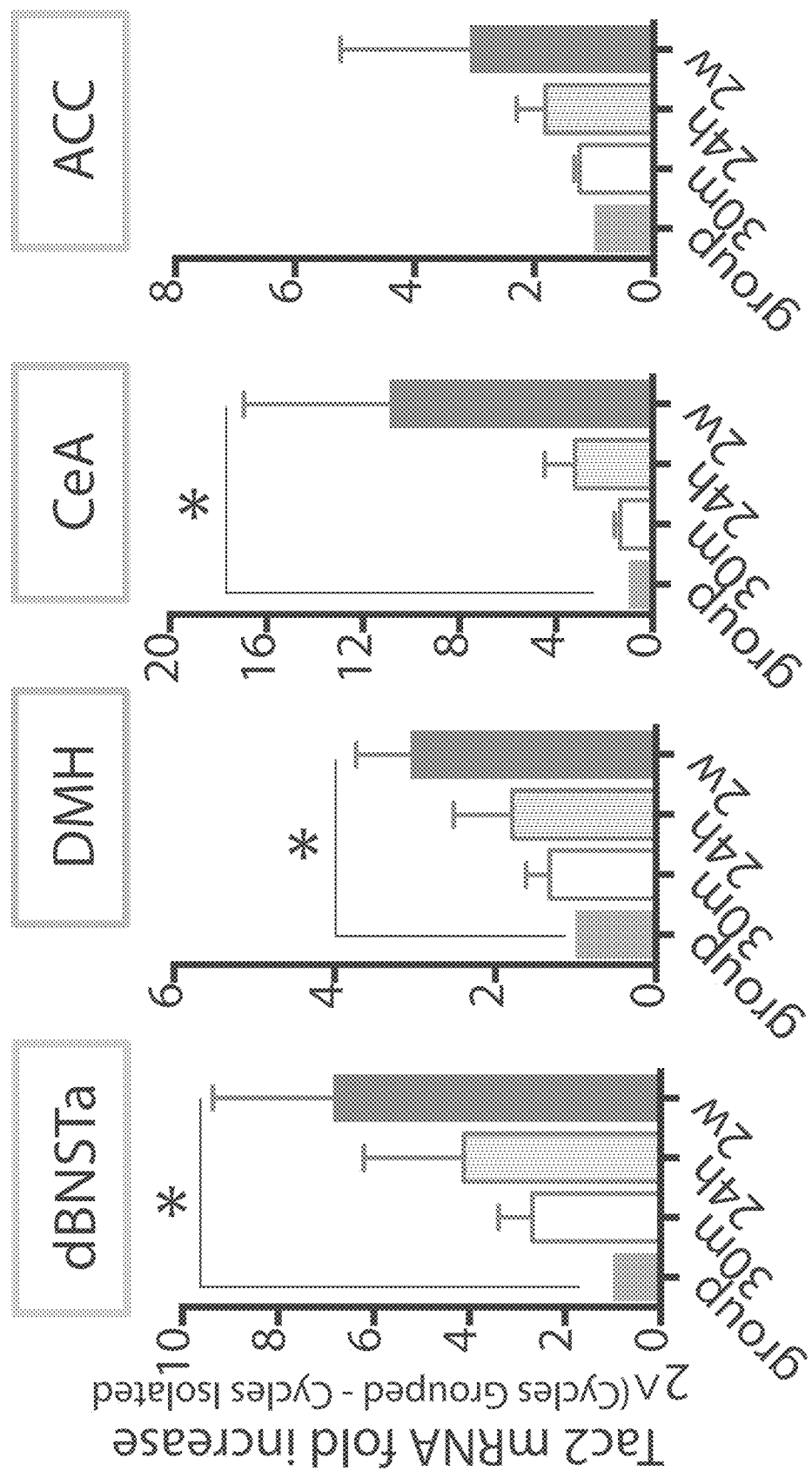

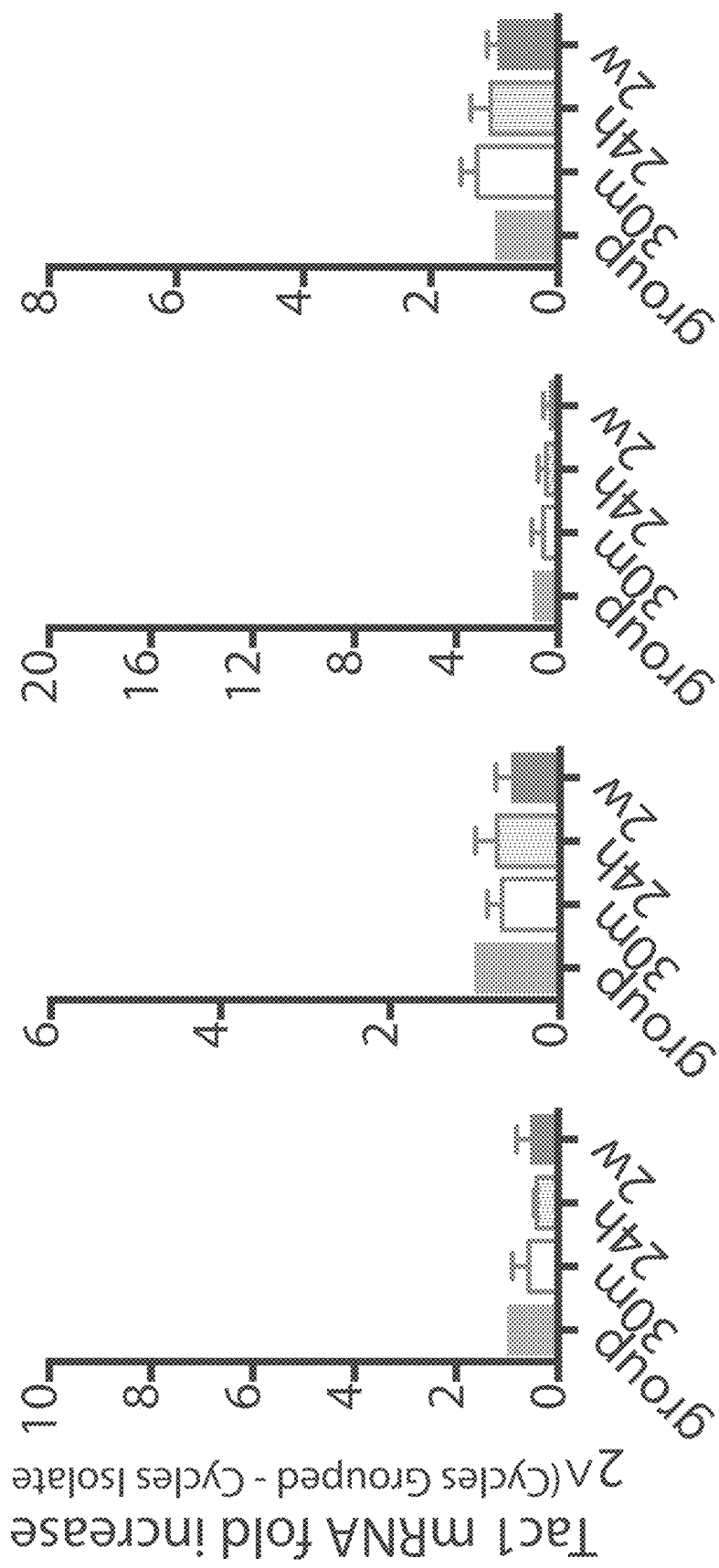

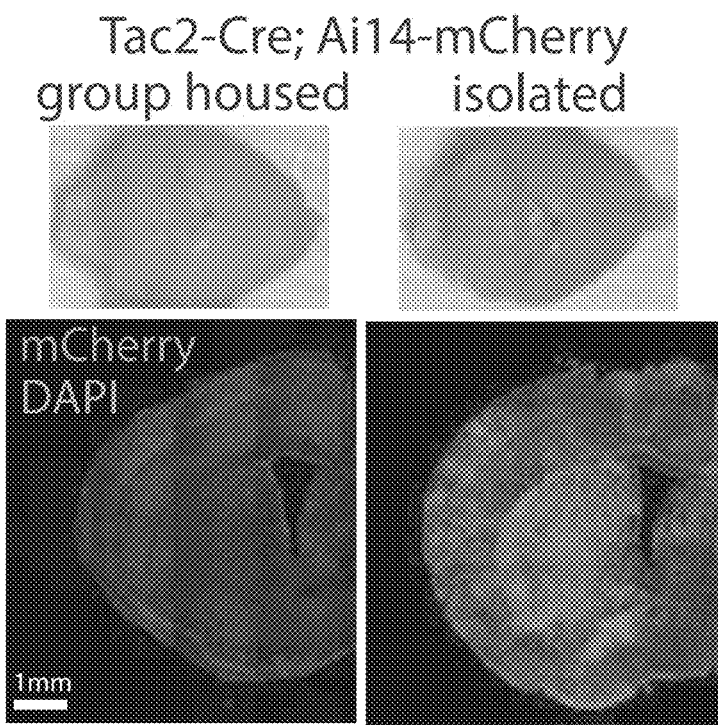
FIG. 9EE
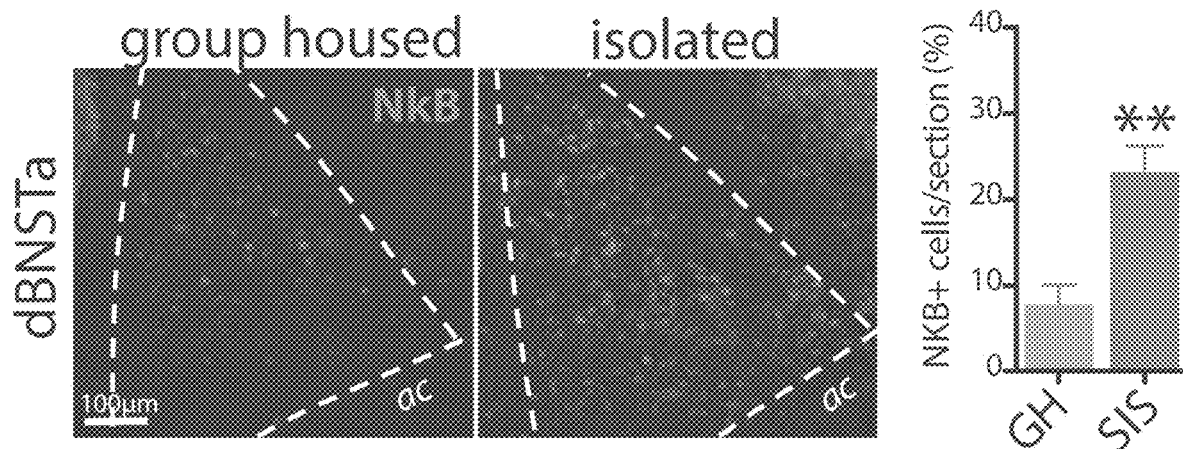
FIG. 9FF
FIG. 9GG social interaction

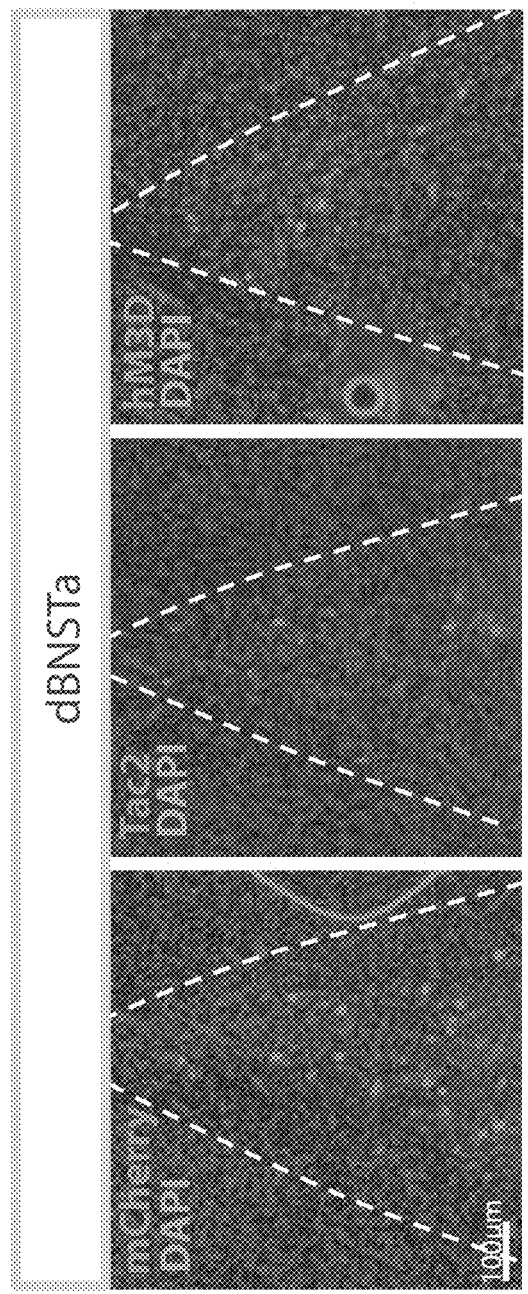
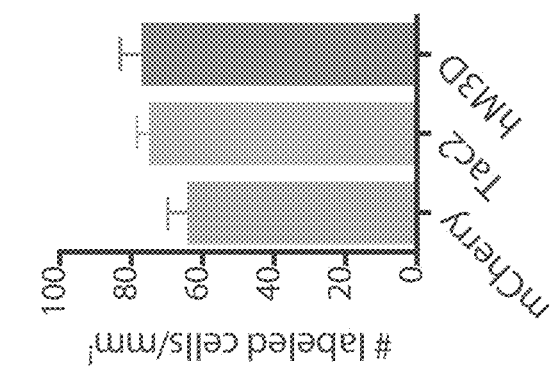
FIG. 14A  FIG. 14B  FIG. 14C  FIG. 14D

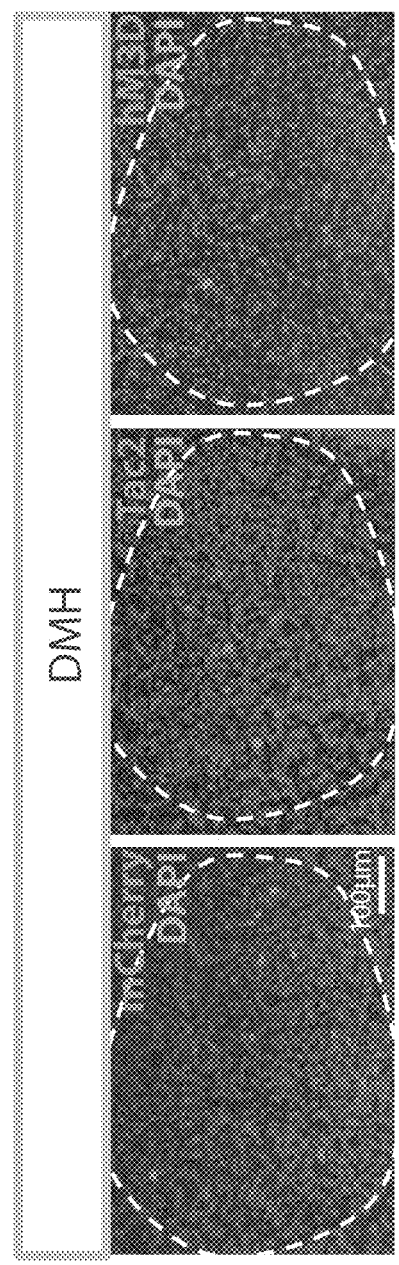
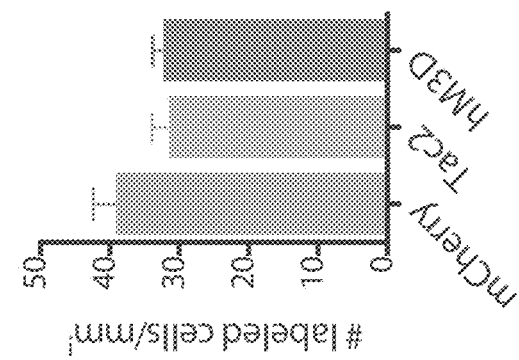
FIG. 14E  FIG. 14F  FIG. 14G  FIG. 14H

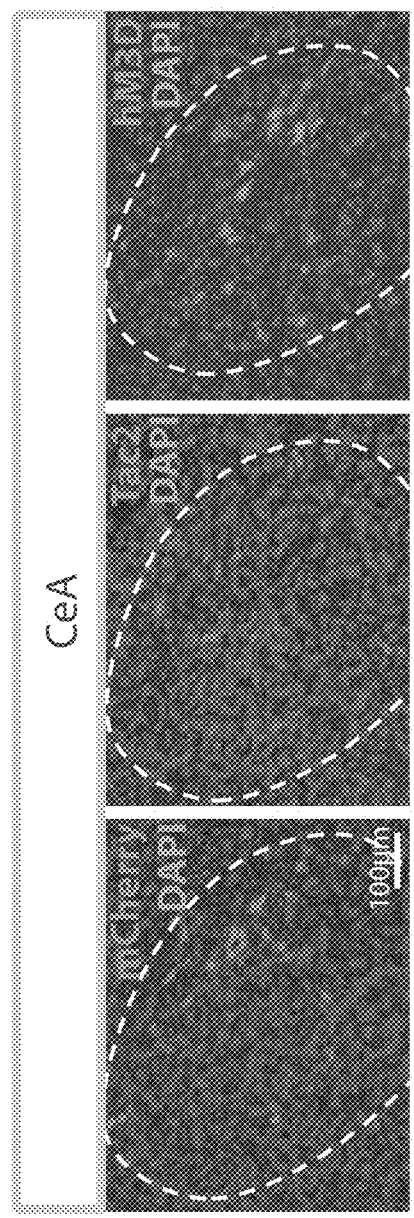
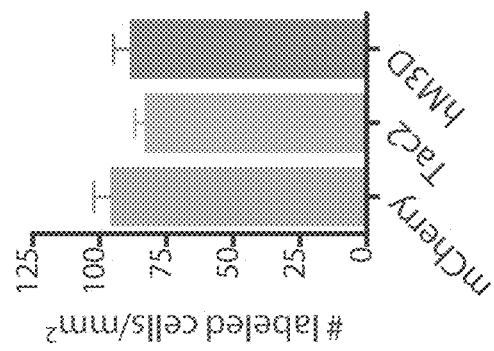
FIG. 14I  FIG. 14J  FIG. 14K  FIG. 14L

SEQUENCE LISTING

<160> NUMBER OF SEQ ID NOS: 33

<210> SEQ ID NO 1
<211> LENGTH: 129
<212> TYPE: PRT
<213> ORGANISM: Homo sapiens

<400> SEQUENCE: 1

Met Lys Ile Leu Val Ala Leu Ala Val Phe Phe Leu Val Ser Thr Gln

```
                1               5                  10                 15
Leu Phe Ala Glu Glu Ile Gly Ala Asn Asp Asp Leu Asn Tyr Trp Ser
                               20                 25                 30

Asp Trp Tyr Asp Ser Asp Gln Ile Lys Glu Glu Leu Pro Glu Pro Phe
                35                 40                 45

Glu His Leu Leu Gln Arg Ile Ala Arg Arg Pro Lys Pro Gln Gln Phe
                50                 55                 60

Phe Gly Leu Met Gly Lys Arg Asp Ala Asp Ser Ser Ile Glu Lys Gln
 65                 70                 75                 80

Val Ala Leu Leu Lys Ala Leu Tyr Gly His Gly Gln Ile Ser His Lys
                    85                 90                 95

Arg His Lys Thr Asp Ser Phe Val Gly Leu Met Gly Lys Arg Ala Leu
                    100                105                110

Asn Ser Val Ala Tyr Glu Arg Ser Ala Met Gln Asn Tyr Glu Arg Arg
                    115                120                125

Arg
```

<210> SEQ ID NO 2
<211> LENGTH: 121
<212> TYPE: PRT
<213> ORGANISM: Homo sapiens

<400> SEQUENCE: 2

```
Met Arg Ile Met Leu Leu Phe Thr Ala Ile Leu Ala Phe Ser Leu Ala
 1               5                  10                 15

Gln Ser Phe Gly Ala Val Cys Lys Glu Pro Gln Glu Glu Val Val Pro
                    20                 25                 30

Gly Gly Gly Arg Ser Lys Arg Asp Pro Asp Leu Tyr Gln Leu Leu Gln
                    35                 40                 45

Arg Leu Phe Lys Ser His Ser Ser Leu Glu Gly Leu Leu Lys Ala Leu
                    50                 55                 60

Ser Gln Ala Ser Thr Asp Pro Lys Glu Ser Thr Ser Pro Glu Lys Arg
 65                 70                 75                 80

Asp Met His Asp Phe Phe Val Gly Leu Met Gly Lys Arg Ser Val Gln
                    85                 90                 95

Pro Asp Ser Pro Thr Asp Val Asn Gln Glu Asn Val Pro Ser Phe Gly
                    100                105                110

Ile Leu Lys Tyr Pro Pro Arg Ala Asp
                    115                120
```

<210> SEQ ID NO 3
<211> LENGTH: 7
<212> TYPE: PRT
<213> ORGANISM: Artificial Sequence
<220> FEATURE:
<223> OTHER INFORMATION: targeting peptide

<400> SEQUENCE: 3

```
Thr Leu Ala Val Pro Phe Lys
 1               5
```

<210> SEQ ID NO 4
<211> LENGTH: 7
<212> TYPE: PRT
<213> ORGANISM: Artificial Sequence
<220> FEATURE:
<223> OTHER INFORMATION: targeting peptide

<400> SEQUENCE: 4

```
Ser Val Ser Lys Pro Phe Leu
1               5

<210> SEQ ID NO 5
<211> LENGTH: 7
<212> TYPE: PRT
<213> ORGANISM: Artificial Sequence
<220> FEATURE:
<223> OTHER INFORMATION: targeting peptide

<400> SEQUENCE: 5

Phe Thr Leu Thr Thr Pro Lys
1               5

<210> SEQ ID NO 6
<211> LENGTH: 7
<212> TYPE: PRT
<213> ORGANISM: Artificial Sequence
<220> FEATURE:
<223> OTHER INFORMATION: targeting peptide

<400> SEQUENCE: 6

Tyr Thr Leu Ser Gln Gly Trp
1               5

<210> SEQ ID NO 7
<211> LENGTH: 7
<212> TYPE: PRT
<213> ORGANISM: Artificial Sequence
<220> FEATURE:
<223> OTHER INFORMATION: targeting peptide

<400> SEQUENCE: 7

Gln Ala Val Arg Thr Ser Leu
1               5

<210> SEQ ID NO 8
<211> LENGTH: 7
<212> TYPE: PRT
<213> ORGANISM: Artificial Sequence
<220> FEATURE:
<223> OTHER INFORMATION: targeting peptide

<400> SEQUENCE: 8

Leu Ala Lys Glu Arg Leu Ser
1               5

<210> SEQ ID NO 9
<211> LENGTH: 62
<212> TYPE: DNA
<213> ORGANISM: Artificial Sequence
<220> FEATURE:
<223> OTHER INFORMATION: shRNA1 first strand

<400> SEQUENCE: 9
ccgacgtggt tgaagagaac accgcttcct gtcacggtgt tctcttcaac cacgtctttt      60
tt                                                                    62

<210> SEQ ID NO 10
<211> LENGTH: 62
<212> TYPE: DNA
<213> ORGANISM: Artificial Sequence
<220> FEATURE:
<223> OTHER INFORMATION: shRNA1 second strand

<400> SEQUENCE: 10
```
aaaaaagacg tggttgaaga gaacaccgtg acaggaagcg gtgttctctt caaccacgtc    60
gg                                                                  62

<210> SEQ ID NO 11
<211> LENGTH: 62
<212> TYPE: DNA
<213> ORGANISM: Artificial Sequence
<220> FEATURE:
<223> OTHER INFORMATION: shRNA2 first strand

<400> SEQUENCE: 11
ccgcctcaac cccatagcaa ttagcttcct gtcactaatt gctatggggt tgaggctttt    60
tt                                                                  62

<210> SEQ ID NO 12
<211> LENGTH: 62
<212> TYPE: DNA
<213> ORGANISM: Artificial Sequence
<220> FEATURE:
<223> OTHER INFORMATION: shRNA2 second strand

<400> SEQUENCE: 12
aaaaaagcct caaccccata gcaattagtg acaggaagct aattgctatg gggttgaggc    60
gg                                                                  62

<210> SEQ ID NO 13
<211> LENGTH: 40
<212> TYPE: DNA
<213> ORGANISM: Artificial Sequence
<220> FEATURE:
<223> OTHER INFORMATION: shRNA1 Forward

<400> SEQUENCE: 13
aaccacgtct tttttaattc tagttattaa tagtaatcaa                          40

<210> SEQ ID NO 14
<211> LENGTH: 33
<212> TYPE: DNA
<213> ORGANISM: Artificial Sequence
<220> FEATURE:
<223> OTHER INFORMATION: shRNA1 Reverse

<400> SEQUENCE: 14
cttcaaccac gtcggctggg aaagagtggt ctc                                 33

<210> SEQ ID NO 15
<211> LENGTH: 40
<212> TYPE: DNA
<213> ORGANISM: Artificial Sequence
<220> FEATURE:
<223> OTHER INFORMATION: shRNA2 Forward

<400> SEQUENCE: 15
ggttgaggct tttttaattc tagttattaa tagtaatcaa                          40

<210> SEQ ID NO 16
<211> LENGTH: 33
<212> TYPE: DNA
<213> ORGANISM: Artificial Sequence
<220> FEATURE:
<223> OTHER INFORMATION: shRNA2 Reverse

<400> SEQUENCE: 16

```
atggggttga ggcggctggg aaagagtggt ctc                                  33
```

<210> SEQ ID NO 17
<211> LENGTH: 18
<212> TYPE: DNA
<213> ORGANISM: Artificial Sequence
<220> FEATURE:
<223> OTHER INFORMATION: mCherry Forward

<400> SEQUENCE: 17

```
ctcctcgccc ttgctcac                                                   18
```

<210> SEQ ID NO 18
<211> LENGTH: 24
<212> TYPE: DNA
<213> ORGANISM: Artificial Sequence
<220> FEATURE:
<223> OTHER INFORMATION: mCherry Reverse

<400> SEQUENCE: 18

```
ggcgcgccat aacttcgtat aatg                                            24
```

<210> SEQ ID NO 19
<211> LENGTH: 48
<212> TYPE: DNA
<213> ORGANISM: Artificial Sequence
<220> FEATURE:
<223> OTHER INFORMATION: pAAV-GFP Forward

<400> SEQUENCE: 19

```
cctggaccta tggtgagcaa gggcgaggag ctgttcaccg ggtggtg                   48
```

<210> SEQ ID NO 20
<211> LENGTH: 55
<212> TYPE: DNA
<213> ORGANISM: Artificial Sequence
<220> FEATURE:
<223> OTHER INFORMATION: pAAV-GFP Reverse

<400> SEQUENCE: 20

```
agcatacatt atacgaagtt atggcgcgcc ctacttgagc tcgagatctg agtac          55
```

<210> SEQ ID NO 21
<211> LENGTH: 1274
<212> TYPE: DNA
<213> ORGANISM: Artificial Sequence
<220> FEATURE:
<223> OTHER INFORMATION: Tac2-P2A-mCherry

<400> SEQUENCE: 21

```
gctagcgcca ccatgaggag cgccatgctg tttgcggctg tcctcgccct cagcttggct     60
tggaccttcg ggctgtgtgt gaggagcca  caggggcagg agggaggct  cagtaaggac    120 tctgatctct atcagctgcc tccgtccctg cttcggagac tctacgacag ccgccctgtc    180
tctctggaag gattgctgaa agtgctgagc aaggcttgcg tgggaccaaa ggagacatca    240
cttccacaga aacgtgacat gcacgacttc tttgtgggac ttatgggcaa gaggaacagc    300
caaccagaca ctcccaccga cgtggttgaa gagaacaccc ccagctttgg catcctcaaa    360
ggaagcggag ctactaactt cagcctgctg aagcaggctg agacgtggga ggagaaccct    420
ggacctatgg tgagcaaggg cgaggaggat aacatggcca tcatcaagga gttcatgcgc    480
ttcaaggtgc acatggaggg ctccgtgaac ggccacgagt cgagatcga gggcgagggc    540 gagggccgcc cctacgaggg cacccagacc gccaagctga aggtgaccaa ggtggcccc    600
```

```
ctgcccttcg cctgggacat cctgtcccct cagttcatgt acggctccaa ggcctacgtg    660
aagcaccccg ccgacatccc cgactacttg aagctgtcct tccccgaggg cttcaagtgg    720
gagcgcgtga tgaacttcga ggacggcggc gtggtgaccg tgaccaggac tcctcccctgc   780 aggacggcga gttcatctac aaggtgaagc tgcgcggcac caacttcccc tccgacggcc    840
ccgtaatgca gaagaagacc atgggctggg aggcctcctc cgagcggatg taccccgagg    900
acggcgccct gaagggcgag atcaagcaga ggctgaagct gaaggacggc ggccactacg    960
acgctgaggt caagaccacc tacaaggcca agaagcccgt gcagctgccc ggcgcctaca   1020
acgtcaacat caagttggac atcacctccc acaacgagga ctacaccatc gtggaacagt   1080
acgaacgcgc cgagggccgc cactccaccg gcggcatgga cgagctgtac aagtaaggcg   1140
cgccataact tcgtataatg tatgctatac gaagttatta agaggtttca tattgctaat   1200
agcagctaca atccagctac cattctgcat aacttcgtat aaagtatcct atacgaagtt   1260
attccggagt cgac                                                    1274

<210> SEQ ID NO 22
<211> LENGTH: 18
<212> TYPE: DNA
<213> ORGANISM: Artificial Sequence
<220> FEATURE:
<223> OTHER INFORMATION: Digoxigenin-labeled Tac2  Forward

<400> SEQUENCE: 22
agccagctcc ctgatcct                                                  18

<210> SEQ ID NO 23
<211> LENGTH: 18
<212> TYPE: DNA
<213> ORGANISM: Artificial Sequence
<220> FEATURE:
<223> OTHER INFORMATION: Digoxigenin-labeled Tac2  Reverse

<400> SEQUENCE: 23
ttgctatggg gttgaggc                                                  18

<210> SEQ ID NO 24
<211> LENGTH: 20
<212> TYPE: DNA
<213> ORGANISM: Artificial Sequence
<220> FEATURE:
<223> OTHER INFORMATION: Tac1 Forward

<400> SEQUENCE: 24
gatgaaggag ctgtccaagc                                                20

<210> SEQ ID NO 25
<211> LENGTH: 20
<212> TYPE: DNA
<213> ORGANISM: Artificial Sequence
<220> FEATURE:
<223> OTHER INFORMATION: Tac1  Reverse

<400> SEQUENCE: 25
tcacgaaaca ggaaacatgc                                                20

<210> SEQ ID NO 26
<211> LENGTH: 19
<212> TYPE: DNA
<213> ORGANISM: Artificial Sequence
<220> FEATURE:
```

<223> OTHER INFORMATION: Tac2 Forward

<400> SEQUENCE: 26
gccatgctgt ttgcggctg                                          19

<210> SEQ ID NO 27
<211> LENGTH: 20
<212> TYPE: DNA
<213> ORGANISM: Artificial Sequence
<220> FEATURE:
<223> OTHER INFORMATION: Tac2 Reverse

<400> SEQUENCE: 27
ccttgctcag cactttcagc                                         20

<210> SEQ ID NO 28
<211> LENGTH: 19
<212> TYPE: DNA
<213> ORGANISM: Artificial Sequence
<220> FEATURE:
<223> OTHER INFORMATION: GAPDH Forward

<400> SEQUENCE: 28
tgaagcaggc atctgaggg                                          19

<210> SEQ ID NO 29
<211> LENGTH: 20
<212> TYPE: DNA
<213> ORGANISM: Artificial Sequence
<220> FEATURE:
<223> OTHER INFORMATION: GAPDH Reverse

<400> SEQUENCE: 29
cgaaggtgga agagtgggag                                         20

<210> SEQ ID NO 30
<211> LENGTH: 20
<212> TYPE: DNA
<213> ORGANISM: Artificial Sequence
<220> FEATURE:
<223> OTHER INFORMATION: 18s Forward

<400> SEQUENCE: 30
gcaattattc cccatgaacg                                         20

<210> SEQ ID NO 31
<211> LENGTH: 20
<212> TYPE: DNA
<213> ORGANISM: Artificial Sequence
<220> FEATURE:
<223> OTHER INFORMATION: 18s Reverse

<400> SEQUENCE: 31
gggacttaat caacgcaagc                                         20

<210> SEQ ID NO 32
<211> LENGTH: 8514
<212> TYPE: DNA
<213> ORGANISM: Homo sapiens

<400> SEQUENCE: 32
cacgcaagcg aaaggagagg aggcggctaa ttaaatattg agcagaaagt cgcgtgggga      60
gaatgtcacg tgggtctgga ggctcaagga ggctgggata aataccgcaa ggcactgagc     120
aggcgaaaga gcgcgctcgg acctccttcc cggcggcagc taccgagagt gcggagcgac    180

```
cagcgtgcgc tcggaggaac cagagaaact cagcaccccg cgggactgtc cgtcgcagta    240
agtgcccgcg cggtgctggc cgcggctgcc cgggtcaccc cgccccgcat ctgtccgagg    300
tggccgcgct gggggcgccg ctgcggcgag ggacagtggg gagactggct tcccaaacgc    360
caacgcccct ctttgtcttc cacctgcaga gtttcctggt ttgaaggtgt gggttggtgg    420 gttaggggc tgggggagtt gggattcagg gagaagaggg ttggagaatc tttgggacgc     480
gattctctcg cctaaccggt acaggtgaga cttcagtcct tatgttttg atcttggttc     540 atccgttgtg gggcagaaaa ttctgttgct ttaactcttg gataaccacc cctaatagat    600
acattatttc tctctttggt gtcttctcct cctaccccctt cccagaaatc caacatgaaa   660
atcctcgtgg ccttggcagt ctttttttctt gtctccactc agctgtttgc agaagaaata   720
ggagccaatg atgatctgaa ttactggtcc gactggtacg acagcgacca gatcaaggtg    780
aggccccttc ccaggacggc ccgcaccctt cttcctgggc tcgggagctg tcaccttccc    840
acgcaacagc accctagtta acgtggcacg caccgccacc acgaaagag gcagcggttg     900 cgtgcgagag gatggaaagg ggcactattt cccgggttcc ccacgggatt ttgtgcccac    960
gattcaagtt tcttcccgag ggctgcaccg tccggcccag gaactccctg cagtagggat    1020
gccctcccgg atgagcccga gatcctcaca aggcgggaaa tctcgtaaga tttcatcccc    1080
caggacctgg gatttcgggg gctccggtcc agctgcactg ccctagcgtc tgggcacggg    1140
cagaggaggg cgcctgggtc gcgggcagca gcgggcacac gcgcgagctg caggggatt    1200 ggagggccgg aggctggagg gaagttaatt tcctgccttc acgtttgttt tgcggacctg    1260
aggatgtagc ttgaagtctc cctttagaaa ctcgtaggct acaggcgctg gggagcgcgc    1320
ctcggaaaaa cggtgaaagt cgtctgtaaa gcgttgtcac ccttcccac cggagcccca     1380 gccccagatc ccacacacct gtgtgcattt agggcggtga ggactctaca aagccggcac    1440
cgagacaaga caaagtcagg tggcggcgca gcagatgagg gaaggtcccc gggctgggag    1500
gaaagagcgg aaagcgctcg aagcttgaag acgccgagcc agctgctaac tcgccctggc    1560
aggcttgcgg ggggcgggac gcgagttcgg cggggagggg cgcagagagg cagcgcctcg    1620
ggagggaccc cgctcagccc gagcgtgggg aaggccgcct ccccacgcct cggggccgga    1680
gtacagcggg gggaagggct cgggttgctg ggtgcctcgc tctggttgcc ttacacgccc    1740
tttgtccgtg cttttgtctc ccaggaggaa ctgccggagc cctttgagca tcttctgcag    1800
agaatcgccc ggagacccaa gcctcagcag ttctttggat taatgggcaa acgggatgct    1860
ggtgagatag gcgaccgtcc ctaggtgtct tgggcagccc gccctgtctg ctcactcctt    1920
cctggagtac cccagggtct ctcgctctga atagagattt ccactccaag aggggtgtaa    1980
ttccccaggc gcgacattgg cccacaccgc actaaggcac gcacgggccc gcggggggag    2040
ggaaagatct ggttcgcatg cctcactgta ttcgagtgaa gcgctcccctt gactaaagat    2100 ccaaactgac aaagggaagg cacgggcctc caggggtagt actgcggatg atccaagtgc    2160
atgtggaaga ggattttata gcattccctg aggtgagagt acatttgtct tgggatagaa    2220
atatcgtttc cttgaattca tcgcacggtc agtggaacat gtagttaatg acaattcgtc    2280
tcttgtcaga ttcctcaatt gaaaacaag tggccctgtt aaaggctctt tatggtaaac     2340
attcctataa atctttattt tactattgtg aaagcacatg taggaaagtg aaataaaatc    2400
ttttatgggg tgaaatacaa gatctgggtc atgcctgttt aataaagaga tggatttgcg    2460
cactctctct cggtttctct ctctctctgt cactctctct gtctctctct ctctgtcact    2520
```

```
ctctctcagt ctctctctct ctctttctct ctctctctca gtgggtggcc agccttgaag   2580
gtgggatgtg ttacagtctt atagttaata agaggcctca gaagtctcat agtcctaggt   2640
ttgaatccca tagaaggcac ttaataaaaa ttccatttgt ttgtttaaat atttagtttt   2700
tatgattaat aatttgttta gcatttatgg ttctgcttta ttcctcagga taatatatag   2760
atagaaaatg ttacatattt tgagaatcaa attattttat aaaagatata atgtagcatc   2820
tttaaaaaca aatctatatg tgtttgctaa ttttatcttt cttctaggac atggccagat   2880
ctctcacaaa agtaagttca aaattatttt gacatttatc aaatttaaat gtaaaattat   2940
attgaatttc actttattta tcttacctta ttttctgtca tgactctagg cttaatatg    3000
tttaatgaag acaatataag aatggggggag attcatatta catccagaat atggttgttt   3060
agacatattg tacttagcaa agagatgcat tatattaaaa aagaaaaaaa tgtcttttaa   3120
gtcccttcaa ttgttagttt tagagaagaa tttcaatcct aggattagaa atctaccata   3180
catatttctt cccagccacc cacccccta gcttactttc actgtaaaca aacaaacaaa    3240
caaacacgaa accccccacaa gcatttatag gcatctccta actcatttta gtatgcttgg   3300
tccaataatg atgtcattta ttagggtcat ccagcagcca attaaatgga atgagtgagt    3360
gaacatgagt agagaatcca tactaaaaat gaagacggta gagatgcagt tttttaatcc   3420
cctaattgaa tgggaaaact cgatcagtaa aacatttctt agggcagcaa agatggcaaa   3480
attgtggtat gtgaaggtca ttaaatttgt ttctcagtta atggaaccgg agttgacaag   3540
aagtggaaag ggtctatctt catcgtattg tccactcacc tattgtaccc tgtcatggat   3600
ttggttcatt gggtggcaga gcaggccaca ttaacgtagc agctctattc tcaactatta   3660
aaataaaaac caagagaaat tctctcacta gcattaaaat agtaacctt ccaaagagtt     3720
catctttgaa aaataaatag tattcatatt tactttctaa ggatttgact ttgaagagaa   3780
ttatatataa aaattctatg taataaaaaa tgtactctgt tcatgtgaaa actaataaac   3840
ttttctgaaa ggagtatctt ttaatatcca ataaaataaa aacagtgacc ttttagaaga   3900
ttataatcat caaggaaagg aatctggttt aattaaggtc tacttgctga gaagtacaac   3960
ttattaataa cacaaggaat tatgcttgga tatttcactc tcacacaaat gtgaaattga   4020
cttcctaaaa aatcaaacct agctcaaata acaatatttt atataaaata ttttagaccc   4080
ttacataaca gataaaatat atgaatagag agtgcttgct aatattaaat atagaattaa   4140
gaaaagtggt ttcattgtat tgttttagtg taatttataa aacttttaag gaatctttat   4200
ttcttcagtc tcaccaaaac ttgaagtaga tagatatta ttatacagac atatattcag    4260
aagcttgctt tgttctggtt ataatagttt gtttcctcaa agatatacat attaaaatac   4320
ccctaaatgt attttttccag gacataaaac agattccttt gttggactaa tgggcaaaag  4380
agctttaaat tctggtatgt atgaaattat gactgaaaat agacagtatc tcaaatctat   4440
ttctattttt tctaagacat agttttaaaa tattaaaaag gagtggtaga tataaaaatg   4500
agtattatgg tggaaaaatt taattgttgt acttgtaacc acaaatggat ttatagctgg   4560
ttaagctaat actaccacag tatctgtcta tttctctcca atcaccattc ttaccagtgt   4620
ctgcccatt taatcattac caacctgaat ctttgggtta gtgctatatt ctttcctata   4680
gatctgttaa ataagccgtg tttaacctta ctgaactaag ggggagtggg gagtgcaggg   4740
aagaatgagg gtgattttca cttgttatca aagtaatttg aaagttttac aagacattac   4800
atttggcgat cttccaatac aaaaataaat tcacaaaaca aattcttat gcaaattaat    4860
cacttttat gaagttgtag aaattcaaaa tctaaacatc ctgatggatg ttggagagga    4920
```

```
caaaagtgat acggtttatt ccagtacttt caaaaaggaa cacaattaaa tatccttgag    4980
tgttataaat tggttctggc tataaactcc ttagagagaa aggatgccac aattctcatt    5040
ttaattctga acaacttttt cgtatgatat aaaggctgca ggtttccttc tcttcaattt    5100
ccatcttctt tgtaaatacc acgtacatat atctgaaaac cattattagt taactcattc    5160
atcacactga tttcaatgta ataaccccct agatcatttt aatagaagct cacttttgt     5220
taagacctta tagctcttac ctctagggct tcttggaaaa gctattcaaa ttctattttg    5280
ccttcagtga aatagaatt aaaatactaa atacgttatt aattataaag taatcagcag     5340
ctgtcttacc catttagaat attccagtt tctagacaat ctataagatg tgctggctta     5400
atccttaatt atctggatcc taggaaaaat aattatccta gtgttttta atggagattt     5460
ttttctttat tgtgaaatgt aagacttggg tacattaaat aaaaccactt tctgtggggc    5520
aaaaatcaaa acgcgcaata gaaaaaaaaa gttaacacaa tctgggctac ggcagaagcc    5580
agagaatata ttcatataat tgaaaagttc taagtgtttc ataattgacc ttttgataca    5640
aaatttccaa taaatctgga atttgaagtt cttggtgaag tccacaggac ttcctagtgt    5700
tcttattggg tccccacttt ctatttagac actaccttg catcttctca ccagtcattt      5760
tgggctgccg aagtgtaaaa gtgtaagaaa ttatcaatgt gccttaatga aaaacttgta    5820
attgttttat taatatgtat tatcttccca cttttggaaa tgaaatataa atttaaacca    5880
caatggcttt tatttgtacc aatacatact agtcctcact taattgtagt tttcttgata    5940
atcatattag tcatcaactt tccatttcca gaattgatat aggtttcaga acatgcttaa    6000
ctttacaaat gtagatattg tacaagttag aacagattaa atacaattaa atgtacttaa    6060
aataataaca taattttaag tagtgataaa aatcactgta gtgaatcagg atcaattat     6120
aactaaatct ttgttcctcc attttagtta aggaaatata aataggtgaa atgtggaaaa    6180
aaatgtgata tgatccacag tcaatcaggg atctttttat gtacctcatt gaggcaaggt    6240
tatcatagcc ttaatctata gccctctgat ctttacccac tcatggtcag ggaccccttt    6300
gacaatctga taaatctaga tagatgccct ttcccagaga aaccctcatc agctcataca    6360
ctcaaaaatt tatatcaggc ttcagagggt tcaaagacca ggtaagaaac tctgcttcca    6420
tgtaagagga cattatgttc cagctaaatc actgtctgtc tttagttggt ttacattagc    6480
tttcatctaa tttctctgag gaatagagtc atgttaccta aagcttgtca gagactgaac    6540
ttgggccatt catcctgttc ctaatataat caaaccagaa tgagaaataa actgtttcct    6600
tccctcacgc ctgtccagtg ttggctcaga ctgttctgcc tcacaagtgc atacttaatt    6660
gatgtaaaat atgcagctta ttgttaaccg cacttaaagg atagctgggt gtttaagacc    6720
agtattaaaa gagggaagtg ataatactgg tgcctttacc tgtcttctct gtcagcaaat    6780
cttctcactg aggaaactgt ttagagtagc acttattatt cctacagatc cttcacagat    6840
ctttctactc tttctgttta cattcagtat tttatacagg ccatactgaa tttcaaaaag    6900
catagtagtt ccactatacc atacgtctaa gtctataagg tattcgttaa ggatgaaaaa    6960
tatcccaaaa tacttttatt gcaacagtct gattttacc cctttgtggt tacagatccc     7020
tttgaaatta tatataataa atataatata atataatata caattttggc attttttgt     7080
ccagataatc aatgtattta aattacttgc tagctatatg ttaaatacct tggaagcaa     7140
taattaatgc ttcacaggcc attaaggtgc tagtgaaaag ttaaacagta tggtatttag    7200
atggctcaac tgacttacct atggtaaatg ggctgttttt agtcttgagg gcagtccatc    7260
```

-continued

| | | | | |
|---|---|---|---|---|
| actgggaggt | atccacaagg | taggaagaga | cccctacaca | attagatgcc ccttgaacaa | 7320 |
| agatcagcaa | acttttcctg | aaaagaaaca | gattataaat | attttaggct ttgtgagcca | 7380 |
| tgtaatctct | gttgcaacta | cccaaatctg | ttattttagg | ccaaagcagc catagacaat | 7440 |
| atgtaaatga | atgagtgtgt | ctgtattcct | ataaacctct | ttacaagaac aaatggtatt | 7500 |
| ctagatttgg | cccatggtct | ctgctagaat | aaaagtccca | catttggttt ttatcctact | 7560 |
| agtattcctg | gttattttag | gcattgtcct | ttctagaatt | cactatgggt atctgccact | 7620 |
| gcttgagaaa | gctgctgaga | atcaacactg | caatatattg | tggaaatatg ctttgggggc | 7680 |
| accaagtata | tgatgaatga | tgaatgaaac | cgagttctgt | ggttagatca tttccaatca | 7740 |
| gaatagagac | tgaggcagga | ttggaagatg | tgcagataac | attcttagaa atacttctgt | 7800 |
| agagggaaaa | tgtcattatg | agtttaaaat | aaattactat | atgccctgaa ctttagttgt | 7860 |
| gtaactccct | cagtgaattc | acttaaaaaa | cactttatct | cttctttgtt ttcagtggct | 7920 |
| tatgaaagga | gtgcaatgca | gaattatgaa | agaagacgtt | aataaactac ctaacattat | 7980 |
| ttattcagct | tcatttgtgt | caatgggcaa | tgacaggtaa | attaagacat gcactatgag | 8040 |
| gaataattat | ttatttaata | acaattgttt | ggggttgaaa | attcaaaaag tgtttatttt | 8100 |
| tcatattgtg | ccaatatgta | ttgtaaacat | gtgttttaat | tccaatatga tgactccctt | 8160 |
| aaaatagaaa | taagtggtta | tttctcaaca | aagcacagtg | ttaaatgaaa ttgtaaaacc | 8220 |
| tgtcaatgat | acagtcccta | agaaaaaaaa | atcattgctt | tgaagcagtt gtgtcagcta | 8280 |
| ctgcggaaaa | ggaaggaaac | tcctgacagt | cttgtgcttt | tcctatttgt tttcatggtg | 8340 |
| aaaatgtact | gagattttgg | tattacactg | tatttgtatc | tctgaagcat gtttcatgtt | 8400 |
| ttgtgactat | atagagatgt | ttttaaaagt | ttcaatgtga | ttctaatgtc ttcatttcat | 8460 |
| tgtatgatgt | gttgtgatag | ctaacatttt | aaataaaaga | aaaaatatct tgaa | 8514 |

<210> SEQ ID NO 33
<211> LENGTH: 6564
<212> TYPE: DNA
<213> ORGANISM: Homo sapiens

<400> SEQUENCE: 33

| | | | | |
|---|---|---|---|---|
| ctttatcagg | gagctgggac | tgagtgactg | cagccttcct | agatcccctc cactcggttt | 60 |
| ctctctttgc | aggagcaccg | gcagcaccag | tgtgtgaggg | gagcaggcag cggtcctagc | 120 |
| cagttccttg | atcctgccag | accacccagc | ccccggcaca | gagctgctcc acaggtaggc | 180 |
| aagtgggaga | atgctggatg | gaccagagct | ggcaccaggg | gacaggagcc agcgtcagga | 240 |
| gggaataaag | cagatggcag | cctctgatag | gggagcaggg | gactgggaag gtgagcacaa | 300 |
| agcacctgta | gggccgagag | ctggttggtg | tttggagcct | gtggctacag actcattctt | 360 |
| tcataccaga | aagttttttgc | ctaagtcttg | ggattatcta | gtactggaaa atagcatcca | 420 |
| ggatccctcc | tccagctgac | tgaggaaaca | gaccagtcca | tgtcctacaa atctatcatc | 480 |
| tttcttggga | gctagagtcc | tcctggcacc | actatagcat | tgcacatctc ctggggagat | 540 |
| atctgatggg | gtagcaggga | aactaagccc | aagggctgta | ccccttctc agaaatactt | 600 |
| tccaccctct | ctccagacca | gggcttggac | agtggagttg | ggggctgggg aagcagggtc | 660 |
| aagccaagct | gctggtaatg | aatgtctctt | gtgtcttcac | ccatgctgta tcttcctctt | 720 |
| ctctccttta | cctgagtcct | gtccctttgc | tctcccaggc | accatgagga tcatgctgct | 780 |
| attcacagcc | atcctggcct | tcagcctagc | tcagagcttt | ggggctgtct gtaaggagcc | 840 |
| acaggaggag | gtggttcctg | gcggggggccg | cagcaaggta | agtctccccct ggcagagtac | 900 |

```
tggggacatc acgggaactt gggactctgc ctgtctggac agctgtagtg aggaaactgg    960 ggtgggggg  ttgtccgtca gagggcattt tgcctcccct tggatttctt tgtttctctg   1020
gtcctttcat gttcccactg tctccaggtg tgtttgtgtc tctgtatctc tgcatgtctt   1080
tgacaccttg tacataaaag gtgccctaca aatatgttgt ttggtgggtt gattgatggg   1140
agacttggtg attggatggt actgtgaggg gtgagctagg gtggtctaag gctctctata   1200
gtctacctca ggtcccttg  caagggacag atctcttcta tttcctggat ggtatgaaac   1260
agtcagaatt tctttcccaa atggttattt gtgtgctatt ttacctatca gttatgtgta   1320
ttgttttatt ttcaaaatgc aaataaattc ccttatcttt tgctcatcca cccccagtaa   1380
cctcaggtgc ttctaagatc ccaaccccct ccttcttctc ttttctccct tgcccgcctc   1440
tatcctctgc ttagtcagga taggaaaaca acaacagcaa aaaaaccaga ttgagcctcg   1500
atttccacag ttcctttacg aaaaagaata ggaattgtca gggtaggggt acaggggag   1560 gatagggagg aagtcttttc aaggttttga aatgacagca attacatcgg tacaaatgct   1620
tttaagatga ttgcgggtgg gacttattac aaattcaatg tgtgaagttt aactgcctct   1680
tcagctcaaa tctgttcagc atctcattat aggaggtggg cagagtattc aacaatttgg   1740
gaaaagtggc tgcctgaaca ccacatgctg ggccaaggga gttatcacca gggcagcctt   1800
gcaggtggca gcagttgtgc catatccaaa aggccagaac cgttaaaaaa aaaaacaccc   1860 agggagtgc  caagtatggg ctggacaccg tttggagcca caagttccag cccaggata    1920 gttagagtat ctgagttctt ctgagacaaa cttgtttcaa gaccttggcc aatgagatgt   1980
cccctctgcc cctcttggtc aatgaatgag agggattgcc atcctacccc ttctccttga   2040
gagtctgtga ggatgaggga aattggggca ggaagagggt agtacatagg tgtgcctagg   2100
caactgggtt ggtatgtgtg ggggtgtgtt ctgtgtaaat gcacttctgt gtgtgcacaa   2160
cagccgaagg atgcctgggt tctggaaaga gaggcgctgc tgagacttga gatttgagat   2220
gaaaatctcc agccatgatc attgttattg tctctctgca gctgcaatta actggctgtg   2280
tggtgtgtgc ccaccaccct gctgtacgca agttgctaaa aaaaaaaaaa aaatcacagg   2340
gacaatcaag agcccgtgct gggcaacagc tctagaactt gggattcagt tgtggagaga   2400
agaagacgtg ccttctgagc atgttgcctt cctggaattc tagacctagg gccaaaaggg   2460
agagggagag aaaactagag gcggaaagcc atggagaata gagaaagagg tggtggaaaa   2520
cagggagaga aacatccatg gacatcgtgc agagtggggg aatcacaggt gcagatgtgt   2580
gcctccaatc tcaccatgca tgtgaatcac ctgggggggct gcttaaaatg cagattctgt   2640
ctcaggaggt ctggggtagg aacaagagtc tgcatttcta acaggctctg tgtagtgctg   2700
gtgttgctgt tggtccacag gtcactcctg gagcacctac ttctcgtcca gtgtgaacca   2760
gaggaaactc tgaaagaaat agggtgtcgg attcaggatg ggctcaggaa gaggctgttt   2820
cttgtgggaa aaggatgagt ggatccgggt gggagcctcc tgcctcaccc ctctttgttt   2880
cttccctaga gggatccaga tctctaccag ctgctccaga gactcttcaa aagccactca   2940
tctctggagg gattgctcaa agccctgagc caggctagca caggtaggag gcggccctag   3000
gggagagggg aatgaggggc aggattctga agataagagg cctgggagat cctttcagat   3060
gggagagaga tgggggatag cttagtgaat cggtgagggt tgtgatctga accccgctct   3120
catcactttc caacttcact ccccatttag acatctgttc ttggtttcac agatcctaag   3180
gaatcaacat ctcccgagaa acgtaagtac cctcttctcc ctccctatct cttgccactt   3240
```

-continued

```
gcccagagct ctgtggggca ttgggcccag gggccatttt gtccagcccc ttctcacctg    3300
gtacaaacaa tatgccagct cccactgctc agccaacctt tcctgaaagg gagaggccat    3360
ccagaactag gaggaagctg gtgtgagggg catggtgggc tctccctctg ctggctggtc    3420
cttggaaaac aaggggatct cttcgtggcc ctgaaaattc caaatcaggc acctgctaga    3480
gcagaaaatt cttgaaatgt ggaggaagga aaggtgagca gagagagtgg gtttagggga    3540
ggcacttgct aactgtgagg agtcatgctt tgacaagaaa aaggaacaga gaccagaaac    3600
ccagtctcag aagtgttgac ccatgtctgg ggagatgctt cactttctca tcatcactgc    3660
tgacaatgtt ggcccttttc tgcaggtgac atgcatgact tctttgtggg acttatgggc    3720
aagaggagcg tccagccagg taggagtgtg tggaggtaca gtggaagggc ttagggtact    3780
ggcagagtat gacagaagtc acgtgcctca tatttgtcac cagagggaaa gacaggacct    3840
ttcttacctt cagtgagggt tcctcggccc cttcatccca atcagcttgg atccacagga    3900
aagtcttccc tgggaacaga ggagcagaga cctttataag gtagtcctgt tgcagctggg    3960
aggaaggata gggagactct gcttccaccc cagtctccca actctgtctt tgaacactgc    4020
ccgtcatagc cagcccttg ctgttggatc agggtgtagt tcacattcag aaagatccct    4080
cttacttaca ctgttcgctt taccctagac tctcctacgg atgtgaatca agagaacgtc    4140
cccagctttg gcatcctcaa gtatccccg agagcagaat agggtaagga ttgttcatta    4200
gagaggggag aggggactgg ggaggggct gtggggttg ccagctgtgc atttcctccc    4260
atgctacagg tattaaagct catagatttg ccctgaaata cactgccaat gcccagcaca    4320
ctgtcggcca aacacaaaga cacttagagg cacgtgtgtt tgtacacatc ccccgtcttt    4380
catctctttc ctctggatca tggacggcag ctgactattg agcaggagtg agtgttggga    4440
gatgaggaga gaggggcttc cccgatgggc aatttctgtt gtttggactt cattcttttg    4500
taatctatgc aaaaagatgg agaaattatt atctgataat tacaaatacc acaaccaatt    4560
cacaggcaag catttgcctc ccaggcaggc tgagcctttc aaatcactca gaatcctggg    4620
ttacggggcc cagaaggtag tcatacacaa ggatgattca ggaagaaatg caaggaactc    4680
tgaaatctaa tggggattag caggaaacca tatctgaatc tctctttagc ataatgaata    4740
agaacaatgg cctgaatgtg aatcctggat ctgccactct atctgtatct ttttggccaa    4800
ggtacatatc ctcctgtgct tcagtttcct catctgaaaa atgaaagtga taatagtatc    4860
tcacagggtt gtggttttga ggattgagta taggtaaagt gttcagaaca gtgccgggtg    4920
cacagtgctg tgtgccaatt ttatgataat tgtcccagtt tgggaggtat gggggatgtc    4980
ctaatgtttc ccctgactgg ctctgtctgg accccaggcc tgagtgggct gacaaattcc    5040
tcacttggta tgcgagtgta agagtccccc agggaagtgt ctagtcaaaa cacgaacctt    5100
ccgccttgac actgtcttcc cacacacagc aagagcagct ccaccaatgg ctttcttttc    5160
actagcttcc aaagaattgg ggtggaggga gtgaaaagga gagggagaga gattgggaag    5220
gctcgtaatc atggagagcc tcctgctttt ctctctgtgt ccctgttacc catactcact    5280
ggtctcaagg tggcacgccc aagacccaag gagctggtgc ttgatgatgc tgcctgtgca    5340
tgaattcctg ggaccagaga ctgagtctgg ccccccattt agtgttgggt gagagggcac    5400
aaagagctat aataactgta acttgctgat tacatggtag ttactgtatc attttgctct    5460
cattagatgg ttatttcagt cctgccgacg gccagataat tatacgagca gctatatctg    5520
gatgacatac tctgctccag cgttatgcac tggccataaa gataattaca gtgcaatttt    5580
gctatagtat tttatacaaa tggcaaaaac aagtgcattg tggaaatcta cttttaatgc    5640
```

```
ttgtttgtgc atccaggctc tttcagaggg acccataatt gcagctttca taatcttacc    5700
attgagggag cattcccaac ctgttaggtg tcaggcagaa taggacataa ggtttctggg    5760
agctggcatt taaagattag atgagatgga tcaacacaga tcattgtgtc atctgatttc    5820
attcatgtga aactgtaagt aatccctggg cctgtgcttc ctctgggagg tttctgggaa    5880
gaggaggaac tggataaggc aggggagca ttcatagtag ggcaccttgg gcagggctgt    5940
gtgtgtgtct ggctcatggt ggtgctagga tggcatgaac ttggttccta catctttggt    6000
ccacatgggc cccactggcc atgcacacag gtgtgtagag taatgtaaat atggcagctg    6060
ggaaggtgca agtacctgcg gctaggagag ttccatcctc aggcccaaag cctggagggc    6120
aggctgaggg tcaagacttg ttctttcctc tctcacagac gcctctcccc ttctctcctg    6180
ctgccacagc aggttttcag tgggactttt ttacaggata taagatgtga tttcagtgtt    6240 ttttttttgtt ttgttttgtt ttttgtcctc agtactccac ttccggactc ctggactgca    6300 ttaggaaagac ctctttccct gtcccaatcc ccaggtgcgc acgctcctgt taccctttct    6360
cttccctgtt cttgtaacat tcttgtgctt tgactccttc tccatctttt ctacctgacc    6420
ctggtgtgga aactgcatag tgaatatccc caaccccaat gggcattgac tgtagaatac    6480
cctagagttc ctgtagtgtc ctacattaaa aatataatgt ctctctctat tcctcaacaa    6540 taaaggatttt ttgcatatga atga                                         6564
```

NEUROKININ ANTAGONISTS AND USES THEREOF

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. The present application claims the benefit of U.S. Provisional Application No. 62/580,834, filed Nov. 2, 2017, which is hereby incorporated by reference in its entirety.

STATEMENT REGARDING FEDERALLY SPONSORED R&D

This invention was made with government support under Grant No. MH085082 & MH108734 awarded by the National Institutes of Health. The government has certain rights in the invention.

REFERENCE TO SEQUENCE LISTING

The present application is being filed along with a Sequence Listing in electronic format. The Sequence Listing is provided as a file CALTE134ASEQUENCE.txt, created and last modified on Oct. 31, 2018, which is 29,729 bytes in size. The information in the electronic format of the Sequence Listing is incorporated herein by reference in its entirety.

FIELD

Some embodiments relate to methods for detecting and treating social isolation stress in a subject in need thereof.

SUMMARY

In some embodiments, a method of inhibiting, ameliorating, reducing the severity of, treating, reducing the likelihood of, or preventing social isolation stress or symptoms thereof in a subject in need thereof is described. The method can comprise administering an effective amount of neurokinin receptor antagonist to the subject. In some embodiments, the neurokinin receptor antagonist is a NK3R antagonist. In some embodiments, the method further comprises obtaining a sample from a peripheral tissue of a subject that is outside of the central nervous system, detecting a level of neurokinin B in the sample, and determining the subject to be in need of the neurokinin receptor antagonist if the level of neurokinin B in the sample is greater than a control level. The NK3R antagonist can be administered to the subject if the level of neurokinin B in the sample is greater than the control level. In some embodiments, the control level of neurokinin B is a level of neurokinin B in a control sample of an individual that does not suffer from social isolation stress or of the subject and collected prior to the induction of social isolation stress. In some embodiments, the method further comprises determining the control level of neurokinin B in the control sample. In some embodiments, the control level of neurokinin B is a stored value. In some embodiments, the subject suffers from at least one of aggression, cancer, major depressive disorder, dysthymic disorder, social phobia, generalized anxiety disorder, alcohol abuse and dependence, drug abuse, nicotine dependence, atherosclerosis, coronary heart disease, ischemic stroke, cognitive impairment, Alzheimer's disease, agoraphobia, post-traumatic stress disorder (PTSD), bereavement, grieving in isolation, or single member living schizophrenia. In some embodiments, the subject suffers from at least one of cancer, major depressive disorder, dysthymic disorder, social phobia, generalized anxiety disorder, alcohol abuse and dependence, drug abuse, nicotine dependence, atherosclerosis, coronary heart disease, ischemic stroke, cognitive impairment, Alzheimer's disease, agoraphobia, post-traumatic stress disorder (PTSD), bereavement, grieving in isolation, or single member living schizophrenia. In some embodiments, the subject suffers from at least one of aggression, major depressive disorder, dysthymic disorder, social phobia, generalized anxiety disorder, alcohol abuse and dependence, drug abuse, nicotine dependence, atherosclerosis, coronary heart disease, ischemic stroke, cognitive impairment, Alzheimer's disease, agoraphobia, post-traumatic stress disorder (PTSD), bereavement, grieving in isolation, or single member living schizophrenia. In some embodiments, the subject suffers from at least one of aggression, cancer, dysthymic disorder, social phobia, generalized anxiety disorder, alcohol abuse and dependence, drug abuse, nicotine dependence, atherosclerosis, coronary heart disease, cognitive impairment, Alzheimer's disease, agoraphobia, post-traumatic stress disorder (PTSD), bereavement, grieving in isolation, or single member living schizophrenia. In some embodiments, the subject suffers from at least one of aggression, cancer, major depressive disorder, social phobia, generalized anxiety disorder, alcohol abuse and dependence, drug abuse, nicotine dependence, atherosclerosis, coronary heart disease, ischemic stroke, cognitive impairment, Alzheimer's disease, agoraphobia, post-traumatic stress disorder (PTSD), bereavement, grieving in isolation, or single member living schizophrenia. In some embodiments, the subject suffers from at least one of aggression, cancer, major depressive disorder, dysthymic disorder, generalized anxiety disorder, alcohol abuse and dependence, drug abuse, nicotine dependence, atherosclerosis, coronary heart disease, ischemic stroke, cognitive impairment, Alzheimer's disease, agoraphobia, post-traumatic stress disorder (PTSD), bereavement, grieving in isolation, or single member living schizophrenia. In some embodiments, the subject suffers from at least one of aggression, cancer, major depressive disorder, dysthymic disorder, social phobia, alcohol abuse and dependence, drug abuse, nicotine dependence, atherosclerosis, coronary heart disease, ischemic stroke, cognitive impairment, Alzheimer's disease, agoraphobia, post-traumatic stress disorder (PTSD), bereavement, grieving in isolation, or single member living schizophrenia. In some embodiments, the subject suffers from at least one of aggression, cancer, major depressive disorder, dysthymic disorder, social phobia, generalized anxiety disorder, drug abuse, nicotine dependence, atherosclerosis, coronary heart disease, ischemic stroke, cognitive impairment, Alzheimer's disease, agoraphobia, post-traumatic stress disorder (PTSD), bereavement, grieving in isolation, or single member living schizophrenia. In some embodiments, the subject suffers from at least one of aggression, cancer, major depressive disorder, dysthymic disorder, social phobia, generalized anxiety disorder, alcohol abuse and dependence, nicotine dependence, atherosclerosis, coronary heart disease, ischemic stroke, cognitive impairment, Alzheimer's disease, agoraphobia, post-traumatic stress disorder (PTSD), bereavement, grieving in isolation, or single member living schizophrenia. In some embodiments, the subject suffers from at least one of aggression, cancer, major depressive disorder, dysthymic disorder, social phobia, generalized anxiety disorder, alcohol abuse and dependence, drug abuse, atherosclerosis, coronary heart disease, ischemic stroke, cognitive impairment, Alzheimer's disease, agoraphobia, post-traumatic stress disorder (PTSD), bereavement, grieving in isolation, or single member living schizophrenia. In some embodiments, the subject suffers from at least one of aggression, cancer, major depressive disorder, dysthymic disorder, social phobia, generalized anxiety disorder, alcohol abuse and dependence, drug abuse, nicotine dependence, coronary heart disease, ischemic stroke, cognitive impairment, Alzheimer's disease, agoraphobia, post-traumatic stress disorder (PTSD), bereavement, grieving in isolation, or single member living schizophrenia. In some embodiments, the subject suffers from at least one of aggression, cancer, major depressive disorder, dysthymic disorder, social phobia, generalized anxiety disorder, alcohol abuse and dependence, drug abuse, nicotine dependence, atherosclerosis, ischemic stroke, cognitive impairment, Alzheimer's disease, agoraphobia, post-traumatic stress disorder (PTSD), bereavement, grieving in isolation, or single member living schizophrenia. In some embodiments, the subject suffers from at least one of aggression, cancer, major depressive disorder, dysthymic disorder, social phobia, generalized anxiety disorder, alcohol abuse and dependence, drug abuse, nicotine dependence, atherosclerosis, coronary heart disease, Alzheimer's disease, agoraphobia, post-traumatic stress disorder (PTSD), bereavement, grieving in isolation, or single member living schizophrenia. In some embodiments, the subject suffers from at least one of aggression, cancer, major depressive disorder, dysthymic disorder, social phobia, generalized anxiety disorder, alcohol abuse and dependence, drug abuse, nicotine dependence, atherosclerosis, coronary heart disease, ischemic stroke, cognitive impairment, agoraphobia, post-traumatic stress disorder (PTSD), bereavement, grieving in isolation, or single member living schizophrenia. In some embodiments, the subject suffers from at least one of aggression, cancer, major depressive disorder, dysthymic disorder, social phobia, generalized anxiety disorder, alcohol abuse and dependence, drug abuse, nicotine dependence, atherosclerosis, coronary heart disease, ischemic stroke, cognitive impairment, Alzheimer's disease, post-traumatic stress disorder (PTSD), bereavement, grieving in isolation, or single member living schizophrenia. In some embodiments, the subject suffers from at least one of aggression, cancer, major depressive disorder, dysthymic disorder, social phobia, generalized anxiety disorder, alcohol abuse and dependence, drug abuse, nicotine dependence, atherosclerosis, coronary heart disease, ischemic stroke, cognitive impairment, Alzheimer's disease, agoraphobia, bereavement, grieving in isolation, or single member living schizophrenia. In some embodiments, the subject suffers from at least one of aggression, cancer, major depressive disorder, dysthymic disorder, social phobia, generalized anxiety disorder, alcohol abuse and dependence, drug abuse, nicotine dependence, atherosclerosis, coronary heart disease, ischemic stroke, cognitive impairment, Alzheimer's disease, agoraphobia, post-traumatic stress disorder (PTSD), grieving in isolation, or single member living schizophrenia. In some embodiments, the subject suffers from at least one of aggression, cancer, major depressive disorder, dysthymic disorder, social phobia, generalized anxiety disorder, alcohol abuse and dependence, drug abuse, nicotine dependence, atherosclerosis, coronary heart disease, ischemic stroke, cognitive impairment, Alzheimer's disease, agoraphobia, post-traumatic stress disorder (PTSD), bereavement, or single member living schizophrenia. In some embodiments, the subject suffers from at least one of aggression, cancer, major depressive disorder, dysthymic disorder, social phobia, generalized anxiety disorder, alcohol abuse and dependence, drug abuse, nicotine dependence, atherosclerosis, coronary heart disease, ischemic stroke, cognitive impairment, Alzheimer's disease, agoraphobia, post-traumatic stress disorder (PTSD), bereavement, or grieving in isolation. In some embodiments, the subject suffers from at least one of aggression, cancer, major depressive disorder, dysthymic disorder, social phobia, generalized anxiety disorder, alcohol abuse and dependence, drug abuse, nicotine dependence, atherosclerosis, coronary heart disease, ischemic stroke, cognitive impairment, Alzheimer's disease, agoraphobia, bereavement, or grieving in isolation. In some embodiments, the subject suffers from at least one of aggression, cancer, major depressive disorder, dysthymic disorder, social phobia, generalized anxiety disorder, alcohol abuse and dependence, drug abuse, nicotine dependence, atherosclerosis, coronary heart disease, ischemic stroke, cognitive impairment, agoraphobia, bereavement, or grieving in isolation. In some embodiments, the subject suffers from at least one of aggression, cancer, major depressive disorder, dysthymic disorder, social phobia, generalized anxiety disorder, alcohol abuse and dependence, drug abuse, nicotine dependence, cognitive impairment, Alzheimer's disease, agoraphobia, post-traumatic stress disorder (PTSD), bereavement, grieving in isolation, or single member living schizophrenia. In some embodiments, the subject suffers from at least one of aggression, cancer, major depressive disorder, dysthymic disorder, social phobia, generalized anxiety disorder, alcohol abuse and dependence, drug abuse, nicotine dependence, agoraphobia, post-traumatic stress disorder (PTSD), bereavement, grieving in isolation, or single member living schizophrenia. In some embodiments, the subject suffers from at least one of aggression, cancer, major depressive disorder, dysthymic disorder, social phobia, generalized anxiety disorder, alcohol abuse and dependence, drug abuse, nicotine dependence, cognitive impairment, Alzheimer's disease, agoraphobia, bereavement, grieving in isolation, or single member living schizophrenia. In some embodiments, the subject suffers from at least one of aggression, cancer, major depressive disorder, dysthymic disorder, social phobia, generalized anxiety disorder, alcohol abuse and dependence, drug abuse, nicotine dependence, agoraphobia, bereavement, grieving in isolation, or single member living schizophrenia. In some embodiments, the subject is at risk of social isolation stress, and the method comprises reducing the likelihood of, or preventing social isolation stress in the subject. In some embodiments, the subject does not suffer from any of schizophrenia, bipolar disorder, or panic disorder. In some embodiments, the subject does not suffer from any of fear memory consolidation, fear conditioning, or PTSD. In some embodiments, the subject has exhibited an induction of expression of neurokinin B in response to a stressor. In some embodiments, the subject exhibits a greater level of neurokinin B than the subject had prior to the induction of neurokinin B in response to the stressor. In some embodiments, the neurokinin receptor antagonist is an NKR3 antagonist selected from the group consisting of: osanetant, talnetant, fezolinetant, pavinetant, SB-222200, and SB-218795, or a combination of two or more of the listed items. In some embodiments, the neurokinin receptor antagonist is an NKR3 antagonist that comprises, consists essentially of, or consists of osanetant. In some embodiments, the NK3R receptor antagonist is administered to the subject prior to the induction of social isolation stress. In some embodiments, the NK3R antagonist is administered to the subject at least 30 minutes prior to the induction of social isolation stress. In some embodiments, the neurokinin receptor antagonist is administered to the subject after the subject exhibits a symptom of social isolation stress. In some embodiments, the neurokinin receptor antagonist is administered to the subject at least two hours after an induction of social isolation stress in the subject.

In some embodiments, a method of determining a risk of social isolation stress in a subject is described. The method can comprise obtaining a sample from a peripheral tissue of the subject that is outside of the central nervous system. The method can comprise detecting a level of neurokinin in the sample. The method can comprise determining the subject to be in need of the neurokinin receptor antagonist if the level of neurokinin in the sample is greater than a control level of neurokinin. In some embodiments, the neurokinin comprises neurokinin B. In some embodiments, the neurokinin receptor antagonist is an NK3R antagonist. In some embodiments, the control level is a level of a control sample of an individual that does not suffer from social isolation stress or of the subject and collected prior to the induction of social isolation stress. In some embodiments, the method further comprises determining the control level in the control sample. In some embodiments, the control level is an electronically stored value. In some embodiments, detecting the level of neurokinin in the sample comprises a technique selected from the group consisting of ELISA, western blot, radioimmunoassay, lateral flow assay, no-wash assay, protein array, quantitative nucleic acid amplification, and nucleic acid hybridization, or two or more of the listed items. In some embodiments, the method is an in vitro method. In some embodiments, the method further comprises administering the NK3R antagonist to the subject.

BRIEF DESCRIPTION OF THE DRAWINGS

FIGS. 1A-R show that prolonged social isolation stress (SIS) alters behavior in accordance with some embodiments. FIGS. 1A-D show alternative models for peptidergic control of an internal state influencing multiple behaviors controlled by different brain regions (dark gray circles, behavior A, behavior B, etc.). Control may be achieved by multiple (FIG. 1A) or a single (FIGS. 1B-D) neuropeptides (pQ, pX, etc.) acting directly on multiple regions (FIG. 1A, FIGS. 1C-D) expressing receptors (RX, RY, etc.) for the peptides, or on a single peptide-responsive "hub" region (FIG. 1B). In FIG. 1D the same peptide (pX) is expressed in different regions (small light gray circles, top) that control different behaviors in different peptide-responsive regions (large dark gray circles, bottom). FIGS. 1E-Q show a comparison between wild-type (WT) group housed (GH) control mice and isolated (SIS) mice (n=8 mice/condition) in the assays indicated (FIG. 1E, FIG. 1K, FIG. 1M, schematics). FIGS. 1F-G show aggression measured by the resident-intruder test. FIGS. 1H-I show freezing responses during ("during") or immediately after ("post") presentations of an overhead looming disk (FIG. 1H) or conditioned tone (FIG. 1I). FIG. 1J shows reactivity to footshock following tone tests. FIG. 1L shows frequency of freezing to a 17-20 kHz ultrasonic sound stimulus (USS). FIGS. 1N-Q show anxiety assays. FIGS. 1N-O show results obtained from open field tests (OFT), FIGS. 1P-Q show results obtained from elevated plus maze (EPM) tests. FIG. 1R shows a summary of results. Dark gray up-pointing arrows indicate isolation-induced increases in behavior, light gray down-pointing arrows indicate isolation-reduced behavioral responding. "n.c.", no change.

In FIGS. 1A-R through FIGS. 7A-I, data are represented as mean±SEM. *$p<0.05$, $p<0.01$, *$p<0.001$. Pairwise contrasts were tested and corrections for multiple comparisons were applied for post-hoc comparisons; bars without asterisks did not reach significance ($p>0.05$). ANOVA's, F values, t values, as well as additional statistical information for this and subsequent figures can be found in Table 2. See also related FIGS. 8A-R.

FIG. 2A is an illustration summarizing tachykinin ligand-receptor specificities. In FIG. 2F, the intensity of zsGreen expression was greater in isolated as compared to group housed mice. In FIG. 2G, the intensity of zsGreen expression was comparably low for both group house and isolated mice.

FIGS. 3A-M show that systemic Nk3R antagonim attenuates the effects of SIS in accordance with some embodiments. FIG. 3A depicts the experimental protocol. Following isolation, SIS or GH mice were injected (i.p.) with osanetant or vehicle and tested for the indicated behaviors (n=6 mice/condition). FIGS. 3B-F show that osanetant blocked SIS-induced aggression (FIGS. 3B-C), post-loom freezing (FIG. 3D), post-tone freezing (FIG. 3E), and increased shock reactivity (FIG. 3F). FIG. 3G shows an experiment to test whether osanetant delivered daily during SIS can protect against its behavioral effects. "osan 1×" indicates an additional control group given a single dose of osanetant 24 hours before testing to control for carry-over of the drug (n=6/condition). FIGS. 3H-L show the effect of osanetant administered during SIS on (FIGS. 3H-I) aggression. (FIG. 3J) post-loom freezing, (FIG. 3K) post-tone freezing. FIG. 3L shows shock reactivity; a trend to protection (SIS-veh vs. osan during) was observed but did not reach the significance threshold (p>0.05). FIG. 3M shows a summary of results. "osan pre-test" indicates osanetant was given 20 min prior to each assay (FIGS. 3B-F) but not during SIS, "osan during SIS" indicates osanetant was given during SIS only (FIGS. 3H-L), and not 20 min before each assay. Faint gray arrows indicate original effects produced by SIS. Black X's indicate SIS-induced effects that were blocked by the manipulation. See also related FIGS. 10A-J.

FIG. 4A shows the experimental protocol. Mice were implanted with bilateral cannulae in dBNSTa, DMH, or CeA, isolated, and given osanetant or vehicle microinfusions (300 nl) 20 min before testing (n=6-7/condition). FIGS. 4B-P show the effect of osanetant infusion into dBNSTa (FIGS. 4B-F), DMH (FIGS. 4G-K), or CeA (FIGS. 4L-P) on indicated assays. Osanetant (bars labeled "osan") selectively blocked persistent freezing in dBNSTa ("post"; FIGS. 4E-F), aggression in DMH (FIGS. 4H-I), and acute freezing in CeA ("during"; FIGS. 4O-P). FIG. 4Q shows a summary of results. Notations are as in FIG. 3M. n/a, not applicable (secondary to lack of freezing during stimulus). Down-pointing arrows indicate manipulation-induced reduction in a behavior not altered by SIS. See also related FIGS. 11A-K.

FIG. 5A shows a schematic of the experimental protocol. Tac2-Cre mice were bilaterally injected in the indicated regions with a Cre-dependent AAV expressing hM4DREADD-mCherry, isolated, and injected (i.p.) with CNO or vehicle prior to testing (n=7-8 mice/condition). FIGS. 5B-P show the effect of vehicle or CNO on mice expressing Tac2-hM4DREADD in dBNSTa (FIGS. 5B-F). DMH (FIGS. 5G-K), or CeA (FIGS. 5L-P) on indicated assays. CNO blocked persistent freezing in dBNSTa ("post"; FIGS. 5E-F), aggression in DMH (FIG. 5H-I), and acute freezing in CeA ("during"; FIGS. 5O-P). FIG. 5Q shows a summary of results. Notations as in FIG. 4Q. CNO had no effect in mCherry-expressing mice (FIG. 12G). See related FIGS. 12A-G.

FIG. 6A shows the experimental protocol. 3 weeks prior to testing, WT mice were injected with an AAV expressing shRNA-zsGreen for specific knockdown of Tac2 (shRNA-1 or shRNA-2), or with an shRNA virus targeting the luciferase gene (control) (n=6-7/mice condition), and maintained in isolation until testing. FIGS. 6E, F). FIG. 6Q shows a summary of results. The effects of shRNA-1 (left column) and shRNA-2 (right column) are presented for each region. See related FIGS. 13A-AA.

FIGS. 7A-I show that activation of Tac2$^+$ neurons plus Tac2 overexpression mimics the effect of SIS in GH mice in accordance with some embodiments. FIG. 7A shows the experimental protocol. GH Tac2-Cre mice were intravenously injected with Cre-dependent AAV-PHP.B viruses expressing the chemogenetic activator hM3DREADD, a Tac2 cDNA, both, or mCherry (controls). Mice remained group housed (4 weeks) with CNO-spiked drinking water provided during the final 2 weeks (for hM3DREADD activation). Mice received an injection of CNO (i.p.) 20 min prior to each assay (n=6 mice/condition). FIGS. 7B-F show the effect of each manipulation on the indicated assays. All animals were treated with CNO and received the same total amount of virus. Only mice receiving both the hM3DREADD and Tac2 cDNA viruses showed a "SIS-like" phenotype (darkest bars), including increased aggression (FIGS. 7B-C), post loom freezing (FIG. 7D), and post-tone freezing (FIG. 7E). FIG. 7F shows reactivity to the footshock. FIG. 7G shows a summary of results. Arrows indicate effects of perturbations to generate SIS-like effects. FIG. 7H is a schematic illustrating how Tac2 and its receptor (Nk3R) control SIS-induced behavior. Without being limited by theory, either the same or different cells may express the peptide and the receptor within each region. FIG. 7I is an illustration summarizing LOF and GOF effects on behavior (Upper). Without being limited by theory, model graphs (Lower) show different thresholds for acute vs. persistent freezing, and different dose-dependencies of freezing on Tac2 levels in dBNSTa vs. CeA (bottom graph), could explain the differential effects of shRNA-1 (weaker) and -2 (stronger; upper graphs) in the two regions (see FIG. 6Q). Without being limited by theory, the model also illustrates how an increase in Tac2 levels caused by SIS (line labeled "CeA") could convert acute (CeA-dependent) to persistent (dBNSTa-dependent) freezing. Dot labelled "GH," baseline levels of Tac2 in GH mice are higher in CeA than in dBNSTa, based on FISH data (FIG. 2W, FIG. 2Y). See related FIGS. 14A-T.

FIGS. 8A-H show that prolonged SIS alters subsequent social and asocial behavior in accordance with some embodiments. FIGS. 8A-F show SIS or GH mice (n=8 mice/condition) tested in various behavioral assays (see also FIG. 1E). Tail rattles during the overhead looming disk assay were elevated in isolated mice (see FIG. 1H for looming data). FIGS. 8C-D show baseline freezing to the tone fear test context averaged across the three minutes of context exposure prior to the initial tone (related tone test data presented in FIG. 1I). No significant generalized freezing to the test context in either group was observed. FIGS. 8E-F show breakdown of tone fear freezing to each tone (30 s. "during") and each trace interval (20 s, "post"). Freezing in SIS mice persisted into each trace interval (see FIG. 1I for averaged values). FIGS. 8G-L show testing of SIS or GH mice (n=8 mice/condition) in the acoustic startle assay (FIGS. 8G-H) and the flinch-vocalization-jump assay (FIGS. 8I-J) to measure reactivity to noxious stimuli presented at varying intensities. Startle responses to a white noise auditory stimulus were enhanced in SIS animals, even at sound decibel (dB) intensities that were sub-threshold for eliciting startle (FIGS. 8G-H). SIS mice showed flinch responses to footshocks of a lower magnitude (milliamp, mA) compared to GH mice (FIGS. 8I-J). FIGS. 8K-L show the percent of mice that jumped off of the EPM within 5 seconds of initial placement in the center of the maze. EPM open vs. closed-arm time data presented in FIGS. 1P-Q. In FIGS. 8M-P. SIS or GH WT mice (n=8 mice/condition) were tested in the social interaction assay. SIS mice spent significantly less time in the zone containing a novel naïve mouse in a pencil cup (left graph), but showed a shorter latency to initially enter the zone containing the mouse (right graph). Representative heatmaps (right panels) reflecting time spent in each location of the interaction apparatus (color scale of maximum time and minimum time shown on the right) for a GH (top) or SIS (bottom) mouse. For group housed mice, maximum time was observed for locations containing a novel naïve mouse (top right panel, circular markings on the right). For isolated mice, maximum time was observed for locations containing an object (lower left panel, circular markings in bottom third). For isolated mice presented with a novel naïve mouse, minimum time was predominant (lower right panel). Group housed mice presented with an object showed interaction ranging from minimum to intermediate (top left panel). In FIGS. 8Q-R, mice that had been tested in the USS assay (FIG. 1K) were tested in a rat exposure assay. GH mice spent significantly more time in the zone farthest away from the rat compared to the other zones. This preference for the "far" zone was absent in SIS mice.

In FIGS. 8A-R to FIGS. 14A-T, *p<0.05, p<0.01, *p<0.001. Bars without asterisks did not reach significance (p>0.05). ANOVA's, F's, and t values as well as additional statistical information for this and subsequent figures can be found in Table S1. Data are represented as mean±SEM.

In FIGS. 9A-P, Tac2-Cre mice were crossed to Ai6-zsGreen reporter mice (see FIG. 2D, FIG. 2F). Representative coronal sections through dBNSTa, DMH, CeA, and ACC (top to bottom) illustrating Tac2-dependent zsGreen expression in GH (left panels) vs. SIS mice (right panels) are shown in FIG. 9A, FIG. 9B, FIG. 9E, FIG. 9F, FIG. 9I, FIG. 9J, FIG. 9M, and FIG. 9N. Quantification of zsGreen+ cell counts (FIGS. 9C, 9G, 9K, and 9O, left) and average fluorescence (FIGS. 9D, 9J, 9L and 9P, right) are presented for each respective region in FIG. 9C (zsGreen+ cell counts for regions in FIGS. 9A-B). FIGS. 9R-Y show quantification of fold increases in Tac2 (R-U) or Tac1 (V-Y) mRNA that revealed significant increases in Tac2, but not Tac1, following 2 weeks of SIS. Data from the GH vs. 2 week condition are also presented in FIGS. 2H-Q and are included here for comparison purposes. FIGS. 9AA-DD show zsGreen+ cells in the dBNSTa co-labeled with the neuronal marker NeuN, the glial marker nuclear factor I-A (NFIA) and the oligodendrocyte marker proteolipid protein (PLP) (top to bottom). Coronal sections and percentage of zsGree+ cells that are double labeled with each respective marker in GH (left) as compared to SIS mice (right) (n=2-4 mice/condition; 3-4 sections/mouse). Up-regulation of Tac2/zsGreen occurred preferentially in neuronal cells. For all panels shown in FIG. 9AA, fluorescent staining of double labeled cells was representative of the quantitations shown in FIGS. 9BB-DD. FIG. 9DD quantitates PLP and zsGreen double staining shown in group housed (GH) and social isolation stress (SIS) mice (See FIG. 9AA, bottom row of panels). The percentage of double labeled cells was similar for isolated and group housed mice for each marker analyzed, with the greatest percentage of double labeling seen with NeuN and relatively lower incidences of double labeling for NFIA and zsGreen(Tac2) and PLP and zsGreen (Tac2).

FIG. 10A shows the general behavioral protocol for results shown in FIGS. 10B-G. FIGS. 10B-C show the number of tail rattles produced during the looming disk assay (see FIG. 3D for looming data). SIS-induced tail rattles were attenuated by osanetant. FIGS. 10D-E show the effects of acutely administered, systemic osanetant on social interaction (n=6 mice/condition). Osanetant attenuated SIS-induced reduction in time spent in the social zone. FIGS. 10F-G show the effects of osanetant on the acoustic startle assay (n=8 mice/condition). Osanetant attenuated SIS-induced increased startle responses. FIG. 10H shows the experimental protocol to test whether osanetant also blocked aggression produced by 2 weeks of sexual experience (2 weeks of continuous co-habitation with a female, no isolation; results shown in FIGS. 10I-J). In contrast to the effect of osanetant to attenuate SIS-induced aggression, it had no effect to attenuate sexual experience-induced aggression (FIGS. 10I-J).

FIGS. 11A-C show representative sagittal sections illustrating Nk3R expression in the indicated regions (Mouse Brain Atlas, Allen Institute for Brain Science; Exp. 80342167; accessible on the world wide web at mouse.brain-map.org/experiment/show/80342167).

FIG. 11D shows that the latency to orient to the looming stimulus was reduced in SIS mice that had osanetant microinfused into DMH (related to FIG. 4J). FIGS. 11E-G show reactivity to the footshock in SIS mice with osanetant microinfused into the indicated region. Only CeA osanetant blocked SIS-enhanced shock reactivity. Data are related to FIGS. 4F, 4K, and 4P. FIGS. 11H-K show the effect of osanetant microinfusions into the ACC or striatum on freezing behavior in the looming assay. No significant effects were observed.

FIGS. 12A-C show representative coronal sections of Cre-dependent hM4DREADD-mCherry viral expression in indicated regions of Tac2-Cre mice. mCherry fluorescent staining was greatest in dBNSTa, followed by CeA that showed a cluster of strong staining in the center and more isolated staining in the periphery of the indicated region. Less mCherry staining was seen in DMH as compared to dBNSTa and CeA, with isolated rather than clustered staining appearing throughout. FIGS. 12D-F show that hM4DREADD-driven chemogenetic silencing of Tac2+ neurons in CeA (FIG. 12F), but not dBNST (FIG. 12D) or DMH (FIG. 12E), attenuated SIS-enhanced shock reactivity. Data are related to FIG. 5F, FIG. 5K, and FIG. 5P. FIG. 12G shows results obtained in tone fear tests for SIS mice injected with AAV2-EF1a-DIO-hM4D-mCherry or AAV2-EF1a-DIO-mCherry control virus in the dBNSTa (n=6-7 mice per condition). CNO administered to hM4DREADD mice attenuated post-tone persistent freezing (see also FIG. 5F), while CNO administered to control mCherry virus-expressing mice produced no significant effects in comparison to vehicle-treated animals.

FIGS. 13A-C show shRNAi-mediated knockdown of Tac2 in CeA (FIG. 13C), but not dBNST (FIG. 13A) or DMH (FIG. 13B), attenuated SIS-enhanced shock reactivity. Data are related to FIG. 6F, FIG. 6K, and FIG. 6P.

Figures 13A, 13B, 13C:
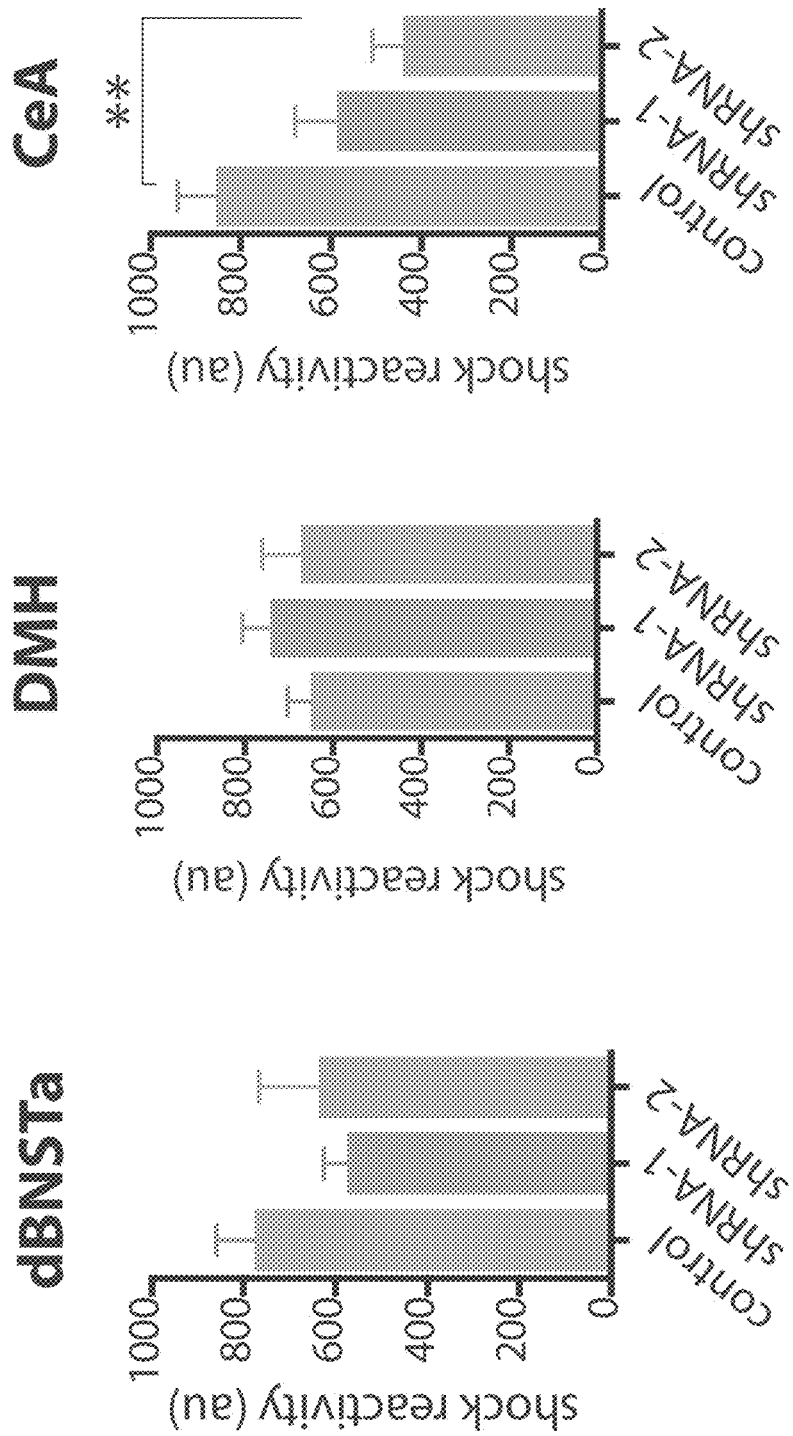
Figure 13D:
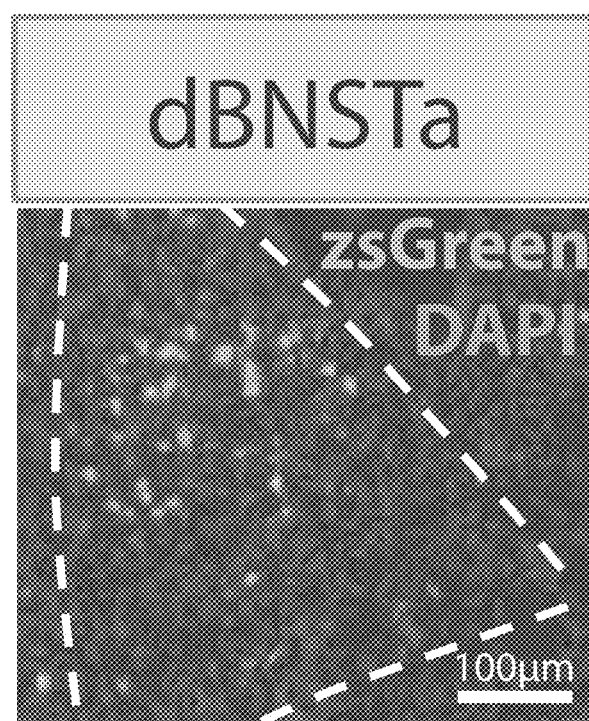
FIG. 13D, FIG. 13F, and FIG. 13H show representative coronal sections of shRNA-2-zsGreen viral expression in indicated regions of WT mice. zsGreen viral expression was seen in dBNSTa, DMH, and CeA as indicated by the presence of fluorescence in each section representative of quantitations shown in FIG. 13E (dBNSTa; corresponding to the region in FIG. 13D), FIG. 13G (DMH; corresponding to the region in FIG. 13E).
Figure 13E:
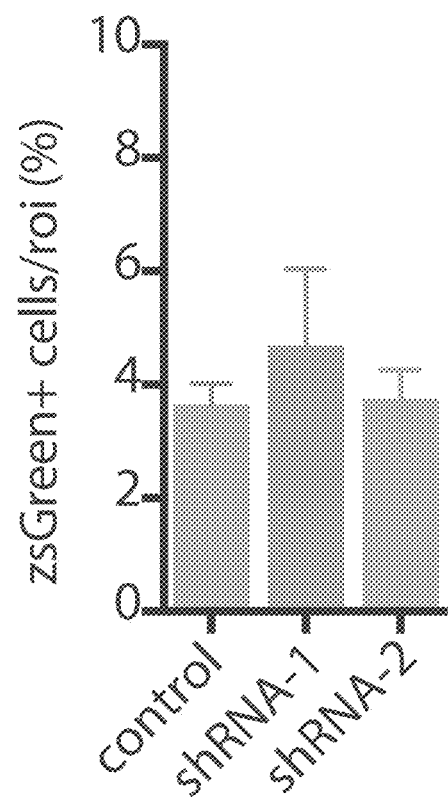
Figure 13F:
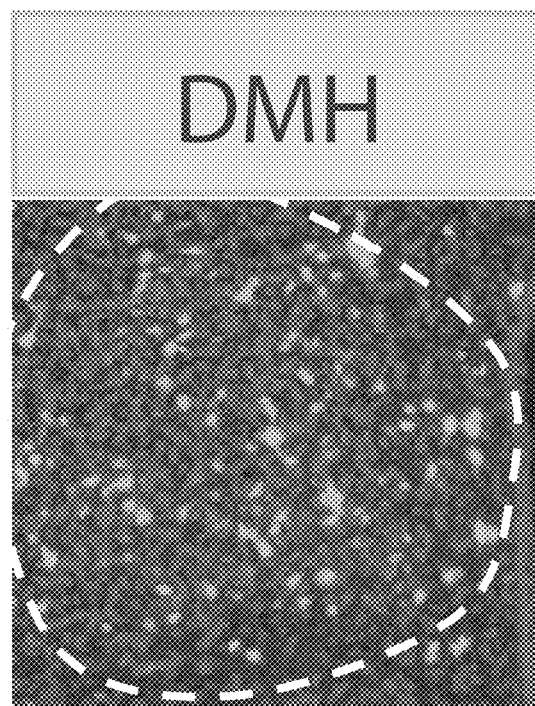
Figure 13G:
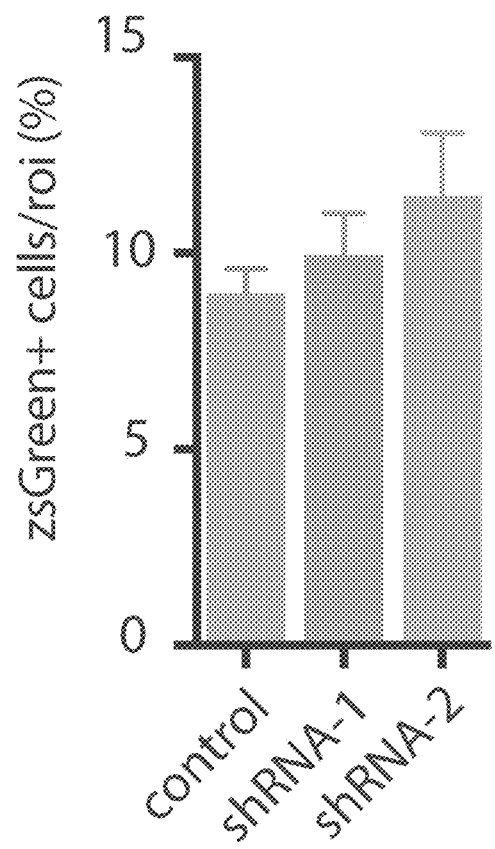
Figure 13H:
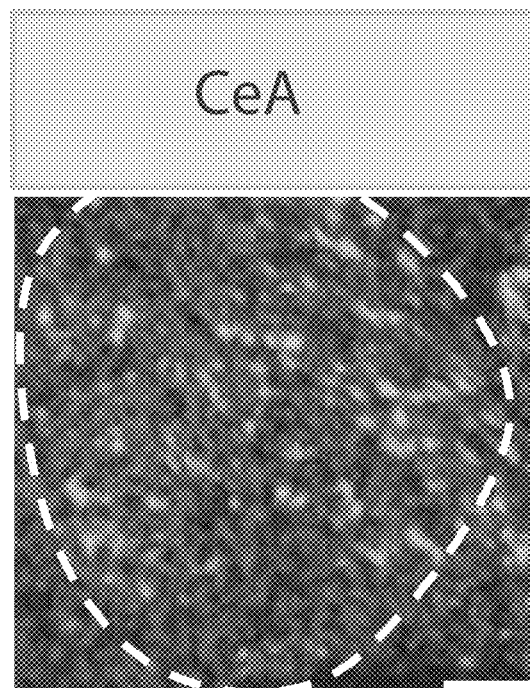
Figure 13I:
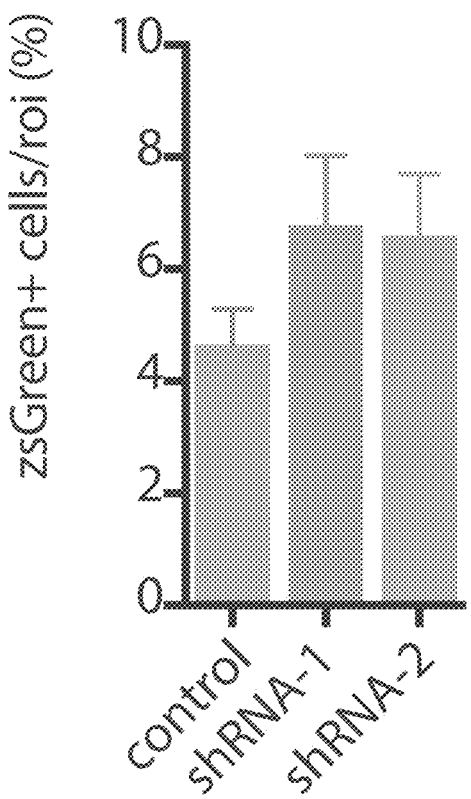
FIG. 13I (CeA; corresponding to the region in FIG. 13I). Lack of any significant difference in the number of zsGree+ cells between Tac2 shRNA virus-injected vs control (luciferase shRNA) virus-injected mice suggests that cell death is not the cause of the Tac2 shRNA phenotypes (FIG. 13E, FIG. 13G, FIG. 13I).
Figures 13J, 13K, 13L, 13M, 13N, 13O:
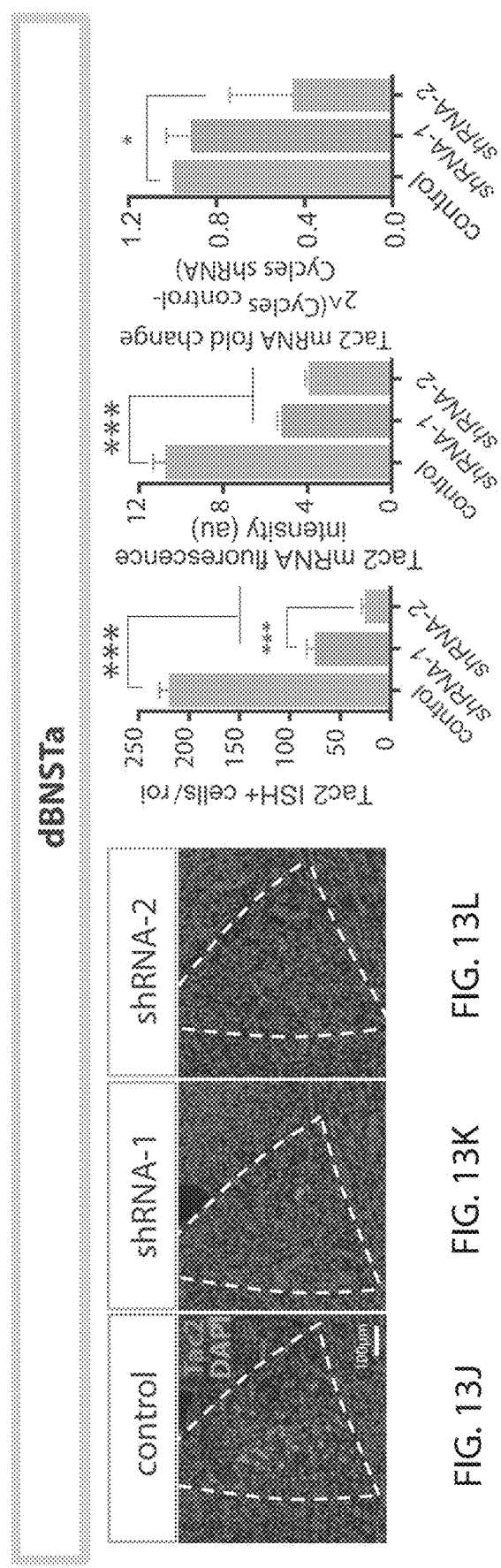
FIGS. 13J-AA show the efficacy of Tac2 shRNAs. Following behavior testing, brain sections and tissue taken from shRNA mice were processed for Tac2 mRNA using FISH or qRT-PCR to confirm knockdown of Tac2. Representative coronal images, Tac2 mRNA cell counts and intensity, and fold changes in Tac2 mRNA were performed for all animals. Significant decreases in Tac2 mRNA were observed in dBNSTa (FIGS. 13J-O). DMH (FIGS. 13P-U), and CeA (FIGS. 13V-AA) (n=6-7 mice per condition; 4-11 sections/mouse). Note that shRNA-2 produces a stronger knockdown than shRNA-1 in many cases. Dashed white outlines indicate regions within which quantifications were made. The quantitations made in FIG. 13D refer to the regions depicted in FIG. 13E. The quantitations made in FIG. 13F refer to the regions depicted in FIG. 13G. The quantitations made in FIG. 13H refer to the regions depicted in FIG. 13I. The quantitations made in FIGS. 13M-O (dBNSTa) refer to the regions depicted in FIGS. 13J-L. The quantitations made in FIGS. 13S-U (DMH) refer to the regions depicted in FIGS. 13P-R. The quantitations made in FIGS. 13Y-AA (CeA) refer to the regions depicted in FIGS. 13V-X.
Figures 13P, 13Q, 13R, 13S, 13T, 13U:
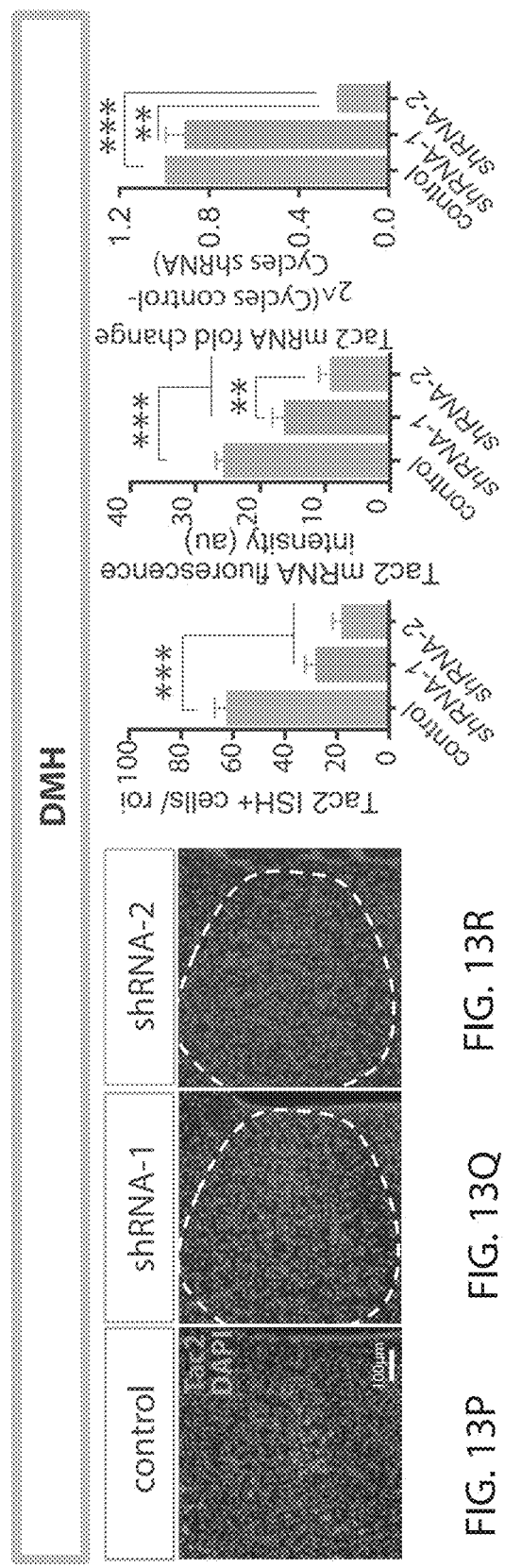
Figures 13A, 13V, 13W, 13X, 13Y, 13Z:
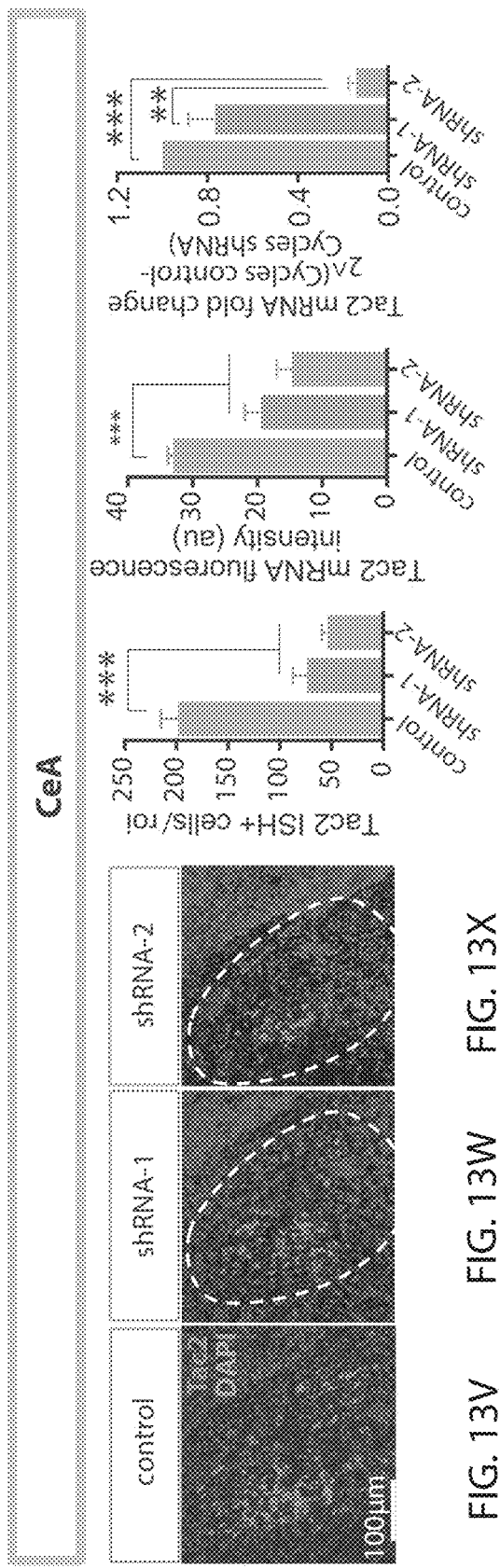
FIGS. 13A-AA show that local Tac2 knockdown attenuates the effects of SIS in some embodiments.

For control sections shown in FIG. 13J and FIG. 13P, fluorescence indicating Tac2 mRNA was seen. This Tac2-identifying fluorescence was reduced in the presence of shRNA-1 or shRNA-2, with few fluorescent cells remaining visible for dBNSTa (FIGS. 13K-L) and DMH (FIGS. 13Q-R). In CeA sections, fluorescence identifying Tac2 mRNA appeared reduced in the presence of shRNA-1 and shRNA-2 relative to control (FIG. 13V-X).

Figure 14P:
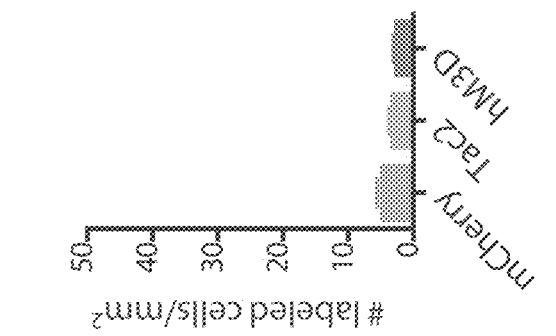
Figures 14M, 14N, 14O:
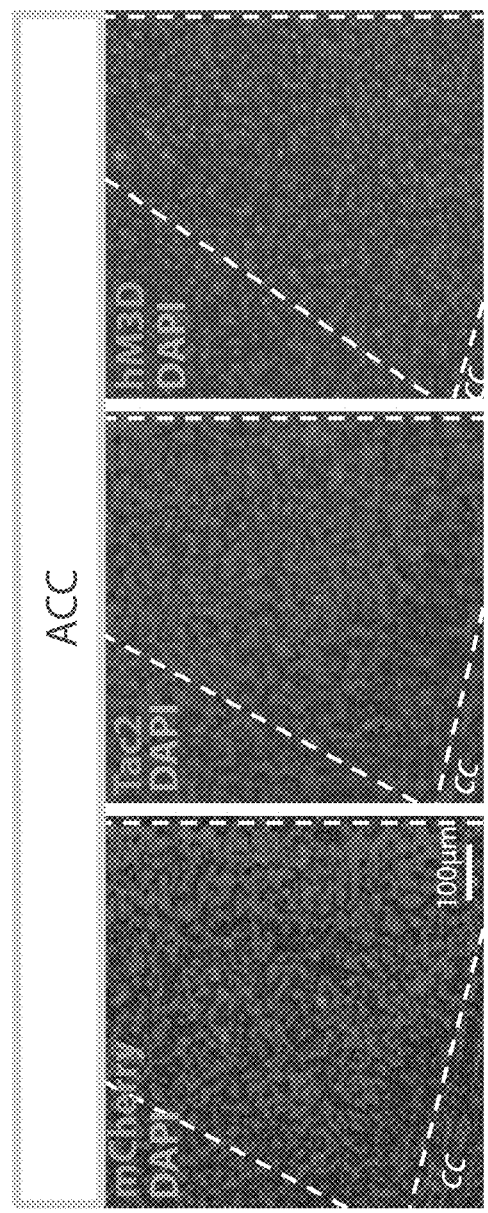
Figures 14Q, 14R, 14S:
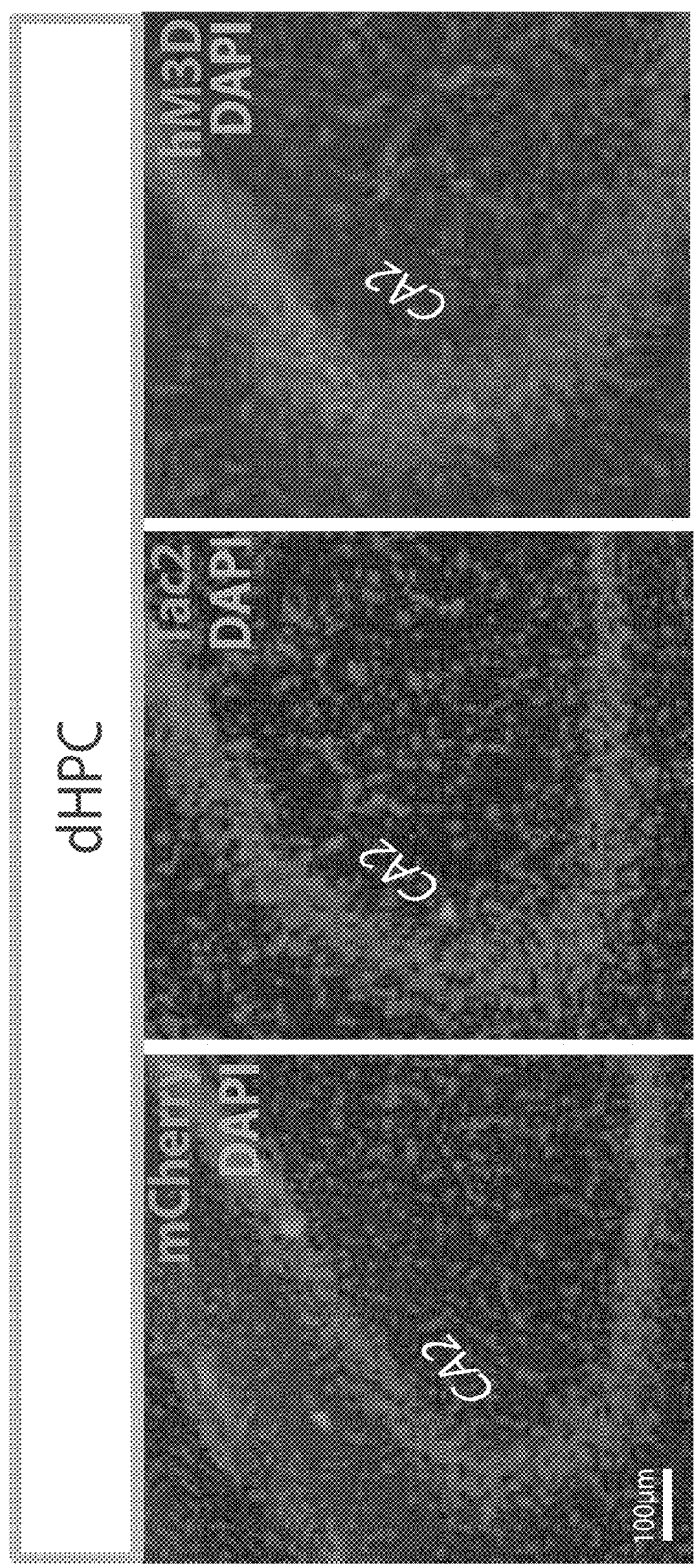
Figure 14T:
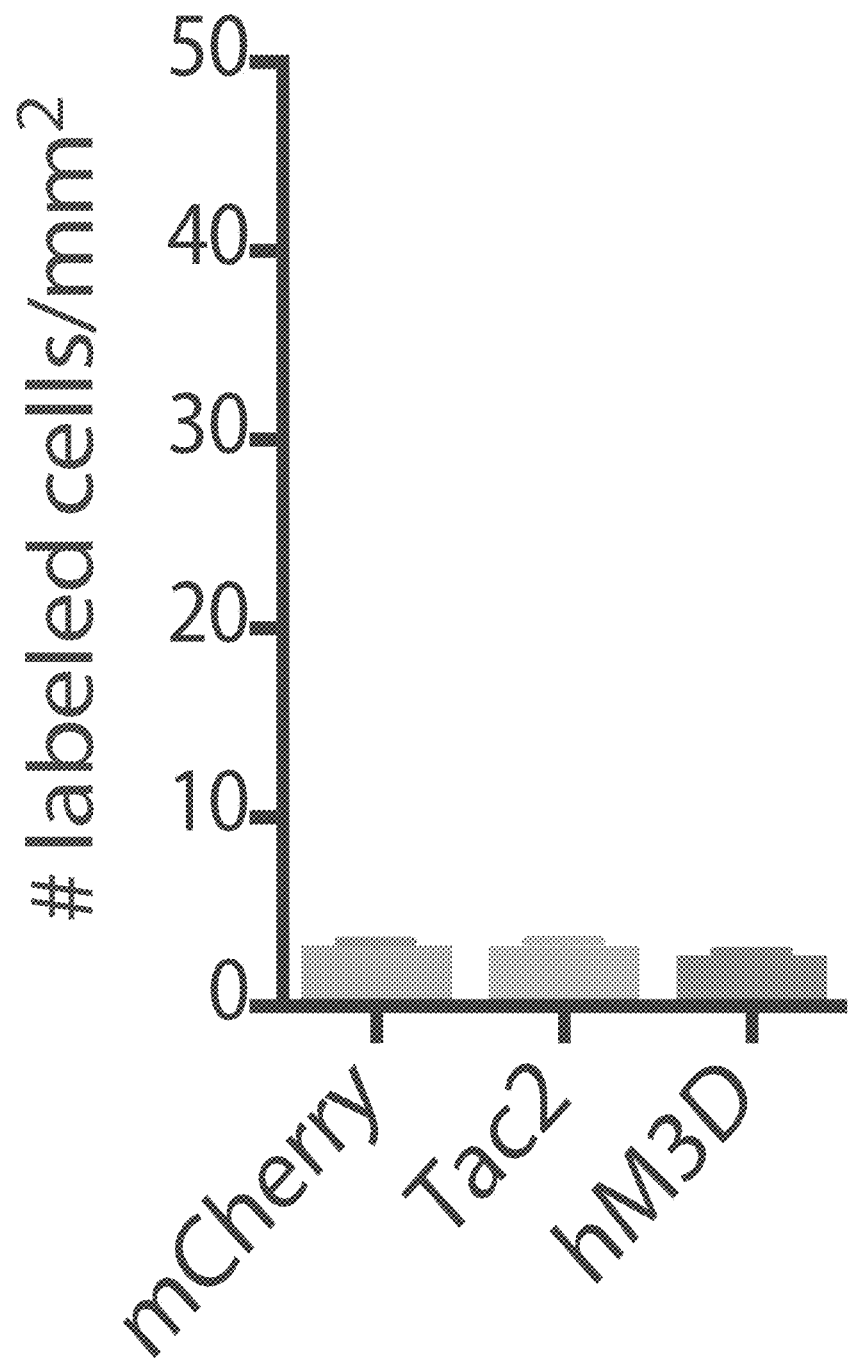

FIGS. 14A-T show Cre-dependent CNS expression from intravenous administration of AAV-PHP.B encoding GOF effectors in some embodiments. FIGS. 14A-C. FIGS. 14E-G, FIGS. 14I-K, FIGS. 14M-O, and FIGS. 14Q-S show representative coronal sections to illustrate expression of the control virus mCherry (left panels), Tac2 cDNA-mCherry virus (center panels), or hM3DREADD-mCherry virus (right panels) in the indicated regions of GH mice injected intravenously with the viruses. Quantification of the number of cells expressing each virus per mm² is presented for each region as follows: FIG. 14D (for regions shown in FIGS. 14A-C), FIG. 14H (for regions shown in FIGS. 14E-G), FIG. 14L (for regions shown in FIGS. 14I-L, FIG. 14P (for regions shown in FIGS. 14M-O), and FIG. 14T (for regions shown in FIGS. 14Q-S). Numbers of mCherry+ cells are low in ACC and dHPC because Tac2-Cre expression is low in these regions in GH mice. "cc", corpus callosum. In sections of dBNSTa (FIGS. 14A-C). DMH (FIGS. 14E-G), and CeA (FIGS. 14I-K), comparable mCherry staining was seen for control virus mCherry (FIGS. 14A, E and I), Tac2 cDNA-mCherry virus (FIGS. 14 B, F, and J), or hM3DREADD-mCherry virus (FIGS. 14C. G, and K) as indicated by the presence of fluorescence. Fluorescence for mCherry (FIGS. 14M and 14Q), Tac2 (FIGS. 14N and 14R) and hM3DREADD-mCherry (FIGS. 14O and 14S) was low to absent in ACC (FIGS. 14M-O) and dHPC sections (FIGS. 14Q-S).

Figure 15A:
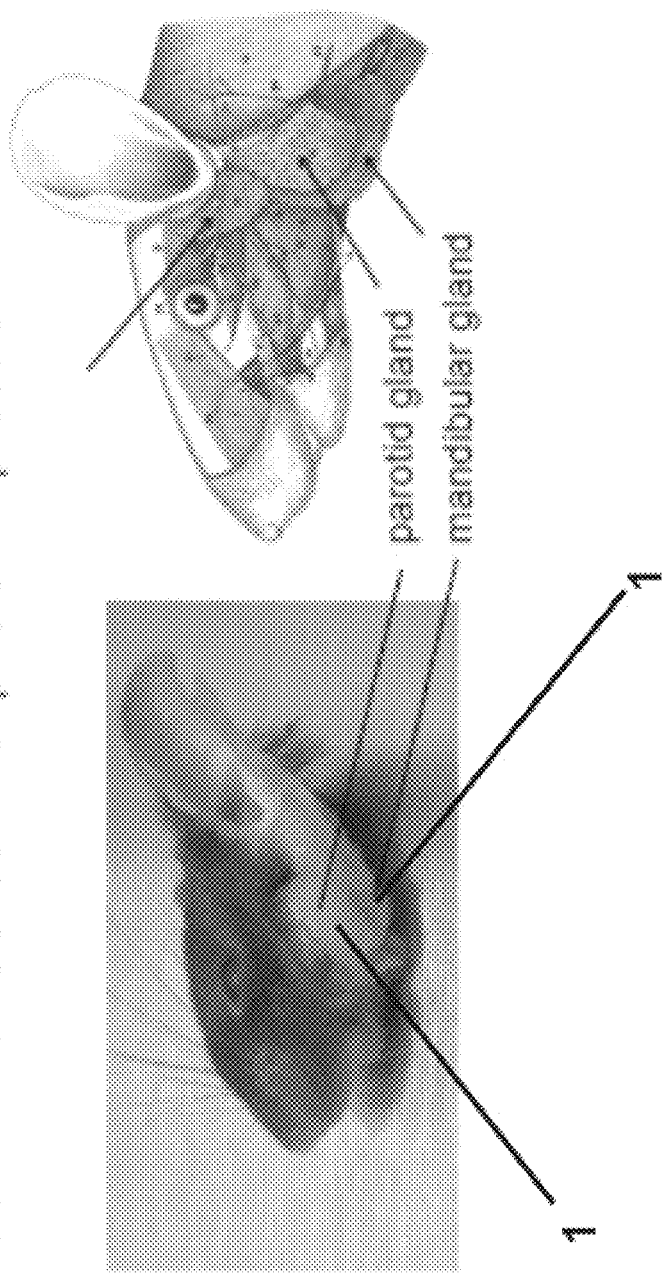
Figure 15B:
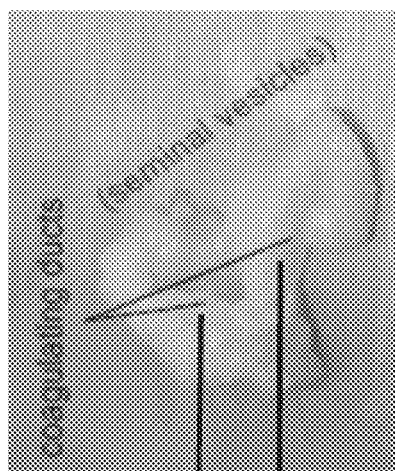
Figure 15C:
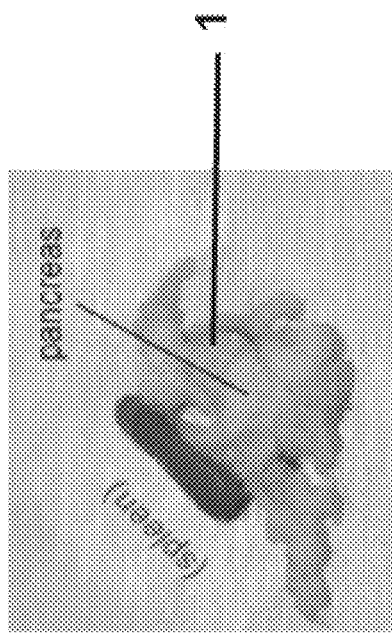
Figure 15D:
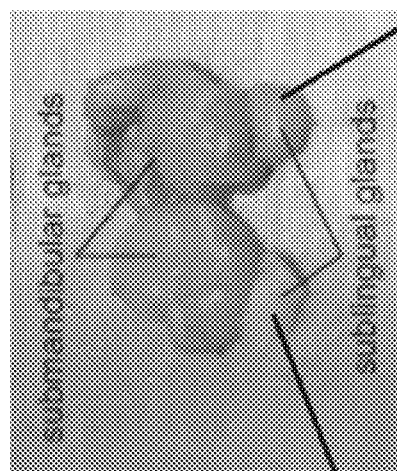
Figure 15E:
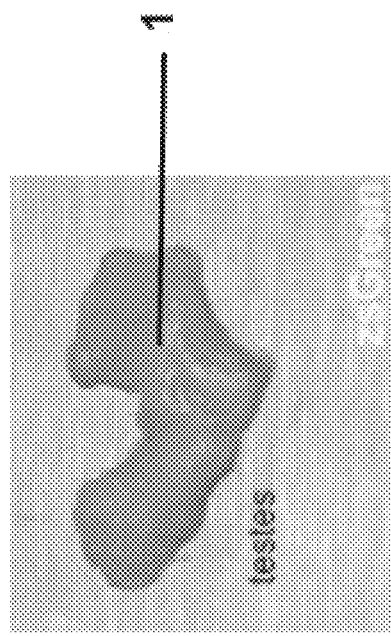

FIGS. 15A-E are a series of images Tac2-IRES2-Cre Ai6-zsGreen mouse organs in some embodiments. zsGreen staining 1 is shown. For reference, FIG. 15A depicts a schematic diagram of the parotid gland and the mandibular gland, as well as an image of zsGreen staining 1 in the Tac2-IRES2-Cre Ai6-zsGreen mouse, indicating that the parotid gland and the mandibular gland had zsGreen staining. Tac2 staining was also observed in the coagulating ducts (FIG. 15B), pancreas (FIG. 15C), sublingual glands (FIG. 15D) and testes (FIG. 15E).

DETAILED DESCRIPTION

Social isolation stress results from an absence of social contact, and can have profound, long-lasting effects on both physical and mental health. It is observed herein that symptoms of social isolation stress are ameliorated by the administration of an antagonist of a neurokinin receptor, for example neurokinin 3 receptor (NK3R). While antagonists of NK3R were initially developed for treatment of schizophrenia and major depressive disorder, efficacy for treatment of treatment of schizophrenia and major depressive disorder was not observed, and a number of these antagonists of NK3R were abandoned. However, these antagonists of NK3R were safe and well-tolerated. It is observed herein that, in accordance with methods of some embodiments herein, antagonists of NK3R are effective in ameliorating, inhibiting, treating, delaying the onset of, and preventing social isolation stress or symptoms thereof. In some embodiments, a subject in need had at least one disorder that would be exacerbated or aggravated by social isolation stress (for example, aggression, cancer, major depressive disorder, dysthymic disorder, social phobia, generalized anxiety disorder, alcohol abuse and dependence, drug abuse, nicotine dependence, atherosclerosis, coronary heart disease, ischemic stroke, cognitive impairment, Alzheimer's disease, agoraphobia, isolated post-traumatic stress disorder (PTSD), bereavement, grieving in isolation, and single member living schizophrenia, or two or more of the listed items. It is contemplated that by ameliorating, treating, inhibiting, preventing, or reducing the likelihood of the social isolation stress, there can also be amelioration, treatment, inhibition, prevention, or reduction in likelihood of the disorder that would be exacerbated by social isolation stress. In some embodiments, a subject in need had at least one disorder that would be exacerbated or aggravated by social isolation stress (for example, aggression, cancer, major depressive disorder, dysthymic disorder, social phobia, generalized anxiety disorder, alcohol abuse and dependence, drug abuse, nicotine dependence, atherosclerosis, coronary heart disease, ischemic stroke, cognitive impairment, Alzheimer's disease, or two or more of the listed items). In some embodiments, a subject in need had at least one disorder that would be exacerbated or aggravated by social isolation stress selected from the group consisting of cancer, major depressive disorder, dysthymic disorder, social phobia, generalized anxiety disorder, alcohol abuse and dependence, drug abuse, nicotine dependence, atherosclerosis, coronary heart disease, ischemic stroke, Alzheimer's disease, or two or more of the listed items.

Social Isolation Stress

As used herein "social isolation stress" and variations of this root term has its customary and ordinary meaning as would be understood by one of ordinary skill in the art in view of this disclosure. It refers to stress that results from an absence of social interaction. The absence of social interaction can be for a matter of days, for example at least about 2 days, such as at least 2, 3, 4, 5, 6, 7 days, or 1, 2, 3, 4, or 5 weeks. It is noted that social isolation stress may occur even if some trivial social interactions take place. Accordingly, while social isolation stress may result from actual physical separation from other individuals, social isolation stress may also result from a lack of meaningful social contacts with other individuals, for example, grieving in isolation (for example, following the loss of a spouse), feelings of isolation as an adolescent, or residing as a patient in a skilled nursing facility. Symptoms of social isolation stress can include, for example, aggression (e.g., higher than a baseline level of aggression), persistent responses to threats, persistent freezing in response to innate and conditioned fear-evoking stimuli, enhanced reactivity to aversive stimuli, and/or reduced social interactions. In some embodiments, social isolation stress comprises, consists essentially of, or consists of aggression and/or persistent responses to threats.

Social isolation stress can exacerbate other disorders. Social isolation stress has been shown to exacerbate cancer (Williams et al. (2009) "A model of gene-environment interaction reveals altered mammary gland gene expression and increased tumor growth following social isolation" Cancer Prev 2: 850-861, which is incorporated by reference in its entirety herein); major depressive disorder, dysthymic disorder, social phobia, and generalized anxiety disorder, alcohol abuse and dependence, drug abuse, and nicotine dependence (Chou et al. (2011) "The association between social isolation and DSM-IV mood, anxiety, and substance use disorders: wave 2 of the National Epidemiologic Survey on Alcohol and Related Conditions" J Clin Psychiatry. 72: 1468-76, which is incorporated by reference in its entirety herein), atherosclerosis and coronary heart disease, ischemic stroke, cognitive impairment, and Alzheimer's disease (Friedler et al. (2015) "One is the Deadliest Number: The Detrimental Effects of Social Isolation on Cerebrovascular Diseases and Cognition" Acta Neuropathol. 129: 493-509, which is incorporated by reference in its entirety herein). Exacerbation of Alzheimer's disease by social isolation stress is also reported by Huang et al. (2015) "Isolation Housing Exacerbates Alzheimer's Disease-Like Pathophysiology in Aged APP/PS 1 Mice: International Journal of Neuropsychopharmacology, doi:10.1093/ijnp/pyu116 1-10.

Accordingly, in the methods and uses of some embodiments, a subject in need of treatment has social isolation stress or is at risk of social isolation stress, and further has a disorder in which social isolation causes or is known to cause exacerbation of the disorder. In the methods and uses of some embodiments, a subject in need of treatment has social isolation stress or is at risk of social isolation stress, and further has a disorder in which social isolation is known to cause exacerbation of the disorder. In some embodiments, a disorder that can be exacerbated by social isolation stress includes, for example, aggression, cancer, major depressive disorder, dysthymic disorder, social phobia, generalized anxiety disorder, alcohol abuse and dependence, drug abuse, nicotine dependence, atherosclerosis, coronary heart disease, ischemic stroke, cognitive impairment, Alzheimer's disease, agoraphobia, isolated post-traumatic stress disorder (PTSD), bereavement, grieving in isolation, or single member living schizophrenia, or two or more of the listed items. In some embodiments, a disorder that can be exacerbated by social isolation stress includes, for example, aggression, cancer, major depressive disorder, dysthymic disorder, social phobia, generalized anxiety disorder, alcohol abuse and dependence, drug abuse, nicotine dependence, atherosclerosis, coronary heart disease, ischemic stroke, cognitive impairment, or Alzheimer's disease, or two or more of the listed items It is also contemplated that consequences of residence in a skilled nursing facility as a patient can be exacerbated by social isolation. In the methods and uses of some embodiments, a subject in need of treatment has social isolation stress or is at risk of social isolation stress, and further suffers from or is at risk of at least one of aggression, depression, anxiety, agoraphobia, isolated PTSD, bereavement, grieving in isolation, or single member living schizophrenia, and/or is a patient in a skilled nursing facility. In the methods and uses of some embodiments, a subject in need of treatment has social isolation stress or is at risk of social isolation stress, and further suffers from or is at risk of at least one of aggression, depression, anxiety, agoraphobia, bereavement, grieving in isolation, or single member living schizophrenia, and/or is a patient in a skilled nursing facility. In the methods and uses of some embodiments, a subject in need of treatment has social isolation stress or is at risk of social isolation stress, and further suffers from or is at risk of at least one of aggression, depression, anxiety, agoraphobia, bereavement, grieving in isolation, and/or single member living schizophrenia. In the methods and uses of some embodiments, a subject in need of treatment has social isolation stress or is at risk of social isolation stress, and further suffers from at least one of aggression, depression, anxiety, agoraphobia, bereavement, and/or grieving in isolation, and/or is a patient in a skilled nursing facility. In the methods and uses of some embodiments, a subject in need of treatment has social isolation stress or is at risk of social isolation stress, and further suffers from at least one of aggression, depression, agoraphobia, anxiety, bereavement, and/or grieving in isolation. In the methods and uses of some embodiments, a subject in need of treatment has social isolation stress or is at risk of social isolation stress, and further suffers from at least one depression, anxiety, agoraphobia, bereavement, and/or grieving in isolation, and/or is a patient in a skilled nursing facility. In the methods and uses of some embodiments, a subject in need of treatment has social isolation stress or is at risk of social isolation stress, and further suffers from at least one of depression, anxiety, agoraphobia, bereavement, bereavement, and/or grieving in isolation. In the methods and uses of some embodiments, a subject in need of treatment has social isolation stress or is at risk of social isolation stress, and further suffers from at least one of depression, anxiety, or agoraphobia. In some embodiments, the subject in need of treatment does not suffer from PTSD.

Neurokinins and Neurokinin Receptors

Neuropeptides such as neurokinins are a class of class of peptide neuromodulators. Neurokinin peptides are encoded by the tachykinins genes. Examples of neurokinins include neurokinin A, neurokinin B, neuropeptide K, neuropeptide gamma, and substance P. In humans, there are three canonical classes of neurokinin receptor, neurokinin 1 receptor (NK1R), neurokinin 2 receptor (NK2R), and neurokinin 3 receptor (NK3R). Neurokinins are the endogenous ligands of neurokinin receptors.

The human TAC1 gene (annotated as GenBank Accession No: CR541730.1) encodes several tachykinins as via alternate splicing and/or post-translational processing, including, neurokinin A, neuropeptide K, and substance P. As murine experiments are also described herein, it is noted that murine Tad is an ortholog of human TAC 1. As such, wherever murine Tac1 is mentioned herein, human TAC 1 (and tachykinins encoded by TAC1) are expressly contemplated. TAC1 encodes protachykinin-1, which can be cleaved into several different neurokinins. An example human TAC1-encoded protachykinin-1 neuropeptide sequence (which can be cleaved into Substance P, Neurokinin A, or Neuropepide K) is (SEQ ID NO: 1; MKILVALAVFFLVSTQLFAEEI-GANDDLNYWSDWYDSDQIKEELPEPFEHLLQRIARR PKPQQFFGLMGKRDADSSIEKQVALLKALYGHGQ-ISHKRHKTDSFVGLMGKRALNS VAYERSAMQNY-ERRR). Upon cleavage of protachykinin-1, Substance P can comprise, consist essentially of, or consist of residues 58-68 of SEQ ID NO: 1. Upon cleavage of protachykinin-1, Neuropeptide K can comprise, consist essentially of, or consist of residues 72-107 of SEQ ID NO: 1. Upon cleavage of protachykinin-1, Neurokinin A can comprise, consist essentially of, or consist of residues 98-107 of SEQ ID NO: 1. It is noted that residues 1-19 of SEQ ID NO: 1 represent a signal peptide.

The human TAC3 gene (annotated as annotated as GenBank Accession No: CR457193.1) encodes neurokinin B. As murine experiments are also described herein, it is noted that murine Tac2 is an ortholog of human TAC3. As such, wherever murine Tac2 is mentioned herein, human TAC3 (and tachykinins encoded by TAC3) are expressly contemplated. An example human TAC3-encoded neurokinin B neuropeptide sequence is (SEQ ID NO: 2; MRIMLLF-TAILAFSLAQSFGAVCKEPQEEVVPGGGRSKRDPD-LYQL LQRLFKSHSSLEGLLKALSQASTDPKESTS-PEKRDMHDFFVGLMGKRSVQPDSPTDV NQENVPSFGILKYPPRAD). It is noted that residues 1-16 of SEQ ID NO: 2 represent a signal peptide.

Under physiological conditions, NK1R has a greater affinity for substance P than other tachykinins. Under physiological conditions, NK2R has a greater affinity for neurokinin A than other tachykinins. Under physiological conditions, NK3R has a greater affinity for neurokinin B than other tachykinins. Accordingly, it will be understood that a NKR3 antagonist may compete with Neurokinin B for binding to NK3R.

When a "neurokinin" is mentioned herein, it will be appreciated that a neurokinin is encoded by a tachykinin gene, and typically binds to a neurokinin receptor. It will be understood that references to neurokinin genes and nucleic acids refer to those genes or nucleic acids that encode neurokinins, including a corresponding tachykinin gene, as appropriate for the context. For example, a "neurokinin nucleic acid" will be understood to refer to a nucleic acid that encodes a neurokinin. For conciseness, the term "tachykinin" may be used herein to refer to a tachykinin gene, or a tachykinin gene product (such as a neurokinin), and it will be understood that the corresponding neurokinin (or neurokinins) and their corresponding receptor are contemplated as is appropriate for the context. For example, if human neurokinin B is mentioned, it will be understood to be encoded by the TAC3 gene, and refer to a higher affinity ligand of NK3R. For example, if murine tac2 or human TAC3 is mentioned, it will be understood to encode neurokinin B, which is the higher affinity ligand for NK3R. Similarly, a "neuropeptide nucleic acid" will be understood to refer to a nucleic acid that encodes a neuropeptide.

Neurokinin Receptor Antagonists

As used herein "neurokinin receptor antagonists" and variations of this root term has its customary and ordinary meaning as would be understood by one of ordinary skill in the art in view of this disclosure. It refers to a compound that has an inhibitory effect on a neurokinin receptor as described herein.

As used herein "NKR3 antagonist" and variations of this root term has its customary and ordinary meaning as would be understood by one of ordinary skill in the art in view of this disclosure. It will be appreciated that a class of NKR3 antagonists has been studied, and several NKR3 antagonists have been shown to be safe and well-tolerated in clinical trials, for example, osanetant and talnetant. Examples of NKR3 antagonists are described in U.S. Pat. Nos. 5,942,523, 7,410,970, 7,435,736, 7,544,694, 7,560,549, 8,138,334, and PCT Pub. Nos. WO 95/32948; WO 2006/130080, WO 2006/050991, WO2006/050992, WO 2008/131779, and WO 2009/130240, each of which is incorporated herein by reference in its entirety.

Examples of NKR3 antagonists are shown below in Table 1. In some embodiments, NKR3 antagonist comprises, consists essentially of, or consists of a compound shown in Table 1 or its salt. In some embodiments, a NKR3 antagonist comprises, consists essentially of, or consists of osanetant, talnetant, fezolinetant, pavinetant, SB-222,200, SB-218,795, a salt of any of the listed items, or a combination of two or more of the listed items. In some embodiments, a NKR3 antagonist comprises, consists essentially of, or consists of fezolinetant, pavinetant, SB-222,200, SB-218,795, a salt of any of the listed items, or a combination of two or more of the listed items. In some embodiments, a NKR3 antagonist comprises, consists essentially of, or consists of talnetant, fezolinetant, pavinetant, SB-222,200, SB-218,795, a salt of any of the listed items, or a combination of two or more of the listed items. In some embodiments, a NKR3 antagonist comprises, consists essentially of, or consists of osanetant, fezolinetant, pavinetant, SB-222,200, SB-218,795, a salt of any of the listed items, or a combination of two or more of the listed items. In some embodiments, the NK3R antagonist does not comprise a peptide.

TABLE 1

| Name | IUPAC name | Synonyms | Formula |
|---|---|---|---|
| Ostenant | N-(1-{3-[(3R)-1-benzoyl-3-(3,4-dichlorophenyl)piperidin-3-yl]propyl}-4-phenylpiperidin-4-yl)-N-methylacetamide | | |
| Talnetant | 3-hydroxy-2-phenyl-N-(1-phenylpropyl)quinoline-4-carboxamide | SB-223,412 | |
| Fezolinetant | (4-fluorophenyl)-[(8R)-8-methyl-3-(3-methyl-1,2,4-thiadiazol-5-yl)-6,8-dihydro-5H-[1,2,4]triazolo[4,3-a]pyrazin-7-yl]methanone | ESN-364 | |
| Pavinetant | 3-(methanesulfonamido)-2-phenyl-N-[(1S)-1-phenylpropyl]quinoline-4-carboxamide | MLE-4901; AZD-4901; AZ-12472520; AZD-2624 | |

TABLE 1-continued

| Name | IUPAC name | Synonyms | Formula |
|---|---|---|---|
| SB 222200 | (S)-3-Methyl-2-phenyl-N-(1-phenylpropyl)-4-quinolinecarboxamide | | |
| SB-218795 | (−)-(R)-N-(α-Methoxycarbonylbenzyl)-2-phenylquinoline-4-carboxamide | | |

In some embodiments, the NK3R antagonist is a compound of the formula:

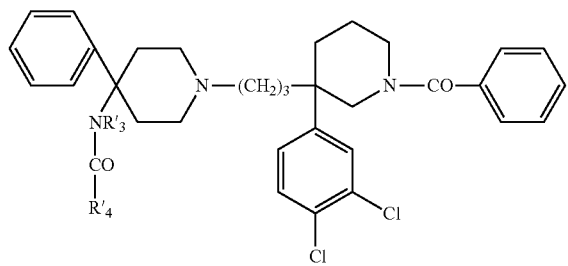

(I)

in which: R'3 represents a hydrogen or methyl; R'4 represents a (C4-C7)alkyl, a phenyl, a benzyl, a pyridyl or a (C3-C7)cycloalkyl which is unsubstituted or substituted by one or more methyls; or R'3 and R'4 together represent a —(CH2)n-group (and n is 3 or 4), as well as their salts.

In some embodiments, the NK3R antagonist is a compound of the formula:

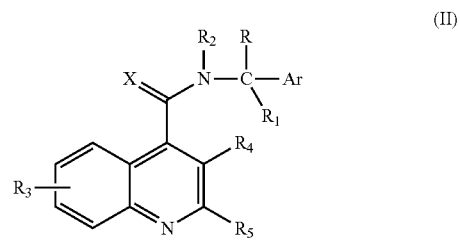

(II)

in which: Ar is an optionally substituted phenyl, naphthyl or $C_{5-7}$ cycloalkdienyl group, or an optionally substituted single or fused ring heterocyclic group, having aromatic character, containing from 5 to 12 ring atoms and comprising up to four heteroatoms in the or each ring selected from S, O, N; R is linear or branched $C_{1-8}$ alkyl, $C_{3-7}$ cycloalkyl, $C_{4-7}$ cycloalkylalkyl, optionally substituted phenyl or phenyl $C_{1-6}$ alkyl, an optionally substituted five-membered heteroaromatic ring comprising up to four heteroatom selected from O and N, hydroxy $C_{1-6}$ alkyl, amino $C_{1-6}$ alkyl, $C_{1-6}$ alkylaminoalkyl, di $C_{1-6}$ alkylaminoalkyl, $C_{1-6}$ acylaminoalkyl, $C_{1-6}$ alkoxyalkyl, $C_{1-6}$ alkylcarbonyl, carboxy, $C_{1-6}$ alkoxyxcarbonyl, $C_{1-6}$ alkoxycarbonyl $C_{1-6}$ alkyl, aminocarbonyl, $C_{1-6}$ alkylaminocarbonyl, di $C_{1-6}$ alkylaminocarbonyl, halogeno $C_{1-6}$ alkyl; or is a group —$(CH_2)_p$— when cyclized onto Ar, where p is 2 or 3. $R_1$ and $R_2$, which may be the same or different, are independently hydrogen or $C_{1-6}$ linear or branched alkyl, or together form a —$(CH_2)_n$— group in which n represents 3, 4, or 5; or $R_1$ together with R forms a group —$(CH_2)_q$—, in which q is 2, 3, 4 or 5. $R_3$ and $R_4$, which may be the same or different, are independently hydrogen, $C_{1-6}$ linear or branched alkyl, $C_{1-6}$ alkenyl, aryl, $C_{1-6}$ alkoxy, hydroxy, halogen, nitro, cyano, carboxy, carboxamido, sulphonamido, $C_{1-6}$ lkoxycarbonyl, trifluoromethyl, acyloxy, phthalimido, amino, mono- and di-$C_{1-6}$ alkylamino, —$O(CH_2)_r$—$NT_2$, in which r is 2, 3, or 4 and T is hydrogen or $C_{1-6}$ alkyl or it forms with the adjacent nitrogen a group

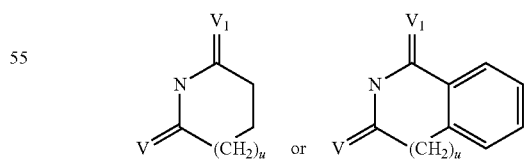

in which V and $V_1$ are independently hydrogen or oxygen and u is 0, 1 or 2; —$O(CH_2)$, —$OW_2$ in which s is 2, 3, or 4 and W is hydrogen or $C_{1-6}$ alkyl; hydroxyalkyl, aminoalkyl, mono- or di-alkylaminoalkyl, acylamino, alkylsulphonylamino, aminoacylamino, mono- or di-alkylaminoacylamino; with up to four $R_3$ substituents being present in the quinoline nucleus; or $R_4$ is a group —$(CH_2)_t$— when cyclized onto $R_5$ as aryl, in which t is 1, 2, or 3; $R_5$ is branched or linear $C_{1-6}$ alkyl, $C_{3-7}$ cycloalkyl, $C_{4-7}$ cycloalkylalkyl, optionally substituted aryl, or an optionally substituted single or fused ring heterocyclic group, having aromatic character, containing from 5 to 12 ring atoms and comprising up to four heteroatoms in the or each ring selected from S, O, N; X is O, S, or N—C.tbd.N. Examples of Ar are phenyl, optionally substituted by hydroxy, halogen, $C_{1-6}$ alkoxy or $C_{1-6}$ alkyl. Examples of halogen are chlorine and fluorine, an example of $C_{1-6}$ alkoxy is methoxy and an example of $C_{1-6}$ alkyl is methyl. Examples of Ar as a heterocyclic group are thienyl and pyridyl. Examples of Ar as a $C_{5-7}$ cycloalkdienyl group is cyclohexadienyl.

Examples of R are as follows: $C_{1-8}$ alkyl: methyl, ethyl, n-propyl, iso-propyl, n-butyl, heptyl; phenyl $C_{1-6}$ alkyl: benzyl; hydroxy $C_{1-6}$ alkyl: —$CH_2OH$, —$CH_2CH_2OH$, CH(Me)OH; amino $C_{1-6}$ alkyl: —$CH_2NH_2$; di $C_{1-6}$ alkylaminoalkyl: —$CH_2NMe_2$; $C_{1-6}$ alkoxylalkyl: $CH_2OMe$; $C_{1-6}$ alkylcarbonyl: COMe; $C_{1-6}$ alkoxycarbonyl: COOMe; $C_{1-6}$ alkoxycarbonyl $C_{1-6}$ alkyl: $CH_2COOMe$; $C_{1-6}$ alkylaminocarbonyl: CONHMe; di $C_{1-6}$ alkylaminocarbonyl: CONMe2, CO(1-pyrrolidinyl); and/or halogen $C_{1-6}$ alkyl: trifluoromethyl; —$(CH_2)_p$— when cyclized onto Ar:

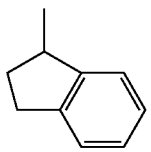

An example of $R_1$ and $R_2$ as $C_{1-6}$ alkyl is methyl. An example of $R_1$ together with R forming a group —$(CH_2)_q$— is spirocyclopentane. Examples of $R_3$ and $R_4$ are methyl, ethyl, n-propyl, n-butyl, methoxy, hydroxy, amino, chlorine, fluorine, bromine, acetyloxy, 2-(dimetylamino)ethoxy, 2-(1-phthaloyl)ethoxy, aminoethoxy, 2-(1-pyrrolidinyl)ethoxy, phthaloyl, dimethylaminopropoxy, dimethylaminoacetylamino, acetylamino, dimethylaminomethyl and phenyl. Examples of $R_5$ are cyclohexyl, phenyl optionally substituted as defined for Ar above; examples of $R_5$ as a heterocyclic group are furyl, thienyl, pyrryl, thiazolyl, benzofuryl and pyridyl.

In some embodiments, the compounds of formula (I) are those in which: Ar is phenyl, optionally substituted by $C_{1-6}$ alkyl or halogen; thienyl or a $C_{5-7}$ cycloalkdienyl group; R is $C_{1-6}$ alkyl, $C_{1-6}$ alkoxycarbonyl, $C_{1-6}$ alkylcarbonyl, hydroxy $C_{1-6}$ alkyl; $R_1$ and $R_2$ are each hydrogen or $C_{1-6}$ alkyl; $R_3$ is hydrogen, hydroxy, halogen, $C_{1-6}$ alkoxy, $C_{1-6}$ alkyl; $R_4$ is hydrogen, $C_{1-6}$ alkyl, $C_{1-6}$ alkoxy, hydroxy, amino, halogen, aminoalkoxy, mono- or di-alkylaminoalkoxy, mono- or di-alkylaminoalkyl, phthaloylalkoxy, mono- or di-alkylaminoacylamino and acylamino; $R_5$ is phenyl, thienyl, furyl, pyrryl and thiazolyl.

In some embodiments, the compounds of formula (I) are those in which: Ar is phenyl, 2-chlorophenyl, 2-thienyl or cyclohexadienyl; R is methyl, ethyl, n-propyl, —COOMe, —COMe; $R_1$ and $R_2$ are each hydrogen or methyl; $R_3$ is hydrogen, methoxy, or hydroxy; $R_4$ is hydrogen, methyl, ethyl, methoxy, hydroxy, amino, chlorine, bromine, dimethylaminoethoxy, 2-(1-phthaloyl)ethoxy, aminoethoxy, 2-(1-pyrrolidinyl)ethoxy, dimethylaminopropoxy, dimethylaminoacetylamino, acetylamino, and dimethylaminomethyl; and $R_5$ is phenyl, 2-thienyl, 2-furyl, 2-pyrryl, 2-thiazolyl and 3-thienyl; and X is oxygen.

Methods of Inhibiting, Ameliorating, Reducing the Severity of, Treating, Reducing the Likelihood of, or Preventing Social Isolation Stress In some embodiments, methods of inhibiting, ameliorating, reducing the severity of, treating, reducing the likelihood of, or preventing social isolation stress or symptoms thereof are described. The method can be performed on a subject in need of inhibiting, ameliorating, reducing the severity of, treating, reducing the likelihood of, or preventing social isolation stress. The method can comprise administering an effective amount of neurokinin receptor antagonist (such as NK3R antagonist) to the subject. The subject can be a human, for example an adult or an adolescent. In some embodiments, the method further comprises identifying the subject as being in need of inhibiting, ameliorating, reducing the severity of, treating, reducing the likelihood of, or preventing social isolation stress or symptoms thereof. In some embodiments, a subject in need of treatment has social isolation stress or is at risk of social isolation stress, and further suffers from at least one of aggression, depression, agoraphobia, isolated PTSD, grieving in isolation, or single member living schizophrenia, and/or is a patient in a skilled nursing facility. In some embodiments, a subject in need of treatment has social isolation stress or is at risk of social isolation stress, and further suffers from at least one of aggression, depression, agoraphobia, grieving in isolation, or single member living schizophrenia, and/or is a patient in a skilled nursing facility. In some embodiments, a subject in need of treatment has social isolation stress or is at risk of social isolation stress, and further suffers from at least one of aggression, cancer, major depressive disorder, dysthymic disorder, social phobia, and generalized anxiety disorder, alcohol abuse and dependence, drug abuse, and nicotine dependence, atherosclerosis and coronary heart disease, ischemic stroke, cognitive impairment, Alzheimer's disease, agoraphobia, isolated post-traumatic stress disorder (PTSD), bereavement, grieving in isolation, single member living schizophrenia, or two or more of the listed items. In some embodiments, a subject in need of treatment has social isolation stress or is at risk of social isolation stress, and further suffers from at least one of aggression, cancer, major depressive disorder, dysthymic disorder, social phobia, and generalized anxiety disorder, alcohol abuse and dependence, drug abuse, nicotine dependence, atherosclerosis, coronary heart disease, ischemic stroke, cognitive impairment, Alzheimer's disease, or two or more of the listed items. In some embodiments, the neurokinin receptor antagonist comprises, consists essentially of, or consists of a NK3R antagonist is selected from the group consisting of: osanetant, talnetant, fezolinetant, pavinetant. SB-222200, and SB-218795. It is noted that wherever a method of inhibiting, ameliorating, reducing the severity of, treating, reducing the likelihood of, or preventing social isolation stress or symptoms thereof comprising administering a neurokinin receptor antagonist (such as NK3R antagonist) antagonist is mentioned herein, the corresponding neurokinin receptor antagonist (such as NK3R antagonist) for use in inhibiting, ameliorating, reducing the severity of, treating, reducing the likelihood of, or preventing social isolation stress or symptoms thereof is also expressly contemplated.

It has been observed herein that levels of neurokinins, such as neurokinin B (or murine Tac2) are elevated in subject in need of social isolation stress treatment using a neurokinin receptor antagonist such as a NK3R antagonist (Example 2). It is contemplated that a subject can be identified in need of inhibiting, ameliorating, reducing the severity of, treating, reducing the likelihood of, or preventing social isolation stress or symptoms thereof based on levels of neurokinin B. Moreover, neurokinins are typically expressed in the central nervous system (CNS), and have a molecular weight that typically prevents their passage to the blood-brain barrier. However, shown in FIGS. 15A-E, it has been observed that neurokinins expressed in response to social isolation stress, for example neurokinin B, are expressed in peripheral organs and tissues such as the parotid gland (FIG. 15A), mandibular gland (FIG. 15A), coagulating ducts (FIG. 15B), pancreas (FIG. 15C), sublingual glands (FIG. 15D) and testes (FIG. 15E). Thus, neurokinins such as neurokinin B are contemplated to be readily accessible in peripheral samples, such as blood, bone marrow, lymphatic fluid, urine, feces, semen, and saliva, without a need to obtain samples from the central nervous system. Accordingly, in methods and uses of some embodiments, peripheral tissue sample is obtained from outside the central nervous system, for example in, such as blood, bone marrow, lymphatic fluid, urine, feces, semen, and saliva, without a need to obtain samples from the central nervous system. A level of neurokinin (such as neurokinin B) can be detected in the sample. The method can further comprise determining the subject to be in need of the neurokinin receptor (such as NK3R) antagonist if the level of neurokinin is greater than a control level. As such, in methods of some embodiments, the neurokinin receptor (such as NK3R) antagonist can be administered to the subject if the level of neurokinin (such as neurokinin B) in the sample is greater than a control level. The control level can be the neurokinin level in a sample of an individual who does not suffer from social isolation stress. In methods of some embodiments, the NK3R antagonist is administered to the subject if the level of neurokinin B in the sample is greater than a control level. In some embodiments, the peripheral tissue sample does not comprise central nervous system tissue or cerebral spinal fluid (CSF). It is also contemplated that the level of neurokinin can be determined based on a level of mRNA encoding the neurokinin. In some embodiments, the level of neurokinin is detected using a technique such as ELISA, radioimmunoassay, lateral flow assay, no-wash assay, protein array, quantitative nucleic acid amplification (for example real-time PCR such as reverse transcriptase PCR), and/or nucleic acid hybridization (for example, microarray).

A "control level" of neurokinin can refer to a level (for example, a concentration, amount, or amount of signal from a detectable moiety) of a control sample. By way of example, a control sample can be a sample of an individual who does not suffer from social isolation stress (or a sample of the subject obtained before the subject suffered from or was at risk of suffering from social isolation stress). In the method of some embodiments, the control level of neurokinin is measured in a control sample as part of the method. The method of some embodiments comprises determining the control level of neurokinin (such as neurokinin B) in the control sample. In the method of some embodiments, the control level of neurokinin (such as neurokinin B) is a stored value, for example an electronically stored value. For example, the control level can have been previously been determined, and the stored value of the control level can be provided a reference for performing the method or use as described herein.

In the method some embodiments, the neurokinin receptor (such as NK3R) antagonist is administered to the subject if the level of neurokinin B in the sample is at least 10% greater than the control level, for example at least 10%, 20%, 30%, 40%, 50%, 60%, 70%, 80%, 90%, 100%, 150%, or 200% greater, including ranges between any two of the listed values, for example, 10%-50% greater, 10%-100% greater, 10%-200% greater, 20%-50% greater, 20%-100% greater, 20%-200% greater, 50%-100% greater, 50%-200% greater, or 100%-200% greater.

In the method of some embodiments, the subject suffers from at least one of aggression, depression, anxiety, post-traumatic stress disorder (PTSD), bereavement, grieving in isolation, agoraphobia, physical isolation, or single member living schizophrenia, and/or is patient in a skilled nursing facility. In the method of some embodiments, the subject suffers from at least one of aggression, depression, anxiety, bereavement stress, agoraphobia, or physical isolation and/or is patient in a skilled nursing facility. In the method of some embodiments, the subject suffers from at least one of aggression, depression, anxiety, or agoraphobia. In the method of some embodiments, the subject suffers from at least one of depression, anxiety, or agoraphobia. In the method of some embodiments, the subject does not suffer from PTSD. In the method of some embodiments, the subject does not suffer from any of fear memory consolidation, fear conditioning, or PTSD. In the method of some embodiments, the subject does not suffer from schizophrenia. In the method of some embodiments, the subject does not suffer from any of schizophrenia, bipolar disorder, or panic disorder. In the method of some embodiments, the subject does not suffer from any of fear memory consolidation, fear conditioning. PTSD, schizophrenia, bipolar disorder, or panic disorder.

In the method (or use) of some embodiments, the subject is at risk of social isolation stress, and the method comprises reducing the likelihood of, or preventing social isolation stress in the subject. For example, the subject can be at risk of social isolation stress based on an anticipated lack of social contact, for example, a subject who is commencing or in the course of physical isolation (such as a quarantine or imprisonment) or social isolation (such as grieving in isolation, or admittance to a skilled nursing facility as a patient). As it has been observed that a subject can exhibit a ramp-up of levels of neurokinin B (tac2) prior to exhibiting symptoms of social isolation stress (Example 2), it is contemplated that the administering a neurokinin receptor (such as NK3R) antagonist to a subject prior to the induction of social isolation stress or appearance of symptoms of social isolation stress can provide a benefit. In the method of some embodiments, a NK3R receptor antagonist is administered to the subject prior to the induction of social isolation stress, for example, at least 0.5, 1, 2, 3, 4, 5, 6, 7, 8, 9, 10, 11, 12, 18 hours, or at least 1, 2, 3, 4, 5, 6, or 7 days prior to induction of social isolation stress, including ranges between any two of the listed values, for example 1 hour-7 days, 1 hour-3 days, 1 hour-1 day, 1-7 days, 1-3 days, 3-7 days, or 3-5 days. In some embodiments, a NK3R receptor antagonist is administered to the subject prior to the appearance of symptoms of social isolation stress, for example, at least 0.5, 1, 2, 3, 4, 5, 6, 7, 8, 9, 10, 11, 12, 18 hours, or at least 1, 2, 3, 4, 5, 6, or 7 days prior to induction of social isolation stress, including ranges between any two of the listed values, for example 1 hour-7 days, 1 hour-3 days, 1 hour-1 day, 1-7 days, 1-3 days, 3-7 days, or 3-5 days. In some embodiments, the neurokinin receptor (such as NK3R) antagonist is administered to the subject at least 30 minutes prior to the induction of social isolation stress. In the method of some embodiments, the neurokinin receptor (such as NK3R) antagonist is administered to the subject at least 1 day prior to the appearance of symptoms of social isolation stress.

In the method of some embodiments, the neurokinin receptor (such as NK3R) antagonist is administered to the subject after the subject exhibits a symptom of social isolation stress. In the method of some embodiments, the NK3R antagonist is administered to the subject at least 2, 4, 6, 8, 10, 12, or 18 hours, or at least 1, 2, 3, 4, 5, 6, or 7 days after an induction of social isolation stress in the subject.

In the method of some embodiments, the subject has exhibited an induction of expression of neurokinin B in response to a stressor, and as such is identified as in need of an neurokinin receptor (such as NK3R) antagonist as described herein. For example, the subject can be identified as having a higher level of neurokinin B in a peripheral sample (not comprising CNS tissue or CSF) that in a sample of the subject prior to exposure to the stressor, and/or compared to a control level in a control sample of an individual who does not suffer from social isolation stress as described herein. As such, in some embodiments, the subject exhibits a greater level of neurokinin B than the subject had prior to the induction of neurokinin B in response to the stressor, indicating that the subject is in need of the NK3R antagonist.

In the method of some embodiments, the neurokinin receptor (such as NK3R) antagonist comprises, consists essentially of, or consists of an NK3R antagonist selected from the group consisting of: osanetant, talnetant, fezolinetant, pavinetant, SB-222200, and SB-218795, or a combination of two or more of the listed items. In the method of some embodiments, the neurokinin receptor (such as NK3R) antagonist comprises, consists essentially of, or consists of: talnetant, fezolinetant, pavinetant. SB-222200, SB-218795, or a combination of two or more of the listed items. In the method of some embodiments, the neurokinin receptor (such as NK3R) antagonist comprises, consists essentially of, or consists of: osanetant, fezolinetant, pavinetant. SB-222200. SB-218795, or a combination of two or more of the listed items. In the method of some embodiments, the neurokinin receptor (such as NK3R) antagonist comprises, consists essentially of, or consists of osanetant, talnetant, or a combination of two or more of the listed items. In the method of some embodiments, the neurokinin receptor (such as NK3R) antagonist comprises, consists essentially of, or consists of osanetant.

In some embodiments, the neurokinin receptor (such as NK3R) antagonist is administered to the subject in a single administration. In some embodiments, the neurokinin receptor (such as NK3R) antagonist is administered to the subject in two or more administrations. For example, the neurokinin receptor (such as NK3R) antagonist can be administered to the subject periodically, for example daily, semiweekly, weekly, biweekly, fortnightly, monthly, and the like. In some embodiments, the neurokinin receptor (such as NK3R) antagonist is administered at different doses in different administrations. In some embodiments, the neurokinin receptor (such as NK3R) antagonist is administered in the same dose for each administration.

The neurokinin receptor (such as NK3R) antagonist may be administered to the subject by a suitable route of administration. Examples of routes of administration for methods and kits of some embodiments herein include, but are not limited to orally, nasally, intracranially, transdermally, or parenterally. In some embodiments, the neurokinin receptor (such as NK3R) antagonist is administered orally or nasally. For oral administration, various oral dosage forms can be used, including such solid forms as tablets, capsules, granules and/or bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and/or melting agents. Further solid dosage forms may comprise milled powders, spray-dried powders, crystalline forms, amorphous forms, and glassy forms, which may be administered as tablets or may be administered as aerosols or airborne particles, for example for nasal or pulmonary delivery. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and/or flavoring agents, or any combination thereof. Further liquid dosage forms may comprise forms for intranasal or pulmonary delivery. Such dosage forms may comprise liquids for intranasal injection, nasal lavage, pulmonary lavage, nebulization or aerosol delivery. In some embodiments, the neurokinin receptor (such as NK3R) antagonist is administered in a dosage form such as a pill, dissolved liquid, oral suspension, buccal film, mouth rinse, spray, cream, lotion, or patch.

In some embodiments, the neurokinin receptor (such as NK3R) antagonist is administered in a pharmaceutically acceptable formulation. Standard pharmaceutical and/or dietary supplement formulation techniques are used, such as those disclosed in Remington's The Science and Practice of Pharmacy, 21st Ed., Lippincott Williams & Wilkins (2005), incorporated herein by reference in its entirety.

In some embodiments, the neurokinin receptor (such as NK3R) antagonist is administered without any other therapeutic agents. In some embodiments, one or more additional therapeutic agents are administered with the neurokinin receptor (such as NK3R) antagonist.

In some embodiments, the neurokinin receptor (such as NK3R) antagonist is administered in an amount effective to inhibit, ameliorate, reduce the severity of, treating, reduce the likelihood of, or prevent social isolation stress or one or more symptoms thereof. In some embodiments, the neurokinin receptor (such as NK3R) antagonist is administered in an amount effective to inhibit aggression in the subject. In some embodiments, the neurokinin receptor (such as NK3R) antagonist is administered in an amount effective to inhibit persistent responses to threats in the subject. In some embodiments, the neurokinin receptor (such as NK3R) antagonist is administered in an amount effective to inhibit persistent freezing in response to innate and conditioned fear-evoking stimuli in the subject. In some embodiments, the neurokinin receptor (such as NK3R) antagonist is administered in an amount effective to inhibit enhanced reactivity to aversive stimuli in the subject. In some embodiments, the neurokinin receptor (such as NK3R) antagonist is administered in an amount effective to increase social interaction in the subject. In some embodiments, the NK3R antagonist is administered in an amount of at least about 0.01 mg/kg, 0.05 mg/kg, 0.1 mg/kg, 0.5 mg/kg, 1 mg/kg, 2 mg/kg, 5 mg/kg, or 10 mg/kg, including ranges between any two of the listed values.

Methods of Determining a Risk of Social Isolation Stress in a Subject

In some embodiments, methods of determining a risk of social isolation stress in a subject are described. The method can comprise obtaining a sample from a peripheral tissue of the subject that is outside of the central nervous system. The method can comprise detecting a level of neurokinin (such as neurokinin B) in the sample. The method can comprise determining the subject to be in need of the neurokinin receptor (such as NK3R) antagonist if the level of neurokinin in the sample is greater than a control level. In some embodiments, the method is an in vitro method. In some embodiments, the method further comprises administering the neurokinin receptor (such as NK3R) antagonist to the subject.

In the method of some embodiments, the sample of the subject comprises at least one of: blood, bone marrow, lymphatic fluid, urine, feces, semen, and saliva. In the method of some embodiments, the sample of the subject does not comprise CNS tissue or CSF.

In the method of some embodiments, the neurokinin receptor antagonist comprises, consists essentially of, or consists of a NK3R antagonist. In the method of some embodiments, the neurokinin comprises, consists essentially of, or consists of neurokinin B.

In the method of some embodiments, the control level of neurokinin (such as neurokinin B) is a level of neurokinin in a control sample of an individual that does not suffer from social isolation stress, or of the subject and collected prior to the induction of social isolation stress in the subject. The control sample can comprise, consist essentially of, or consist of the same of material as the sample of the subject (for example, blood).

In the method of some embodiments, the control level is determined in the control sample. The control level can be determined in the control sample at the same time as in the sample of the subject, or at a different time. In some embodiments, the control level is provided as a stored value, for example an electronically stored value. The level of neurokinin B in the sample of the subject can be compared to the stored value of the control level. In some embodiments, the method comprises determining the control level of neurokinin in the control sample.

In the method of some embodiments, detecting the level of neurokinin in the sample (and/or control sample) comprises a technique selected from the group consisting of ELISA, radioimmunoassay, western blot, lateral flow assay, no-wash assay, protein array, quantitative nucleic acid amplification (for example real-time PCR such as reverse transcriptase PCR), and nucleic acid hybridization (such as FISH or microarray), or two or more of the listed items. In the method of some embodiments, detecting the level of neurokinin in each of the sample and control sample comprises a technique selected from the group consisting of ELISA, radioimmunoassay, western blot, lateral flow assay, no-wash assay, protein array, quantitative nucleic acid amplification (for example real-time PCR such as reverse transcriptase PCR), and nucleic acid hybridization (such as FISH or microarray), or two or more of the listed items.

Additional Embodiments

Some embodiments relate to uses of drugs that are at least in part antagonists of tachykinin receptors, such as NK3R. (Maggio, 1988; Culman and Unger, 1995; Beaujouan et al., 2004). Antagonists of NK3R include Osanetant, Talnetant and many other related drugs. Osanetant and Talnetant were tested in human trials for treatment of Schizophrenia and Major Depressive Disorder. They exhibited safety in Phase I, but were abandoned due to lack of efficacy in Phase I/III (Griebel and Holsboer, 2012). Currently there are no FDA-approved uses of NK3R antagonists in humans. To Applicant's knowledge, the drugs are not being actively pursued by the pharmaceutical industry.

It is reported herein that in mice, treatment with Osanetant protects and prevents the behavioral effects of 2 weeks of social isolation stress (SIS). These behavioral effects include 1) increased aggression; 2) persistent freezing to innate and conditioned fear-evoking stimuli; 3) enhanced reactivity to aversive stimuli; 4) reduced social interactions, and several other effects. Notably, these effects do not appear to be simple reversal of a state of anxiety promoted by SIS. The effect on aggressiveness was unexpected and has not previously been reported. For example, SIS mice cannot be returned to a cage with other males (even littermates), because they will attack and kill them. Treatment with Osanetant, either during or following SIS, prevents aggression and allows the mice to be safely returned to group housing conditions.

Without being limited by theory, it is contemplated that Osanetant and other NK3R antagonists may have failed in earlier clinical trials because they were tested for the wrong indications. Data described herein identify different indications and NK3R antagonists.

In addition to the disclosure elsewhere herein, the following options are described:

1. A method of inhibiting, ameliorating, reducing the severity of, treating, reducing the likelihood of, or preventing social isolation stress or symptoms thereof in a subject in need thereof, the method comprising administering an effective amount of neurokinin receptor antagonist to the subject.

2. The method of option 1, wherein the neurokinin receptor antagonist is a NK3R antagonist.

3. The method of any one of options 1-2, further comprising:
    obtaining a sample from a peripheral tissue of a subject that is outside of the central nervous system;
    detecting a level of neurokinin B in the sample; and
    determining the subject to be in need of the neurokinin receptor antagonist if the level of neurokinin B in the sample is greater than a control level,
    wherein the NK3R antagonist is administered to the subject if the level of neurokinin B in the sample is greater than the control level.

4. The method of option 3, wherein the control level of neurokinin B is a level of neurokinin B in a control sample of an individual that does not suffer from social isolation stress or of the subject and collected prior to the induction of social isolation stress.

5. The method of 4, the method further comprising determining the control level of neurokinin B in the control sample.

6. The method of any one of options 3-5, wherein the control level of neurokinin B is a stored value.

7. The method of any one of options 1-6, wherein the subject further suffers from at least one of aggression, cancer, major depressive disorder, dysthymic disorder, social phobia, generalized anxiety disorder, alcohol abuse and dependence, drug abuse, nicotine dependence, atherosclerosis, coronary heart disease, ischemic stroke, cognitive impairment, Alzheimer's disease, agoraphobia, post-traumatic stress disorder (PTSD), bereavement, grieving in isolation, or single member living schizophrenia.

8. The method of any one of options 1-7, wherein the subject suffers from at least one of aggression, cancer, major depressive disorder, dysthymic disorder, social phobia, generalized anxiety disorder, alcohol abuse and dependence, drug abuse, nicotine dependence, atherosclerosis, coronary heart disease, ischemic stroke, cognitive impairment, Alzheimer's disease, agoraphobia, bereavement, or grieving in isolation.

9. The method of any one of options 1-8, wherein the subject is at risk of social isolation stress, and wherein the method comprises reducing the likelihood of, or preventing social isolation stress in the subject.

10. The method of any one of options 1-9, wherein the subject does not suffer from any of schizophrenia, bipolar disorder, or panic disorder.

11. The method of any one of options 1-10, wherein the subject does not suffer from any of fear memory consolidation, fear conditioning, or PTSD.

12. The method of any one of options 1-11, wherein the subject has exhibited an induction of expression of neurokinin B in response to a stressor.

13. The method of any one of options 1-12, wherein the subject exhibits a greater level of neurokinin B than the subject had prior to the induction of neurokinin B in response to the stressor.

14. The method of any one of options 1-13, wherein the neurokinin receptor antagonist is an NKR3 antagonist selected from the group consisting of: osanetant, talnetant, fezolinetant, pavinetant, SB-222200, and SB-218795, or a combination of two or more of the listed items.

15. The method of any one of options 1-14, wherein the neurokinin receptor antagonist is an NKR3 antagonist that comprises, consists essentially of, or consists of osanetant.

16. The method of any one of options 1-15, wherein the NK3R receptor antagonist is administered to the subject prior to the induction of social isolation stress.

17. The method of option 16, wherein the NK3R antagonist is administered to the subject at least 30 minutes prior to the induction of social isolation stress.

18. The method of any one of options 1-17, wherein the neurokinin receptor antagonist is administered to the subject after the subject exhibits a symptom of social isolation stress.

19. The method of option 18, wherein the neurokinin receptor antagonist is administered to the subject at least two hours after an induction of social isolation stress in the subject.

20. A method of determining a risk of social isolation stress in a subject, the method comprising:
   obtaining a sample from a peripheral tissue of the subject that is outside of the central nervous system;
   detecting a level of neurokinin in the sample; and
   determining the subject to be in need of the neurokinin receptor antagonist if the level of neurokinin in the sample is greater than a control level of neurokinin.

21. The method of option 20, wherein the neurokinin comprises neurokinin B.

22. The method of option 20 or 21, wherein the neurokinin receptor antagonist is an NK3R antagonist.

23. The method of any one of options 20-22, wherein the control level is a level of a control sample of an individual that does not suffer from social isolation stress or of the subject and collected prior to the induction of social isolation stress.

24. The method of option 23, further comprising determining the control level in the control sample.

25. The method of any one of options 20-24 wherein the control level is an electronically stored value.

26. The method of any one of options 20-25, wherein detecting the level of neurokinin in the sample comprises a technique selected from the group consisting of ELISA, western blot, radioimmunoassay, lateral flow assay, no-wash assay, protein array, quantitative nucleic acid amplification, and nucleic acid hybridization, or two or more of the listed items.

Materials and Methods for Examples 1-9

Animals

C57BL/6N male mice (experimental), C57BL/6N female mice (for sexual experience), and BALB/c (intruder) WT male mice were obtained from Charles River (at 6-10 weeks of age). For visualization of Tac2 and Tad expression, we used previously described Cre-dependent Ai6-zsGreen and Ai14-mCherry fluorescent reporter mice (Madisen et al., 2010; incorporated by reference in its entirety), Tac2-IRES2-Cre (Cai et al., 2014; incorporated by reference in its entirety), and Tac1-IRES2-Cre knockin mice (obtained from the Allen Institute for Brain Science), which were backcrossed to the C57BL/6N background in the Caltech animal facility. Tac2-Cre mice were used for Cre-dependent LOF/GOF experiments (FIGS. 5A-Q, FIGS. 7A-I). Animals were housed and maintained on a reverse 12-hr light-dark cycle with food and water ad libitum. Behavior was tested during the dark cycle. Care and experimental manipulation of animals were in accordance with the National Institute of Health Guide for Care and Use of Laboratory Animals and approved by the Caltech Institutional Animal Care and Use Committee. As shown in FIGS. 15A-D, in the Tac2-Cre mice Ai6-zsGreen mice, zsGreen staining was observed in the parotid gland and mandibular gland (FIG. 15A), coagulating ducts (FIG. 15B), pancreas (FIG. 15C), sublingual glands (FIG. 15D) and testes (FIG. 15E). Thus, it can be concluded that Tac2 is transcribed outside of the CNS in periperphal tissues such as the parotid gland (FIG. 15A), mandibular gland (FIG. 15A), coagulating ducts (FIG. 15B), pancreas (FIG. 15C), sublingual glands (FIG. 15D) and testes (FIG. 15E).

Social Isolation Stress

WT males (Charles River) were housed in isolation (1 animal per cage), or in groups of 3. Tac2-Cre males (bred in-house) were housed in isolation, or in groups of 2-5. Animals were isolated post-weaning, at 8-16 weeks of age. All cage conditions remained otherwise identical for group-housed mice compared to isolated animals, and mice were housed on the same rack in the same vivarium. Except as otherwise indicated, social isolation was maintained for at least 2 weeks (this period was extended in the case of surgical experiments, i.e. when adequate time for recovery and viral expression levels were required). All mice were between 12-20 weeks of age at the time of behavioral testing.

Viral Constructs

AAV2-EF1a-DIO-hM4D(Gq)-mCherry and AAV2-EF1a-DIO-mCherry were acquired from the University of North Carolina (UNC) viral vector core. The pAAV-Tac2-shRNA1-CMV-zsGreen, pAAV-Tac2-shRNA2-CMV-zsGreen, and pAAV-shRLuc-CMV-zsGreen plasmids were constructed as described below and serotyped with AAV5 coat proteins and packaged in-house (see viral packaging below). The pAAV-hSyn-Tac2-P2A-mCherry and pAAV-hSyn-Tac2-P2A-GFP plasmids were constructed as described below and packaged into AAV-PHP.B (see PHP.B section below). The pAAV-hSyn-DIO-hM3D(Gq)-mCherry and pAAV-hSyn-DIO-mCherry were acquired from Addgene and packaged into AAV-PHP.B (see below).

Construction of Small Hairpin RNA Expressing AAV Vector

Small hairpin RNA (shRNA) for the mouse Tac2 gene (NM_009312.2) were designed using the online designing tool siDirect 2.0 (http://sidirect2.rnai.jp/) (Naito et al., 2009; incorporated by reference in its entirety).

Oligonucleotides encoding Tac2 shRNAs were purchased from IDT. Oligonucleotides used were as follows: shRNA1, 5'-CCGACGTGGTIGAAGAGAACACCGCTICCTGT-CACGGTGTICTCTCAACCACGT C TTTTTT-3' (SEQ ID NO: 9) and 5'-AAAAAAGACGTGGTT-GAAGAGAACACCGTGACAGGAAGCGGTGTTCTCT-CAAC C ACGTCGG-3' (SEQ ID NO: 10); shRNA2, 5'-CCGCCTCAACCCCATAGCAATTAGCTTCCTGT-CACTAATTGCTATGGGGTTGAGG C TTTTTT-3' (SEQ ID NO: 11) and 5'-AAAAAAGCCTCAACCCCAT-AGCAATTAGTGACAGGAAGCTAATTGCTATGGGGT TG AGGCGG-3' (SEQ ID NO: 12).

pAAV.H1.shRLuc.CMV.ZsGreen.SV40 (Luc shRNA) plasmid (PL-C-PV1781, Penn Vector Core) was used as shRNA AAV vector backbone and control shRNA construct. The entire Luc shRNA plasmid except the luciferase shRNA sequence was amplified by PCR with the following primers: shRNA1, Forward—AACCACGTCTTTTTAATTCTAGT-TATTAATAGTAATCAA (SEQ ID NO: 13); Reverse—CTTCAACCACGTCGGCTGGGAAAGAGTGGTCTC (SEQ ID NO: 14); shRNA2, Forward—GGT-GAGGCTTTTTAATTCTAGTTATTAATAGTAATCAA (SEQ ID NO: 15); Reverse—ATGGGGTT-GAGGCGGCTGGGAAAGAGTGGTCTC (SEQ ID NO: 16). All PCR reactions were performed using PrimeSTAR Max DNA Polymerase (Takara Bio, Kusatsu, Japan). After PCR amplification, template plasmid was digested by DpnI (NEB, Ipswich, Mass.) and PCR amplicons were ligated with annealed shRNA oligos using the GeneArt Seamless Cloning and Assembly Kit (Thermo Fisher Scientific, Waltham, Mass.) following the manufacturer's instructions.

Construction of Tac2-Overexpression AAV Vectors

The Tac2-P2A-mCherry gene fragment was synthesized in the form of IDT gBlocks (see below), pAAV-hSyn-Tac2-P2A-mCherry was generated via ligation to the AccI/NheI site of pAAV-hSyn-DIO-hM3D(Gq)-mCherry plasmid (Addgene #44361) using DNA Ligation Kit Mighty Mix (Takara Bio, Kusatsu, Japan). To generate the pAAV-hSyn-Tac2-P2A-GFP plasmid, the entire pAAV-hSyn-Tac2-P2A-mCherry plasmid except mCherry sequence was amplified by PCR with the following primers: Forward—CTCCTCGCCCTTGCTCAC (SEQ ID NO: 17); Reverse—GGCGCGCCATAACTTCGTATAATG (SEQ ID NO: 18) and the GFP sequence was amplified from the pAAV-GFP plasmid (AAV-400, Cell Biolabs Inc, San Diego, Calif.) with the following primers: Forward—CCTGGACCTATGGT-GAGCAAGGGCGAGGAGCTGTCACCGGGGTGGTG (SEQ ID NO: 19); Reverse—AGCATACAT-TATACGAAGTTATGGCGCGCCCTACTT-GAGCTCGAGATCTGAGTAC (SEQ ID NO: 20). Both PCR amplicons were treated with DpnI (NEB) and ligated together using the GeneArt Seamless Cloning and Assembly Kit (Thermo Fisher scientific) following the manufacturer's instructions.

The synthesized Tac2-P2A-mCherry gene fragment was as follows:

```
                                          (SEQ ID NO: 21)
GCTAGCGCCACCATGAGGAGCGCCATGCTGTTTGCGGCTGTCCTCGCCCT

CAGCTTGGCTTGGACCTTCGGGGCTGTGTGTGAGGAGCCACAGGGGCAGG

GAGGGAGGCTCAGTAAGGACTCTGATCTCTATCAGCTGCCTCCGTCCCTG

CTTCGGAGACTCTACGACAGCCGCCCTGTCTCTCTGGAAGGATTGCTGAA

AGTGCTGAGCAAGGCTTGCGTGGGACCAAAGGAGACATCACTTCCACAGA

AACGTGACATGCACGACTTCTTTGTGGGACTTATGGGCAAGAGGAACAGC
```

```
-continued
CAACCAGACACTCCCACCGACGTGGTTGAAGAGAACACCCCCAGCTTTGG

CATCCTCAAAGGAAGCGGAGCTACTAACTTCAGCCTGCTGAAGCAGGCTG

GAGACGTGGAGGAGAACCCTGGACCTATGGTGAGCAAGGGCGAGGAGGAT

AACATGGCCATCATCAAGGAGTTCATGCGCTTCAAGGTGCACATGGAGGG

CTCCGTGAACGGCCACGAGTTCGAGATCGAGGGCGAGGGCGAGGGCCGCC

CCTACGAGGGCACCCAGACCGCCAAGCTGAAGGTGACCAAGGGTGGCCCC

CTGCCCTTCGCCTGGGACATCCTGTCCCCTCAGTTCATGTACGGCTCCAA

GGCCTACGTGAAGCACCCCGCCGACATCCCCGACTACTTGAAGCTGTCCT

TCCCCGAGGGCTTCAAGTGGGAGCGCGTGATGAACTTCGAGGACGGCGGC

GTGGTGACCGTGACCAGGACTCCTCCCTGCAGGACGGCGAGTTCATCTAC

AAGGTGAAGCTGCGCGGCACCAACTTCCCCTCCGACGGCCCCGTAATGCA

GAAGAAGACCATGGGCTGGGAGGCCTCCTCCGAGCGGATGTACCCCGAGG

ACGGCGCCCTGAAGGGCGAGATCAAGCAGAGGCTGAAGCTGAAGGACGGC

GGCCACTACGACGCTGAGGTCAAGACCACCTACAAGGCCAAGAAGCCCGT

GCAGCTGCCCGGCGCCTACAACGTCAACATCAAGTTGGACATCACCTCCC

ACAACGAGGACTACACCATCGTGGAACAGTACGAACGCGCCGAGGGCCGC

CACTCCACCGGCGGCATGGACGAGCTGTACAAGTAAGGCGCGCCATAACT

TCGTATAATGTATGCTATACGAAGTTATTAAGAGGTTTCATATTGCTAAT

AGCAGCTACAATCCAGCTACCATTCTGCATAACTTCGTATAAAGTATCCT

ATACGAAGT TATTCCGGAGTCGAC.
```

Viral Packaging rAAVs were produced by polyethylenimine (PEI) triple transfection of HEK293T cells. Briefly, 40 μg of equimolar pHelper, pXR5 and pAAV-trans DNA plasmids were mixed with 120 μl of 1 mg/ml Polyethylenimine HCl MAX (Polysciences) in PBS and incubated at RT for 5 minutes, 90% confluent HEK293 cells grown on 15 cm tissue culture plates were transfected with the plasmid/PEI mixture. Cells were collected 72 hours post transfection, freeze-thawed 3 timed and incubated with Benzonase (Millipore) at 5 units/mL for 1 hour. The solution was then centrifuged at 5000×g for 20 minutes. The supernatant was layered on top of a discontinuous gradient of iodixanol and centrifuged at 200,000×g for 2 hours at 18° C. The 40% iodixanol fraction was collected, concentrated, and buffer exchanged with PBS using a Millipore 100 kD centrifugal filter. AAV genomic titers were determined by real-time PCR using primers against the ITR and normalized by dilution with PBS to $1\times10^{12}$ genome copies per mL virus.

AAV-PHP.B Production and Intravenous Administration

The AAV-hSyn-DIO-Tac2-P2A-mCherry, AAV-hSyn-DIO-hM3D-mCherry, and AAV-hSyn-DIO-mCherry recombinant AAV genomes were separately packaged into the AAV-PHP.B capsid by triple transfection of HEK293T cells and purified with iodixanol step gradients as previously described (Deverman et al., 2016; incorporated by reference in its entirety). $5\times10^{11}$ vector genomes (vg) of each virus were administered intravenously (via the retro-orbital sinus) to Tac2-Cre animals individually or in combination. To equalize the amount of virus given to each mouse, $5\times10^{11}$ vg of AAV-PHP.B-hSyn-DIO-mCherry was administered to each animal to bring the amount of virus up to the amount injected in the double Tac2+hM3DREAAD group. Each animal received a total vector dose of $1 \times 10^{12}$ vg.

Surgery and Cannula Implants 8-16 week old mice were anesthetized with isoflurane and mounted in a stereotaxic apparatus (Kopf Instruments). Anesthesia was maintained throughout surgery at 1-1.5% isoflurane. The skull was exposed and small burr holes produced dorsal to each injection site using a stereotaxic mounted drill. Virus was backfilled into pulled fine glass capillaries (~50 μm diameter at tip) and pressure injections of 300 nl were made bilaterally into either the dBNSTa (AP +0.25, ML ±0.85, DV −4.1), DMH (AP −1.3, ML±0.35, DV −5.6), or CeA (AP −1.4, ML ±2.6, DV −4.73) at a rate of 30 nl per minute using a nanoliter injector (Nanoliter 2000, World Precision Instruments) controlled by an ultra microsyringe pump (Micro4, World Precision Instruments). Capillaries remained in place for 5 minutes following injections to allow for full diffusion of virus and to reduce backflow up the injection tract. Skin above the skull was then drawn together and sealed with GLUture (Zoetis). For bilateral cannula implantations, single or double guide cannulas (custom, Plastics One) aimed 0.5 mm above each region were implanted and held in place with dental cement (Parkell). Compatible dummy cannulas with a 0.5 mm protrusion at the tip were inserted to prevent cannula clogging. Directly following surgery, mice were given a subcutaneous injection of ketoprofen (2 mg/kg) and supplied with drinking water containing 400 mg/L sulphamethoxazole and 200 mg/L ibuprofen and monitored for 7 days. Dummies were replaced every 2-3 days to keep cannula tracts clean. All injections were subsequently verified histologically.

Immunohistochemistry

Immunofluorescence staining proceeded as previously described (Anthony et al., 2014; Cai et al., 2014; Hong et al., 2014; Kunwar et al., 2015; incorporated by reference in their entirety). Briefly, mice were perfused transcardially with 0.9% saline followed by 4% paraformaldehyde (PFA) in 1×PBS. Brains were extracted and post-fixed in 4% PFA overnight at 4° C. followed by 48 hours in 15% sucrose. Brains were embedded in OCT mounting medium, frozen on dry ice, and stored at −80° C. for subsequent imaging. Sections 40-50 μm thick were cut on a cryostat (Leica Biosystems). Sections were either directly mounted onto Superfrost slides for histological verification of injections/cannula placements or were cut free floating for antibody staining. For antibody staining, brain sections were washed 3× in 1×PBS and blocked in PBS-T (0.3% Triton X-100 in 1×PBS) with 10% normal goat or donkey serum for 1 hr at room temperature (RT). Sections were then incubated in primary antibody diluted in blocking solution at 4° C. for 48-72 hours. Sections were stained for neurokinin B (rabbit anti-proNKB; 1:1000; Ressler lab); the glial marker nuclear factor I-A (rabbit anti-mouse NFIA; 1:1000; Deneen lab) (Deneen et al., 2006; incorporated by reference in its entirety); the oligodendrocyte marker proteolipid protein (chicken anti-PLP; 1:1,000; Millipore) or the nuclear marker NeuN (rabbit anti-NeuN; 1:1000; Millipore). Sections were then washed 3× and incubated in secondary antibodies diluted in blocking buffer (goat anti-rabbit, goat anti-chicken, Alexa Fluor 594, 1:500) overnight at 4° C. Sections were then washed 3×, incubated for 20 minutes at RT in DAPI diluted in 1×PBS (1:2000) for counterstaining, washed again, mounted on Superfrost slides, and coverslipped for imaging on a confocal microscope (Olympus FluoView FV1000).

Fluorescent In Situ Hybridization

Digoxigenin-labeled Tac2 RNA probe was generated following a previously described protocol (http://help.brain-map.org/display/mousebrain/Documentation) (Lein et al., 2007; incorporated by reference in its entirety) with the following primer sets: Forward—AGCCAGCTCCCT-GATCCT (SEQ ID NO: 22); Reverse—TTGC-TATGGGGTTGAGGC (NM_009312.2, 36-608 bp) (SEQ ID NO: 23). Fluorescent in situ hybridization (FISH) was carried out according to the protocol described in (Thompson et al., 2008; incorporated by reference in its entirety) with modifications. Briefly, mice were transcardially perfused with 1×PBS followed by 4% paraformaldehyde/PBS (PFA) in 1×PBS. Brains were fixed in 4% PFA for 3-4 hours at 4° C. and cryoprotected overnight in 15% sucrose at 4° C. Brains were embedded in OCT Compound (Fisher Scientific) and cryosectioned at 30 μm thickness and mounted on Superfrost Plus slides (Fisher Scientific). Sections were fixed in 4% PFA for 30 minutes, acetylated with 0.25% acetic anhydride in 0.1 M triethanolamine for 10 minutes, dehydrated with increasing concentrations of EtOH (50, 70, 95 and 100%), gently treated with proteinase K (6.3 μg/mL in 0.01M Tris-HCl pH 7.4 and 0.001M EDTA) for 10 minutes, and fixed in 4% PFA for 20 minutes. All procedures were performed at room temperature (RT). The hybridization buffer contained 50% deionized formamide, 3× standard saline citrate (SSC), 0.12 M PB (pH 7.4), 10% dextran sulfate, 0.12 mg/ml yeast tRNA, 0.1 mg/mL calf thymus DNA, and 1× Dehardt solution. The sections were prehybridized at 63° C. in hybridization buffer for 30 minutes and then hybridized with the digoxigenin-labeled Tac2 RNA probe (300 ng/ml) in hybridization buffer at 63° C. for 16 hours. After hybridization, the sections were washed with 5×SSC for 10 minutes, 4×SSC/50% formamide for 20 minutes, 2×SSC/50% formamide for 30 minutes, and 0.1× SSC for 20 minutes twice each at 61° C. The sections were blocked with 4% sheep serum in TNT buffer (Tris-HCl pH7.5, 0.15 M NaCl and 0.00075% Tween 20) for 30 minutes and TNB Blocking buffer (TSA blocking reagent, PerkinElmer, Waltham, Mass.) for 30 minutes at RT. The sections were incubated overnight at RT with anti-digoxigenin-POD antibody (1:600, Roche Diagnostics) in TNB buffer. The sections were washed with TNT buffer and tyramide-biotin signal amplification was performed using the TSA Plus Biotin Kit (PerkinElmer). Signals were visualized after 1 hour incubation with Alexa Fluor 594 Streptavidin (Jackson ImmunoResearch) or Alexa Fluor 488 Streptavidin (Invitrogen) at RT. Sections were counterstained with DAPI (0.5 μg/mL in PBS), washed with 1×PBS, and coverslipped using Fluoro-Gel with Tris Buffer (Electron Microscopy Sciences). Tissue images of entire coronal brain sections were taken using an Olympus VS120-S6-W slide-scanner and cells positive for the probe were counted.

Cell Counting

Following confocal or slide-scanner imaging, quantification of labeled cells was performed using ImageJ and Metamorph. Cells were counted by an observer blind to experimental conditions. Brain images were converted to greyscale (16-bit) in ImageJ and adjusted using automatic thresholding and watershed separation. Cells were either counted automatically using ImageJ's particle analysis algorithm (random sections were counted manually to cross-check that automated scoring was consistent with manual human scoring); otherwise, cells were counted manually using MetaMorph. Cells that were not entirely contained within a given region of interest (ROI) were excluded from analyses. Relative fluorescent intensities were measured automatically using MetaMorph for a given ROI. Raw cell counts within an ROI were divided by the size of the ROI ($mm^2$) to produce the number of positively labeled cells/$mm^2$.

Quantitative Real-Time Reverse Transcription PCR

Group housed or isolated (30 minutes, 24 hours, 2 weeks) mice were decapitated and brains were quickly removed and placed in RNA Later (Qiagen) at 4° C. Tissue from dBNSTa, DMH, CeA, ACC, and dHPC was microdissected and placed in RNA Later. Tissue was then homogenized and RNA purified using an RNAeasy Plus Mini Kit (Qiagen). 150 ng of total RNA/region/condition was then incubated with 3 μl of Turbo DNase, 1 μl of Murine RNase Inhibitor in 1× Turbo DNase buffer for 15 minutes at 37° C. to remove any contaminating genomic DNA. Samples were subsequently purified using Dynabeads MyOne Silane beads and eluted in 11 μl. The eluted RNA was used as input into a 20 l reverse transcriptase reaction (SuperScript III). 1 μl of 100 μM random 9-mers (NNNNNNNNN—IDT corporation) served as primers. The reverse transcriptase reaction was inactivated at 70° C. prior to qPCR analysis on the Light-Cycler 480 Instrument II. The following primers, ordered from Integrated DNA Technologies, were used: Tad (Forward—GATGAAGGAGCTGTCCAAGC (SEQ ID NO: 24); Reverse—TCACGAAACAGGAAACATGC (SEQ ID NO: 25)); Tac2 (Forward-GCCATGCTGTTIGCGGCTG (SEQ ID NO: 26); Reverse—CCTTGCTCAGCACTTTCAGC (SEQ ID NO: 27)); GAPDH (Forward—TGAAGCAGGCATCTGAGGG (SEQ ID NO: 28); Reverse—CGAAGGTGGAAGAGTGGGAG (SEQ ID NO: 29)); and 18s (Forward—GCAATTATTCCC-CATGAACG (SEQ ID NO: 30); Reverse—GGGACT-TAATCAACGCAAGC (SEQ ID NO: 31)). GAPDH and 18s served as housekeeping genes to which Tad and Tac2 were normalized. Primers were resuspended in ddH$_2$O to 100 μM. A 25 μM mix of each primer was used as input for qRT-PCR reactions. Four technical replicates were run for each sample primer pair and the Cp (Crossing Point) value was determined using Lightcycler II Software. The median value of the four technical replicates was used as the representative value for the set. Final mRNA fold increase values were determined by normalizing raw fluorescent values of experimental animals to controls using the following formula: $2^{(Cycles\ Control-\ Cycles\ Experimental)}$. Thus, for example, if the control sample required 8 cycles and the experimental sample 3 cycles to reach the Cp, then the fold-increase for experimental/control would be $2^{(8-3)}=2^5=32$-fold.

Resident Intruder Assay

Testing for aggression using the resident intruder assay (Blanchard et al., 2003; incorporated by reference in its entirety) was performed as previously described (Hong et al., 2015; Hong et al., 2014; Lee et al., 2014; incorporated by reference in their entirety). Briefly, experimental mice ("residents") were transported in their homecage to a novel behavior testing room (cagemates in group housed mice were removed from the homecage prior to transport for this and all other behavioral tests), where they acclimated for 5-15 minutes. Homecages were then slotted into a customized behavioral chamber lit with a surround panel of infrared lights and equipped with two synchronized infrared video cameras (Pointgrey) placed at 90-degree angles from each other to allow for simultaneous behavior recording with a front and top view. Synchronized video was acquired using Hunter 4.0 software (custom, Pietro Perona lab, Caltech). Following a two-minute baseline period, an unfamiliar male BALB/c mouse ("intruder") was placed in the homecage of the resident for 10 minutes and mice were allowed to freely interact. Group housed BALB/c males were used as intruders because they are a relatively submissive strain, thereby reducing any intruder-initiated fighting. Behavior videos were hand-annotated by an observer blind to experimental conditions (Behavior Annotator, Piotr's MATLAB toolbox; http://vision.ucsd.edul~pdollar/toolbox/doc/). Fighting bouts were scored on a frame-by-frame basis and were defined as a frame during which the resident male was engaged in an episode of biting or intense aggressive behavior immediately surrounding a biting episode. Annotation files were then batch analyzed for behavior, including number of fighting bouts, using in-house customized programs in MATLAB (A. Kennedy, Caltech).

Looming Disk Assay

Freezing behavior to presentation of an overhead looming disk proceeded as previously described (Kunwar et al., 2015; Yilmaz and Meister, 2013; incorporated by reference in their entirety). Briefly, mice were transported to a novel behavioral testing room. After 5 minutes of acclimation, mice were placed inside a novel, custom-built open top Plexiglas arena (48×48×30 cm) covered with a flat screen monitor placed directly above and with illumination provided by infrared LEDs (Marubeni). Mice were given a 5 minute baseline period in the arena, after which entry into the center of the arena triggered presentation of a single, 10 second overhead looming disk stimulus (comprised of a single looming disk presentation 0.5 seconds in duration, which was repeated 10 times with an inter-stimulus interval of 0.5 seconds). The stimulus was controlled by custom MATLAB code (M. Meister, Caltech) run on a dedicated computer in an adjacent room. Mice remained in the area for an additional 2 minutes before being transported back. Behavior was recorded using a video recorder attached to a laptop equipped with video capture software (Corel Video-Studio Pro). Acute freezing behavior to the looming disk ("during") as well as in the 30 seconds following the last disk ("post") were scored manually (Behavior Annotator, MATLAB) by an observer blind to environmental conditions.

Tone Fear Conditioning and Shock Reactivity

The protocol for tone trace fear conditioning was performed as previously described (Cushman et al., 2014; incorporated by reference in its entirety) using fear conditioning boxes previously described in detail (Haubensak et al., 2010; Kunwar et al., 2015; incorporated by reference in their entirety). Briefly, mice were transported in squads of four on a white cart to a novel behavioral testing room containing 4 sound-attenuating fear-conditioning chambers (Med Associates). This "training context" was comprised of flat grid flooring (wired to a shock generator and scrambler for footshock delivery, Med Associates), houselights, and the presence of an internal fan for background noise. Chambers were sprayed with 70% Simple Green solution on the underlying chamber pan to generate a unique contextual scent and chambers were cleaned with 70% EtOH between squads. Trace fear conditioning consisted of a 3 minute baseline period followed by 3 tone-shock trials consisting of a 20 second tone conditional stimulus (CS; 75 dB, 2800 Hz), a 20 second trace interval and a 2 second footshock unconditional stimulus (US; 0.7 mA). The inter-trial interval (ITI) between trials was 60 seconds. Mice remained in the chambers an additional 60 seconds before being transported back to the vivarium. The following day, mice were transported in fresh cardboard boxes to a novel behavioral testing room consisting of 4 distinct fear-conditioning boxes to test for tone fear. The "test context" consisted of the houselights and fan turned off, uneven grid flooring, a 1% acetic acid scent and a black plastic insert used to generate a triangular roof. Testing was performed identical to training with the exception that shocks were omitted from test trials to allow for behavior assessment to the tone. A single shock was administered in the last minute of testing to assess activity burst responding to the shock. This allowed assessment of reactivity to the shock under our various manipulations performed during testing without disrupting fear acquisition by performing manipulations during training. All experimental manipulations and data shown herein were performed during the test phase of fear conditioning (training data not shown). Training and testing context were counterbalanced across mice. Freezing behavior during the baseline period as well as during each tone presentation ("during") and trace interval ("post") were assessed as previously described (Zelikowsky et al., 2014; incorporated by reference in its entirety) using automated near-infrared video tracking equipment and computer software (VideoFreeze, Med Associates). Shock reactivity (motion, arbitrary units) was measured during the 2 second shock US as well as the 3 seconds immediately following.

Ultrasonic Sound Stimulus Assay

Behavior was tested as previously described (Mongeau et al., 2003; incorporated by reference in its entirety). Briefly, mice were brought into a novel experimental testing room in their homecages and allowed to acclimate for 5 minutes. Behavior in the homecage to an ultrasonic sound stimulus (USS) was then recorded using a digital video camera connected to a portable laptop equipped with video capture software (Corel VideoStudio Pro). Mice were permitted a 2-minute baseline period of behavior followed by three, 1-minute presentations of the USS (100 ms frequency sweeps between 17 and 20 kHz, 85 dB, alternately ON 2 sec/OFF 2 sec) with a 1-minute inter-trial interval. Following testing, mice were returned to the vivarium. Freezing behavior to each USS and post-USS period (ITI) was manually scored by an observer blind to experimental conditions (Behavior Annotator, MATLAB).

Open Field Test

Open field testing (OFT) was performed as previously described (Anthony et al., 2014; Cai et al., 2014; Kunwar et al., 2015; incorporated by reference in their entirety) to examine anxiety-like behavior (thigmotaxis) in a novel open arena. Briefly, mice were brought into a novel behavior testing room in squads of 4. They were then individually placed in plastic open top arenas (50×50×30 cm) and allowed to freely move for a 10-minute period. Video was captured using an overhead mounted video camera connected to a dedicated computer in an adjacent room equipped with Mediacruise (Canopus) video capture software. Ethovision software was used to generate trajectory maps and analyze time spent in the center of the arena (center 50%) and average velocity.

Elevated Plus Maze

Elevated plus maze (EPM) testing was performed as previously described (Cai et al., 2014; Kunwar et al., 2015; incorporated by reference in their entirety). Briefly, mice were brought into a behavioral testing room and tested for anxiety-like behavior on an elevated plus maze. The EPM was comprised of a platform (74 cm above the floor) with four arms—two opposing open arms (30×5 cm) and two opposing closed arms (30×5×14 cm). Mice were placed in the center of the EPM and their behavior was tracked for 5 minutes using Mediacruise (Canopus) for video capture and Ethovision for trajectory maps, analyses of time spent in each arm, and number of entries. Mice were also scored for whether or not they jumped off of the center of the platform within 5 seconds of being initially placed on the EPM.

Acoustic Startle Response

Startle responding to an acoustic stimulus (Koch, 1999; incorporated by reference in its entirety) was measured using a startle chamber (SR-LAB; San Diego Instruments) as previously described (Shi et al., 2003; incorporated by reference in its entirety). Briefly, mice (in squads of 3) were brought into a novel behavioral testing room in their homecages and allowed to acclimate for 5-10 minutes. Mice were then placed into sound-attenuating startle chambers comprised of a Plexiglas cylinder (5.1 cm diameter) mounted on a platform (20.4×12.7×0.4 cm) with a piezoelectric accelerometer unit attached below to detect startle motion. The chambers contained an overhead loudspeaker and light. Following a 3-minute baseline, mice were presented with a series of 8 noise presentations ramping up from 67-124 dB (67, 78, 86, 95, 104, 109, 115, 124 dB) across a 4 minute period (~30 sec variable inter-trial interval; ITI). The delivery of acoustic stimuli and acquisition of startle motion was controlled by SR-LAB software on a dedicated computer. Prior to each behavioral testing session, sound levels were calibrated with a sound-level meter (Radio Shack), and response sensitivities were calibrated using the SR-LAB Startle Calibration System. Startle chambers were cleaned with 70% EtOH between squads.

Flinch-Vocalize-Jump Assay

Sensitivity to a noxious footshock stimulus was assessed using the flinch-vocalize-jump assay (Kim et al., 1991; incorporated by reference in its entirety). Mice were transported to a behavioral testing room and individually tested in a fear conditioning box (Med Associates) for reactivity to a series of manually delivered shocks ramping up in amplitude. Shocks were administered every 5 seconds beginning from 0.05 mA to 0.6 mA, with each shock increasing by 0.05 mA. The shock intensity level at which a mouse displayed flinching (first perceptible reaction to the shock), vocalization (sound audible to a human observer), and jumping (simultaneous lifting of all 4 paws off the grid) were noted for each mouse.

Social Interaction Assay

Mice were tested for interactive behavior towards a new mouse using the social interaction assay. Behavior testing proceeded as previously described (Hsiao et al., 2013; incorporated by reference in its entirety). Briefly, mice were brought to a behavioral testing room in squads of 4 and individually placed in a long Plexiglass apparatus (50×75 cm) consisting of three chambers—a center chamber and two side chambers each containing an empty pencil cup flipped upside-down. Following a 5-minute baseline period, an unfamiliar male mouse (BALB/c) was placed under one pencil cup, and a novel object (50 mL falcon tube cut in half) was placed under the other (placements counterbalanced across mice). Sociability across a 10-minute time period was assessed. Video was captured using an overhead mounted video camera connected to a dedicated computer in an adjacent room equipped with Mediacruise (Canopus) video capture software. Ethovision software (Noldus) was used to analyze time spent in each chamber and generate an output file containing information on XY coordinates (location). XY coordinates were then used to generate heat maps reflecting the amount of time spent at each location in the social interaction apparatus (Matlab).

Rat Exposure Assay

Behavior was tested as previously described in (Kunwar et al., 2015; incorporated by reference in its entirety). Briefly, mice were tested for behavior towards an intact rat predator (Blanchard et al., 2005; incorporated by reference in its entirety), weighing 300-500 grams. Mice were brought into a novel testing environment in their homecage. Behavior was recorded using a digital video camera attached to a portable laptop running video acquisition software (Corel VideoStudio Pro). Following a 3-minute baseline period, a rat was lowered onto one side of the mouse's homecage in a custom-made mesh enclosure (16×11×15 cm) for a 5-minute time period. To assess where the mouse spent its time, the homecage was divided into three equal zones, with Zone 1 closest to the rat and Zone 3 farthest. Time spent in each zone and freezing behavior (not shown) was calculated using EthovisionXT software (Noldus).

Pharmacology

Mice were administered the Nk3R antagonist osanetant (Axon Medchem, Axon 1533) either systemically or intrabrain region. Osanetant was dissolved in saline with 0.1% Tween 20 (vehicle). For systemic administration mice received an intraperitoneal (i.p.) injection (5 mg/kg) 20 minutes prior to behavioral testing. For microinfusions, guide cannulas were removed from mice and replaced with injector cannulas (Plastics One), which protruded 0.5 mm from the tip of the guide cannula. Injectors were attached to 5 µl Hamilton syringes with PE tubing (Plastics One) and mounted on a microinfusion pump (Harvard Apparatus) for controlled infusion of osanetant (0.3 µl vehicle with 375 ng dose per site injected over 6 minutes). For experiments using systemic administration of clozapine-N-oxide (CNO), CNO (Enzo Life Sciences-Biomol, BML-NS105-0005) was dissolved in saline (9 g/L NaCl) and injected (i.p.) at 5 mg/kg for hM4DREADD silencing or 2 mg/kg for hM3DREADD activation 20 minutes prior to behavioral testing. CNO was also administered chronically in drinking water (0.5 mg CNO/100 ml water).

Quantification and Statistical Analyses

All behavioral data was scored by a trained observer blind to experimental conditions or scored using an automated system (Ethovision, Med Associates). Data were then processed and analyzed using MATLAB, Excel, Prism 6, and G*Power. Statistical analyses were conducted using ANOVAs followed by Bonferroni post hoc tests, Fisher's LSD tests, and unpaired t tests when appropriate. The n value, the mean values ±SEM for each data set, and statistically significant effects are reported in each figure/figure legend. The significance threshold was held at $\alpha$=0.05, two-tailed (not significant, ns, $p>0.05$; *$p<0.05$; $p<0.01$; *$p<0.001$). Full statistical analyses corresponding to each data set, including 95% confidence intervals (CIs) and effect size (12), are presented in Table 2.

TABLE 2

STATISTICAL ANALYSES

Figures 1A, 1B, 1C, 1D:
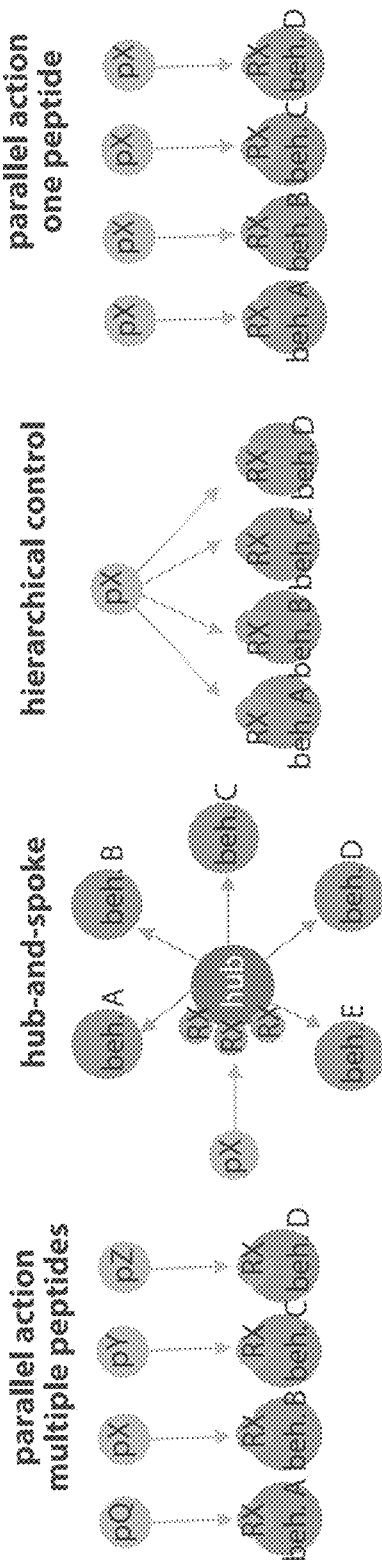
Figure 1E:
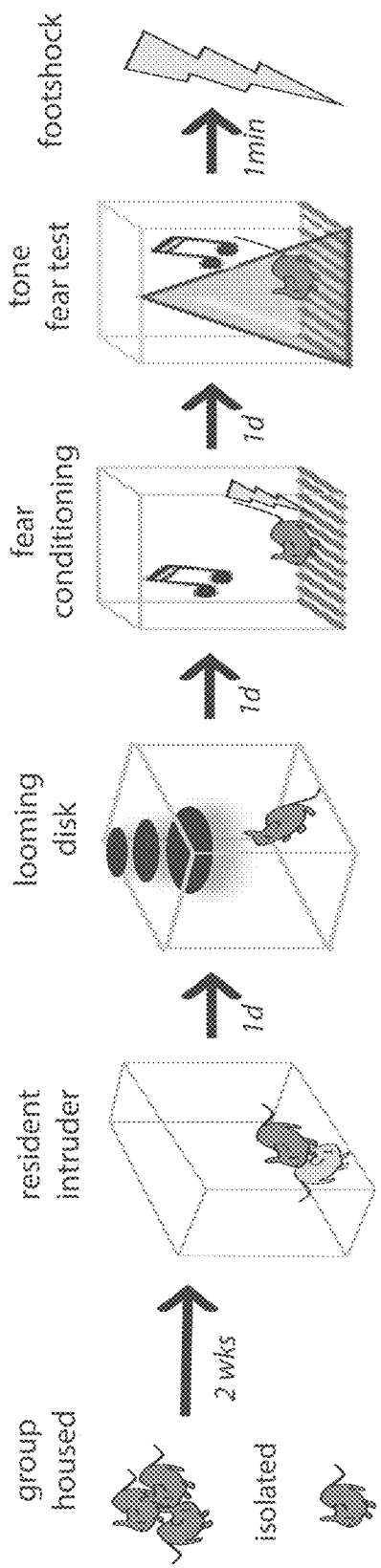
Figure 1R:
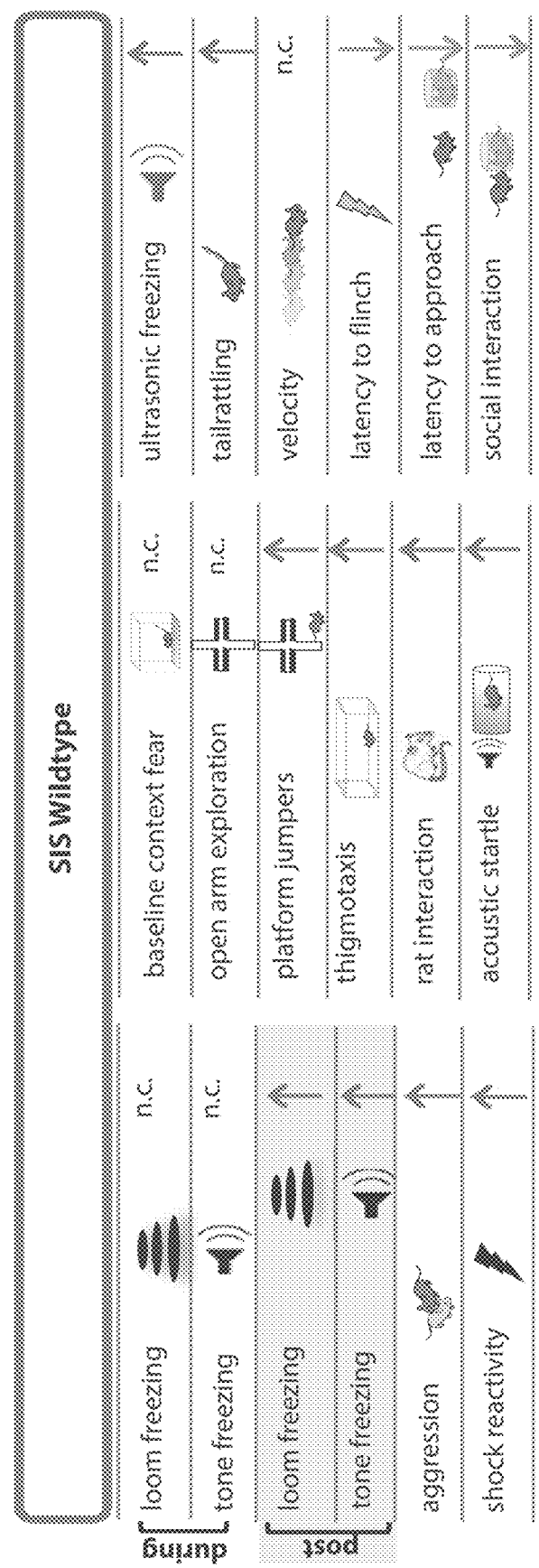

| FIGURE/ASSAY | TEST | F, t VALUE | p VALUE | CI | $\eta^2$ |
|---|---|---|---|---|---|
| FIG. 1 | | | | | |
| F; resident intruder | unpaired t-test | $t_{1,14}$ = 8.972 | <0.0001 | 19.21-31.29 | 0.852 |
| G; looming disk | RM ANOVA | time: $F_{1,14}$ = 11.19 | =0.005 | | |
| | Bonferroni | post: $t_{1,28}$ = 2.74 | <0.05 | -83.28--6.055 | |
| H; fear conditioning | RM ANOVA | time: $F_{1,13}$ = 11.80 | =0.004 | | |
| | | stress: | =0.066 | | |
| | | $F_{1,13}$ = 4.042 | | | |
| | | X: $F_{1,13}$ = 6.239 | =0.0267 | | |
| | Bonferroni | post: $t_{1,26}$ = 2.905 | <0.05 | -61.04--6.147 | |
| I; footshock | unpaired t-test | $t_{1,14}$ = 2.653 | =0.019 | 27.84-262.8 | 0.335 |
| K; ultrasonic sound | RM ANOVA | stim: $F_{5,45}$ = 9.397 | <0.0001 | | |
| | | stress: | 0.0096 | | |
| | | $F_{1,9}$ = 10.72 | | | |
| | | X: $F_{5,45}$ = 3.292 | 0.0128 | | |
| | Bonferroni | USS1: $t_{1,54}$ = 4.31 | <0.001 | -50.76--11.32 | |
| | | USS3: | <0.01 | -44.97--5.525 | |
| | | $t_{1,54}$ = 3.506 | | | |
| M; open field | unpaired t-test | $t_{1,14}$ = 2.362 | =0.0332 | -48.01--2.311 | 0.285 |
| FIG. 2 | | | | | |
| E; Tac2 qRTPCR | OW ANOVA | See FIG. S2 | | | |
| | Fisher's LSD | dBNST: | =0.029 | -11.01--0.697 | |
| | | $t_{1,12}$ = 2.474 | | | |
| | | DMH: $t_{1,12}$ = 2.808 | =0.016 | -3.656--0.461 | |
| | | CEA: $t_{1,12}$ = 2.271 | =0.042 | -19.43--0.403 | |
| | | ACC: $t_{1,12}$ = 1.330 | =0.2081 | -5.492-1.328 | |
| | | dHPC: $t_{1,2}$ = 1.921 | =0.1948 | -3.085-8.06 | |
| L; FISH, dBNSTa | unpaired t-test | cells: $t_{1,18}$ = 2.197 | =0.041 | 5.499-245.0 | 0.212 |
| | | inten: $t_{1,19}$ = 7.562 | <0.0001 | 21.90-38.67 | 0.751 |
| M; FISH, DMH | unpaired t-test | cells: $t_{1,4}$ = 7.451 | =0.002 | 83.99-183.8 | 0.933 |
| | | inten: $t_{1,4}$ = 9.156 | =0.001 | 38.51-72.03 | 0.955 |
| N; FISH, CeA | unpaired t-test | cells: $t_{1,17}$ = 2.127 | =0.048 | 1.145-285.5 | 0.21 |
| | | inten: $t_{1,15}$ = 2.503 | =0.024 | 4.118-51.33 | 0.295 |
| O; FISH, ACC | unpaired t-test | cells: $t_{1,20}$ = 0.561 | =0.581 | -17.80-30.89 | 0.015 |
| | | inten: $t_{1,12}$ = 2.832 | =0.015 | 1.310-10.05 | 0.401 |
| P; FISH, dHPC | unpaired t-test | cells: $t_{1,25}$ = 0.983 | =0.335 | -6.229-17.60 | 0.037 |
| | | inten: $t_{1,44}$ = 4.68 | <0.0001 | 3.611-9.073 | 0.332 |

TABLE 2-continued

STATISTICAL ANALYSES

| FIGURE/ASSAY | TEST | F, t VALUE | p VALUE | CI | $\eta^2$ |
|---|---|---|---|---|---|
| | | FIG. 3 | | | |
| B; resident intruder | OW ANOVA | $F_{3,20}$ = 3.213 | =0.045 | | 0.325 |
| | Fisher's LSD | veh grp vs. veh SIS: $t_{1,20}$ = 2.449 | =0.024 | −22.22−−1.781 | |
| | | veh SIS vs. osan SIS: $t_{1,20}$ = 2.245 | =0.036 | 0.781-21.22 | |
| C; looming disk | RM ANOVA | time: $F_{1,20}$ = 65.08 | <0.0001 | | |
| | Fisher's LSD | veh grp vs. veh SIS: $t_{1,40}$ = 2.661 | 0.011 | −68.24−−9.325 | |
| | | veh SIS vs. osan SIS: $t_{1,40}$ = 2.198 | 0.034 | 2.584-61.5 | |
| D; fear conditioning | RM ANOVA | time: $F_{1,20}$ = 20.34 | =0.0002 | | |
| | Fisher's LSD | veh grp vs. veh SIS: $t_{1,40}$ = 2.134 | =0.039 | −62.8−−1.712 | |
| | | veh SIS vs. osan SIS: $t_{1,40}$ = 3.155 | =0.003 | 17.14-78.22 | |
| E; footshock | unpaired t-test | veh SIS vs. osan SIS: $t_{1,10}$ = 3.095 | =0.011 | −329.6−−53.66 | 0.48 |
| G; resident intruder | OW ANOVA | $F_{3,20}$ = 2.282 | =0.11 | | 0.255 |
| | Fisher's LSD | veh grp vs. veh SIS: $t_{1,20}$ = 2.257 | =0.035 | −23.09−−0.91 | |
| | | veh SIS vs. daily osan: $t_{1,20}$ = 2.257 | =0.035 | 0.9097-23.09 | |
| H; looming disk | RM ANOVA | time: $F_{1,20}$ = 43.99 | <0.0001 | | |
| | Fisher's LSD | veh SIS vs. daily osan: $t_{1,40}$ = 2.452 | =0.019 | 6.224-64.58 | |
| I; fear conditioning | RM ANOVA | time: $F_{1,20}$ = 2.882 | =0.105 | | |
| | Fisher's LSD | veh grp vs. 24 hr osan: $t_{1,40}$ = 2.116 | =0.041 | −36.23-23.75 | |
| | | 24 hr osan vs. daily osan: $t_{1,40}$ = 2.726 | =0.010 | −21.5-38.48 | |
| | | FIG. 4 | | | |
| C; looming disk | RM ANOVA | time: $F_{1,10}$ = 12.41 | =0.006 | | |
| | | X: $F_{1,10}$ = 21.33 | =0.001 | | |
| | Bonferroni | $t_{1,20}$ = 4.33 | <0.001 | 23.36-82.73 | |
| D; fear conditioning | RM ANOVA | time: $F_{1,10}$ = 11.73 | =0.007 | | |
| | Bonferroni | $t_{1,20}$ = 2.496 | <0.05 | 0.925-62.43 | |
| E; resident intruder | unpaired t-test | $t_{1,10}$ = 2.231 | =0.049 | −19.65−−0.012 | 0.332 |
| I; looming disk | RM ANOVA | time: $F_{1,11}$ = 7.232 | =0.021 | | |
| | | osan: $F_{1,11}$ = 188.1 | <0.0001 | | |
| | Bonferroni | during: $t_{1,22}$ = 7.947 | <0.0001 | 54.38-101.6 | |
| | | post: $t_{1,22}$ = 4.343 | <0.001 | 19.02-66.23 | |
| J; fear conditioning | RM ANOVA | time: $F_{1,11}$ = 9.612 | =0.01 | | |
| | | osan: $F_{1,11}$ = 9.711 | =0.01 | | |
| | Bonferroni | during: $t_{1,22}$ = 2.542 | <0.05 | 1.996-72.09 | |
| | | post: $t_{1,22}$ = 3.016 | <0.05 | 8.893-78.98 | |
| | | FIG. 5 | | | |
| C; looming disk | RM ANOVA | time: $F_{1,12}$ = 23.22 | =0.0004 | | |
| | | CNO: $F_{1,12}$ = 11.65 | =0.005 | | |
| | | X: $F_{1,12}$ = 5.222 | =0.041 | | |
| | Bonferroni | $t_{1,24}$ = 4.082 | <0.001 | 19.2-73.51 | |
| D; fear conditioning | RM ANOVA | time: $F_{1,12}$ = 11.13 | =0.006 | | |
| | | CNO: $F_{1,12}$ = 10.94 | =0.006 | | |
| | | X: $F_{1,12}$ = 8.695 | =0.012 | | |
| | Bonferroni | $t_{1,20}$ = 4.412 | <0.001 | 18.25-61.43 | |
| E; resident intruder | unpaired t-test | $t_{1,14}$ = 1.865 | =0.042 | −12.63-0.882 | 0.199 |
| I; looming disk | RM ANOVA | time: $F_{1,14}$ = 28.94 | <0.0001 | | |
| | | CNO: $F_{1,14}$ = 7.353 | =0.017 | | |
| | Bonferroni | during: $t_{1,28}$ = 2.689 | <0.05 | 4.427-69.88 | |
| | | post: $t_{1,28}$ = 2.464 | <0.05 | 1.326-66.78 | |
| J; fear conditioning | RM ANOVA | time: $F_{1,14}$ = 28.79 | <0.0001 | | |
| | | CNO: $F_{1,14}$ = 8.405 | 0.012 | | |
| | Bonferroni | during: $t_{1,28}$ = 2.643 | <0.05 | 3.854-70.39 | |
| | | post: $t_{1,28}$ = 2.9 | <0.05 | 7.464-74 | |

TABLE 2-continued

| | STATISTICAL ANALYSES | | | | |
|---|---|---|---|---|---|
| FIGURE/ASSAY | TEST | F, t VALUE | p VALUE | CI | $\eta^2$ |
| | | FIG. 6 | | | |
| C; looming disk | RM ANOVA | time: $F_{1,15}$ = 42.94 | <0.0001 | | |
| | | shRNA: $F_{2,15}$ = 10.69 | =0.001 | | |
| | Bonferroni | during; con vs. shRNA2: $t_{1,30}$ = 2.889 | <0.05 | 4.473-68.62 | |
| | | post; con vs. shRNA1: $t_{1,30}$ = 3.367 | <0.01 | 10.51-74.65 | |
| | | post; con vs. shRNA2: $t_{1,30}$ = 4.495 | <0.001 | 24.78-88.92 | |
| D; fear conditioning | RM ANOVA | time: $F_{1,9}$ = 15.08 | =0.004 | | |
| | | shRNA: $F_{2,9}$ = 16.95 | =0.001 | | |
| | | X: $F_{2,9}$ = 4.878 | =0.037 | | |
| | Bonferroni | during; con vs. shRNA2: $t_{1,18}$ = 4.481 | <0.001 | 22.12-85.49 | |
| | | during; shRNA1 vs. shRNA2: $t_{1,18}$ = 3.833 | <0.01 | 14.33-77.7 | |
| | | post; con vs. shRNA1: $t_{1,18}$ = 3.833 | <0.01 | 14.33-77.7 | |
| | | post; con vs. shRNA2: $t_{1,18}$ = 5.423 | <0.001 | 33.42-96.79 | |
| E; resident intruder | unpaired t-test | con vs. shRNA1: $t_{1,10}$ = 2.049 | =0.034 | −14.61-0.611 | 0.296 |
| | unpaired t-test | con vs. shRNA2: $t_{1,10}$ = 1.883 | =0.045 | −14.19-1.192 | 0.262 |
| I; looming disk | RM ANOVA | time: $F_{1,14}$ = 58.3 | <0.0001 | | |
| | | shRNA: $F_{2,14}$ = 12.56 | =0.001 | | |
| | Bonferroni | during; con vs. shRNA1: $t_{1,28}$ = 3.18 | <0.05 | 7.01-63.38 | |
| | | during; con vs. shRNA2: $t_{1,28}$ = 3.02 | <0.05 | 5.239-61.61 | |
| | | post; con vs. shRNA1: $t_{1,28}$ = 3.141 | <0.05 | 6.58-62.95 | |
| | | post; con vs. shRNA2: $t_{1,28}$ = 3.345 | <0.01 | 8.837-65.2 | |
| J; fear conditioning | RM ANOVA | time: $F_{1,14}$ = 13.09 | =0.003 | | |
| | | shRNA: $F_{2,14}$ = 10.79 | =0.002 | | |
| | Bonferroni | during; con vs. shRNA2: $t_{1,28}$ = 3.58 | <0.01 | 12.17-72.15 | |
| | | post; con vs. shRNA2: $t_{1,28}$ = 4.408 | <0.001 | 21.93-81.91 | |
| | | FIG. 7 | | | |
| B; resident intruder | OW ANOVA | $F_{3,20}$ = 4.149 | =0.019 | | 0.384 |
| | Bonferroni | mCherry vs. Tac2 + hM3D: $t_{1,20}$ = 2.971 | <0.05 | −22.17--0.166 | |
| | | Tac2 vs. Tac2 + hM3D: $t_{1,20}$ = 3.016 | <0.05 | −22.33--0.332 | |
| C; looming disk | RM ANOVA | time: $F_{1,20}$ = 37.33 | <0.0001 | | |
| | Bonferroni | post; mCherry vs. Tac2 + hM3D: $t_{1,40}$ = 2.517 | <0.05 | −98.26--0.351 | |

TABLE 2-continued

STATISTICAL ANALYSES

| FIGURE/ASSAY | TEST | F, t VALUE | p VALUE | CI | $\eta^2$ |
|---|---|---|---|---|---|
| | | FIG. 8 | | | |
| B; tone fear test | RM ANOVA | trial: $F_{5,65} = 4.488$ | =0.001 | | |
| | | stress: $F_{1,13} = 5.037$ | =0.043 | | |
| | | X: $F_{5,65} = 2.895$ | =0.020 | | |
| | Bonferroni | trace1: $t_{1,78} = 2.376$ | =0.020 | −61.24−−5.404 | |
| | | trace2: $t_{1,78} = 2.467$ | =0.016 | −62.51−−6.675 | |
| | | trace3: $t_{1,78} = 3.352$ | =0.001 | −74.92−−19.09 | |
| C; looming (1$^{st}$) | RM ANOVA | time: $F_{1,9} = 18.78$ | =0.002 | | |
| | | stress: $F_{1,9} = 10.64$ | =0.010 | | |
| | Bonferroni | post: $t_{1,18} = 2.95$ | <0.05 | −65.71−−6.128 | |
| D; tone fear (1$^{st}$) | RM ANOVA | time: $F_{1,14} = 27.08$ | =0.0001 | | |
| | | X: $F_{1,14} = 5.44$ | =0.035 | | |
| | Bonferroni | post: $t_{1,28} = 3.04$ | <0.05 | −56.73−−7.083 | |
| E; tail rattles | unpaired t-test | $t_{1,24} = 2.276$ | =0.039 | 0.129-4.371 | 0.27 |
| G; rat exposure | RM ANOVA | zone: $F_{2,16} = 9.563$ | =0.002 | | |
| | Bonferroni | group; rat vs. far: $t_{1,16} = 5.45$ | <0.001 | −274.7−−93.91 | |
| | | group; center vs. far: $t_{1,16} = 4.56$ | <0.001 | −244.6−−63.82 | |
| H; flinch voc. jump | unpaired t-test | flinch: $t_{1,14} = 2.688$ | =0.018 | −0.090−−0.010 | 0.340 |
| I; acoustic startle | RM ANOVA | trial: $F_{7,98} = 40.43$ | <0.0001 | | |
| | | stress: $F_{1,14} = 6.905$ | =0.020 | | |
| | Fisher's LSD | 95: $t_{1,112} = 2.019$ | =0.046 | −596.1−−5.656 | |
| | | 109: $t_{1,112} = 2.138$ | =0.035 | −613.7−−23.28 | |
| | | 115: $t_{1,112} = 2.64$ | =0.001 | −688.6−−98.16 | |
| | | 124: $t_{1,112} = 2.482$ | =0.015 | −665−−74.53 | |
| J; social interaction | RM ANOVA | zone: $F_{2,28} = 4.608$ | =0.019 | | |
| | | X: $F_{2,28} = 2.282$ | =0.024 | | |
| | Bonferroni | mouse zone: $t_{1,42} = 2.743$ | =0.027 | 6.909-144.9 | |
| J; latency | unpaired t-test | $t_{1,8} = 2.376$ | =0.045 | −28.59−−0.430 | 0.414 |
| | | FIG. 9 | | | |
| B; Tac2-Cre; Ai6-zsGreen | unpaired t-test | dBNSTa; cells: $t_{1,17} = 7.22$ | <0.0001 | 141.1-257.6 | 0.754 |
| | | inten: $t_{1,17} = 11.50$ | <0.0001 | 50.20-72.76 | 0.886 |
| | | DMH; cells: $t_{1,30} = 5.934$ | <0.0001 | 58.14-119.2 | 0.54 |
| | | inten: $t_{1,30} = 20.19$ | <0.0001 | 62.73-76.84 | 0.931 |
| | | CeA; cells: $t_{1,21} = 5.161$ | <0.0001 | 77.50-182.1 | 0.559 |
| | | inten: $t_{1,20} = 9.402$ | <0.0001 | 39.89-62.63 | 0.816 |
| | | ACC; cells: $t_{1,17} = 21.49$ | <0.0001 | 641.8-781.5 | 0.965 |
| | | inten: $t_{1,17} = 23.48$ | <0.0001 | 74.87-89.66 | 0.97 |
| F; Tac2 qRTPCR | OW ANOVA | dBNSTa: $F_{3,12} = 2.194$ | =0.142 | | 0.354 |
| | Fisher's LSD | Group vs. 2w: $t_{1,12} = 2.474$ | =0.029 | | |
| | OW ANOVA | DMH: $F_{3,12} = 3.034$ | =0.071 | | 0.431 |
| | Fisher's LSD | Group vs. 2w: $t_{1,12} = 2.808$ | =0.0158 | | |
| | OW ANOVA | CeA: $F_{3,12} = 2.251$ | =0.135 | | 0.36 |
| | Fisher's LSD | Group vs. 2w: $t_{1,12} = 2.271$ | =0.042 | | |
| | OW ANOVA | ACC: $F_{3,12} = 0.706$ | =0.567 | | 0.15 |
| | Fisher's LSD | Group vs. 2w: $t_{1,12} = 1.330$ | =0.208 | | |
| H; Tac2 CeA FISH | TW ANOVA | stress: $F_{1,67} = 9.987$ | =0.002 | | |
| | Fisher's LSD | CeM: $t_{1,67} = 2.018$ | =0.048 | −399.9−−2.191 | |
| | | CeL: $t_{1,67} = 2.103$ | =0.039 | −425.9−−11.12 | |

TABLE 2-continued

| | STATISTICAL ANALYSES | | | | |
|---|---|---|---|---|---|
| FIGURE/ASSAY | TEST | F, t VALUE | p VALUE | CI | $\eta^2$ |
| I; NkB staining | TW ANOVA | stress: $F_{1,17} = 59.26$ | <0.0001 | | |
| | | region: $F_{2,17} = 8.602$ | =0.0026 | | |
| | Bonferroni | dBNSTa: $t_{1,17} = 4.182$ | <0.01 | −52.09−−11.63 | |
| | | DMH: $t_{1,17} = 4.561$ | <0.001 | −52.16−−13.78 | |
| | | CeA: $t_{1,17} = 4.619$ | <0.001 | −64.00−−17.28 | |
| | | FIG. 10 | | | |
| G; tail rattles | OW ANOVA | $F_{3,20} = 3.247$ | 0.044 | | 0.328 |
| | Bonferroni | veh; group vs SIS: $t_{1,20} = 2.59$ | <0.05 | −6.129−−0.205 | |
| | | SIS: veh vs osan: $t_{1,20} = 2.454$ | <0.05 | 0.038-5.962 | |
| H; social interaction | OW ANOVA | $F_{3,20} = 2.981$ | 0.056 | | 0.309 |
| | Bonferroni | veh; group vs SIS: $t_{1,20} = 2.334$ | 0.030 | 9.423-168 | |
| | | SIS: veh vs osan: $t_{1,20} = 2.688$ | 0.014 | −181.5−−22.91 | |
| I; acoustic startle | RM ANOVA | time: $F_{7,140} = 28.12$ | <0.0001 | | |
| | Bonferroni | 124 dB: veh; SIS vs group: $t_{1,160} = 2.704$ | <0.05 | 47.76-858.6 | |
| | | 124 dB: SIS; veh vs osan: $t_{1,160} = 2.943$ | <0.05 | 87.76-898.6 | |
| M; looming disk | RM ANOVA | time: $F_{1,16} = 28.23$ | <0.0001 | | |
| | | osan: $F_{1,16} = 12.64$ | =0.0026 | | |
| | | X: $F_{1,16} = 24.3$ | =0.0002 | | |
| | Bonferroni | post: $t_{1,32} = 5.767$ | <0.0001 | 33.78-80.3 | |
| | | FIG. 11 | | | |
| E; latency to orient | unpaired t-test | $t_{1,10} = 2.33$ | 0.042 | 0.2-8.937 | 0.352 |
| H; footshock CeA | unpaired t-test | $t_{1,11} = 4.201$ | 0.002 | −331−−103.4 | 0.616 |
| | | FIG. 12 | | | |
| B; cfos dBNSTa | OW ANOVA | $F_{4,94} = 48.27$ | <0.0001 | | 0.673 |
| | Bonferroni | HC: GH vs SIS: $t_{1,94} = 1.244$ | >0.05 | −7.542-21.94 | |
| | | SIS: HC vs LD: $t_{1,94} = 9.377$ | <0.0001 | −63.47−−36.36 | |
| | | SIS: HC vs FC: $t_{1,94} = 8.528$ | <0.0001 | −76.92−−41.54 | |
| C; cfos DMH | OW ANOVA | $F_{4,98} = 19.34$ | <0.0001 | | 0.441 |
| | Bonferroni | HC: GH vs SIS: $t_{1,98} = 2.188$ | >0.05 | | |
| | | SIS: HC vs RI: $t_{1,98} = 6.219$ | <0.0001 | −38.2−−16.02 | |
| D; cfos CeA | OW ANOVA | $F_{4,101} = 25.45$ | <0.0001 | | 0.502 |
| | Bonferroni | HC: GH vs SIS: $t_{1,101} = 1.243$ | >0.05 | −7.8-22.72 | |
| | | SIS: HC vs LD: $t_{1,101} = 3.239$ | <0.01 | −35.21−−4.239 | |
| | | SIS: HC vs FC: $t_{1,101} = 7.913$ | <0.0001 | −65.79−−33.79 | |
| H; footshock CeA | unpaired t-test | $t_{1,14} = 2.68$ | 0.018 | −355.8−−39.48 | 0.339 |
| N; tone fear test | RM ANOVA | time: $F_{1,22} = 32.77$ | <0.0001 | | |
| | | group: $F_{3,22} = 10.73$ | =0.0002 | | |
| | | X: $F_{3,22} = 3.16$ | =0.045 | | |
| | Bonferroni | CNO; mCherry vs. hM4D: $t_{1,44} = 5.014$ | <0.0001 | 23.10-79.78 | |
| | | hM4D; veh vs. CNO: $t_{1,44} = 4.92$ | <0.0001 | 22.97-81.79 | |

TABLE 2-continued

STATISTICAL ANALYSES

| FIGURE/ASSAY | TEST | F, t VALUE | p VALUE | CI | $\eta^2$ |
|---|---|---|---|---|---|
| FIG. 13 | | | | | |
| C; footshock CeA | OW ANOVA Bonferroni | $F_{2,14} = 6.064$<br>con vs shRNA2:<br>$t_{1,14} = 3.455$ | 0.013<br><0.01 | <br>112.6-710.4 | 0.464 |
| E; Tac2 mRNA dBNSTa: FISH cells | OW ANOVA Bonferroni | $F_{2,27} = 183.8$<br>con vs shRNA-1:<br>$t_{1,27} = 13.69$<br>con vs shRNA-2:<br>$t_{1,27} = 18.47$<br>shRNA-1 vs shRNA-2:<br>$t_{1,27} = 4.781$ | <0.0001<br><0.0001<br><br><0.0001<br><br><0.001 | <br>117.4 to 171.2<br><br>167.8 to 221.6<br><br>23.49 to 77.31 | 0.932 |
| E; Tac2 mRNA dBNSTa:FISH inten | OW ANOVA Bonferroni | $F_{2,168} = 68.24$<br>con vs shRNA-1:<br>$t_{1,168} = 8.486$<br>con vs shRNA-2:<br>$t_{1,168} = 10.73$ | <0.0001<br><0.0001<br><br><0.0001 | <br>3.93-7.062<br><br>5.284-8.358 | 0.448 |
| E; Tac2 mRNA dBNSTa: qRTPCR | OW ANOVA Fisher's LSD | $F_{2,5} = 4.113$<br>con vs shRNA-2:<br>$t_{1,5} = 2.733$ | =0.088<br>=0.041 | | 0.622 |
| F; Tac2 mRNA DMH: FISH cells | OW ANOVA Bonferroni | $F_{2,51} = 32.65$<br>con vs shRNA-1:<br>$t_{1,51} = 5.947$<br>con vs shRNA-2:<br>$t_{1,51} = 7.529$ | <0.0001<br><0.0001<br><br><0.0001 | <br>19.86-48.18<br><br>29.40-58.21 | 0.562 |
| F; Tac2 mRNA DMH: FISH inten | OW ANOVA Bonferroni | $F_{2,75} = 27.47$<br>con vs shRNA-1:<br>$t_{1,75} = 4.235$<br>con vs shRNA-2:<br>$t_{1,75} = 7.386$<br>shRNA-1 vs shRNA-2: $t_{1,75} = 3.151$ | <0.0001<br><0.001<br><br><0.0001<br><br><0.01 | <br>4.334-14.51<br><br>11.34-21.52<br><br>2.577-11.44 | 0.423 |
| F; Tac2 mRNA DMH: qRTPCR | OW ANOVA Bonferroni | $F_{2,5} = 47.44$<br>con vs shRNA-2:<br>$t_{1,5} = 9.172$<br>shRNA-1 vs shRNA-2:<br>$t_{1,5} = 8.126$ | =0.0006<br><0.001<br><br><0.01 | <br>0.476-1.074<br><br>0.388-0.985 | 0.95 |
| G; Tac2 mRNA CeA: FISH cells | OW ANOVA Bonferroni | $F_{2,47} = 39.04$<br>con vs shRNA-1:<br>$t_{1,47} = 6.827$<br>con vs shRNA-2:<br>$t_{1,47} = 8.39$ | <0.0001<br><0.0001<br><br><0.0001 | <br>79.71-170.8<br><br>101.4-186.6 | 0.624 |
| G; Tac2 mRNA DMH: FISH inten | OW ANOVA Bonferroni | $F_{2,102} = 30.68$<br>con vs shRNA-1:<br>$t_{1,102} = 4.919$<br>con vs shRNA-2:<br>$t_{1,102} = 7.54$ | <0.0001<br><0.0001<br><br><0.0001 | <br>7.248-19.72<br><br>12.77-23.80 | 0.376 |
| G; Tac2 mRNA DMH: qRTPCR | OW ANOVA Bonferroni | $F_{2,6} = 40.01$<br>con vs shRNA-2:<br>$t_{1,6} = 8.646$<br>shRNA-1 vs shRNA-2:<br>$t_{1,6} = 6.311$ | =0.0003<br><0.001<br><br><0.01 | <br>0.532-1.184<br><br>0.300-0.953 | 0.93 |

Example 1

This example describes the effect of chronic social isolation stress (SIS) on multiple defensive behaviors.

Figure 8A:
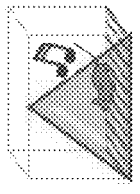
Figure 8C:
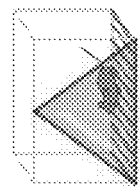
Figure 8E:
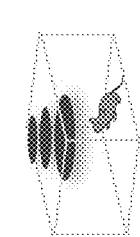
Figure 8B:
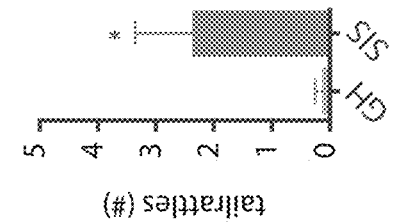
Figure 8D:
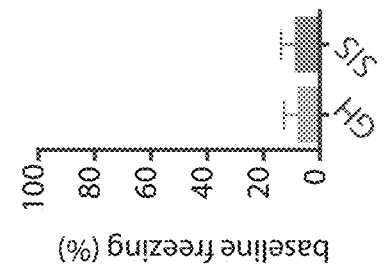
Figure 8F:
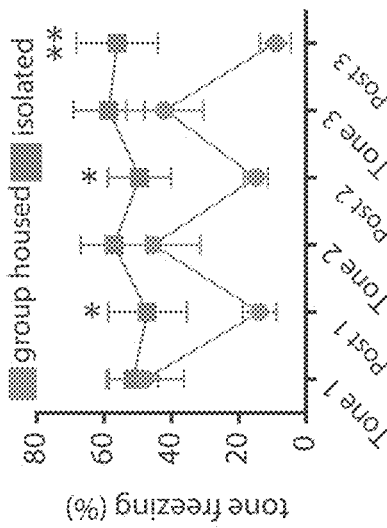

As an initial step, we broadly examined the behavioral effects produced by prolonged social isolation stress (SIS). Wildtype C57B16/N mice were subjected to two weeks of SIS or group housed (GH) with male littermates, and tested in multiple behavioral assays: aggression in the resident intruder assay (Thurmond, 1975; incorporated by reference in its entirety herein), innate freezing to an overhead looming disk (Yilmaz and Meister, 2013; incorporated by reference in its entirety herein), learned freezing to a conditioned tone (2.8 kHz) (Fanselow, 1980; incorporated by reference in its entirety herein), and reactivity to a footshock (0.7 mA) (FIGS. 1E-J and FIGS. 8A-F). Consistent with previous studies (Valzelli, 1969; Matsumoto et al., 2005; Toth et al., 2011; incorporated by reference in their entirety herein), SIS produced a robust increase in offensive aggression towards a submissive intruder, compared to non-aggressive group housed controls (FIGS. 1F-G). The magnitude of acute freezing (during the stimulus) to both the overhead looming disk and the conditioned tone was unaffected by SIS (FIG. 1H, FIG. 1I, during). However, in SIS mice, freezing persisted beyond the termination of the stimulus (FIG. 1H, FIG. 1I, post, dark gray bars labelled "SIS"), in contrast to GH controls where it terminated with stimulus offset. In addition, SIS mice showed significantly enhanced reactivity to a footshock (FIG. 1J) and increased freezing to a threatening ultrasonic stimulus (USS) (Mongeau et al., 2003; incorporated by reference in its entirety herein) (FIGS. 1K-L). SIS mice also exhibited increased tail rattling to the looming disk (FIGS. 8A-B), increased sensitivity to subthreshold acoustic startle stimuli (FIGS. 8G-H), and a decreased latency to flinch to a mild footshock (FIGS. 8I-J).

Mice were also tested for anxiety-like behavior in the open field test (OFT) and the elevated plus maze (EPM) (FIGS. 1M-Q, FIGS. 8K-L). SIS mice showed a modest but significant reduction in time spent in the center of the OFT arena, without a change in velocity (FIGS. 1N-O), but were no different from GH mice in the EPM test (FIGS. 1P-Q). However, SIS mice showed an increased propensity to jump off the EPM platform (FIGS. 8 K-L).

Lastly, mice were tested in a 3-chamber social interaction test with a conspecific mouse and in a rat exposure test. SIS mice spent less time interacting with a new mouse in a social interaction assay, although their latency to initially approach the mouse was reduced (FIGS. 8M-P). In addition, SIS mice spent more time closer to a rat than farther away (FIGS. 8Q-R). Collectively, these findings demonstrate that SIS produces penetrant, persistent, and pervasive effects on a variety of behavioral responses to various stimuli (summarized in FIG. 1R). This profile appears behaviorally distinct from that typically indicative of anxiety (Blanchard et al., 2003; Bourin et al., 2007; incorporated by reference in their entirety herein), consistent with earlier studies in mice (Hilakivi et al., 1989; incorporated by reference in its entirety herein). Moreover, the observation that prolonged deprivation of social contact produces effects on subsequent social behavior, such as enhanced aggression, distinguishes SIS from other stressors including short-term social isolation (Matthews et al., 2016; incorporated by reference in its entirety herein), which does not promote aggression in mice.

The data show that, in accordance with some embodiments, chronic social isolation stress (SIS) produces widespread effects on multiple defensive behaviors, including, but not limited to, enhanced aggressiveness towards a submissive intruder, increased freezing, increased sensitivity to the looming disk, increased sensitivity to acoustic startle stimuli, decreased latenency to flinch to a mild footshock, and increased anxiety-like behavior.

Example 2

This example describes the effect of chronic social isolation stress (SIS) on Tac2 transcription.

In *Drosophila*, an unbiased screen of peptidergic neurons identified DTK (*Drosophila* tachykinin)-expressing neurons, and identified the DTK peptide, as required for social isolation-induced aggression (Asahina et al., 2014; incorporated by reference in its entirety herein). To determine whether this role might extend to mammals, we investigated the role of tachykinins in SIS. In rodents, the tachykinin gene family comprises Tac1 and Tac2 (Maggio, 1988; incorporated by reference in its entirety herein). Tac1 encodes the peptides substance P (SP), as well as neurokinin A (NkA); Tac2 encodes neurokinin B (NkB). These peptides bind with the highest affinities to the Nk1, Nk2, and Nk3 receptors, respectively (FIG. 2A) (Ebner et al., 2009; incorporated by reference in its entirety herein). Notably, Tac1 and Tac2 are expressed in a variety of brain regions that have been implicated in emotion and social behavior (FIGS. 2B-C) (Culman and Unger, 1995; incorporated by reference in its entirety herein).

Figures 9A, 9B, 9C, 9D:
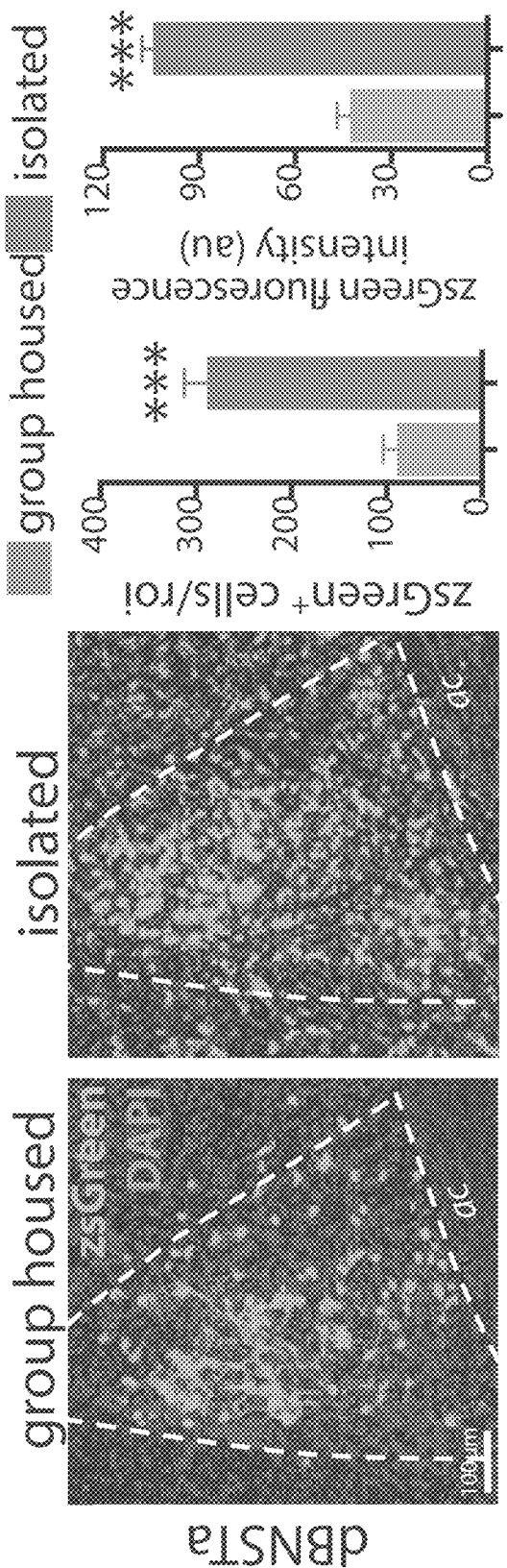
FIGS. 9A-GG show that SIS produces an increase in Tac2 expression in accordance with some embodiments.
FIG. 9D (average fluorescence for regions in FIGS. 9A-B), FIG. 9G (for zsGreen+ cell counts for regions in FIGS. 9E-F), FIG. 9H (average fluorescence for regions in FIGS. 9R-F), FIG. 9K (zsGreen+ cell counts for regions in FIGS. 9I-J), FIG. 9L (average fluorescence for regions in FIGS. 9I-J), FIG. 9O (zsGreen+ cell counts for regions in FIGS. 9M-N), and FIG. 9P (average fluorescence for regions in FIGS. 9H-N). Counts/fluorescence were restricted to each region as outlined (white dashed line). SIS produced significant increases in zsGreen expression across regions. For all panels shown in FIG. 9A, FIG. 9B, FIG. 9E, FIG. 9F, FIG. 9I, FIG. 9J, FIG. 9M, and FIG. 9N, the intensity of fluorescent staining was representative of the quantitations shown in FIG. 9C, FIG. 9D, FIG. 9G, FIG. 9H, FIG. 9K, FIG. 9L, FIG. 9O, and FIG. 9P. For example, greater fluorescent intensity was seen in isolated mice as compared to group housed mice for dBNSTa. DMH, CeA, and ACC, with fluorescent intensity lowest in ACC of group housed mice.
FIG. 9BB quantitates NeuN and zsGreen double staining shown in group housed (GH) and social isolation stress (SIS) mice (See FIG. 9AA, top row of panels).
FIG. 9CC quantitates NFIA and zsGreen double staining shown in group housed (GH) and social isolation stress (SIS) mice (See FIG. 9AA, middle row of panels).
Figure 9H:
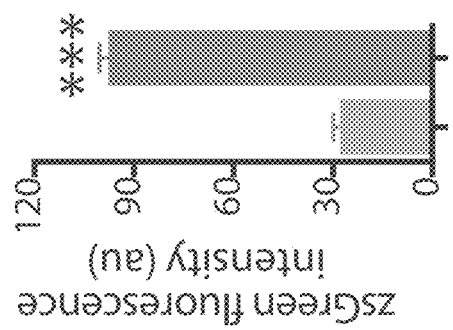
Figure 9G:
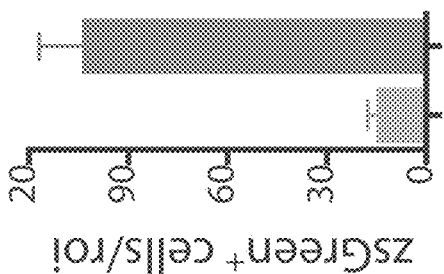
Figure 9F:
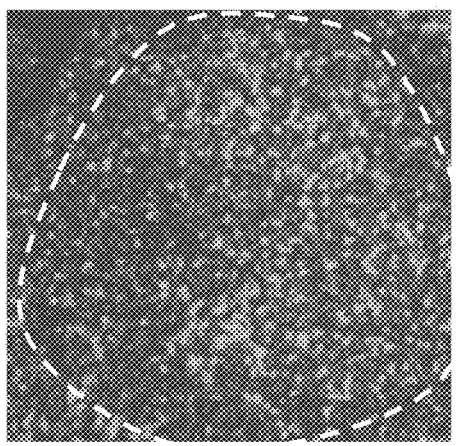
FIGS. 9FF-GG show neurokinin B (NkB)-like immunoreactivity in dBNSTa following 2 weeks of SIS compared to group housing (n=4 mice/condition). Representative confocal image (FIG. 9FF, left) and quantification (FIG. 9GG, right) show elevated signal in SIS mice. BLA, basolateral amygdala. AC, anterior commissure. For the panels shown in FIG. 9FF, the intensity of fluorescent staining was representative of quantitations shown in FIG. 9GG. It is noted that greater fluorescent intensity was seen in isolated mice as compared to group housed mice.
Figure 9E:
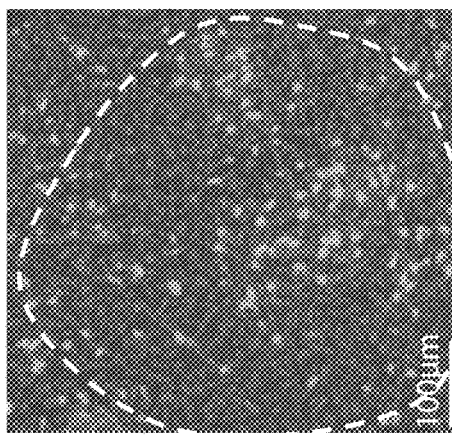
In FIG. 9EE, Tac2-Cre mice were crossed to Ai14-mCherry reporter mice and GH or isolated to confirm that the SIS-induced increase in zsGreen expression was not an artifact due to the reporter mouse (n=4 mice/condition). Representative coronal sections illustrating increased Tac2-mCherry. Robust mCherry staining was seen in isolated mice. By contrast, mCherry staining was weak to undetectable in group housed mice.
Figure 9P:
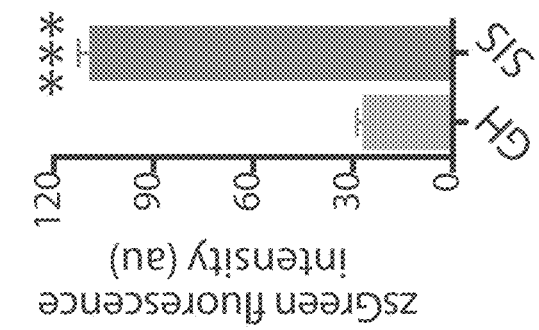
Figure 9O:
Figure 9N:
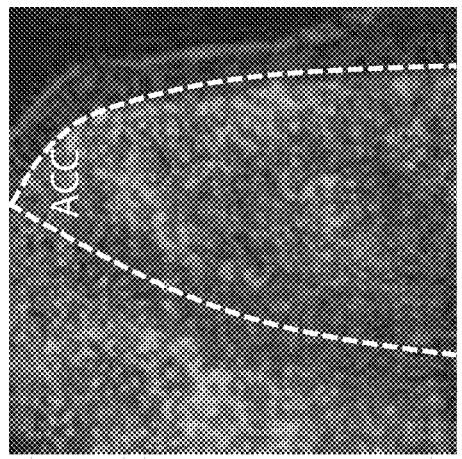
Figure 9M:
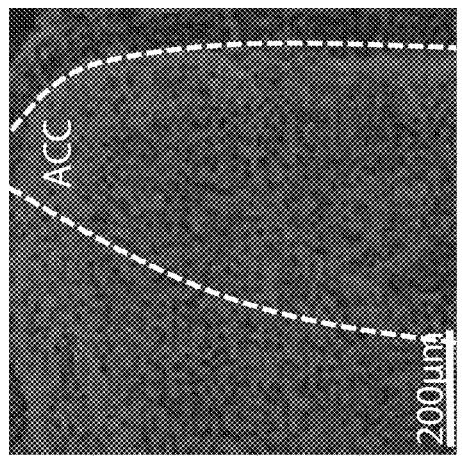
Figure 9Q:
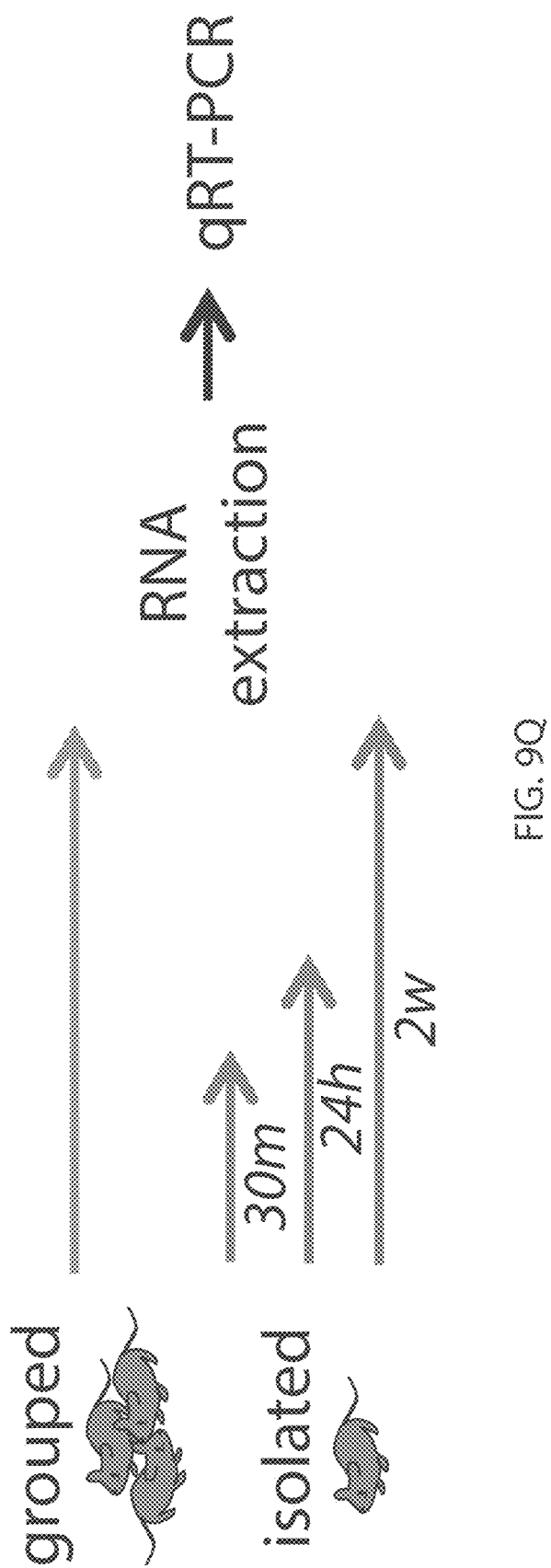
FIG. 9Q shows an experimental schematic. Mice were GH or isolated for 2 weeks, 24 hrs. or 30 minutes (n=4 mice/condition), and tissue for each indicated region was dissected and processed for qRT-PCR analyses.
Figure 9Z:
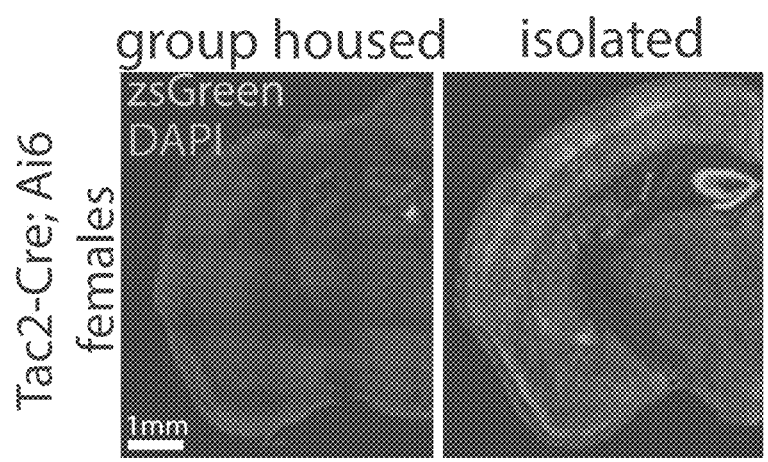
FIG. 9Z shows coronal images of Tac2-Cre; Ai6-zsGreen female mice illustrating that zsGreen expression is increased in females as well as in males (See FIGS. 2A-AA). Greater fluorescent intensity was seen in isolated females as compared to group housed females.
Figure 9A:
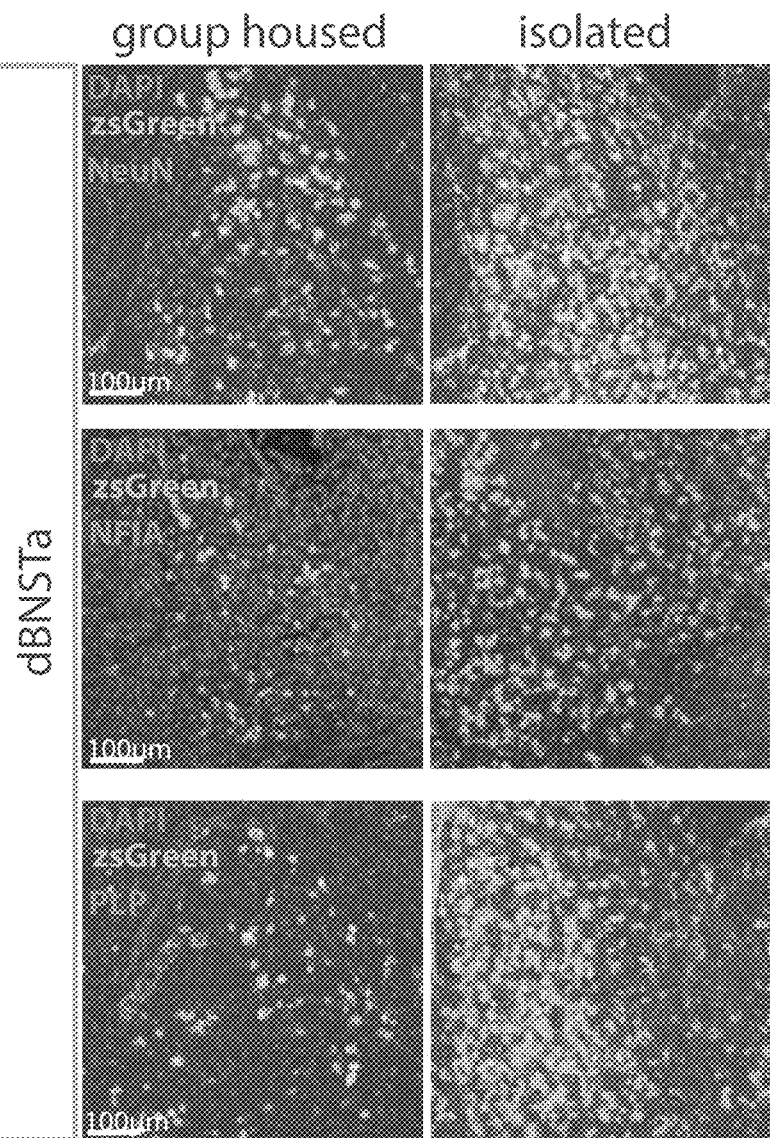
Figure 9B:
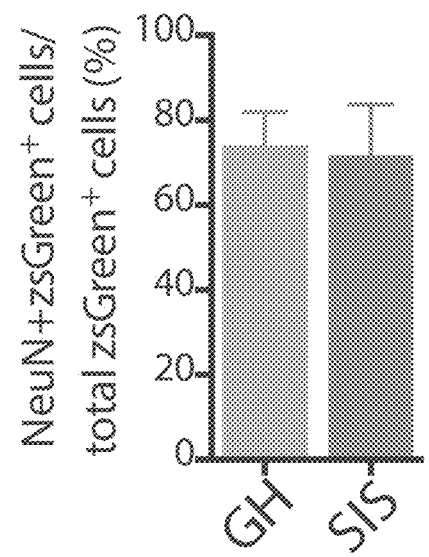
Figure 9C:
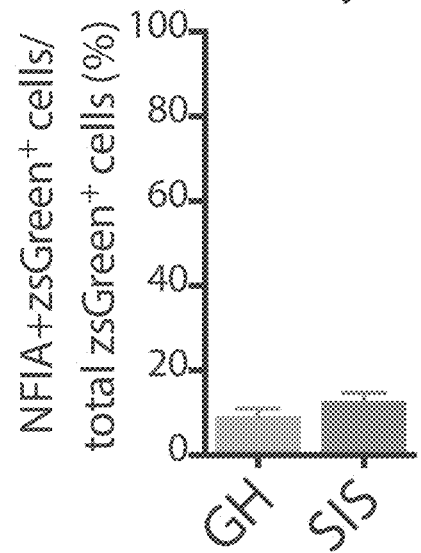
Figure 9D:
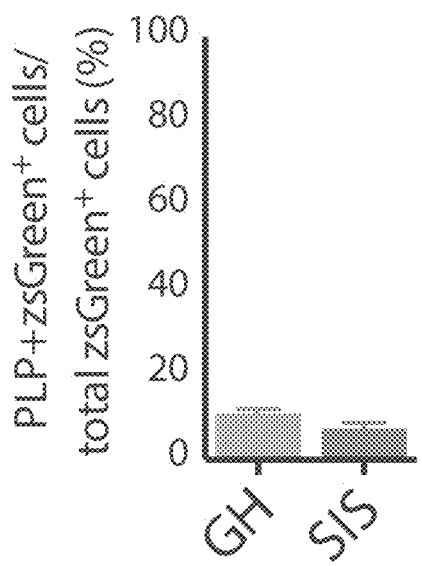

To determine whether Tac expression is affected by SIS, we crossed Tac2-IRES-Cre or Tac1-IRES-Cre knock-in mice (Tasic et al., 2016; incorporated by reference in its entirety herein) to Cre-reporter mice expressing zsGreen from the Rosa-26 locus under control of the ubiquitous CAG promoter-enhancer (line Ai6) (Madisen et al., 2010; incorporated by reference in its entirety herein). Double-heterozygous mice were socially isolated for two weeks or group housed prior to sacrifice. Strikingly, freshly dissected brains from isolated Tac2-Cre; Ai6 mice exhibited broadly enhanced zsGreen expression that could be detected by the naked eye under ambient lighting (FIG. 2D). Sectioning confirmed a widespread increase in zsGreen expression throughout the brain, in both males (FIG. 2F) and females (FIG. 9Z). Induction was apparent in the anterior dorsal bed nucleus of the stria terminalis (dBNSTa), central nucleus of the amygdala (CeA), dorsomedial hypothalamus (DMH), and anterior cingulate cortex (ACC) (FIGS. 9A-P). Counterstaining with neuronal and glia markers indicated that most zsGreen expression occurred in neuronal cells (FIGS. 9AA-DD). Increased zsGreen expression was also detected in peripheral endocrine tissues, such as the pancreas, testes and submandibular gland (not shown).

Similar results were obtained using a different Cre reporter mouse, Ai14 (Madisen et al., 2010; incorporated by reference in its entirety herein) expressing mCherry (FIG. 9EE), indicating that the induction was not a peculiarity of the Ai6 line. Notably, no such change was observed in socially isolated Tac1-Cre; Ai6 mice (FIG. 2E, FIG. 2G). Without being limited by theory, these data suggest that the broad induction of zsGreen observed in SIS mice is specific to the Tac2Cre allele, and is not a non-specific effect of SIS to increase Cre-mediated recombination at the Rosa-26 locus or a peculiarity of the zsGreen reporter.

Figure 2A:
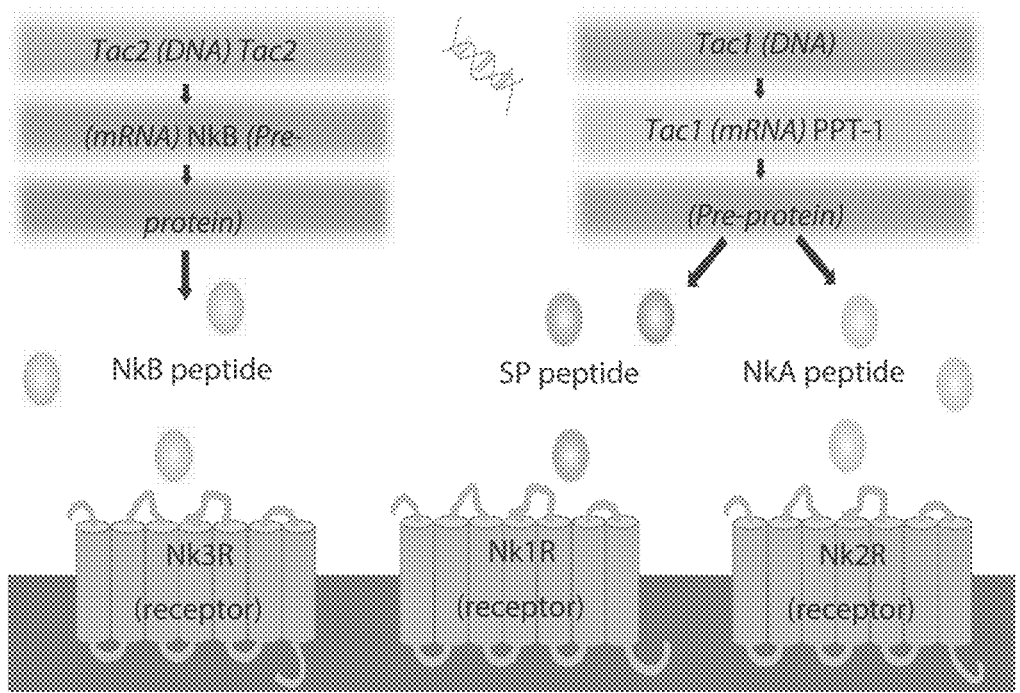
FIGS. 2A-AA show that SIS causes an increase in Tac2 expression in accordance with some embodiments.
Figure 2B:
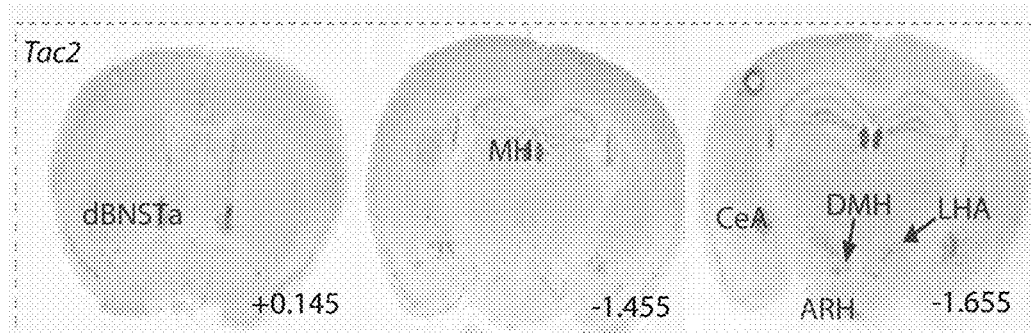
FIGS. 2B-C show Tac2 (top panels) and Tad (bottom panels) mRNA expression (coronal sections) revealed by in situ hybridization (ISH) (data from Mouse Brain Atlas, Allen Institute of Brain Science; Tac2, Exp. 72339556; accessible on the world wide web at mouse-.brain-map.org/experiment/show/72339556; Tac1, Exp.1038; accessible on the world wide web at mouse.brain-map.org/experiment/show/1038). Abbreviations: dBNSTa, antero-dorsal bed nucleus of the stria terminalis; MH, medial habenula; CeA, central amygdala; DMH, dorsomedial hypothalamus; ARH, arcuate nucleus; LHA, lateral hypothalamus; CP, caudate putamen; MeA, medial amygdala; VMH, ventral medial hypothalamus; ZI, zona incerta.
Figure 2C:
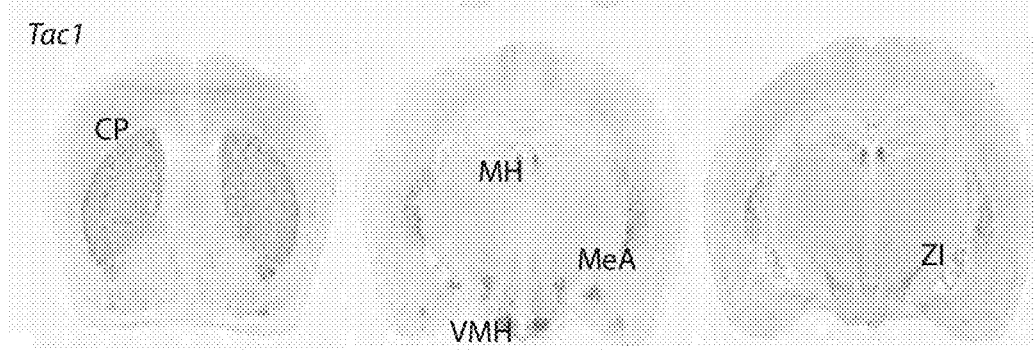
Figure 2R:
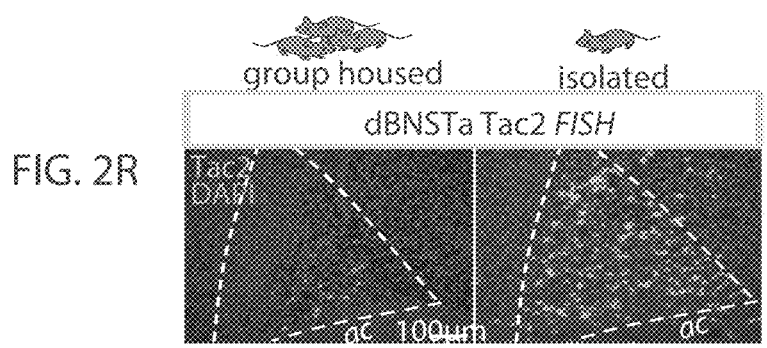
FIGS. 2R-V show Tac2 mRNA detected by FISH in GH or SIS mice in the indicated regions (n=3-4 mice/condition, 1-4 sections/region/mouse); representative sections from each area are shown. Dashed lines indicate regions of interest (ROIs) used for quantification.
Figure 2S:
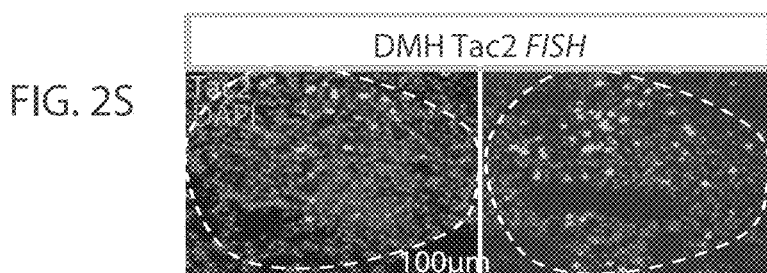
Figure 2T:
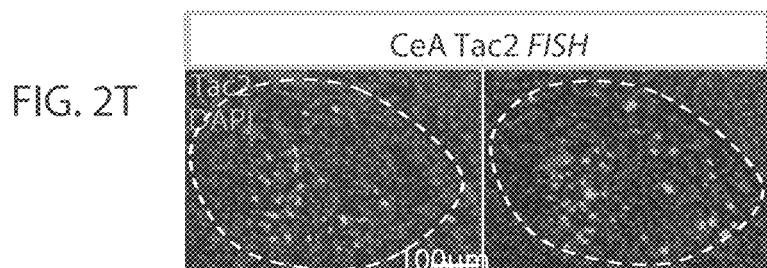
Figure 2U:
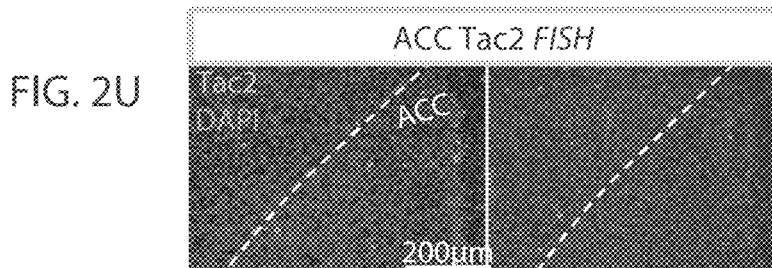
Figure 2V:
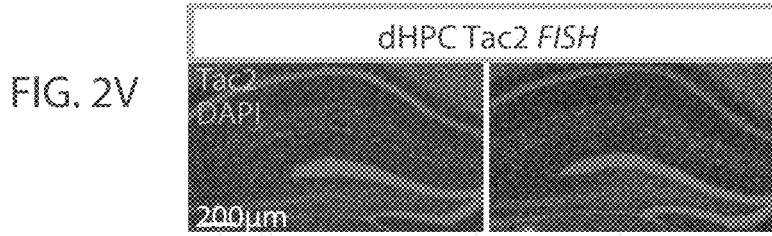
Figure 2W:
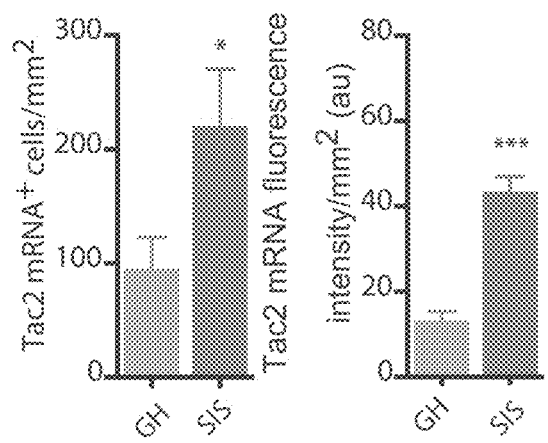
FIGS. 2W-AA show the average number of Tac2 mRNA$^+$ cells/mm$^2$ in ROIs (left) and the average fluorescence intensity/mm$^2$ (right) in the regions shown in FIGS. 2R-V, respectively. Fold-increases in Tac2 mRNA fluorescence intensity are greater than increases in cell number, indicating an increase in expression level per cell. See, also related FIGS. 9A-GG. For all panels shown in FIGS. 2R-V, the intensity of fluorescent staining was representative of the quantitations shown in FIGS. 2W-AA. Greater fluorescent intensity was seen in isolated mice as compared to group housed mice for dBNSTa, DMH, and CeA, while fluorescent intensity was comparably low for isolated and group housed mice in ACC and dHPC.
Figure 2X:
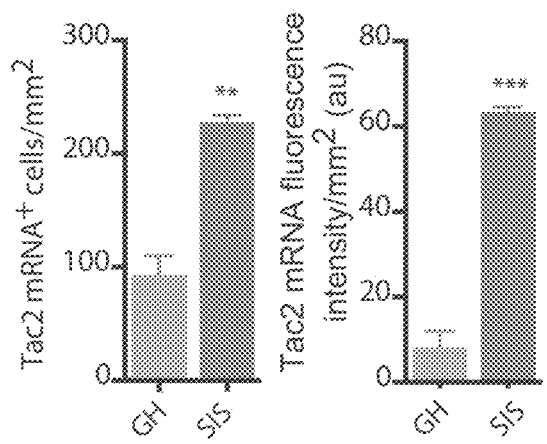
FIGS. 2D-G show expression of zsGreen in GH vs. 2 week-isolated Tac2-Cre (FIG. 2D, FIG. 2F) or Tac1-Cre (FIG. 2E, FIG. 2G) mice crossed to Ai6 (zsGreen) Cre reporter mice. Intact brains under ambient light (FIG. 2D, FIG. 2E) or coronal sections (FIG. 2F, FIG. 2G) are shown.
FIGS. 2H-Q show quantification of Tac2 or Tac1 mRNAs by qRT-PCR in the indicated regions, hand-dissected from the brains of GH or SIS mice (n=4 mice/condition).
Figure 2Y:
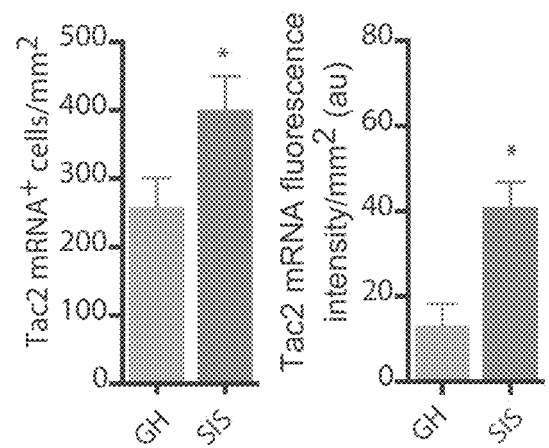
Figure 2Z:
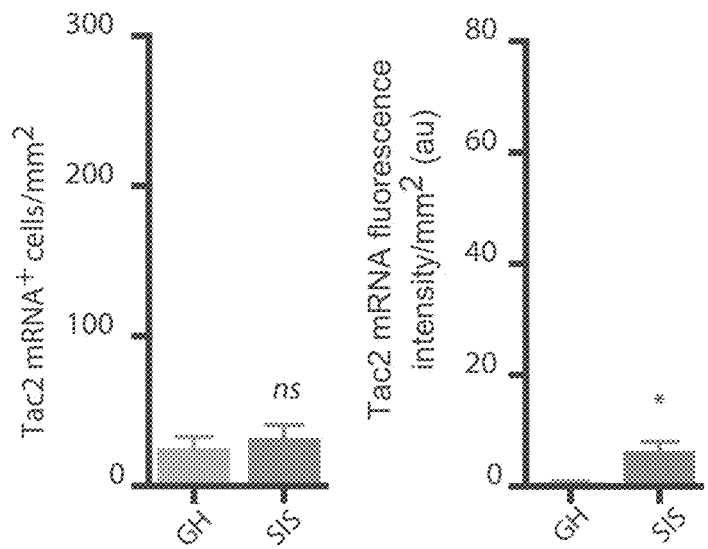
Figure 2A:
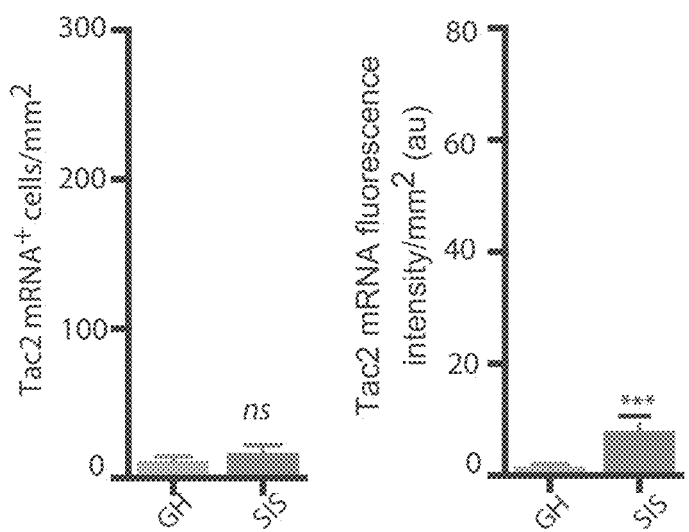

To confirm that SIS up-regulated endogenous Tac2 expression, we quantified Tac2 mRNA in selected brain regions from SIS or GH wild-type mice, using qRT-PCR. QRT-PCR analyses indicated that SIS caused a large (~3-8-fold) and statistically significant increase in Tac2 mRNA levels in the dBNSTa, DMH and CeA, with trends that did not reach significance observed in the ACC and dHPC (FIGS. 2H-L). A time-course revealed an increase in Tac2 mRNA from 30 min to 2 weeks of SIS (FIGS. 9Q-U). No increase in Tac1 mRNA was observed in these regions (FIG. 2M-Q, FIG. 9V-Y). An increase in NkB protein expression was also observed in the dBNSTa by immunostaining (FIGS. 9FF-GG). Endogenous Tac2 mRNA up-regulation was also observed in wild-type mice in dBNSTa, CeA and DMH using RNA fluorescent in situ hybridization (FISH) (FIGS. 2R-T). The fold-increase in fluorescence intensity per mm2 was much greater than the fold-increase in the number of Tac2 mRNA+ cells (FIGS. 2W-Y), suggesting a broad increase in expression per cell, rather than in the number of strongly positive cells. This likely explains why the Cre reporter mouse, which integrates and amplifies expression, yielded a larger fold-increase in the number of positive cells (FIGS. 9A-P). This difference was particularly evident in the ACC or dHPC, where the intensity of Tac2 mRNA FISH signal increased only slightly but a pronounced increase in the number of zsGreen+ cells was observed (FIGS. 2U-V, FIGS. 2Z-AA and FIGS. 9A-P). Despite these quantitative differences between methods, the data indicate that SIS up-regulates Tac2 mRNA expression in multiple brain regions.

In sum, the data show that, in accordance with some embodiments, chronic social isolation stress (SIS) causes widespread upregulation of Tac2 but not Tac1 transcription.

Example 3

This example shows the effect of acute systemic antagonism on the effects of social isolation stress (SIS).

Figure 3A:
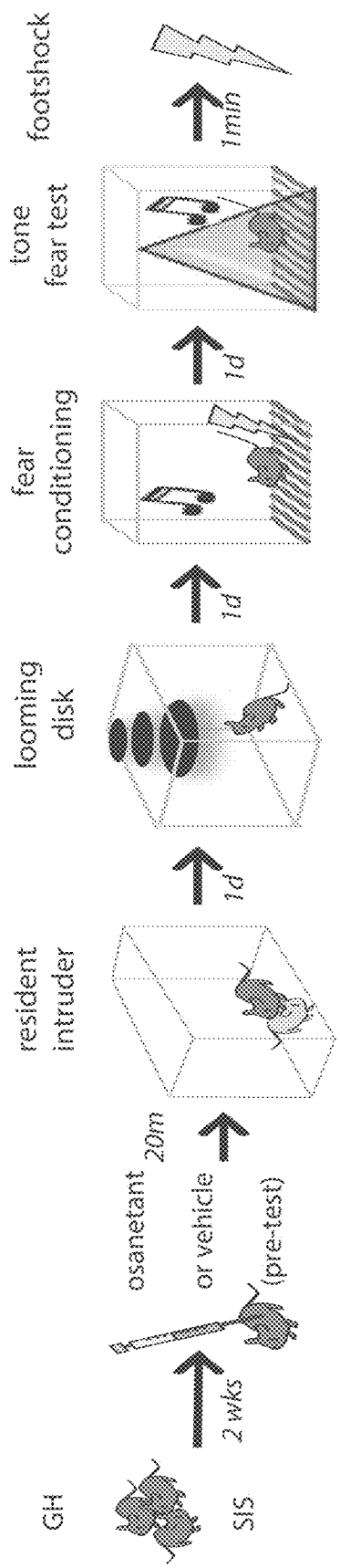
Figures 3B, 3C, 3D:
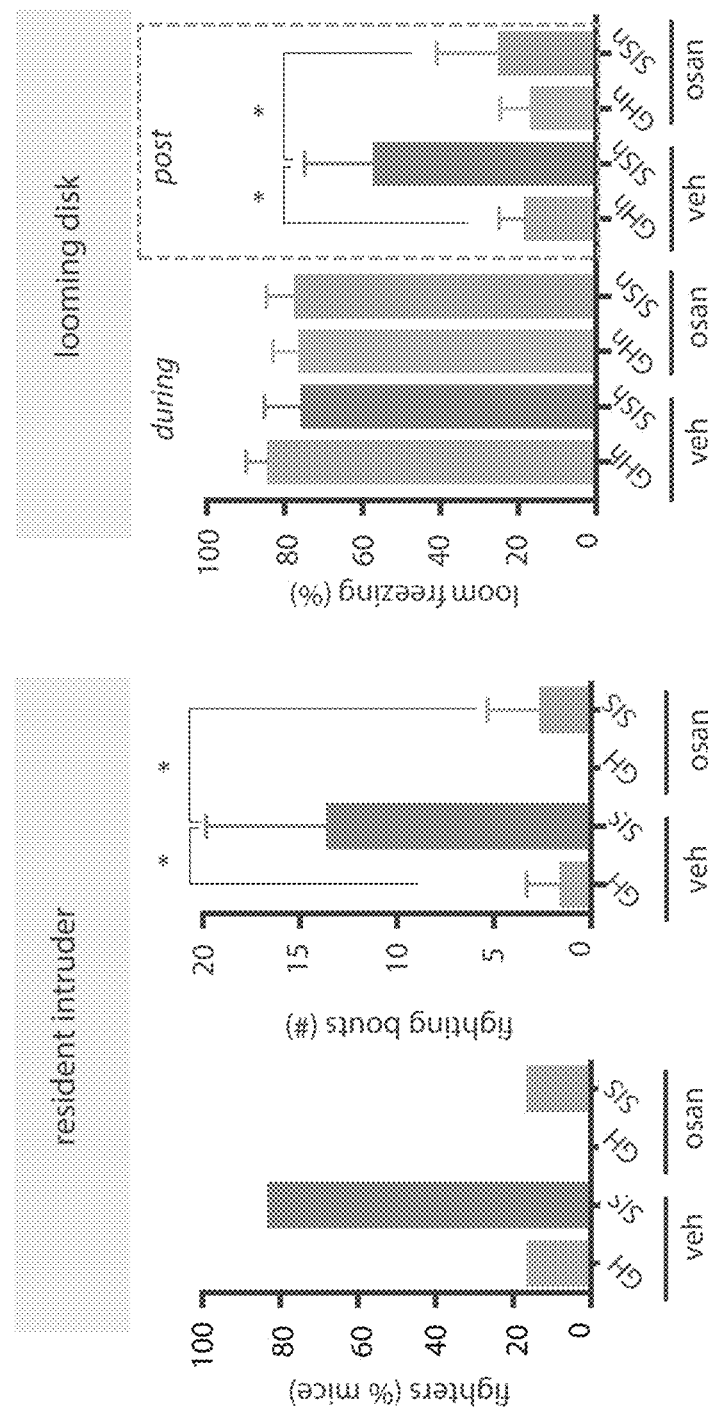
Figures 3E, 3F:
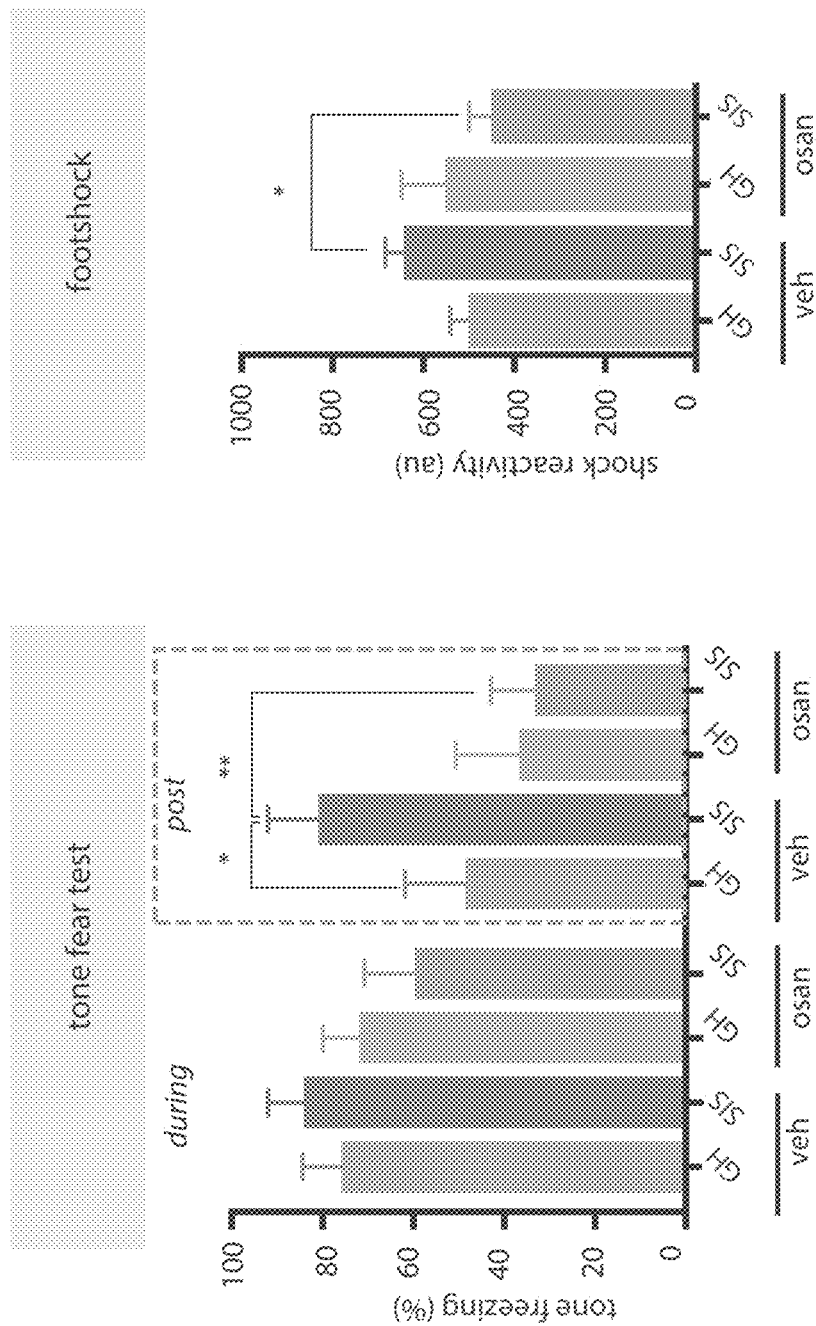
Figure 10A:
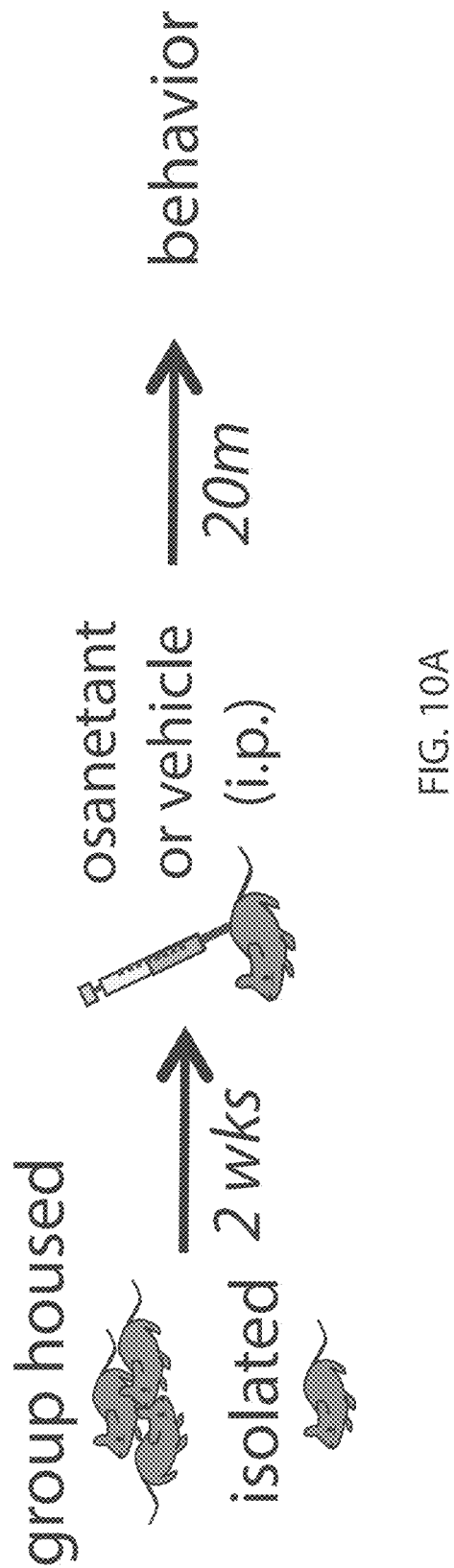
FIGS. 10A-J show the effects of systemic acute osanetant on behavior in some embodiments.
Figure 10B:
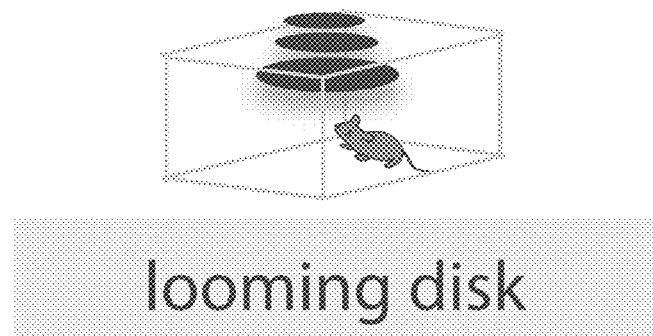
Figure 10C:
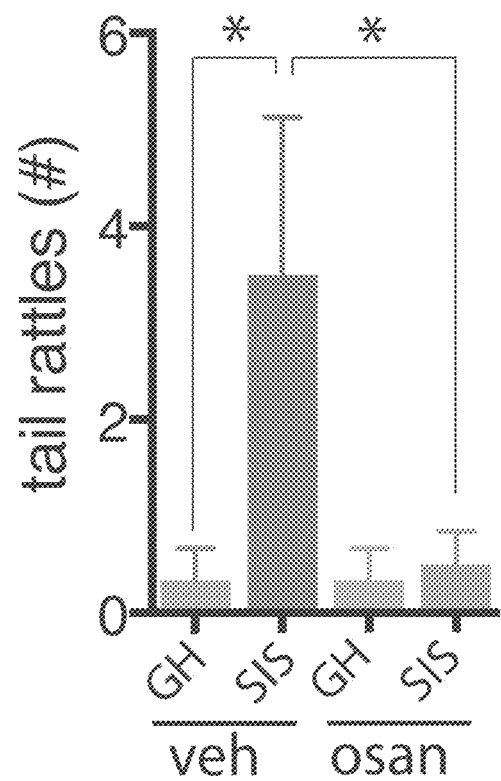
Figure 10D:
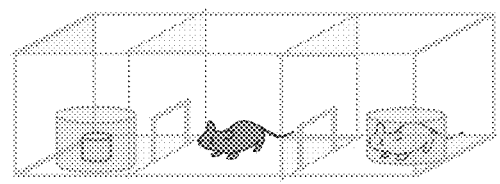
Figure 10E:
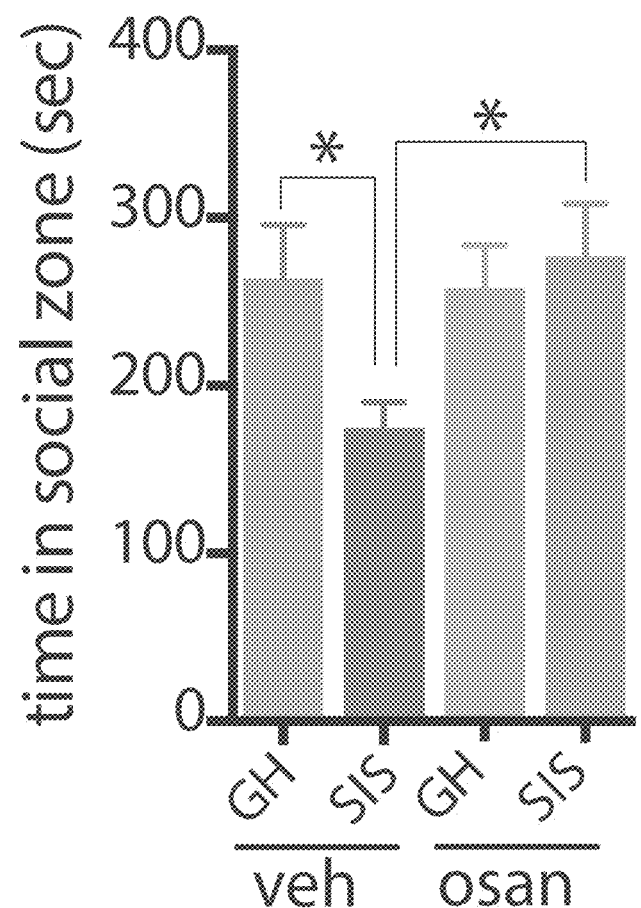
Figure 10F:
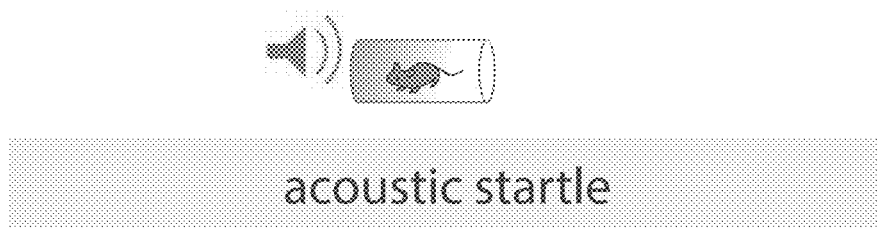
Figure 10G:
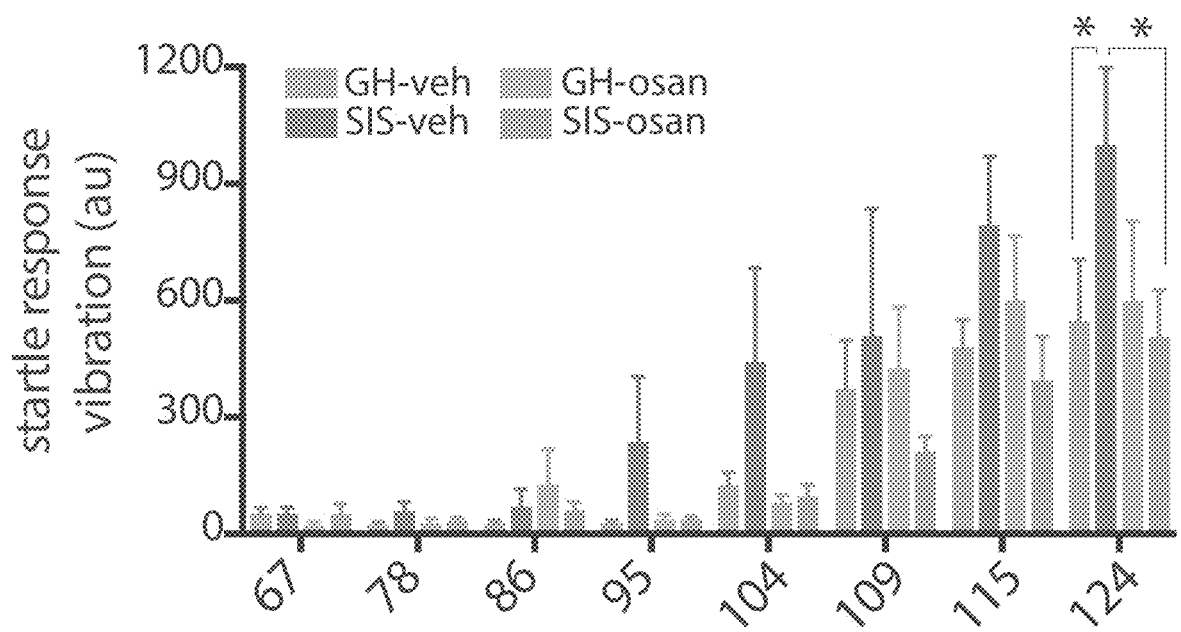
Figure 10H:
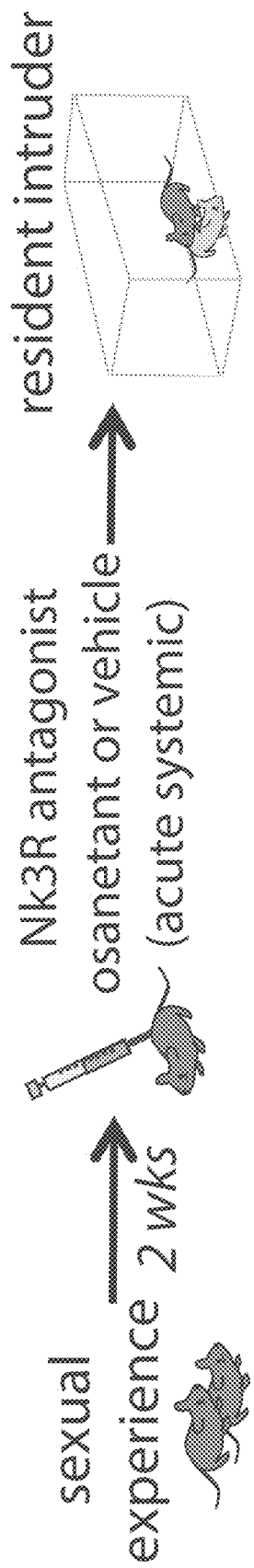
Figure 10I:
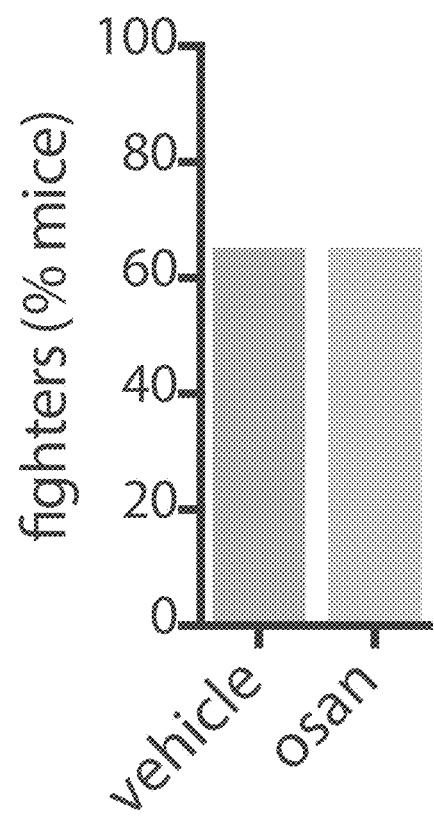
Figure 10J:
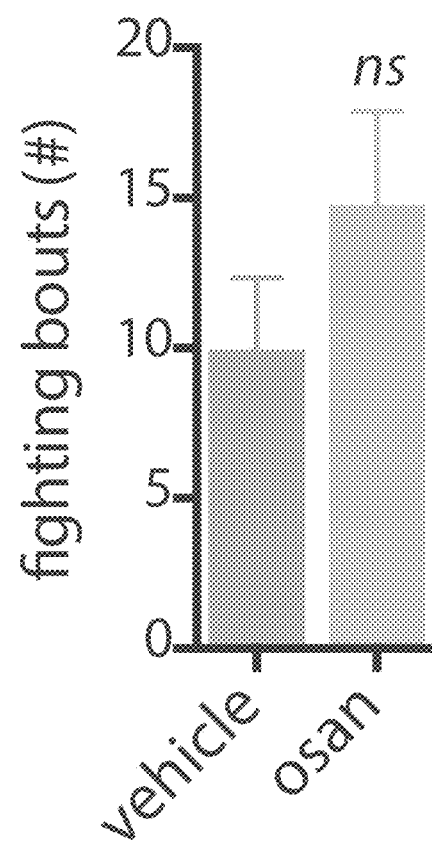

As a first step to investigate whether the induction of Tac2 expression reflects a causal role for this peptide in mediating the behavioral effects of SIS, we inhibited NkB signaling by systemic administration of osanetant (FIG. 3A) (Emonds-Alt et al., 1995; incorporated by reference in its entirety herein), a specific Nk3R antagonist that crosses the blood-brain barrier (Spooren et al., 2005; incorporated by reference in its entirety). Osanetant (5 mg/kg) administered 20 minutes prior to each behavioral assay strongly reduced SIS-enhanced aggression (FIGS. 3B-C), but had no effect on aggression promoted by sexual experience (Remedios et al., 2017; incorporated by reference in its entirety herein) (FIGS. 10H-J). Osanetant also attenuated the SIS-induced enhancement of persistent freezing to both the looming disk and the fear-conditioned tone (FIG. 3D, FIG. 3E, post). There were no significant differences between groups during the presentation of these threatening stimuli. Osanetant also blocked other SIS-induced alterations in behavior including increased shock reactivity (FIG. 3F), increased tail-rattling (FIGS. 10 B-C), decreased social interaction (FIGS. 10 D-E) and enhanced responding in the acoustic startle assay (FIGS. 10 F-G). Thus, systemic antagonism of Nk3Rs administered prior to testing was able to block virtually all of the measured behavioral effects of chronic SIS, while leaving other, non-SIS altered behaviors (e.g. acute freezing, sexual-experience-dependent aggression) intact.

The data show that acute systemic antagonism attenuates the effects of SIS, including, but not limited to, SIS-enhanced aggression, SIS-induced enhancement of persistent freezing, increased shock reactivity, increased tail rattling, decreased social interaction, and enhanced responses in the acoustic startle assay.

Example 4

This example shows the protective effect of chronic systemic antagonism of Nk3Rs during social isolation stress (SIS).

Figure 3G:
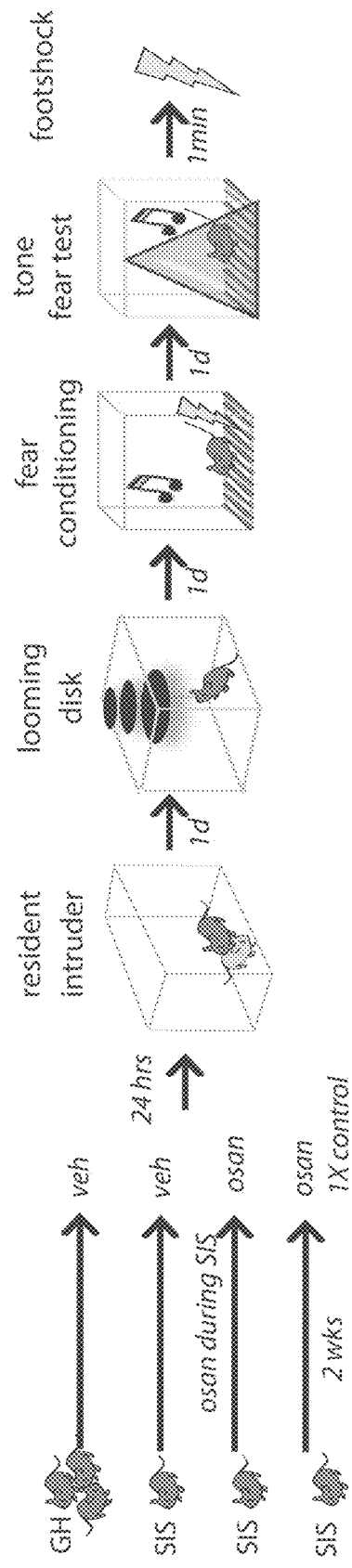

We asked whether Tac2 signaling is required during the period of social isolation to observe the changes in behavior. Mice were administered osanetant daily in their home cage during the two-week social isolation period, but were then tested off-drug. To control for carry-over of the drug from the final homecage administration into the testing period (24 hrs later), an additional group of mice was subjected to two weeks of SIS without drug, and given a single home-cage administration of osanetant 24 hours prior to testing (FIG. 3G).

Figure 3K:
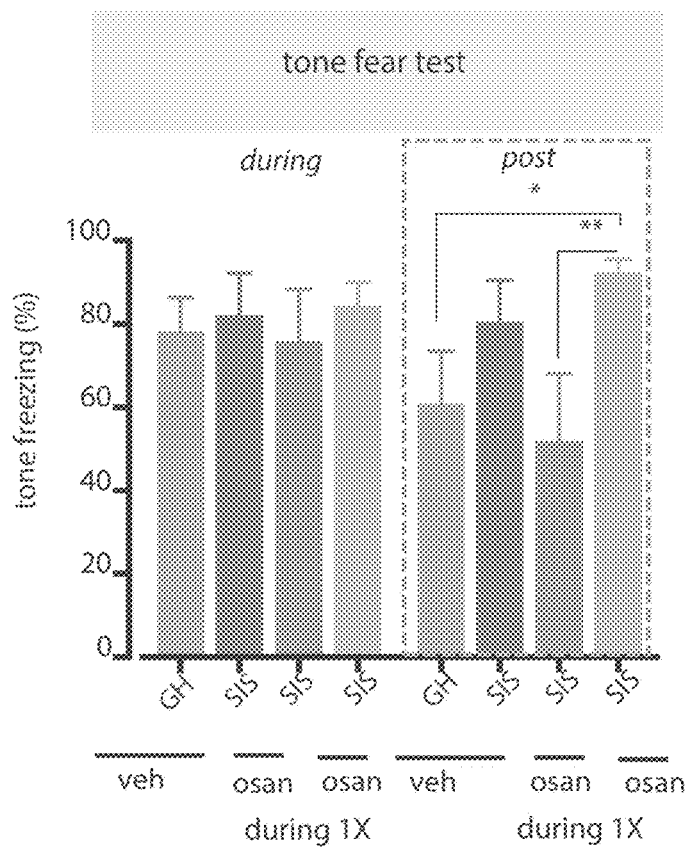
Figure 3L:
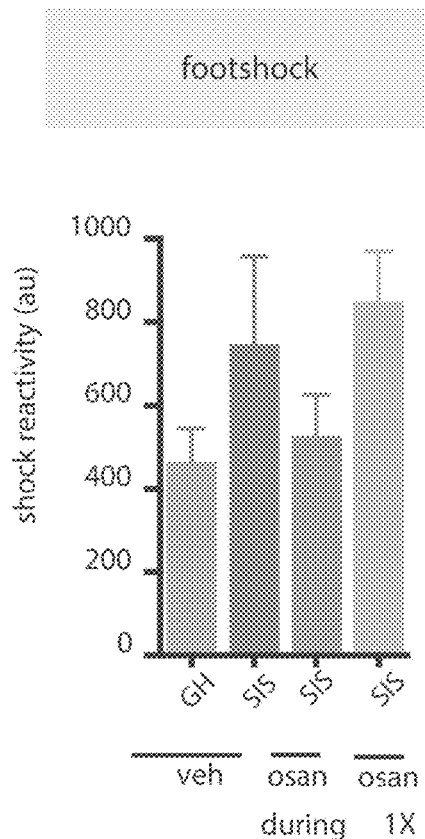
Figure 3M:
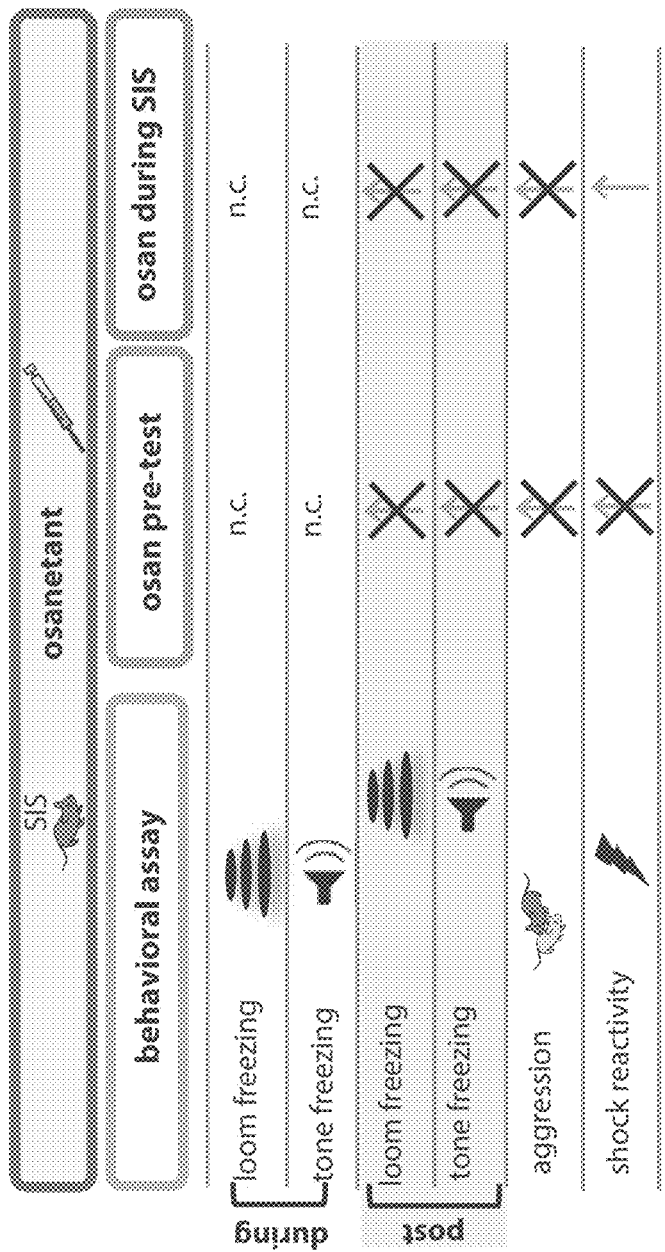

Remarkably, treatment with daily osanetant during isolation prevented SIS-enhanced aggression (FIGS. 3H-I), persistent freezing to the looming disk (FIG. 3J), and persistent freezing to the fear conditioned tone (FIG. 3K). The SIS-induced increase in shock reactivity was reduced, but not significantly (FIG. 3L, FIG. 3M). Mice that had been treated with osanetant during SIS could be returned to housing with their pre-isolation cagemates without any subsequent fighting observed, in contrast to control SIS mice which vigorously attacked their cagemates when reintroduced to the group (data not shown).

The data show that, in accordance with some embodiments, chronic systemic antagonism of Nk3Rs during SIS has a protective effect by preventing SIS-enhanced aggression and presistent freezing behaviors.

Example 5

This example shows the role of Nk3Rs in dBNSTa, CeA, and DMH in mediating the effects of social isolation stress (SIS) on different behaviors.

Figure 4A:
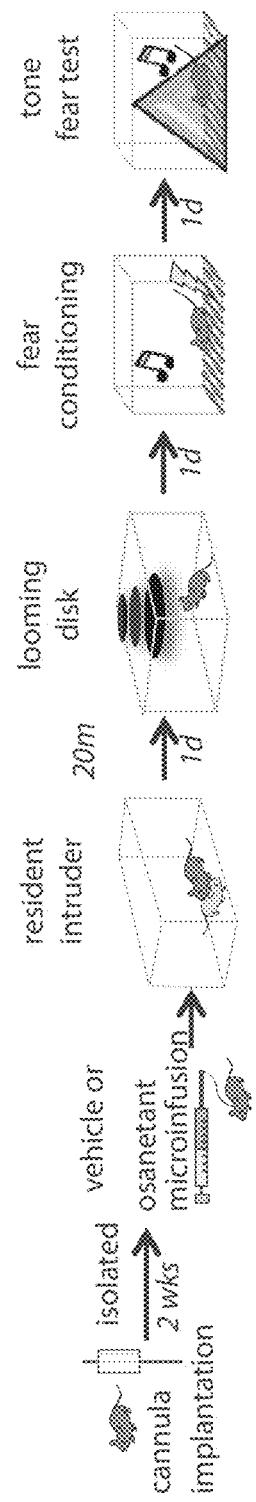
FIGS. 4A-Q show that targeted Nk3R antagonism in dBNSTa, DMH, or CeA attenuates different effects of SIS in a dissociable manner in accordance with some embodiments.
Figure 4K:
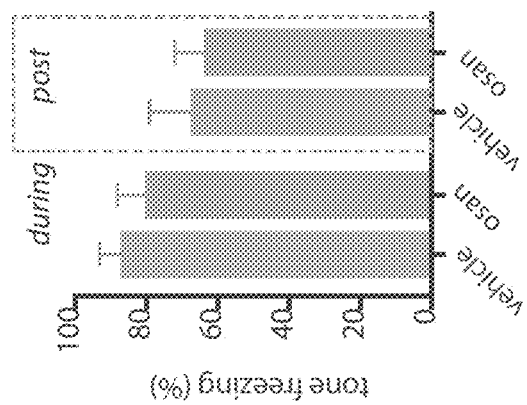
Figure 4J:
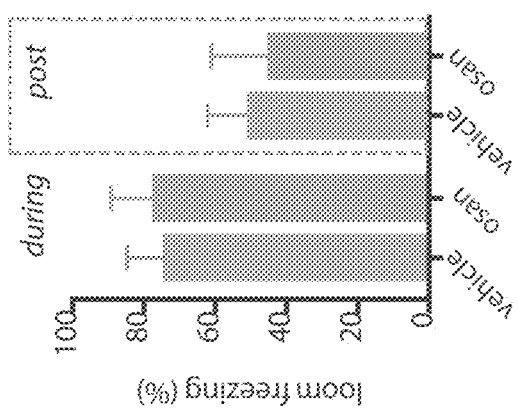
Figure 4I:
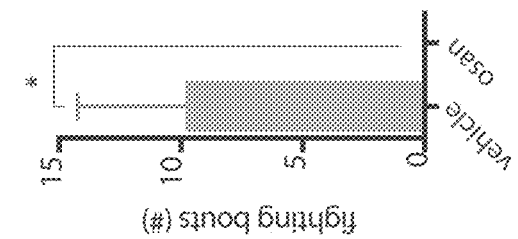
Figure 4H:
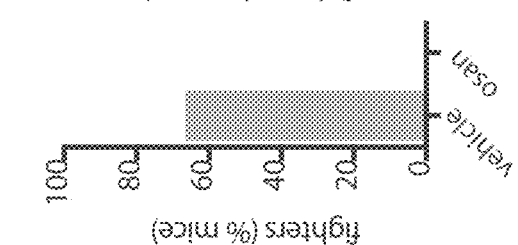
Figure 4G:
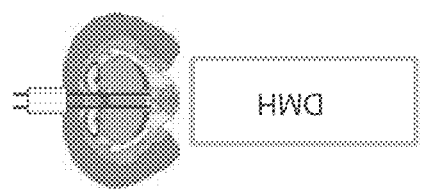
Figure 4P:
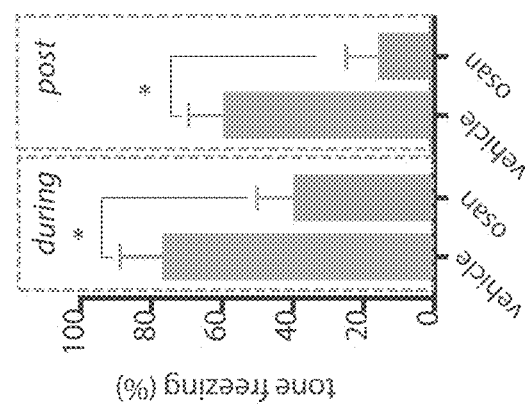
Figure 4O:
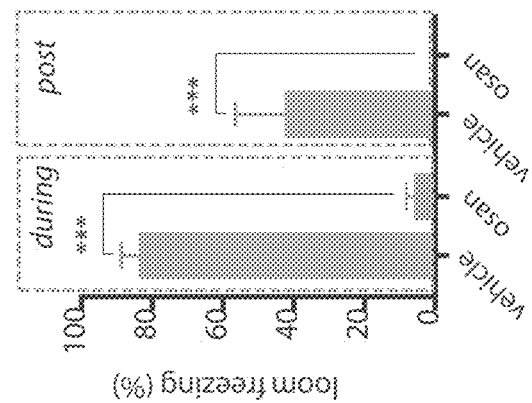
Figure 4N:
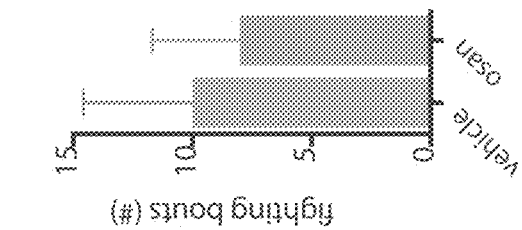
Figure 4M:
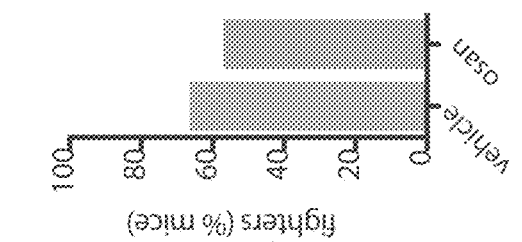
Figure 4L:
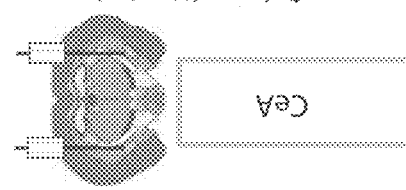
Figure 4Q:
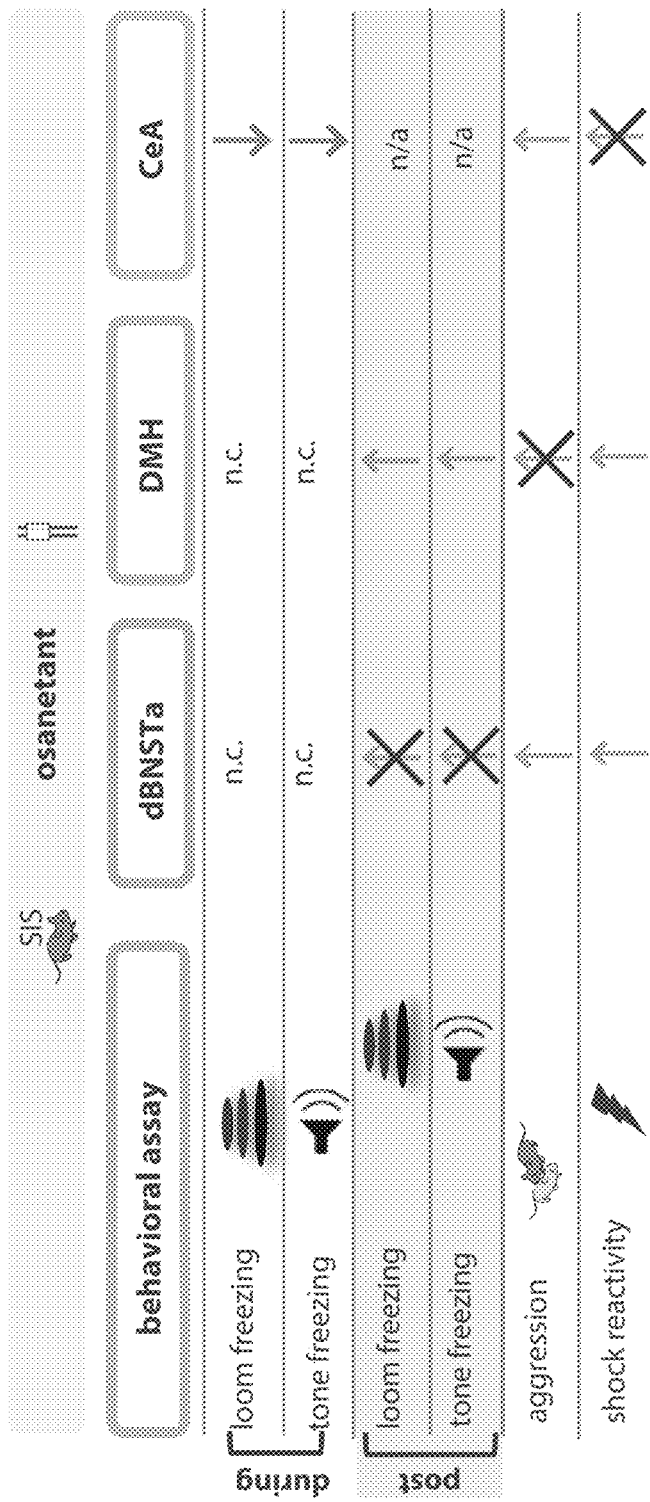

Without being limited by theory, the foregoing results suggested that Tac2/NkB signaling is required for the effect of chronic SIS to alter multiple defensive behaviors. We next asked where in the brain this signaling is required. As a first step, we pharmacologically inhibited Nk3Rs in dBNSTa, DMH, and CeA, as these regions contain cells expressing Nk3Rs (FIGS. 11A-C), and exhibited a strong induction of Tac2 expression following SIS (FIGS. 2A-AA). Cannulated mice were subjected to SIS and then received bilateral microinfusions of osanetant into the region of interest 20 minutes prior to each behavioral test (FIG. 4A). We selected four assays—the resident intruder assay, looming disk, fear conditioning, and shock reactivity—because they exhibited robust SIS-induced changes and could be performed sequentially within the same animals without affecting each other (as indicated by initial pilot experiments in which each assay was performed independently). This multiplexed approach allowed comparison of 4 different behavioral effects of SIS in animals with multiple manipulations in each of 3 different brain regions, without requiring an exponential increase in the number of implanted animals.

Figures 11A, 11B, 11C:
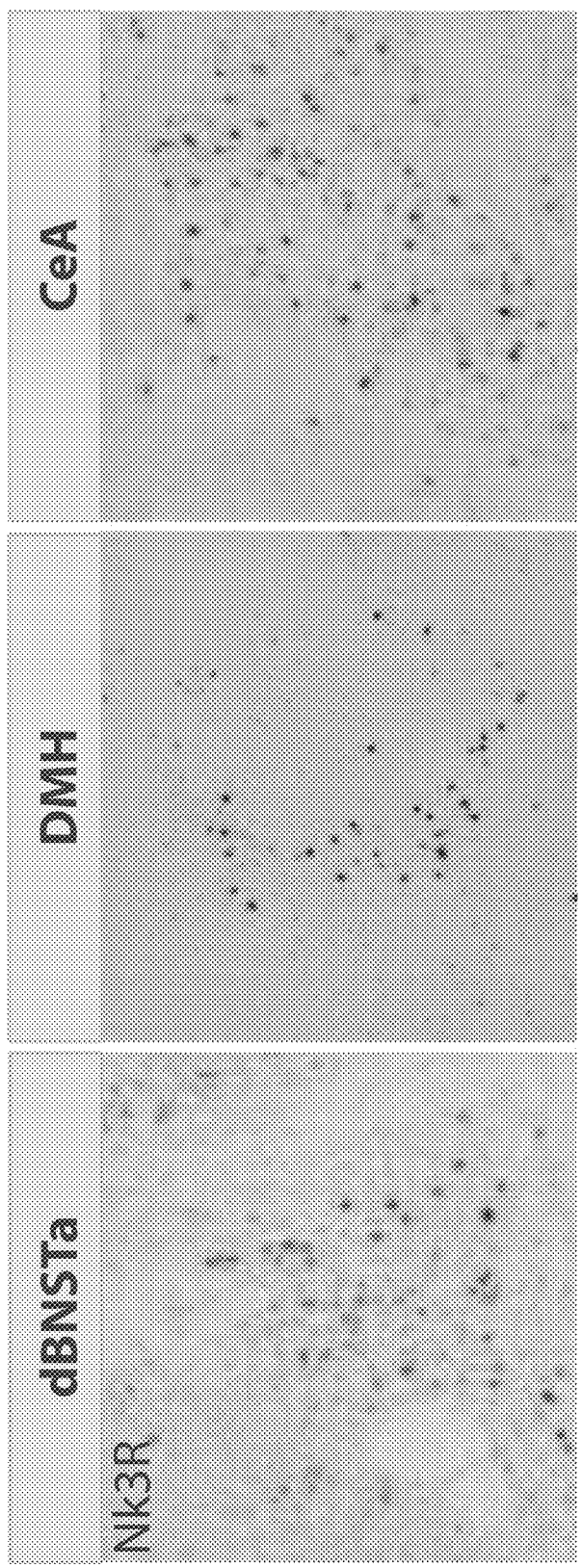
FIGS. 11A-K show that local Nk3R antagonism in dBNSTa, DMH, and CeA blocks dissociable effects of SIS on behavior in some embodiments.
Figure 11D:
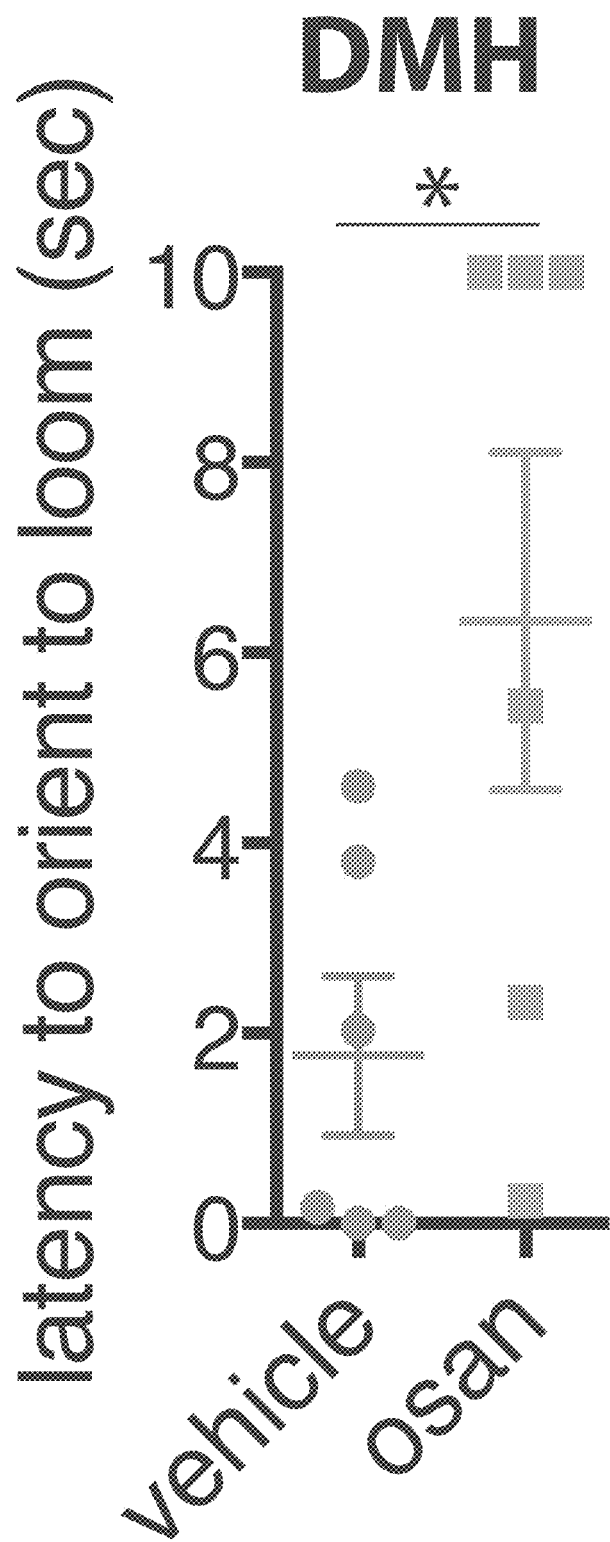
Figures 11E, 11F, 11G:
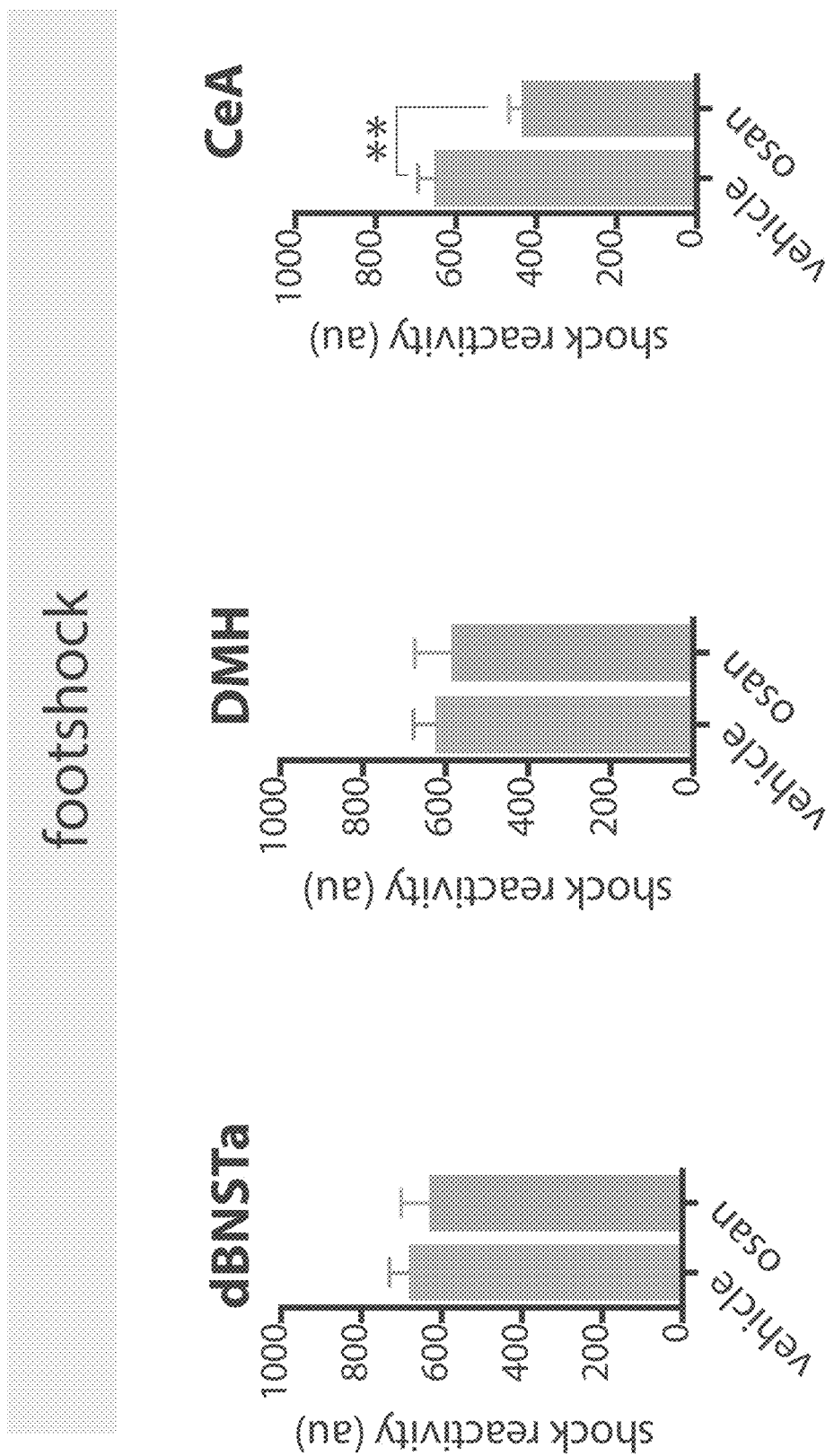
Figure 11H:
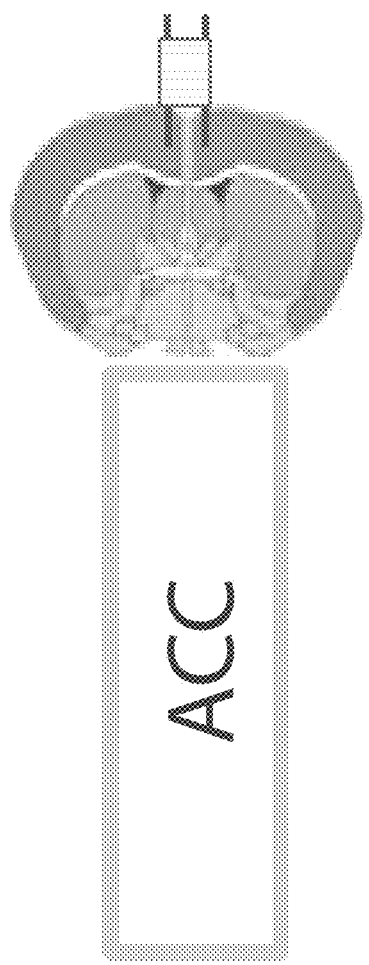
Figure 11I:
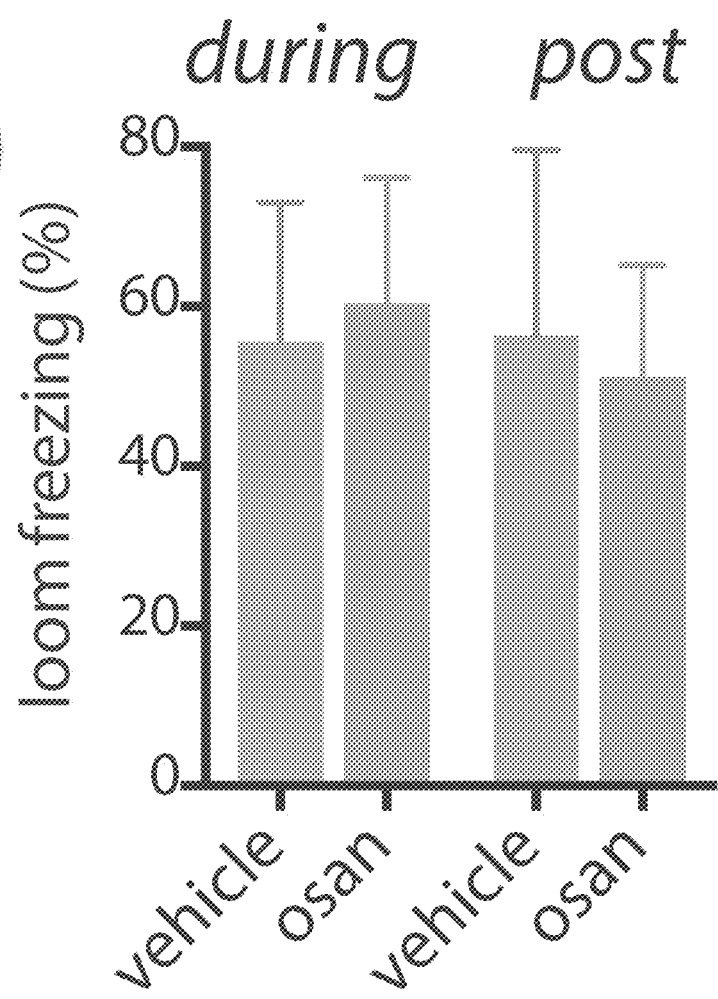
Figure 11J:
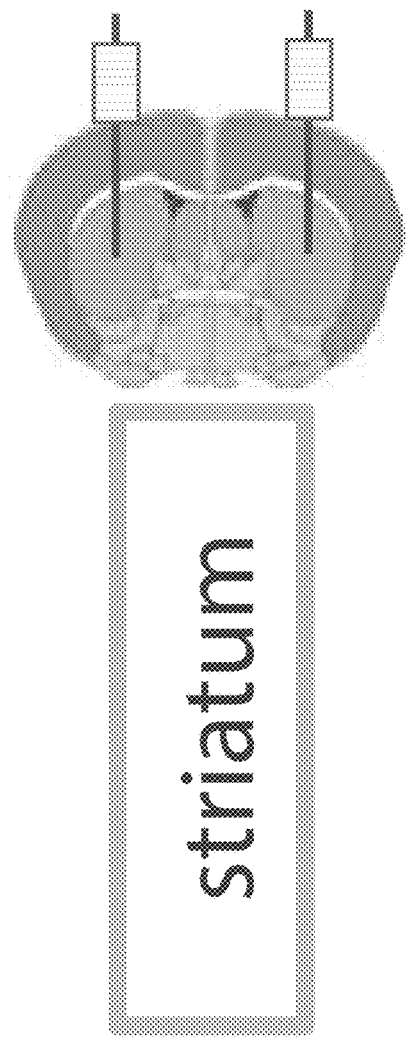
Figure 11K:
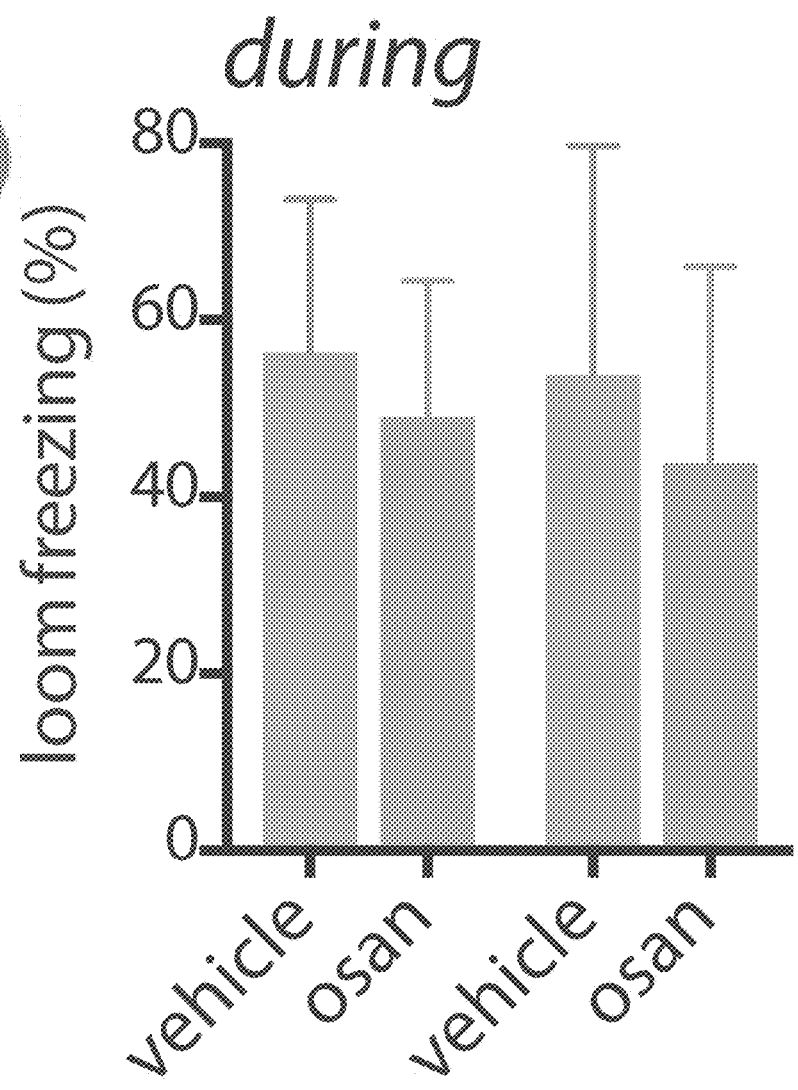
Figures 12A, 12B, 12C:
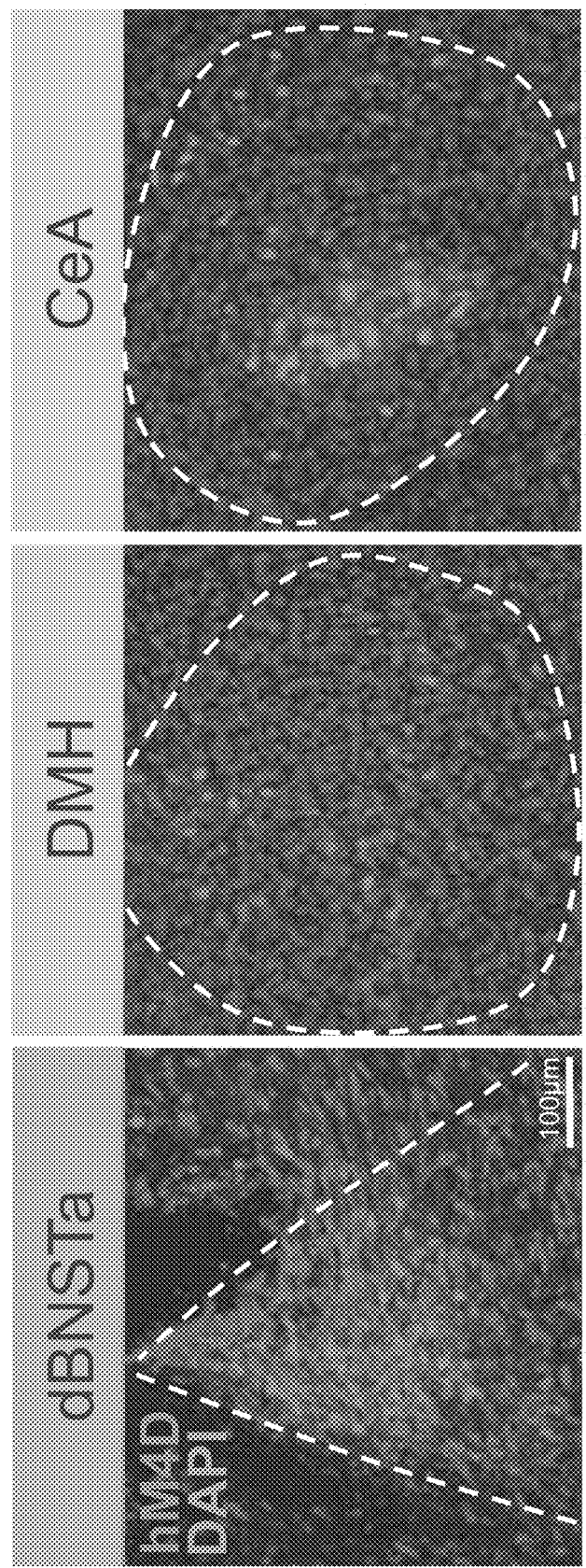
FIGS. 12A-G show that local chemogenetic silencing of Tac2+ neurons reduces the effects of SIS in some embodiments.
Figures 12D, 12E, 12F:
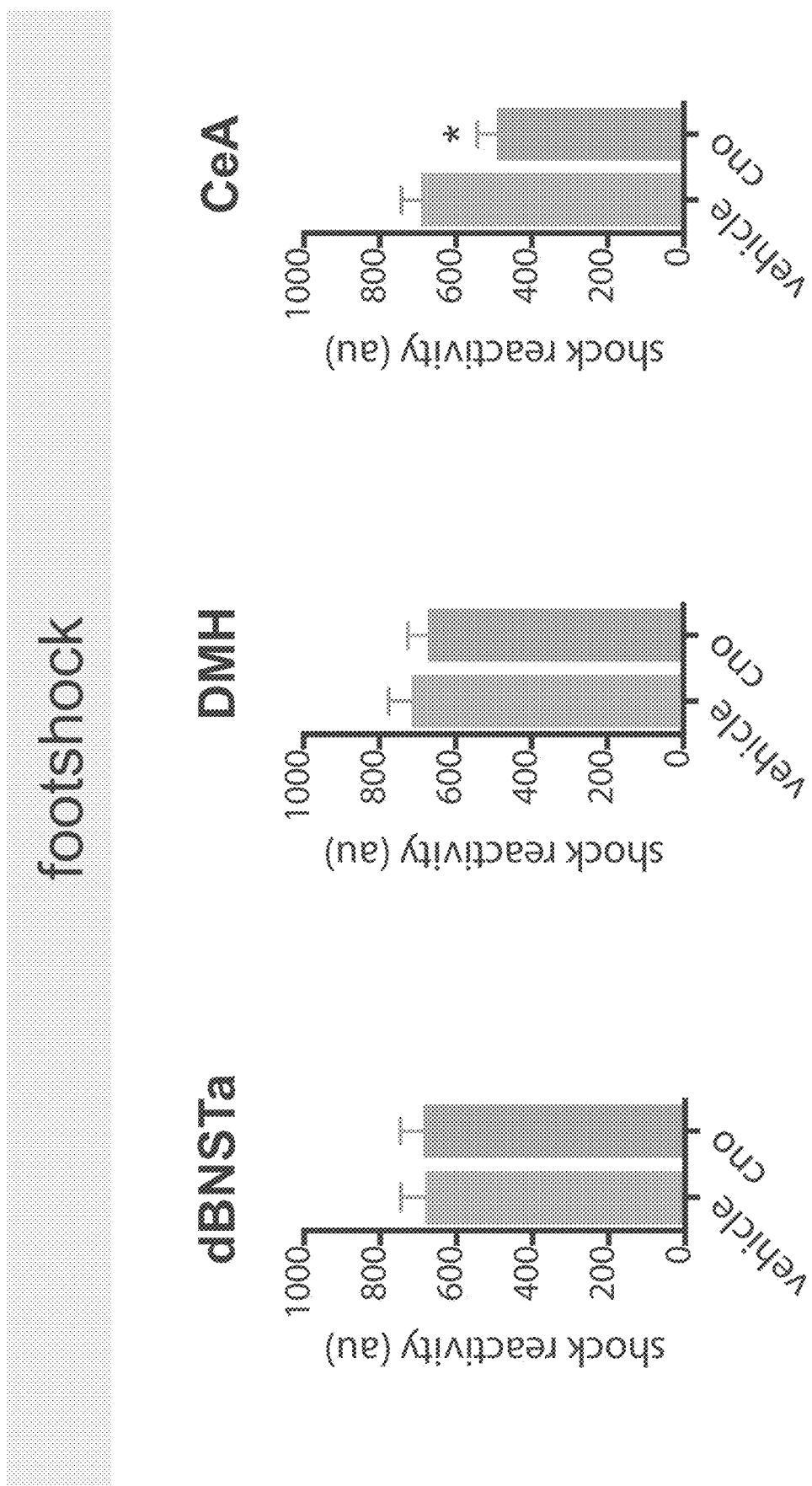
Figure 12G:
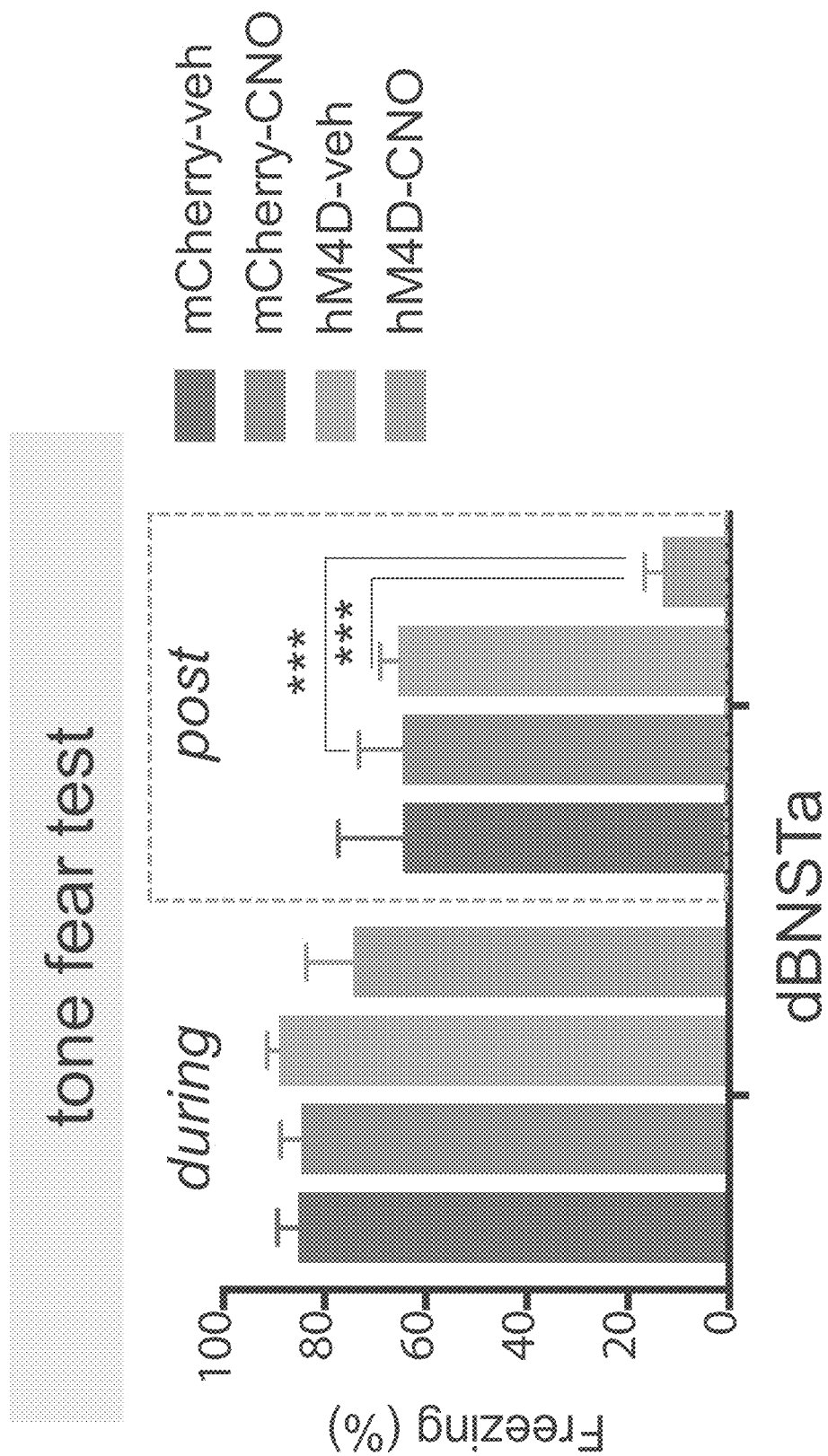

Local infusion of osanetant in dBNSTa selectively inhibited the SIS-induced persistent (but not acute) freezing to both the looming disk and the conditioned tone (FIGS. 4E-F), with no effect on aggression (FIGS. 4C-D) or shock reactivity (FIG. 11E). By contrast, osanetant microinfused into the DMH abolished SIS-induced aggression (FIG. 4H-I), but had no effect on persistent responses to the looming stimulus (FIG. 4J) or the conditioned tone (FIG. 4K), or on responses to the footshock (FIG. 11F). However, DMH-infused mice showed an increase in latency to first orient and freeze to the looming stimulus (FIG. 11D). Lastly, osanetant injection into the CeA left aggression unaffected, but reduced acute (and thereby persistent) freezing to innate and conditioned threatening stimuli, as well as reactivity to footshock (FIGS. 4L-Q, FIG. 11G). Experiments targeting osanetant to the ACC or striatum failed to yield significant effects on the SIS-induced persistent freezing to the looming disk (FIGS. 11H-K).

The data show that, in accordance with some embodiments, Nk3Rs in dBNSTa, CeA, and DMH dissociably mediate the effects of SIS on different behaviors, with the dBNSTa region selectively regulating SIS-induced persistent freezing, the DMH region selectively regulating SIS-induced aggression, and the CeA region selectively regulating acute (and thus presistent) freezing as well as reactivity to footshock.

The Mouse Connectivity Atlas, Allen Institute for Brain Science identifies connectivity for projection target regions of the dBNST (Experiment #265138021); DMH (Experiment #300927483); and CeA (Experiment #241279261). Tac2 neurons of the dBNSTa have been identified as projecting to the Reticular nucleus of the thalamus (RT), Vascular organ of the lamina terminalis (OV), Supramammillary nucleus (SUM), Tuberomammillary nucleus, ventral part (TMv), Paraventricular hypothalamic nucleus, descending division (PVHd), Lateral hypothalamic area (LHA), Lateral preoptic area (LPO), Preparasubthalamic nucleus (PST), Parasubthalamic nucleus (PSTN), Subthalamic nucleus (STN), Tubueral nucleus (TU), Midbrain trigeminal nucleus (MEV), Ventral tegmental area (VTA), Midbrain reticular nucleus, retrorubral area (RR), Midbrain reticular nucleus (MRN), Periaqueductal gray (PAG), Cuneiform nucleus (CUN), Edinger-Westphal nucleus (EW), Substantia nigra, compact part (SNc), Pedunculopontine nucleus (PPN), Rostral linear nucleus raphe (RL), Central linear nucleus raphe (CLI), Dorsal nucleus raphe (DR), Parabrachial nucleus (PB), Barrington's nucleus (B), Supratrigeminal nucleus (SUT), External cuneate nucleus (ECU), Nucleus ambiguus (MB), Lateral reticular nucleus (LRN), Magnocellular reticular nucleus (MARN), Parvicellular reticular nucleus (PARN), Paragigantocellular reticular nucleus, lateral part (PGRN1), Parapyramidal nucleus (PPY), Nucleus raphe magnus (RM), Nucleus raphe pallidus (RPA), and Nucleus raphe obscurus (RO). Tac 2 neurons of the DMH have been identified as projecting to the Induseum griseum (IG), Hypothalamus (HY), Dorsal medial hypothalamus (DMH), Ventrolateral preoptic nucleus (VLPO), Supramammallary nucleus (SUM), Ventral tuberomammallary nucleus (TMv), Dorsal premammillary nucleus (PMd), Ventral premammillary nucleus (PMv), Posterior hypothalamic nucleus (PH), Lateral hypothalamic area (LHA), Parasubthalamic nucleus (PSTN), Tuberal nucleus (TU), Medulla (MY), and Nucleus raphe pallidus (RPA). Tac 2 neurons of the CEA have been identified as projecting to the Central amygdalar nucleus (CEA), Pallidum (PAL), Globus pallidus, internal segment (GPi), Substantia innominate (SI), Subparafascicular nucleus, magnocellular part (SPFm), Subparafascicular nucleus, parvicellular part (SPFp), Subparafascicular area (SPA), Peripeduncular nucleus (PP), Reticular nucleus of the thalamus (RT), Paraventricular hypothalamic nucleus, descending division (PVHd), Lateral hypothalamic area (LHA), Lateral preoptic area (LPO), Preparasubthalamic nucleus (PST), Parasubthalamic nucleus (PSTN), Subthalamic nucleus (STN), Zona incerta (ZI), Midbrain trigeminal nucleus (MEV), Ventral tegmental area (VTA), Midbrain reticular nucleus, retrorubral area (RR), Midbrain reticular nucleus (MRN), Periaqueductal gray (PAG), Edinger-Westphal nucleus (EW), Trochlear nucleus (IV), Substantia nigra, compact part (SNc), Pedunculopontine nucleus (PPN), Parabrachial nucleus (PB), Pontine reticular nucleus, caudal part (PRNc), Supratrigeminal nucleus (SUT), Tegmental reticular nucleus (TRN), Accessory facial motor nucleus (ACVII), Inferior salivatory nucleus (ISN), Magnocellular reticular nucleus (MARN), Parvicellular reticular nucleus (PARN), Parapyramidal nucleus (PPY), Nucleus raphe magnus (RM), Nucleus raphe pallidus (RPA), and Nucleus raphe obscurus (RO).

Example 6

This example shows the effect of region-specific chemogenetic silencing of Tac2+ neurons on behavioral responses to social isolation stress (SIS).

Figure 5A:
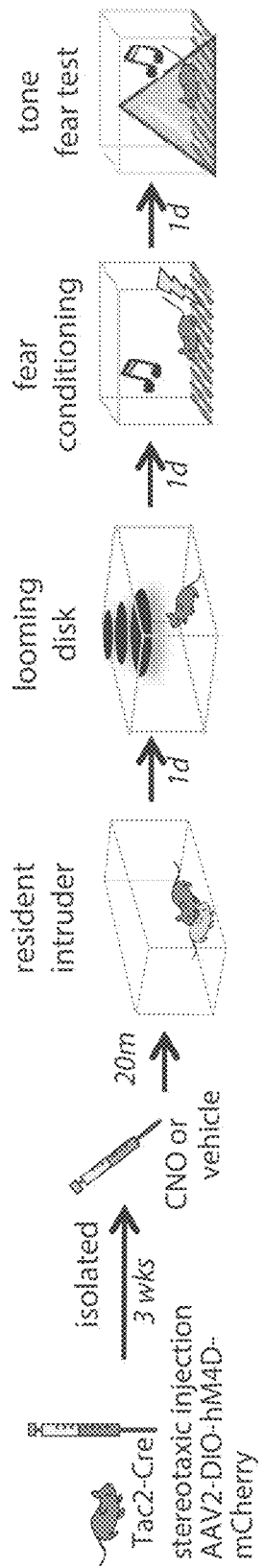
FIGS. 5A-Q show that targeted chemogenic silencing of Tac2$^+$ cells attenuates the effects of SIS in accordance with some embodiments.
Figure 5Q:
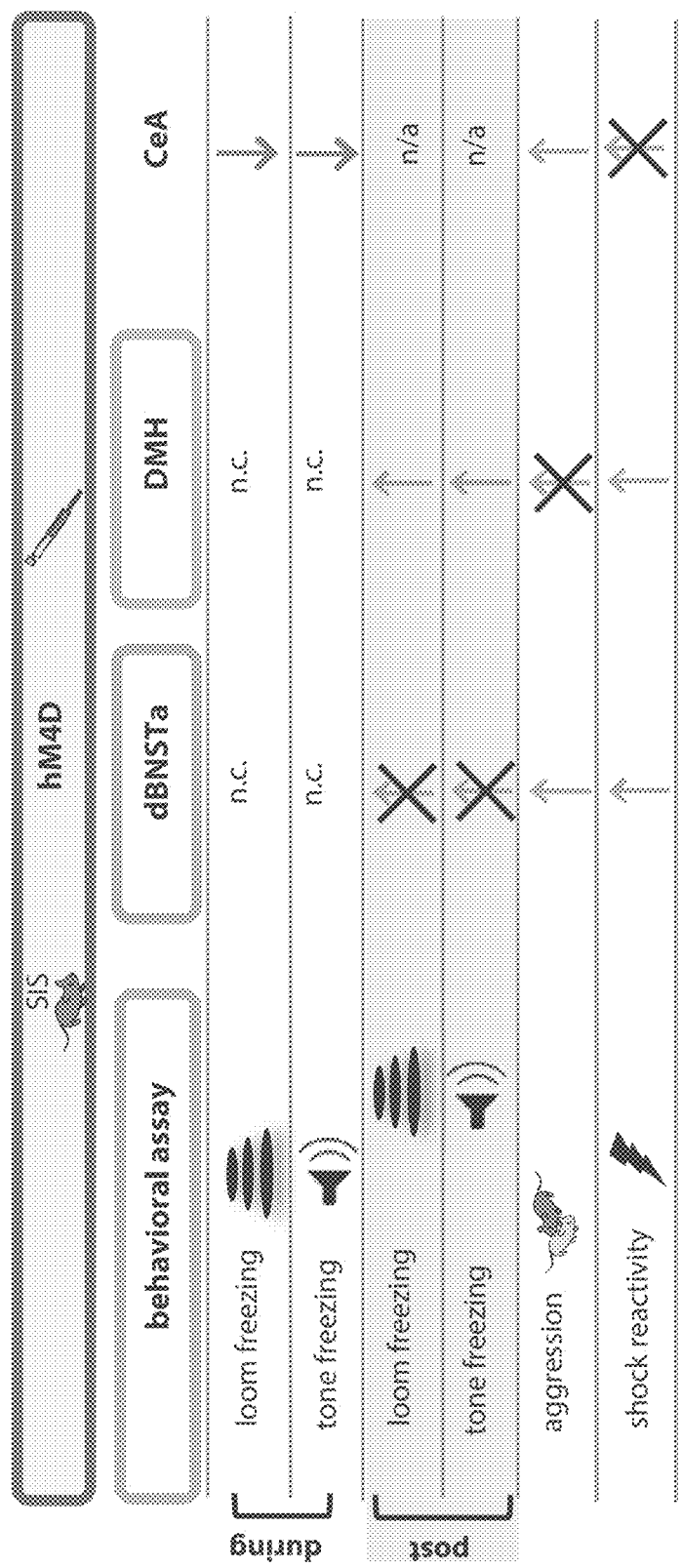

To determine whether the induction of Tac2 mRNA in dBNSTa, DMH and CeA reflected a requirement for NkB release in these structures, we first asked whether the activity of Tac2+ neurons in these regions was required for the effects of SIS. Tac2-Cre mice were bilaterally injected with a Cre-dependent AAV encoding hM4DREADD (AAV2-DIO-hM4D-mCherry) for neuronal inhibition of Tac2+ cells (Conklin et al., 2008; incorporated by reference in its entirety). Following 3 weeks to allow for adequate viral expression (FIGS. 12 A-C), mice were tested for SIS-induced behavior following injection of clozapine-N-oxide (CNO) or vehicle (FIG. 5A).

Chemogenetic silencing of Tac2+ cells in dBNSTa, DMH, and CeA essentially phenocopied the effect of local osanetant infusions. In dBNSTa, persistent freezing responses were selectively attenuated (FIGS. 5B-F), in DMH, aggression was inhibited (FIGS. 5G-K), and in CeA, acute freezing and shock reactivity were suppressed (FIGS. 5L-Q, FIG. 12F). Notably, the effects of CNO were dependent on hM4DREADD expression, as we did not observe any effects of CNO in mCherry control mice (FIG. 12G) (Gomez et al., 2017; incorporated by reference in its entirety). Without being limited by theory, these results demonstrate that the activity of Tac2+ neurons plays differential roles in each of these regions for different behavioral effects of SIS.

In sum, the data show, in accordance with some embodiments, that region-specific chemogenetic silencing of Tac2$^+$ neurons in dBNSTa, DMH, and CeA blocks distinct behavioral responses to SIS.

Example 7

This example shows that Tac2 synthesis impacts distinct behavioral responses to social isolation stress (SIS).

Figure 6A:
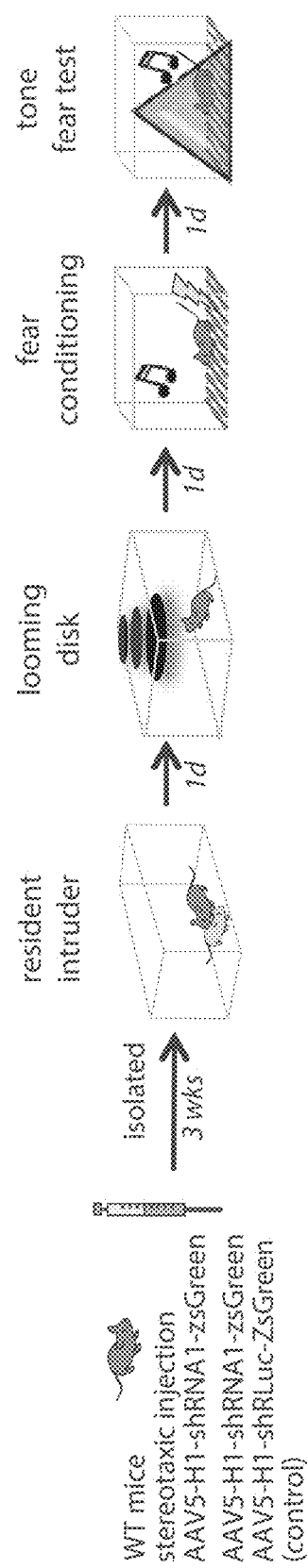
FIGS. 6A-Q show that targeted knockdown of Tac2 attenuates the effects of SIS in accordance with some embodiments.
Figure 6F:
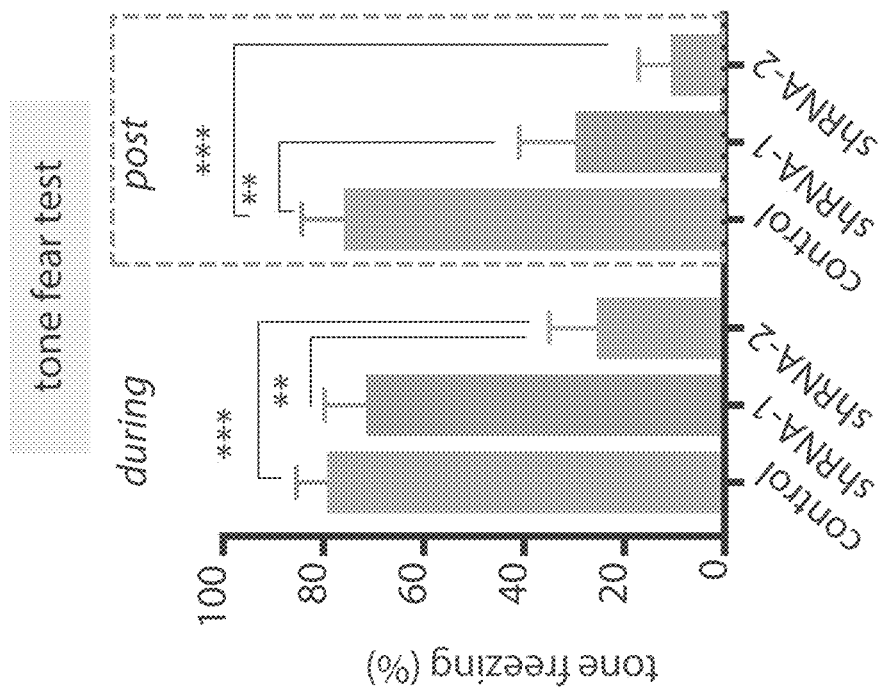
FIGS. 6E-F); aggression in DMH (FIG. 6H-I) and freezing in CeA (FIGS. 6O-P). shRNA-2 (bars labelled "shRNA-2") yielded similar effects but additionally reduced acute freezing in dBNSTa ("during"
Figure 6E:
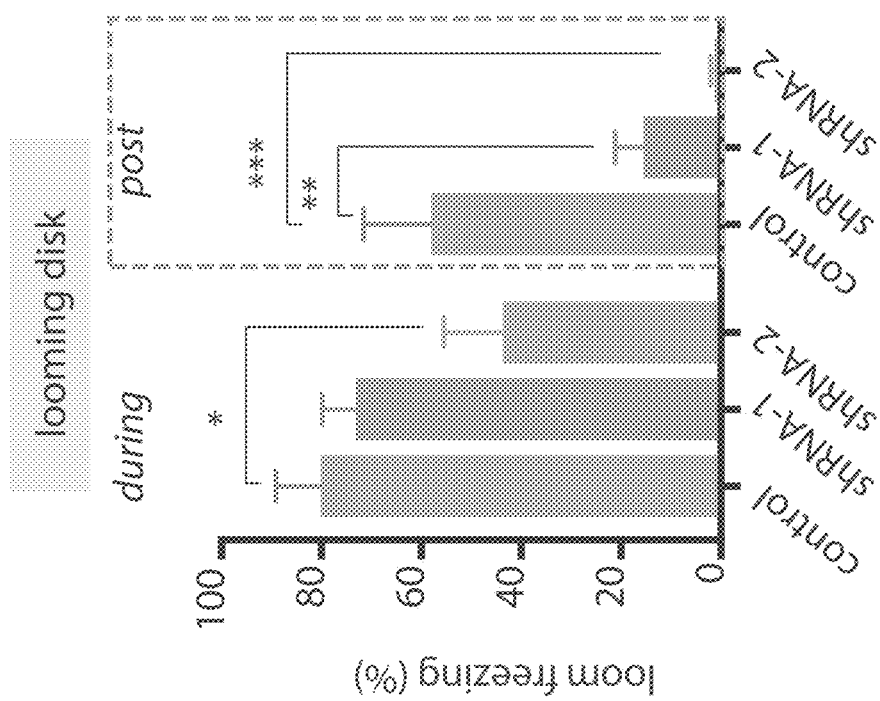
Figure 6I:
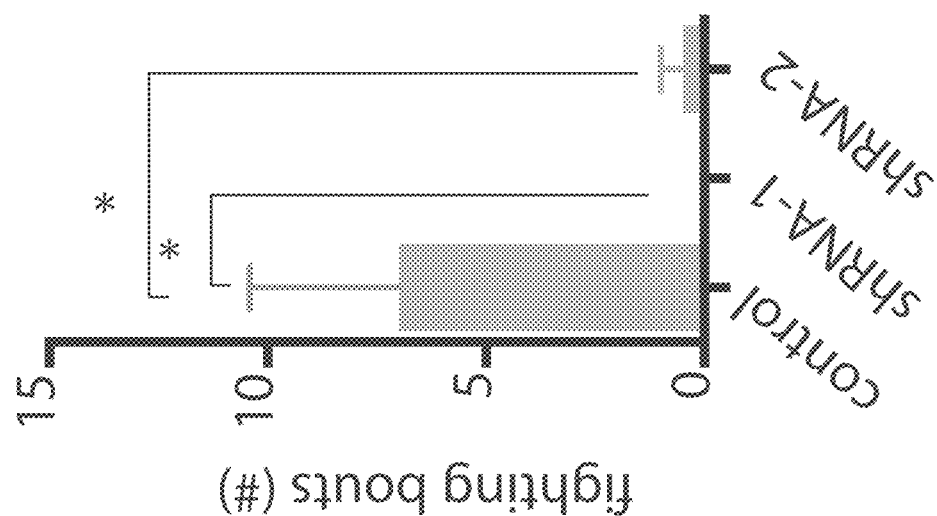
FIGS. 6B-P show the effect of shRNAs in dBNSTa (FIGS. 6B-F); DMH (FIGS. 6G-K), or CeA (FIGS. 6L-P) on indicated assays. shRNA-1 (bars labelled "shRNA-1") blocked persistent freezing in dBNSTa ("post"
Figure 6H:
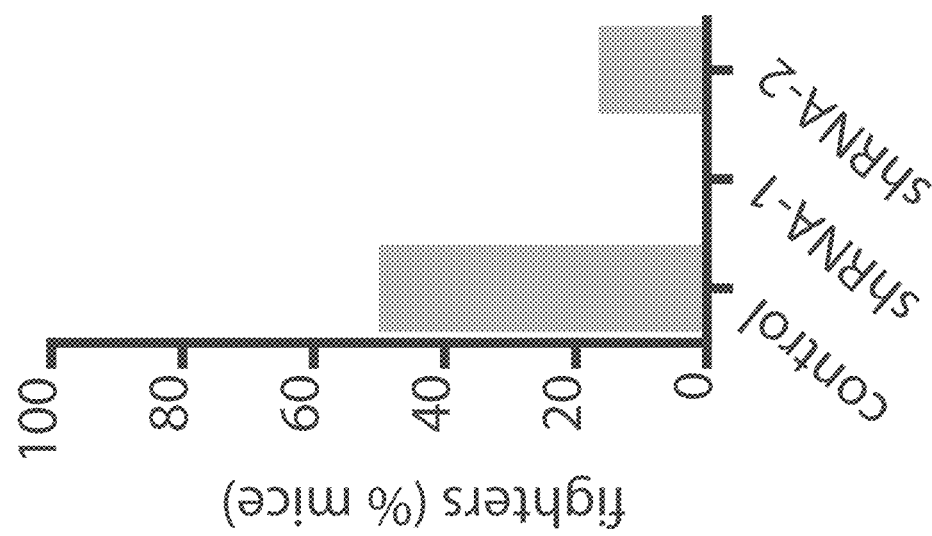
Figure 6G:
Figure 6K:
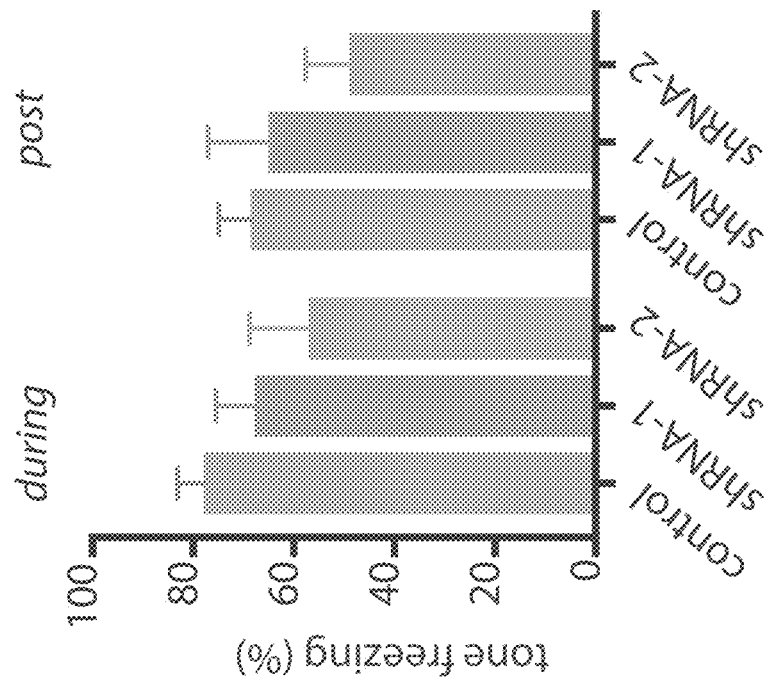
Figure 6J:
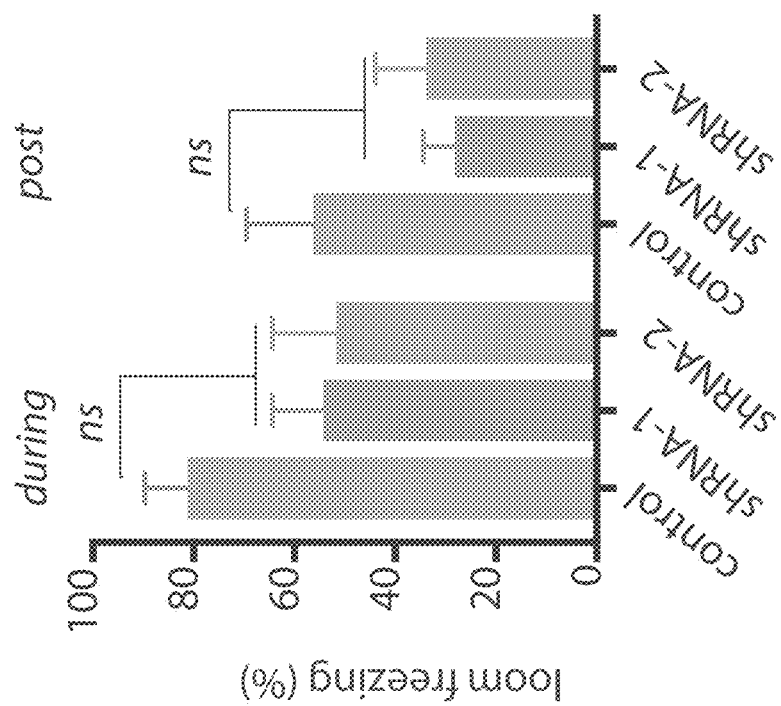
Figure 6P:
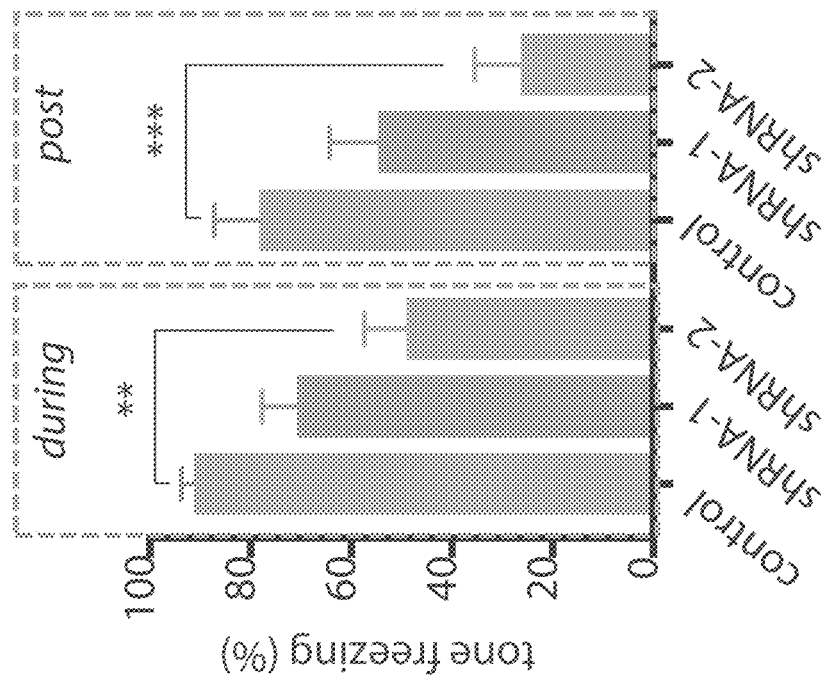
Figure 6O:
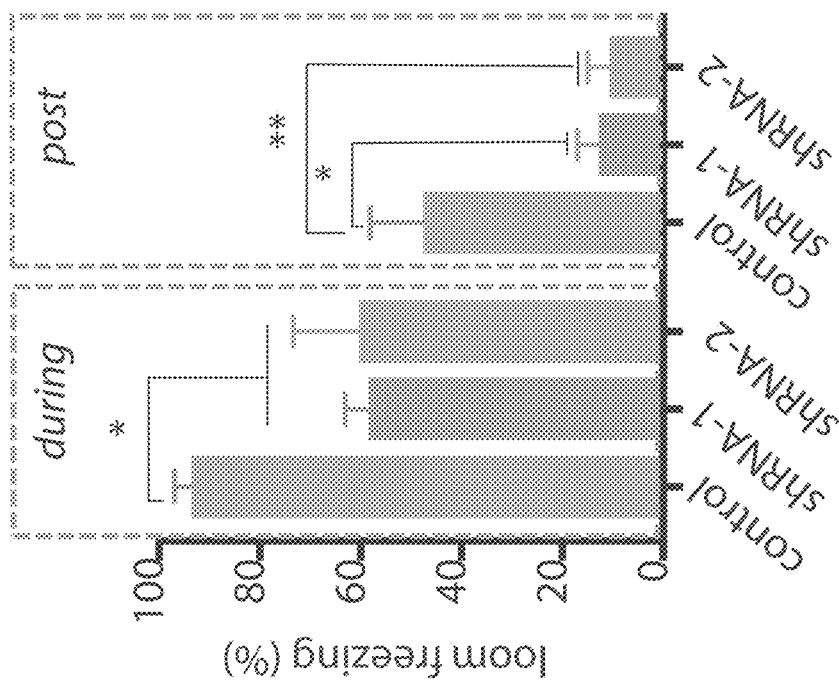

To further investigate a role for local Tac2 release in mediating different effects of SIS, we asked next whether Tac2 synthesis played a role in each of the three brain regions studied, via targeted shRNAi-mediated knockdown of Tac2. Mice were injected stereotaxically in dBNSTa, DMH, or CeA with adeno-associated viruses (AAVs) expressing small hairpin RNAs (shRNAs), together with a CMV promoter-driven zsGreen fluorescent reporter to assess cell viability (AAV5-H1-shRNA-CMV-zsGreen). Of four different shRNAs originally generated, two (shRNA-1 and shRNA-2) proved effective as determined by FISH and qRT-PCR, with shRNA-2 yielding the strongest reductions in Tac2 mRNA (FIGS. 13J-AA). Control mice were injected with an AAV encoding an shRNA targeted to the luciferase gene. Injections were histologically verified by zsGreen fluorescence. The number of zsGreen+ neurons was not significantly different between animals injected with control vs. experimental shRNAs, suggesting that the reduction in the number of Tac2 mRNA+ cells was not due to cell death (FIGS. 13 D-I). Following virus injections, mice were isolated for three weeks and tested for behavior (FIG. 6A).

Figure 6Q:
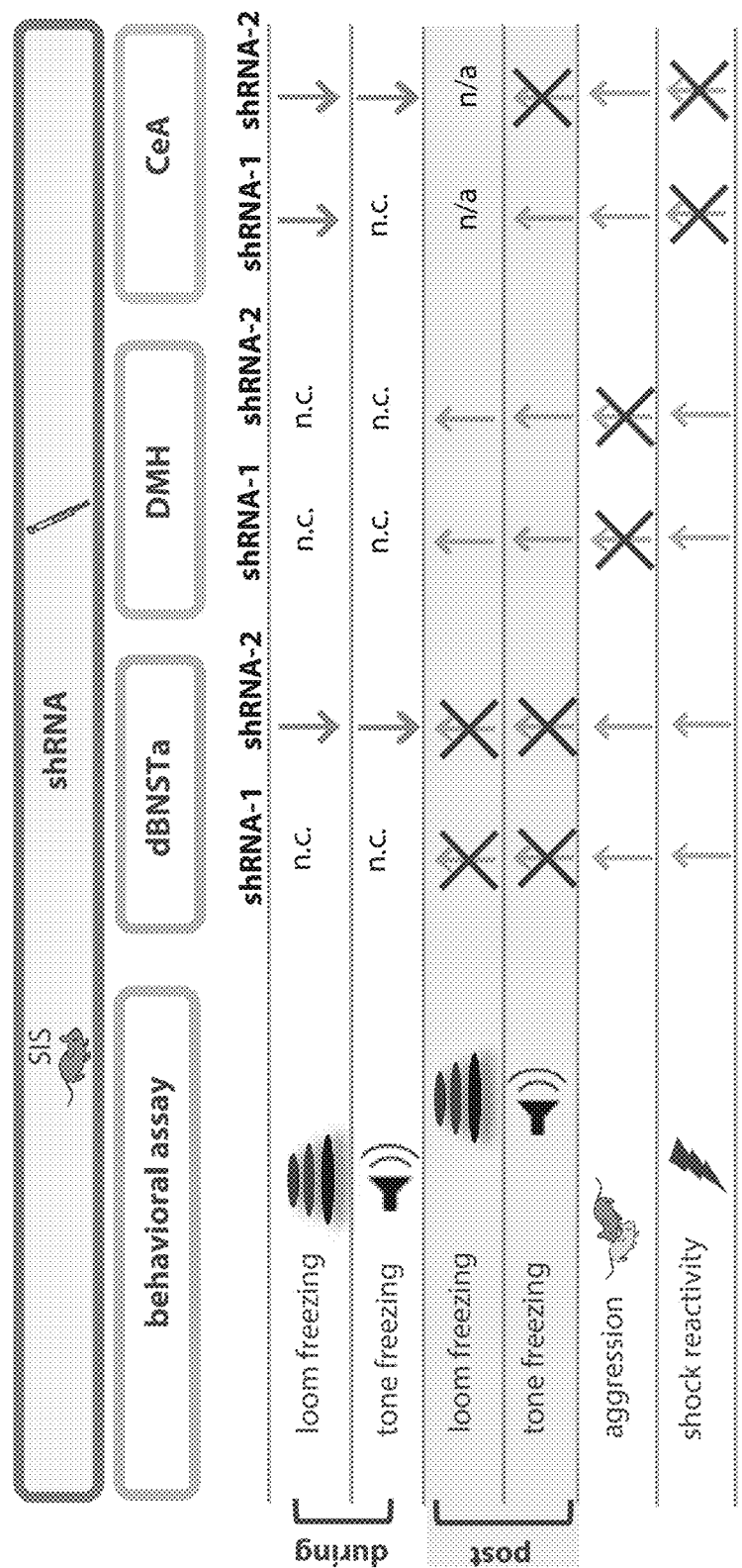

In DMH, both shRNAs strongly attenuated SIS-induced aggression, but had no significant effect on freezing (FIGS. 6G-K), similar to the effect of Tac2+ neuron silencing or local infusion of osanetant in this region (FIGS. 4G-K and FIGS. 5G-K). Conversely, in the dBNSTa, shRNA-1 strongly reduced persistent freezing to both the looming disk and the conditioned tone (FIGS. 6E-F, bars labelled "shRNA-1," post), but had no effect on SIS-induced aggression (FIGS. 6C-D) or acute freezing to the threatening stimuli (FIG. 6E, FIG. 6F, bars labelled "shRNA-1," during). Unlike Tac2+ neuron silencing and local osanetant infusion, the more effective shRNA-2 in dBNSTa significantly reduced acute freezing during presentation of both the looming disk and conditioned tone, to an extent similar to that observed in CeA (FIGS. 6E-F, O-P, during, bars labelled "shRNA-2"). In CeA, Tac2 shRNAs reduced acute freezing during stimulus presentation (FIG. 6O), and had no effect on aggression (FIGS. 6M-N). Together these data support a region-specific effect of local Tac2 synthesis in the control of different SIS-induced behaviors (FIG. 6Q).

The data show that Tac2 synthesis in dBNSTa, CeA, and DMH in accordance with some embodiments results in distinct behavioral responses to SIS.

Example 8

This example shows the effects of enhanced Tac2 expression and neuronal activation on Tac2+ neurons on behavior.

The foregoing findings indicate that Tac2 is up-regulated in several brain regions by SIS, and that Tac2 signaling in several of these brain regions results in the collective behavioral effects of SIS. However, because there already is Tac2 expression in these regions in group housed mice (FIGS. 2B-C, FIG. 2F), these data do not address whether Tac2 up-regulation per se mediates the behavioral effects of SIS, or whether Tac2 is simply involved in a permissive manner with respect to these behaviors. To address this question, we asked whether increasing the level and/or release of Tac2 was sufficient to mimic any of the behavioral effects of SIS, in group housed animals.

Figure 7A:
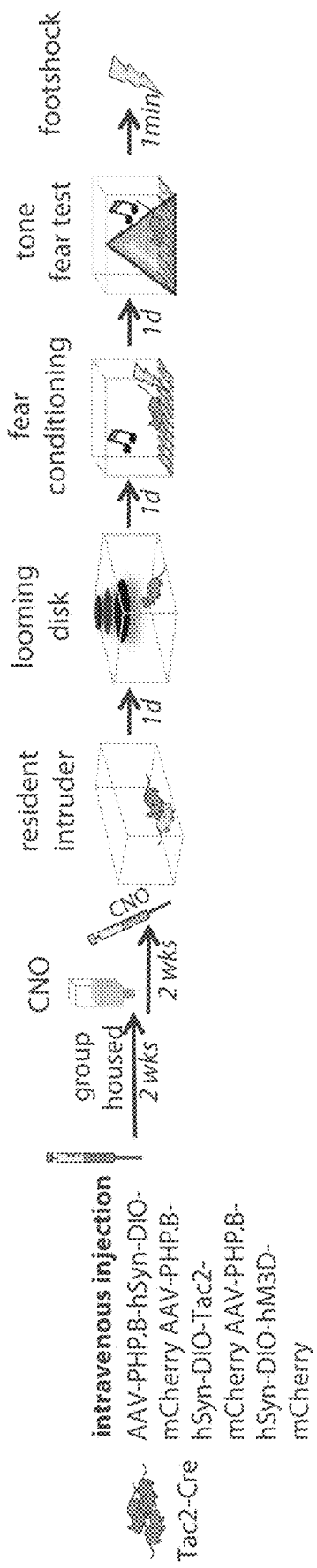
Figures 7B, 7C, 7D:
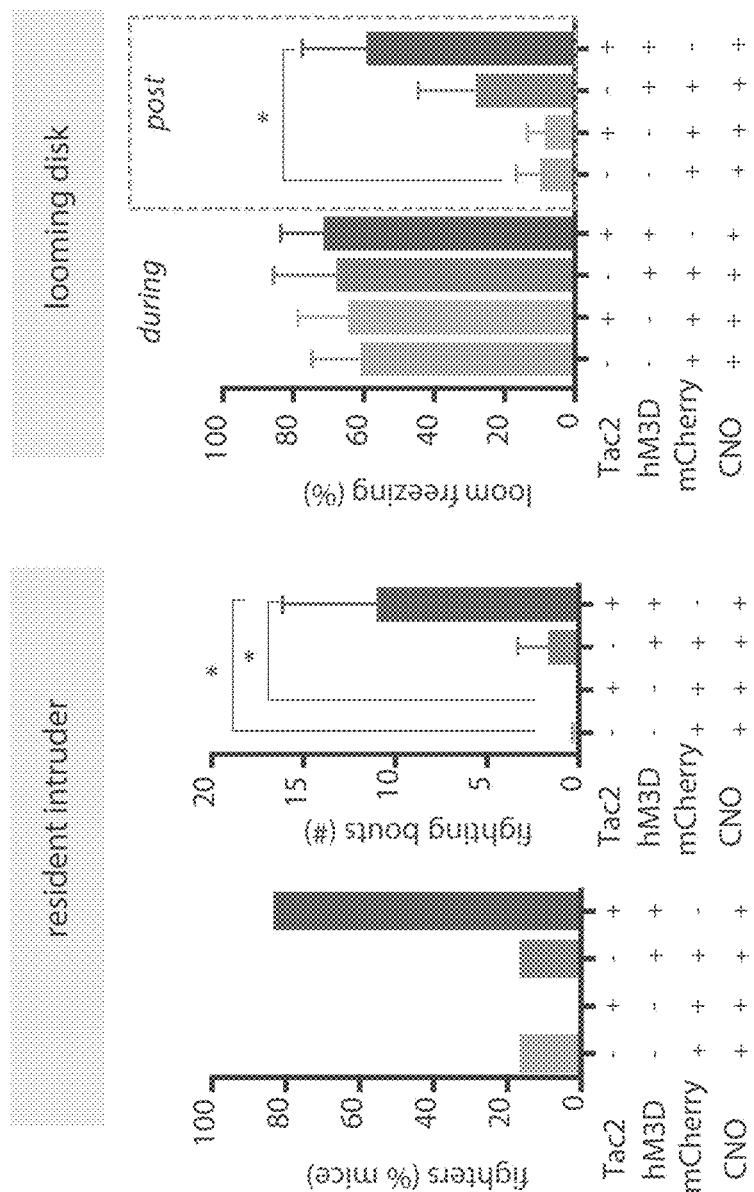
Figure 7E:
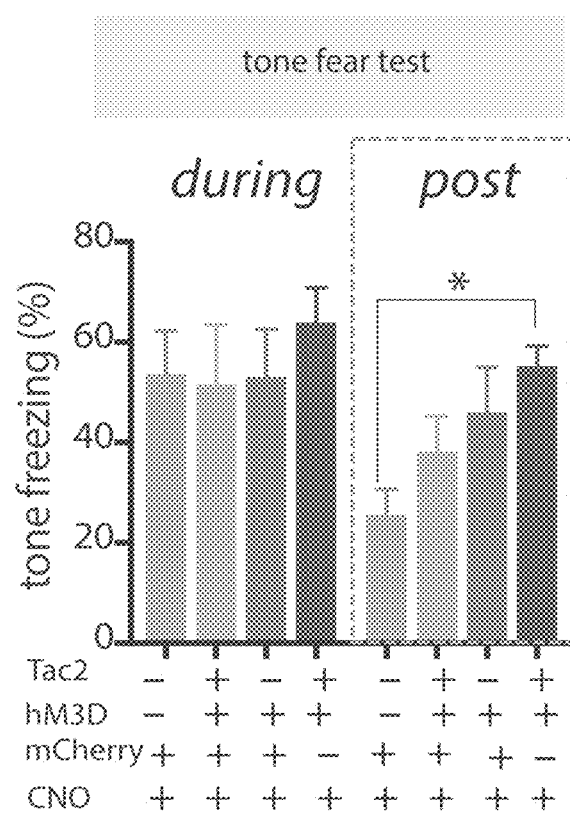
Figure 7F:
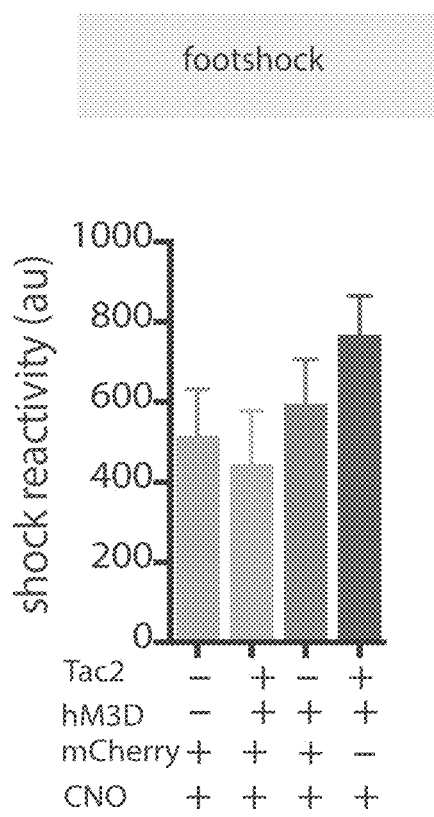
Figure 7G:
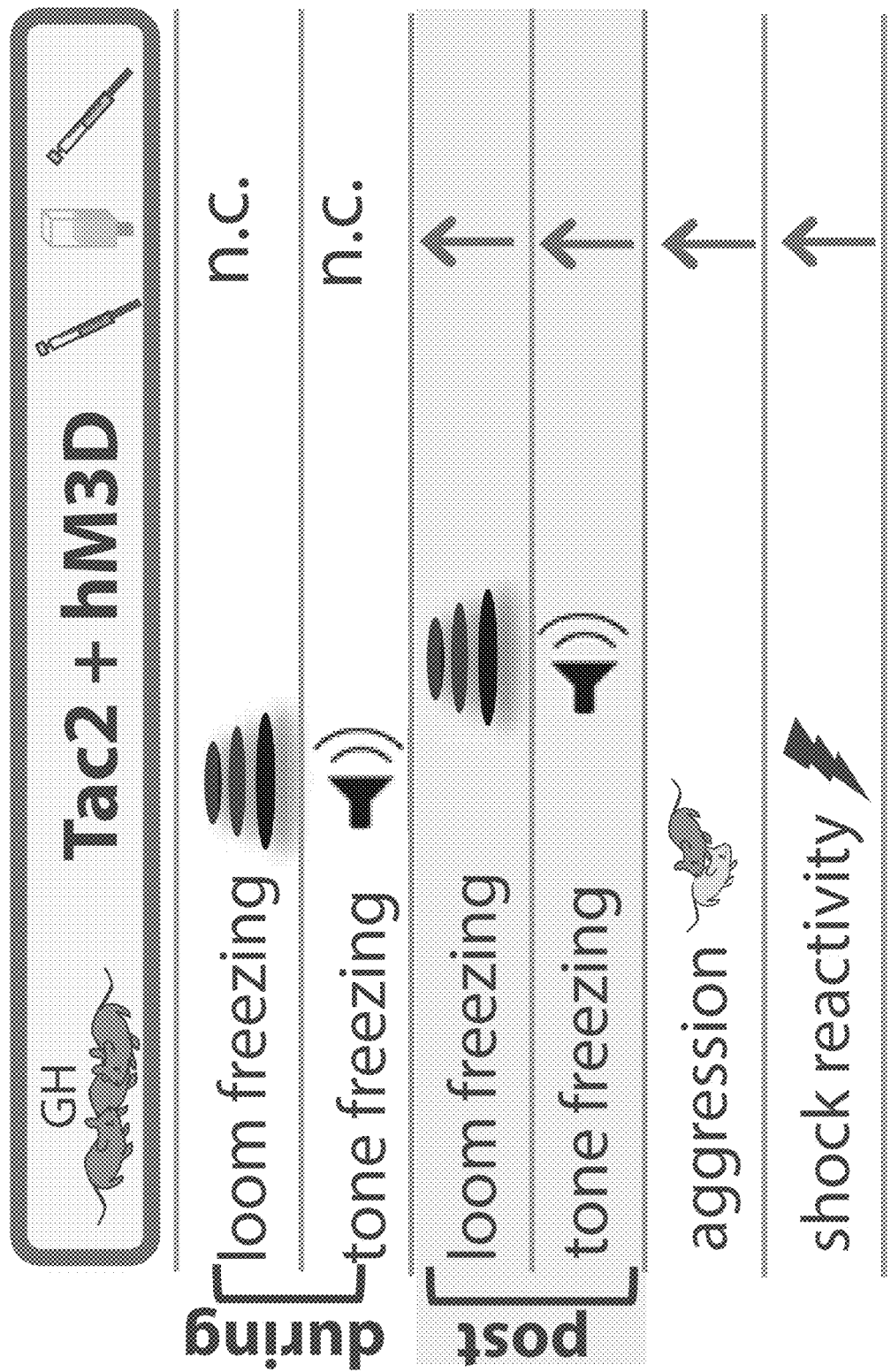

We packaged Cre-dependent vectors encoding the DREADD neuronal activator hM3D, a Tac2 cDNA or control mCherry, in AAV-PHP.B—a viral capsid that crosses the blood-brain barrier (Deverman et al., 2016; incorporated by reference in its entirety). These viruses were intravenously injected (individually or in combination) into GH Tac2-Cre mice (FIGS. 14A-T). Following three weeks to allow for viral expression, all mice (including mCherry-expressing controls) were given CNO in their drinking water for 2 weeks. Mice were then behaviorally tested following a CNO injection (FIG. 7A). This procedure was designed to achieve Tac2 over-expression and/or neuronal activation during both a two-week mock SIS period, as well as during testing.

Increasing Tac2 expression or activating Tac2+ neurons on its own was insufficient to generate significant SIS-like effects in any of our assays (FIGS. 7B-F, second and third bars from left, including "during" and "post" conditions). In contrast, concomitant over-expression of the Tac2 cDNA and activation of Tac2+ neurons using CNO/hM3DREADD recapitulated key behavioral effects of SIS in GH mice, including increased aggression and persistent freezing to threats (FIGS. 7B-E; summarized in FIG. 7G). No such effects were observed in control mice injected with mCherry-only virus and treated with CNO, indicating that the results are not due to CNO itself (Gomez et al., 2017; incorporated by reference in its entirety herein). Histological analysis confirmed expression of mCherry-tagged AAV cargo genes in the dBNSTa, CeA, and DMH (FIGS. 14A-L), as well as in several additional regions (FIGS. 14M-T).

The data show that enhancement of both Tac2 expression and neuronal activity in $Tac^2$ neurons, in accordance with some embodiments, mimics the effects of social isolation stress (SIS) in group housed mice.

Example 9: Discussion of Examples 1-8

The conventional view of stress has been dominated by the HPA axis activation paradigm, focusing research on corticotropin releasing hormone (CRH) and related neuropeptides as substantial mediators of brain responses to psychogenic stress (Koob, 1999; Sapolsky et al., 2000; McEwen, 2007; Bruchas et al., 2009; Bruchas et al., 2010; Griebel and Holsboer, 2012; Kormos and Gaszner, 2013; McCall et al., 2015; Chen, 2016; incorporated by reference in their entirety herein). However this view is largely based on studies using acute or intermittent chronic stressors. There is ongoing debate as to whether the effects of prolonged, continuous stress differ only quantitatively or are qualitatively different from that of acute stress (McEwen, Bowles, et al., 2015; Musazzi et al., 2017; incorporated by reference in their entirety herein). Here, we have studied the effects of continuous chronic stress produced by prolonged social isolation. The significance of this mechanism across many species is consistent with the results of a screen in *Drosophila* (Asahina et al., 2014; incorporated by reference in its entirety herein). Thus, without being limited by theory, it is contemplated that Tac2/NkB represents a significant mediator of chronic SIS effects on the brain, which to Applicant's knowledge has previously been overlooked.

Tac2/NkB Acts in a Distributed Manner to Control Multiple Components of the SIS Response Multiple neuropeptides have been implicated in stress (Kormos and Gaszner, 2013; incorporated by reference in its entirety herein). However, with few exceptions (Regev et al., 2011; Regev et al., 2012; incorporated by reference in their entirety herein), conventional studies of a given peptide have typically focused on a single brain region, stressor and/or behavior (e.g., the BNST and anxiety assays; reviewed in Kash et al., 2015 and incorporated by reference in its entirety herein), and have used a single type of manipulation (but see (McCall et al., 2015; incorporated by reference in its entirety herein). Conventionally, this made it difficult to determine whether and how a given neuropeptide acts in different brain regions to contribute to a stress-induced brain state (Kormos and Gaszner, 2013; Chen, 2016; incorporated by reference in their entirety herein).

The multiplexed approach described herein permitted comparison of the results of the same experimental manipulation in different brain regions, or of different types of manipulations in the same brain region, using a battery of behavioral assays. Surprisingly, in each of the regions studied, targeted loss-of-function (LOF) manipulations of Tac2/NkB peptide (via shRNAi), Tac2+ neurons (via hM4DREADD), or Nk3Rs (via osanetant), yielded qualitatively similar results. Without being limited by theory, taken together with the fact that Tac2/NkB and its receptor Nk3R are both expressed in each of these regions (Allen Institute for Brain Science; (Beaujouan et al., 2004; Duarte et al., 2006; incorporated by reference in their entirety herein), these data are suggestive of local actions of the peptide within each structure, with the possibility that the same or different cells express both the peptide and the receptor. However, our results do not rule out effects of the peptide at distal targets as well.

Together, these results reveal that Tac2/NkB acts in multiple areas to control different aspects of the SIS-induced state, in a dissociable manner. This finding is counter-intuitive to conventional understanding, because one might have expected that, to the contrary, such global control would be most efficiently exerted in a hierarchical manner, with release of the peptide from a single region modulating multiple downstream sites (e.g. FIG. 1B, FIG. 1C, Example 1). Nevertheless, without being limited by theory, such a distributed mechanism to coordinate the influences of a neuropeptide is reminiscent of that played by Pigment-Dispersing Factor (PDF) in controlling circadian circuits in *Drosophila* (Taghert and Nitabach, 2012; Dubowy and Sehgal, 2017; incorporated by reference in their entirety herein), or roaming vs. dwelling states in *C. elegans* (Flavell et al., 2013; incorporated by reference in its entirety herein), and may explain some of the diverse functions of CRF (Regev et al., 2011; McCall et al., 2015; each of which is incorporated by reference in its entirety herein).

Activation and Peptide Overexpression in $Tac2^+$ Neurons Mimics the Effects of SIS It was surprising that combined overexpression of Tac2 and activation of $Tac2^+$ neurons recapitulated multiple effects of SIS in GH mice. It has been set forth that a stress peptide can elicit behavioral responses, e.g., when injected into the brain (reviewed in (Koob, 1999; Kormos and Gaszner, 2013; each of which is incorporated by reference in is entirety herein). However, this case represents, to our knowledge, the first example of a neuropeptide that mimics many of the effects of a stressor in unstressed animals. For example, it has been posited that even CRF when exogenously administered to unstressed animals in low arousal conditions does not produce stress-like responses (Koob, 1999; incorporated by reference in its entirety herein). Furthermore, overexpression of CRF using genetic methods has been posited to produce different responses, depending on the mode and site of expression, leading to conflicting results (Regev et al., 2011; Flandreau et al., 2012; Regev et al., 2012; Sink et al., 2012; Kash et al., 2015; each of which is incorporated by reference in its entirety herein).

We observed that simply overexpressing Tac2 in Tac2$^+$ neurons had no behavioral effect. When this manipulation was combined with chemogenetic activation of Tac$^2$ neurons, a phenotype was observed; neuronal activation on its own had little effect. Without being limited by theory, these data suggest that neuronal activity is limiting for effects of neuropeptide overexpression. These experiments were facilitated by an experimental design that affords the ability to independently manipulate the expression of Tac2, and the activity of Tac$^2$ neurons, in a brain-wide, non-invasive manner in adult mice (Deverman et al., 2016; Chan et al., 2017; each of which is incorporated by reference in its entirety herein), without the need to employ complex transgenic strategies (Lu et al., 2008; incorporated by reference in its entirety herein).

Figure 7H:
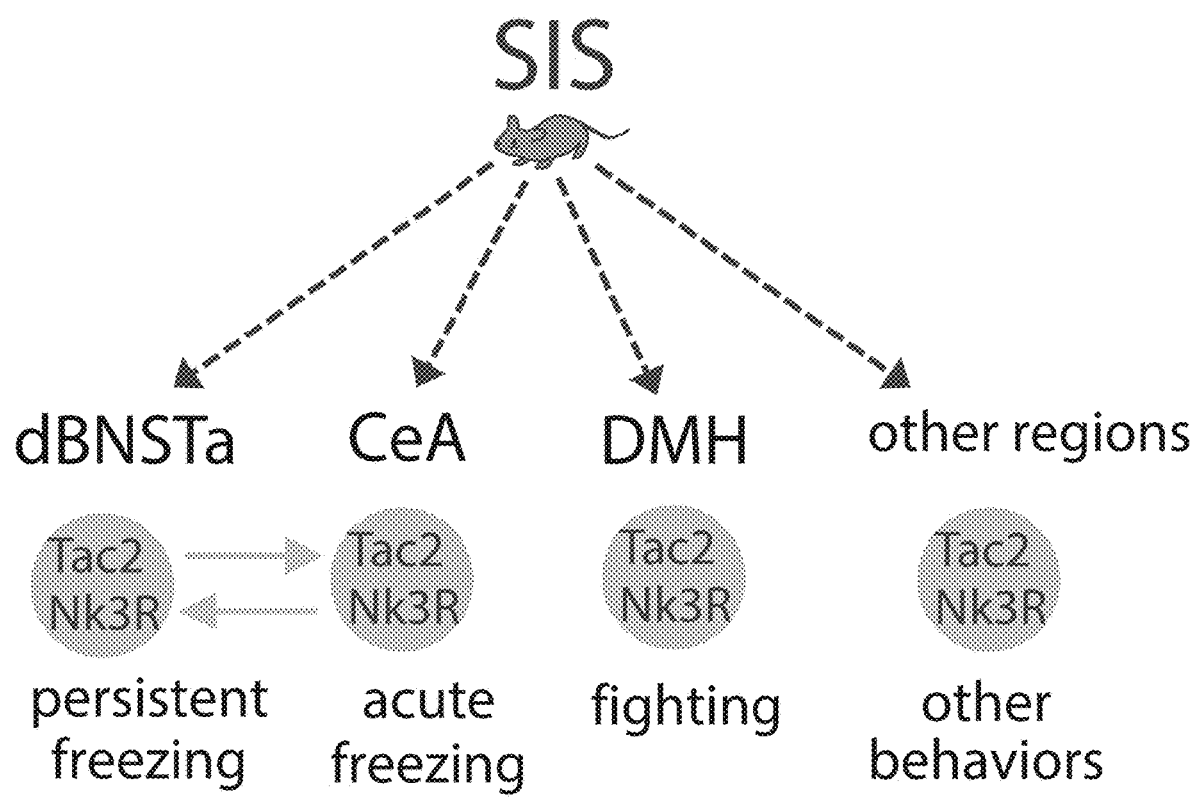
Figure 7I:
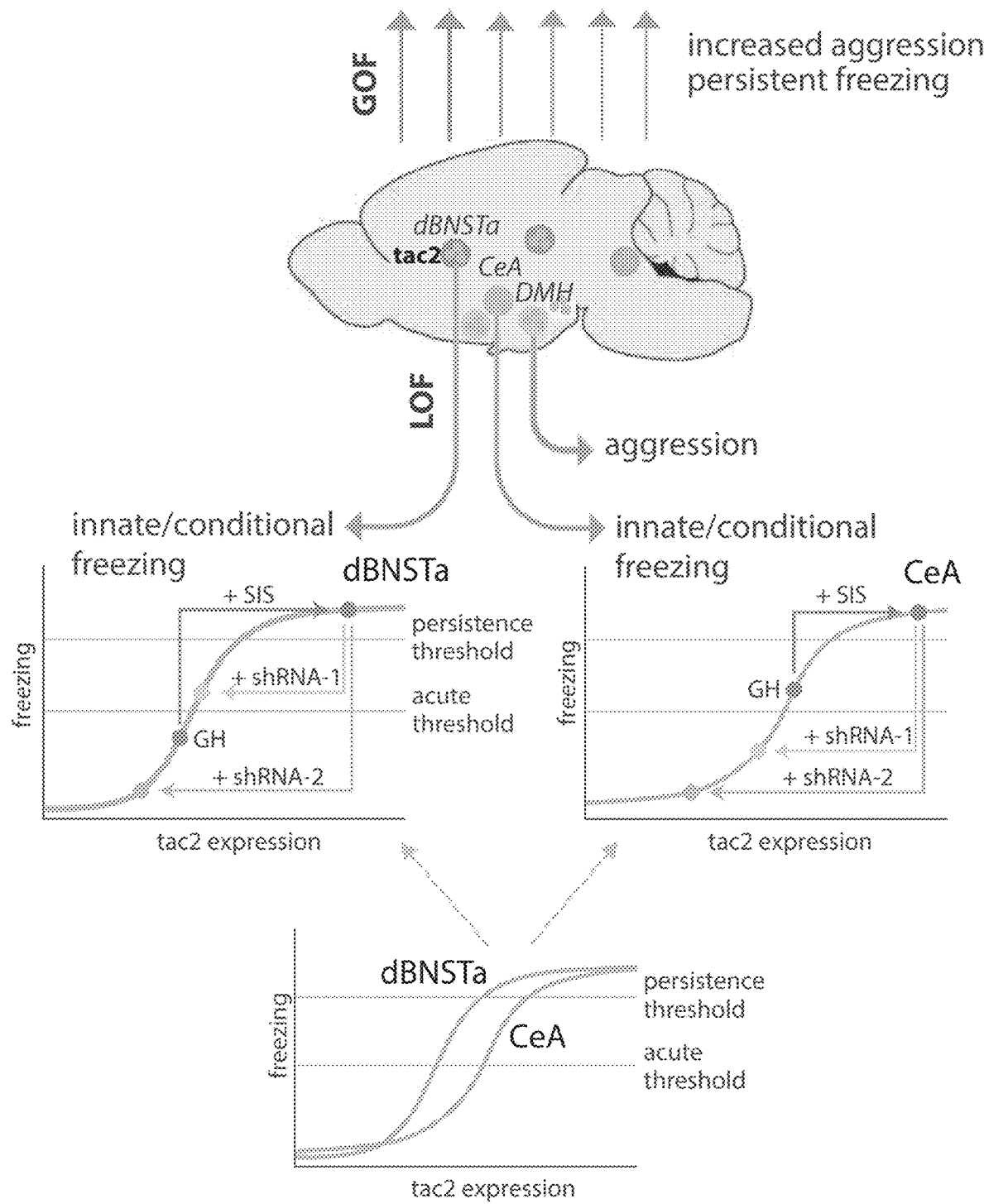

Tac2/NkB Controls Both Acute and Persistent Responses to Threats Depending on Level of the Peptide In dBNSTa, most of our LOF manipulations reduced persistent but not acute (during stimulus) freezing, while in CeA these same manipulations inhibited acute freezing. Without being limited by theory, while persistent freezing was also inhibited in CeA, there was no manipulation in this region that prevented persistent but not acute freezing, suggesting that the lack of persistence is secondary to the reduced acute response. This dissociation is consistent with the conventional view that CeA controls phasic, stimulus-locked responses to threats, while dBNSTa controls more persistent responses (Walker et al., 2009; Kash et al., 2015; incorporated by reference in its entirety). However, without being limited by theory, closer inspection of the data indicates that the functional distinction between these regions is more subtle. Specifically, in dBNSTa, the more potent shRNA-2 also reduced acute freezing during the stimulus, while the less potent shRNA-1 only reduced post-stimulus freezing. Without being limited by theory, these data suggest that the effects of Tac2/NkB signaling on acute vs. enduring responses to threats are not determined simply by the region(s) in which the neuropeptide acts, but also by the level of its expression and the "dose-response" properties or threshold sensitivity of each region to the neuropeptide (FIG. 7I, Example 8). Without being limited by theory, reciprocal connections between CeA and dBNST (Dong et al., 2001; Dong and Swanson, 2006b, a; incorporated by reference in their entirety herein) may contribute to their partially overlapping functions as well (FIG. 7H, Example 8).

We find that acute freezing responses to threats in GH animals can be converted to persistent ones simply by artificially promoting Tac2 expression and release. Preliminary data indicate that Tac2 plays a role in acute freezing in GH animals as well. Without being limited by theory, together, these data suggest that the up-regulation of Tac2 expression may convert defensive reactions to threats from transient to more enduring responses. In this way, the scalable property of neuropeptides—their concentration is a continuous variable—may be used to promote persistence, another feature of emotion states (Anderson and Adolphs, 2014; incorporated by reference in its entirety).

Identification of Tac2/NkB as a Substantial Mediator of Brain Responses to Chronic SIS In addition to CRF, a large number of other neuropeptides have been posited to play a role in stress responses, including the urocortins (UCNs 1-3), neuropeptide Y (NPY), vasopressin (AVP), pituitary adenyl cyclase-activating peptide (PACAP), neuropeptide S and others (reviewed in (Kormos and Gaszner, 2013; Kash et al., 2015; Chen, 2016; incorporated by reference in their entirety herein). Conventionally, most work on the tachykinins in stress has focused on Tac1/Substance P/NkA (Bilkei-Gorzo et al., 2002; Beaujouan et al., 2004; Ebner et al., 2004; Ebner et al., 2008; incorporated by reference in their entirety herein). Conventional pharmacological and genetic studies have yielded conflicting results regarding the direction of NkB influences on stress responses (Ebner et al., 2009; incorporated by reference in its entirety herein). Without being limited by theory, our data identify Tac2/NkB as a significant and previously unrecognized mediator of chronic SIS influences on the brain.

The role of Tac2/NkB to mediate SIS-enhanced aggression (Hatch et al., 1963; Valzelli, 1969; incorporated by reference in their entirety herein) distinguishes it from peptides involved in other forms of stress, which typically decrease rather than increase aggression (Maier, 1984; Hammack et al., 2012; each of which is incorporated by reference in its entirety herein). Without being limited by theory, the effect of Tac2/NkB on aggression is dissociable from its role in SIS-enhanced defensive behavior, and is exerted via the hypothalamus and not the amygdala, as generally assumed (Chattarji et al., 2015; incorporated by reference in its entirety herein). Without being limited by theory, the finding that tachykinins play a role in the control of social isolation-induced aggression in both flies (Asahina et al., 2014; incorporated by reference in its entirety herein) and mice is consistent with evidence supporting an evolutionary conservation of neuropeptide function in behavior across phylogeny (Bargmann, 2012; Katz and Lillvis, 2014; incorporated by reference in their entirety herein). In that context, without being limited by theory, it is possible that Tac2/NkB may play a role in the effect of solitary confinement to increase aggressiveness in humans (Arrigo and Bullock, 2008; incorporated by reference in its entirety herein).

While we uncovered a role for Tac2 in the SIS paradigm, and without being limited by theory, the role of Tac2 may be specific to SIS or extend to other stressors as well. Our SIS paradigm differs from acute and repeated intermitted stressors (footshock, restraint, forced swim) not only in its quality, but also in its extended duration and continuous nature. Without being limited by theory, the engagement of the Tac2/NkB system, therefore, could reflect any of these differences. However, it is currently difficult to directly compare acute stressors to SIS using the same continuous schedule. Nevertheless, a role for Tac2/NkB in consolidation of a conditioned fear memory in CeA, acting on a time scale of a day, has been proposed (Andero et al., 2014; incorporated by reference in its entirety herein). Therefore, without being limited by theory, Tac2 may play a broader role in responses to stressors other than SIS.

Nk3R Antagonists as Treatments for Effects of Long-Term Isolation

It has been set forth that social isolation promotes poor health, clinical psychiatric symptoms and increased mortality in humans (Cacioppo and Hawkley, 2009; Umberson and Montez, 2010; Cacioppo et al., 2015; Holt-Lunstad et al., 2015; incorporated by reference in their entirety herein). Osanetant and several other Nk3R antagonists have been tested in clinical trials as therapies for schizophrenia, bipolar and panic disorder (Spooren et al., 2005; incorporated by reference in its entirety herein). Although these drugs were well tolerated, they were abandoned for lack of efficacy (Griebel and Holsboer, 2012; incorporated by reference in its entirety herein). Without being limited by theory, the profound effect of osanetant to prevent and reverse an SIS-induced global brain state in accordance with some embodiments herein suggests that Nk3R antagonists may merit re-examination as potential indications for, e.g., mood disorders caused by extended periods of social isolation in humans as well as in animals.

REFERENCES

Each of the following references is incorporated herein by reference in its entirety:

Beaujouan, J. C., Torrens, Y., Saffroy, M., Kemel, M. L., and Glowinski, J. (2004). A 25 year adventure in the field of tachykinins. Peptides 25, 339-357.

Culman, J., and Unger, T. (1995). Central Tachykinins—Mediators of Defense Reaction and Stress Reactions. Canadian Journal of Physiology and Pharmacology 73, 885-891.

Griebel, G., and Holsboer, F. (2012). Neuropeptide receptor ligands as drugs for psychiatric diseases: the end of the beginning? Nature review Drug discovery, 1-17.

Maggio, J. E. (1988). Tachykinins. Annual review of neuroscience 11, 13-28.

Anthony, T. E., Dee, N., Bernard, A., Lerchner, W., Heintz, N., and Anderson, D. J. (2014). Control of stress-induced persistent anxiety by an extra-amygdala septohypothalamic circuit. Cell 156, 522-536.

Blanchard, D. C., Blanchard, R. J., and Griebel, G. (2005). Defensive responses to predator threat in the rat and mouse. Current protocols in neuroscience Chapter 8, Unit 8 19.

Blanchard, D. C., Griebel, G., and Blanchard, R. J. (2003). The Mouse Defense Test Battery: pharmacological and behavioral assays for anxiety and panic. European journal of pharmacology 463, 97-116.

Cai, H., Haubensak, W., Anthony, T. E., and Anderson, D. J. (2014). Central amygdala PKC-delta(+) neurons mediate the influence of multiple anorexigenic signals. Nature neuroscience 17, 1240-1248.

Cushman, J. D., Moore, M. D., Olsen, R. W., and Fanselow, M. S. (2014). The role of the delta GABA(A) receptor in ovarian cycle-linked changes in hippocampus-dependent learning and memory. Neurochemical research 39, 1140-1146.

Deneen, B., Ho, R., Lukaszewicz, A., Hochstim, C. J., Gronostajski, R. M., and Anderson, D. J. (2006). The transcription factor NFIA controls the onset of gliogenesis in the developing spinal cord. Neuron 52, 953-968.

Deverman, B. E., Pravdo, P. L., Simpson, B. P., Kumar, S. R., Chan, K. Y., Banerjee, A., Wu, W. L., Yang, B., Huber, N., Pasca, S. P., et al. (2016). Cre-dependent selection yields AAV variants for widespread gene transfer to the adult brain. Naturebiotechnology 34, 204-209.

Haubensak, W., Kunwar, P. S., Cai, H., Ciocchi, S., Wall, N. R., Ponnusamy, R., Biag, J., Dong, H. W., Deisseroth, K., Callaway, E. M., et al. (2010). Genetic dissection of an amygdala microcircuit that gates conditioned fear. Nature 468, 270-276.

Hong, W., Kennedy, A., Burgos-Artizzu, X. P., Zelikowsky, M., Navonne, S. G., Perona, P., and Anderson, D. J. (2015). Automated measurement of mouse social behaviors using depth sensing, video tracking, and machine learning. Proceedings of the National Academy of Sciences of the United States of America 112, E5351-5360.

Hong, W., Kim, D. W., and Anderson, D. J. (2014). Antagonistic control of social versus repetitive self-grooming behaviors by separable amygdala neuronal subsets. Cell 158, 1348-1361.

Hsiao, E. Y., McBride, S. W., Hsien, S., Sharon, G., Hyde, E. R., McCue, T., Codelli, J. A., Chow, J., Reisman, S. E., Petrosino, J. F., et al. (2013). Microbiota modulate behavioral and physiological abnormalities associated with neurodevelopmental disorders. Cell 155, 1451-1463.

Kim, J. J., DeCola, J. P., Landeira-Fernandez, J., and Fanselow, M. S. (1991). N-methyl-D-aspartate receptor antagonist APV blocks acquisition but not expression of fear conditioning. Behavioral neuroscience 105, 126-133.

Koch, M. (1999). The neurobiology of startle. Progress in neurobiology 59, 107-128.

Kunwar, P. S., Zelikowsky, M., Remedios, R., Cai, H., Yilmaz, M., Meister, M., and Anderson, D. J. (2015). Ventromedial hypothalamic neurons control a defensive emotion state. eLife 4.

Lee, H., Kim, D. W., Remedios, R., Anthony, T. E., Chang, A., Madisen, L., Zeng, H., and Anderson, D. J. (2014). Scalable control of mounting and attack by Esr1+ neurons in the ventromedial hypothalamus. Nature 509, 627-632.

Lein, E. S., Hawrylycz, M. J., Ao, N., Ayres, M., Bensinger, A., Bernard, A., Boe, A. F., Boguski, M. S., Brockway, K. S., Byrnes, E. J., et al. (2007). Genome-wide atlas of gene expression in the adult mouse brain. Nature 445, 168-176.

Madisen, L., Zwingman, T. A., Sunkin, S. M., Oh, S. W., Zariwala, H. A., Gu, H., Ng, L. L., Palmiter, R. D., Hawrylycz, M. J., Jones, A. R., et al. (2010). A robust and high-throughput Cre reporting and characterization system for the whole mouse brain. Nature neuroscience 13, 133-140.

Mongeau, R., Miller, G. A., Chiang, E., and Anderson, D. J. (2003). Neural correlates of competing fear behaviors evoked by an innately aversive stimulus. The Journal of neuroscience: the official journal of the Society for Neuroscience 23, 3855-3868.

Naito, Y., Yoshimura, J., Morishita, S., and Ui-Tei, K. (2009). siDirect 2.0: updated software for designing functional siRNA with reduced seed-dependent off-target effect. BMC bioinformatics 10, 392.

Shi, L., Fatemi, S. H., Sidwell, R. W., and Patterson, P. H. (2003). Maternal influenza infection causes marked behavioral and pharmacological changes in the offspring. The Journal of neuroscience: the official journal of the Society for Neuroscience 23, 297-302.

Thompson, C. L., Pathak, S. D., Jeromin, A., Ng, L. L., MacPherson, C. R., Mortrud, M. T., Cusick, A., Riley, Z. L., Sunkin, S. M., Bernard, A., et al. (2008). Genomic anatomy of the hippocampus. Neuron 60, 1010-1021.

Yilmaz, M., and Meister, M. (2013). Rapid innate defensive responses of mice to looming visual stimuli. Current biology: CB 23, 2011-2015.

Zelikowsky, M., Hersman, S., Chawla, M. K., Barnes, C. A., and Fanselow, M. S. (2014). Neuronal ensembles in amygdala, hippocampus, and prefrontal cortex track differential components of contextual fear. The Journal of neuroscience: the official journal of the Society for Neuroscience 34, 8462-8466.

With respect to the use of substantially any plural and/or singular terms herein, those having skill in the art can translate from the plural to the singular and/or from the singular to plural as is appropriate to the context and/or application. The various singular/plural permutations can be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Wherever a method of using a compound (e.g., a method comprising administering a NK3R antagonist) is disclosed herein, the corresponding compound for use is also expressly contemplated. For example, for the disclosure of a method of inhibiting, ameliorating, reducing the severity of, treating, reducing the likelihood of, or preventing social isolation stress or symptoms thereof in a subject in need thereof comprising administering a NK3R antagonist, the corresponding NK3R antagonist for use in inhibiting, ameliorating, reducing the severity of, treating, reducing the likelihood of, or preventing social isolation stress or symptoms thereof is also contemplated.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of inhibiting, ameliorating, reducing the severity of, or treating one or more symptoms caused by social isolation stress, the method comprising:
   identifying a subject as suffering from social isolation stress and in need of inhibiting, ameliorating, reducing the severity of, or treating one or more symptoms caused by the social isolation stress, wherein the subject does not have Alzheimer's disease or schizophrenia; and
   administering an effective amount of a neurokinin receptor antagonist to the subject, wherein the neurokinin receptor antagonist is a NK3R antagonist, to thereby inhibit, ameliorate, reduce the severity of, or treat the one or more symptoms caused by the social isolation stress.

2. The method of claim 1, further comprising:
   obtaining from the subject a sample from a peripheral tissue that is outside of the central nervous system; and
   detecting a level of neurokinin B in the sample.

3. The method of claim 1, wherein the subject suffers from at least one of aggression, cancer, major depressive disorder, dysthymic disorder, social phobia, generalized anxiety disorder, alcohol abuse and dependence, drug abuse, nicotine dependence, atherosclerosis, coronary heart disease, ischemic stroke, cognitive impairment, agoraphobia, post-traumatic stress disorder (PTSD), bereavement, or grieving in isolation.

4. The method of claim 1, wherein the subject has exhibited an induction of expression of neurokinin B in response to a lack of social interaction or contact.

5. The method of claim 4, wherein the subject, before administering the NK3R antagonist, exhibits a greater level of neurokinin B than the subject had prior to the induction of neurokinin B in response to the lack of social interaction or contact.

6. The method of claim 1, wherein the neurokinin receptor antagonist is an NK3R antagonist selected from the group consisting of: osanetant, talnetant, fezolinetant, pavinetant, SB-222200, and SB-218795, or a combination of two or more of the listed items.

7. The method of claim 1, wherein the neurokinin receptor antagonist is an NK3R antagonist that comprises osanetant.

8. The method of claim 1, wherein the subject is exposed to an innate or conditioned fear-evoking stimulus, or an aversive stimulus after the administering, whereby the one or more symptoms of social isolation stress in response to the innate or conditioned fear-evoking stimulus, or the aversive stimulus is inhibited, ameliorated, reduced in severity or treated.

9. The method of claim 8, wherein the neurokinin receptor antagonist is administered to the subject between 30 minutes to 1 day prior to the exposure to the innate or conditioned fear-evoking stimulus, or the aversive stimulus.

10. The method of claim 1, wherein the one or more symptoms of social isolation stress comprises one or more of aggression, a persistent response to threats, a persistent freezing in response to innate and conditioned fear-evoking stimuli, an enhanced reactivity to aversive stimuli, and reduced social interactions.

11. A method of treating a subject for one or more symptoms caused by social isolation stress, comprising:
   identifying a subject as suffering from social isolation stress, wherein the subject does not have Alzheimer's disease or schizophrenia; and
   administering an effective amount of a neurokinin receptor antagonist to the subject, to thereby treat one or more symptoms caused by social isolation stress,
   wherein the neurokinin receptor antagonist is a NK3R antagonist, and
   wherein the subject, before administering the neurokinin receptor antagonist, has an elevated level of neurokinin B induced by deprivation of social interaction or contact.

12. The method of claim 11, wherein the lack of social interaction or contact comprises physical separation of the subject from other individuals.

13. The method of claim 11, wherein the lack of social interaction or contact comprises lack of social interaction or contact due to grieving in isolation, residing as a patient in a skilled nursing facility, being in quarantine, imprisonment, solitary confinement, or experiencing feelings of isolation as an adolescent.

14. The method of claim 11, wherein the lack of social interaction or contact is for at least 1 week.

15. The method of claim 1, wherein the subject has social isolation stress due to physical separation of the subject from other individuals.

16. The method of claim 1, wherein the subject has social isolation stress due to grieving in isolation, residing as a patient in a skilled nursing facility, being in quarantine, imprisonment, solitary confinement, or experiencing feelings of isolation as an adolescent.

17. The method of claim 1, wherein the subject has social isolation stress due to a lack of social interaction or contact for at least 1 week.

18. The method of claim 1, wherein the subject does not have social phobia or agoraphobia.

19. The method of claim 11, wherein the subject does not have social phobia or agoraphobia.

20. The method of claim 1, wherein the subject is a human subject.

21. The method of claim 11, wherein the subject is a human subject.

22. The method of claim 1, wherein the subject is identified as having at least one of the following caused by deprivation of social interaction or contact: increased aggression, increased anxiety, a persistent response to an innate or conditioned fear-evoking stimulus, and an enhanced reactivity to an aversive stimulus.

23. The method of claim 1, wherein the subject is identified as having at least increased aggression caused by deprivation of social interaction or contact.

\* \* \* \* \*